US009611317B2

(12) United States Patent
Throsby et al.

(10) Patent No.: US 9,611,317 B2
(45) **Date of Patent: *Apr. 4, 2017**

(54) HUMAN BINDING MOLECULES CAPABLE OF NEUTRALIZING INFLUENZA VIRUS H3N2 AND USES THEREOF

(71) Applicant: Crucell Holland B.V., Leiden (NL)

(72) Inventors: Mark Throsby, Utrecht (NL); Robert H. E. Friesen, Leiden (NL); Theodorus H. J. Kwaks, Voorschoten (NL); Mandy A. C. Jongeneelen, Leiden (NL)

(73) Assignee: Crucell Holland B.V., Leiden (NL)

( * ) Notice: Subject to any disclaimer, the term of this patent is extended or adjusted under 35 U.S.C. 154(b) by 547 days.

This patent is subject to a terminal disclaimer.

(21) Appl. No.: 13/897,843

(22) Filed: May 20, 2013

(65) Prior Publication Data

US 2013/0309248 A1 Nov. 21, 2013
US 2015/0175677 A9 Jun. 25, 2015

Related U.S. Application Data

(63) Continuation of application No. 13/138,941, filed as application No. PCT/EP2010/056217 on May 6, 2010, now Pat. No. 8,470,327.

(60) Provisional application No. 61/215,890, filed on May 11, 2009.

(30) Foreign Application Priority Data

May 11, 2009 (EP) .................................... 09159947
Jan. 20, 2010 (EP) .................................... 10151155

(51) Int. Cl.

*A61K 39/145* (2006.01)
*C12Q 1/70* (2006.01)
*C07K 16/10* (2006.01)
*A61K 39/12* (2006.01)
*A61K 39/00* (2006.01)

(52) U.S. Cl.

CPC .......... *C07K 16/1018* (2013.01); *A61K 39/12* (2013.01); *A61K 2039/505* (2013.01); *A61K 2039/507* (2013.01); *A61K 2039/545* (2013.01); *C07K 2317/21* (2013.01); *C07K 2317/33* (2013.01); *C07K 2317/34* (2013.01); *C07K 2317/55* (2013.01); *C07K 2317/622* (2013.01); *C07K 2317/76* (2013.01); *C07K 2317/92* (2013.01); *C12N 2760/16111* (2013.01)

(58) Field of Classification Search

None
See application file for complete search history.

(56) References Cited

U.S. PATENT DOCUMENTS

| | | | |
|---|---|---|---|
| 5,696,108 A | 12/1997 | Heath, Jr. et al. | |
| 6,265,150 B1 | 7/2001 | Terstappen et al. | |
| 8,470,327 B2 * | 6/2013 | Throsby et al. | 424/159.1 |
| 2008/0014205 A1 | 1/2008 | Horowitz et al. | |
| 2008/0152657 A1 | 6/2008 | Horowitz et al. | |
| 2009/0092620 A1 | 4/2009 | Moste et al. | |
| 2009/0311265 A1 | 12/2009 | Van Den Brink et al. | |

FOREIGN PATENT DOCUMENTS

| | | |
|---|---|---|
| WO | WO8403564 | 9/1984 |
| WO | WO9309872 | 5/1993 |
| WO | WO9815833 | 4/1998 |
| WO | WO0063403 | 10/2000 |
| WO | WO02103012 | 12/2002 |
| WO | WO2007067046 | 6/2007 |
| WO | WO2008028946 | 3/2008 |
| WO | WO2008110937 | 9/2008 |
| WO | WO2009035420 | 3/2009 |
| WO | WO2009036157 | 3/2009 |
| WO | WO2009053604 | 4/2009 |
| WO | WO2009079259 | 6/2009 |
| WO | WO2009115972 | 9/2009 |
| WO | WO2010130636 | 11/2010 |

OTHER PUBLICATIONS

Stropkovská et al. (Acta Virol. Mar. 2009;53 (1):15-20).*
Presta LG (Curr Opin Immunol. Aug. 2008;20(4):460-70).*
Search Report for PCT/EP2010/056217, 2010.*
Ekiert et al., A Highly Conserved Neutralizing Epitope on Group 2 Influenza A Viruses, Science, Aug. 12, 2011, pp. 843-850, vol. 333.
Yoshida et al., Cross-protective potential of a novel monoclonal antibody directed against antigenic site B of the hemagglutinin of influenza A viruses, PLOS Pathogens, Mar. 2009, pp. E1000350, vol. 5, No. 3.
Stropkovska et al., Broadly cross-reactive monoclonal antibodies against HA2 glycopeptide of Influenza A virus hemagglutinin of H3 subtype reduce replication of influenza A viruses of human and avian origin, ACTA Virologica, 2009, pp. 15-20, vol. 53, No. 1.
Gocnik et al., Antibodies specific to HA2 glycopolypeptide of influenza A virus haemagglutinin with fusion-inhibition activity contribute to the protection of mice against lethal infection, Journal of General Virology, Mar. 2007, pp. 951-955, vol. 88, No. Part 3.

(Continued)

*Primary Examiner* — Agnieszka Boesen
(74) *Attorney, Agent, or Firm* — TraskBritt P.C.

(57) ABSTRACT

Described are binding molecules, e.g., human monoclonal antibodies, that bind to influenza virus comprising HA of the H3 subtype, e.g., H3N2, and have a broad neutralizing activity against such influenza virus. Described are polynucleotides encoding the binding molecules, their sequences and compositions comprising the binding molecules and methods of identifying or producing the binding molecules. The binding molecules can be used in the diagnosis, prophylaxis, and/or treatment of influenza virus H3N2 infection. The binding molecules may provide cross-subtype protection, such that infections with H3, H7, and/or H10-based influenza subtypes can be prevented and/or treated.

11 Claims, 17 Drawing Sheets

(56) References Cited

OTHER PUBLICATIONS

Throsby et al., Heterosubtypic neutralizing monoclonal antibodies cross-protective against H5N1 and H1N1 recovered from human IgM+ memory B cells, PLOS ONE 2008, pp. E3942, vol. 3, No. 12.
Kashyap et al., Combinatorial antibody libraries from survivors of the Turkish H5N1 avian influenza outbreak reveal virus neutralization strategies, Proceedings of the National Academy of Sciences of USA, Apr. 22, 2008, pp. 5986-5991, vol. 105, No. 16, National Academy of Science, Washington, DC, US.
Liu et al., Panorama phylogenetic diversity and distribution of Type A influenza virus, PLOS One, 2009, pp. E5022, vol. 4, No. 3.
Sui et al., Structural and functional bases for broad-spectrum neutralization of avian and human influenza A viruses, Nature Structural and Molecular Biology, Mar. 1, 2009, pp. 265-273, vol. 16, No. 3, Nature Publishing Group, US.
PCT International Search Report, PCT/EP2010/056217, dated Jul. 14, 2010.
PCT International Preliminary Report on Patentability, PCT/EP2010/056217, dated Jul. 18, 2011.
Shibuya T, Yamashiro T, Masaike Y, Ohuchi M, Uechi G, Nishizono A. Identification of a human monoclonal Fab with neutralizing activity against H3N2 influenza A strain from a newly constructed human Fab library. Microbial Immunol. Mar. 2008;52(3):162-70.
Vareckova E et al. Inhibition of fusion activity of influenza A haemagglutinin mediated by HA2-specific monoclonal antibodies. Arch Virol. Mar. 2003;148(3):469-86.
Stropkovska A et al. Broadly cross-reactive monoclonal antibodies against HA2 glycopeptide of Influenza A virus hemagglutinin of H3 subtype reduce replication of influenza A viruses of human and avian origin. Acta Virol. 2009;53 (1):15-20.
Presta LG. Molecular engineering and design of therapeutic antibodies. Curr Opin Immunol. Aug. 2008;20(4):460-70.

* cited by examiner

A.

B.

C.

CR8020 CR8041 CR8043 CR8057

A.

B.

C.

A.

B.

C.

A.

B.

C.

A.

B.

C.

A.

B.

C.

A.

B.

C.

A.

B.

C.

SEQUENCE LISTING

<160> NUMBER OF SEQ ID NOS: 258

<210> SEQ ID NO 1
<211> LENGTH: 339
<212> TYPE: DNA
<213> ORGANISM: Artificial
<220> FEATURE:
<223> OTHER INFORMATION: SC08-001 VH DNA

<400> SEQUENCE: 1
gaggtgcagc tggtggagtc tggaggaggc ctgatccagc cggggggtc cctgagactc 60 tcctgtgcag cctctggatt caccgtcagt agcaactacg tgagctgggt ccgccaggcc 120
ccagggaagg ggctggagtg gctctcactt atttacacgg gtggtaccac atactacgca 180
gactccgtga agggccgatt caccatctcc agagacaact ccaagaatac ggtgtttctt 240
caaatgaaca gcctgagagc cgaggacgcg gccatgtatt actgtgcgag agtgtcagca 300
ttacggtttt tgcagtggcc aaactacgcg atggacgtc 339

<210> SEQ ID NO 2
<211> LENGTH: 113
<212> TYPE: PRT
<213> ORGANISM: Artificial
<220> FEATURE:
<223> OTHER INFORMATION: SC08-001 VH PROTEIN

<400> SEQUENCE: 2

Glu Val Gln Leu Val Glu Ser Gly Gly Gly Leu Ile Gln Pro Gly Gly
1 5 10 15

Ser Leu Arg Leu Ser Cys Ala Ala Ser Gly Phe Thr Val Ser Ser Asn
20 25 30

Tyr Val Ser Trp Val Arg Gln Ala Pro Gly Lys Gly Leu Glu Trp Leu
35 40 45

Ser Leu Ile Tyr Thr Gly Gly Thr Thr Tyr Tyr Ala Asp Ser Val Lys
50 55 60

Gly Arg Phe Thr Ile Ser Arg Asp Asn Ser Lys Asn Thr Val Phe Leu
65 70 75 80

Gln Met Asn Ser Leu Arg Ala Glu Asp Ala Ala Met Tyr Tyr Cys Ala
85 90 95

Arg Val Ser Ala Leu Arg Phe Leu Gln Trp Pro Asn Tyr Ala Met Asp
100 105 110

Val

<210> SEQ ID NO 3
<211> LENGTH: 303
<212> TYPE: DNA
<213> ORGANISM: Artificial
<220> FEATURE:
<223> OTHER INFORMATION: SC08-001 VL DNA

<400> SEQUENCE: 3
cagtctgccc tgactcagcc tgcctccgtg tctgggtctc ctggacggtc gatcaccatc 60
tcctgctctg gaacccgcag tgacgttggt ggtcataatt atgtctcctg gtaccaacaa 120
cacccaggca aagcccccaa actcatgatt tatgaggtca gtcatcggcc ctcaggggtt 180
tctaatcgct tctctggctc caagtctggc agcacggcct ccctgaccat ctctggcctc 240
cagtctgagg acgaggctga ttattactgc agctcttata caggtgaagg ccccctagga 300
gtg 303

<210> SEQ ID NO 4
<211> LENGTH: 101
<212> TYPE: PRT
<213> ORGANISM: Artificial
<220> FEATURE:
<223> OTHER INFORMATION: SC08-001 VL PROTEIN

<400> SEQUENCE: 4

```
Gln Ser Ala Leu Thr Gln Pro Ala Ser Val Ser Gly Ser Pro Gly Arg
1               5                   10                  15

Ser Ile Thr Ile Ser Cys Ser Gly Thr Arg Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Glu Val Ser His Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80

Gln Ser Glu Asp Glu Ala Asp Tyr Tyr Cys Ser Ser Tyr Thr Gly Glu
                85                  90                  95

Gly Pro Leu Gly Val
            100
```

<210> SEQ ID NO 5
<211> LENGTH: 342
<212> TYPE: DNA
<213> ORGANISM: Artificial
<220> FEATURE:
<223> OTHER INFORMATION: SC08-003 VH DNA

<400> SEQUENCE: 5

```
gaggtgcagc tggtggagac cggggggagac ttggtccagc ctggggggtc cctgagactc      60

tcctgttcag cctctgaatt cagcttcagt agttattgga tgagctgggt ccgccaggct     120

ccagggaaag ggctggagtg ggtggccaac atgaagcaag atggaagtga gaagtactat     180

gtggactctg tgaagggccg gttcaccatc tccagagaca acgccaagaa ctcattatat     240

ctgcaaatga acagcctgag aggcgaggac acggctgtgt attactgtgc gaggggttcc     300

tgtgacgatt cttggactgg ttgtcatgat gcttttgaca tc                        342
```

<210> SEQ ID NO 6
<211> LENGTH: 114
<212> TYPE: PRT
<213> ORGANISM: Artificial
<220> FEATURE:
<223> OTHER INFORMATION: SC08-003 VH PROTEIN

<400> SEQUENCE: 6

```
Glu Val Gln Leu Val Glu Thr Gly Gly Asp Leu Val Gln Pro Gly Gly
1               5                   10                  15

Ser Leu Arg Leu Ser Cys Ser Ala Ser Glu Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Met Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
```

```
                85                  90                  95

Ala Arg Gly Ser Cys Asp Asp Ser Trp Thr Gly Cys His Asp Ala Phe
            100                 105                 110

Asp Ile


<210> SEQ ID NO 7
<211> LENGTH: 291
<212> TYPE: DNA
<213> ORGANISM: Artificial
<220> FEATURE:
<223> OTHER INFORMATION: SC08-003 VL DNA

<400> SEQUENCE: 7

gtgttgacgc agccgccctc ggtgtcagtg gccccaggac agacggccag gattgcctgt      60

gggggaaaca acattgggag taaaagtgtg cactggtacc agcagaagcc aggccaggcc     120

cctgtgctgg tcgtctatga tgatagcgcc cggccctcag ggatccctga gcgattctct     180

ggctccaatt ctgggaacac ggccaccctg accatcagca gggtcgaggc cggggatgaa     240

gccgactatt actgtcaggt gtgggagagt ggtagtgatc tacgactgct t              291


<210> SEQ ID NO 8
<211> LENGTH: 97
<212> TYPE: PRT
<213> ORGANISM: Artificial
<220> FEATURE:
<223> OTHER INFORMATION: SC08-003 VL PROTEIN

<400> SEQUENCE: 8

Val Leu Thr Gln Pro Pro Ser Val Ser Val Ala Pro Gly Gln Thr Ala
1               5                   10                  15

Arg Ile Ala Cys Gly Gly Asn Asn Ile Gly Ser Lys Ser Val His Trp
            20                  25                  30

Tyr Gln Gln Lys Pro Gly Gln Ala Pro Val Leu Val Val Tyr Asp Asp
        35                  40                  45

Ser Ala Arg Pro Ser Gly Ile Pro Glu Arg Phe Ser Gly Ser Asn Ser
    50                  55                  60

Gly Asn Thr Ala Thr Leu Thr Ile Ser Arg Val Glu Ala Gly Asp Glu
65                  70                  75                  80

Ala Asp Tyr Tyr Cys Gln Val Trp Glu Ser Gly Ser Asp Leu Arg Leu
                85                  90                  95

Leu


<210> SEQ ID NO 9
<211> LENGTH: 342
<212> TYPE: DNA
<213> ORGANISM: Artificial
<220> FEATURE:
<223> OTHER INFORMATION: SC08-015 VH DNA

<400> SEQUENCE: 9

caggtgcagc tgcaggagtc gggggagac ttggtccagc ctgggggtc cctgagactc      60

tcctgttcag cctctgaatt cagcttcagt agttattgga tgagctgggt ccgccaggct     120

ccagggaaag ggctggagtg ggtggccaac atgaagcaag atggaagtga gaagtactat     180

gtggactctg tgaagggccg gttcaccatc tccagagaca acgccaagaa ctcattatat     240

ctgcaaatga acagcctgag aggcgaggac acggctgtgt attactgtgc gaggggttcc     300

tgtgacgatt cttggactgg ttgtcatgat gcttttgaca tc                        342
```

<210> SEQ ID NO 10
<211> LENGTH: 114
<212> TYPE: PRT
<213> ORGANISM: Artificial
<220> FEATURE:
<223> OTHER INFORMATION: SC08-015 VH PROTEIN

<400> SEQUENCE: 10

```
Gln Val Gln Leu Gln Glu Ser Gly Gly Asp Leu Val Gln Pro Gly Gly
1               5                   10                  15

Ser Leu Arg Leu Ser Cys Ser Ala Ser Glu Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Met Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Gly Ser Cys Asp Asp Ser Trp Thr Gly Cys His Asp Ala Phe
            100                 105                 110

Asp Ile
```

<210> SEQ ID NO 11
<211> LENGTH: 288
<212> TYPE: DNA
<213> ORGANISM: Artificial
<220> FEATURE:
<223> OTHER INFORMATION: SC08-015 VL DNA

<400> SEQUENCE: 11

```
gtgttgacgc agccgccctc ggtgtcagtg gccccaggac agacggccaa gattacctgt     60

gggggagaca acattggaag aaaaagtgtg cactggtacc agcagaagcc aggcctggcc    120

cctgtgctgg tcgtcaatga taatagcgac cggccctcag ggatccctgc gcgattctct    180

ggctccaact ctgggaacac ggccaccctg accatcagca gggtcgaagc cggggatgag    240

gccgactatt actgtcacgt gtggggtagt agtcgtgacc attatgtc                 288
```

<210> SEQ ID NO 12
<211> LENGTH: 96
<212> TYPE: PRT
<213> ORGANISM: Artificial
<220> FEATURE:
<223> OTHER INFORMATION: SC08-015 VL PROTEIN

<400> SEQUENCE: 12

```
Val Leu Thr Gln Pro Pro Ser Val Ser Val Ala Pro Gly Gln Thr Ala
1               5                   10                  15

Lys Ile Thr Cys Gly Gly Asp Asn Ile Gly Arg Lys Ser Val His Trp
            20                  25                  30

Tyr Gln Gln Lys Pro Gly Leu Ala Pro Val Leu Val Val Asn Asp Asn
        35                  40                  45

Ser Asp Arg Pro Ser Gly Ile Pro Ala Arg Phe Ser Gly Ser Asn Ser
    50                  55                  60

Gly Asn Thr Ala Thr Leu Thr Ile Ser Arg Val Glu Ala Gly Asp Glu
65                  70                  75                  80

Ala Asp Tyr Tyr Cys His Val Trp Gly Ser Ser Arg Asp His Tyr Val
```

85 90 95

<210> SEQ ID NO 13
<211> LENGTH: 342
<212> TYPE: DNA
<213> ORGANISM: Artificial
<220> FEATURE:
<223> OTHER INFORMATION: SC08-016 VH DNA

<400> SEQUENCE: 13
gaggtgcagc tggtggagtc tgggggagac ttggtccagc ctgggggtc cctgagactc 60 tcctgttcag cctctgaatt cagcttcagt agttattgga tgagctgggt ccgccaggct 120
ccagggaaag ggctggagtg ggtggccaac atgaagcaag atggaagtga gaagtactat 180
gtggactctg tgaagggccg gttcaccatc tccagagaca acgccaagaa ctcattatat 240
ctgcaaatga acagcctgag aggcgaggac acggctgtgt attactgtgc gaggggttcc 300
tgtgacgatt cttggactgg ttgtcatgat gcttttgaca tc 342

<210> SEQ ID NO 14
<211> LENGTH: 114
<212> TYPE: PRT
<213> ORGANISM: Artificial
<220> FEATURE:
<223> OTHER INFORMATION: SC08-016 VH PROTEIN

<400> SEQUENCE: 14

Glu Val Gln Leu Val Glu Ser Gly Gly Asp Leu Val Gln Pro Gly Gly
1 5 10 15

Ser Leu Arg Leu Ser Cys Ser Ala Ser Glu Phe Ser Phe Ser Ser Tyr
20 25 30

Trp Met Ser Trp Val Arg Gln Ala Pro Gly Lys Gly Leu Glu Trp Val
35 40 45

Ala Asn Met Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Gly Glu Asp Thr Ala Val Tyr Tyr Cys
85 90 95

Ala Arg Gly Ser Cys Asp Asp Ser Trp Thr Gly Cys His Asp Ala Phe
100 105 110

Asp Ile

<210> SEQ ID NO 15
<211> LENGTH: 303
<212> TYPE: DNA
<213> ORGANISM: Artificial
<220> FEATURE:
<223> OTHER INFORMATION: SC08-016 VL DNA

<400> SEQUENCE: 15
cagtctgtcg tgacgcagcc gccctcagtg tctggggccc cagggcagag ggtcaccatc 60
tcctgcactg ggagcagctc caacatcggg gcaggttatg atgtacactg gtaccagcag 120
cttccaggaa cagcccccaa actcctcatc tatggtaaca acaatcggcc ctcaggggtc 180
cctgaccgat tctctggatc caggtctggc cctttagccc tcctggccat cactgggctc 240
caggctgagg atgaggctga ttattactgc cagtcctatg acagcagcct gagtgtttat 300
gtc 303

```
<210> SEQ ID NO 16
<211> LENGTH: 101
<212> TYPE: PRT
<213> ORGANISM: Artificial
<220> FEATURE:
<223> OTHER INFORMATION: SC08-016 VL PROTEIN

<400> SEQUENCE: 16

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Arg Ser Gly Pro Leu Ala Leu Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Tyr Val
            100


<210> SEQ ID NO 17
<211> LENGTH: 342
<212> TYPE: DNA
<213> ORGANISM: Artificial
<220> FEATURE:
<223> OTHER INFORMATION: SC08-017 VH DNA

<400> SEQUENCE: 17

gaggtgcagc tggtggagac tggggagac ttggtccagc ctggggggtc cctgagactc      60

tcctgttcag cctctgaatt cagcttcagt agttattgga tgagctgggt ccgccaggct     120

ccagggaaag ggctggagtg ggtggccaac atgaagcaag atggaagtga gaagtactat     180

gtggactctg tgaagggccg gttcaccatc tccagagaca acgccaagaa ctcattatat     240

ctgcaaatga acagcctgag aggcgaggac acggctgtgt attactgtgc gaggggttcc     300

tgtgacgatt cttggactgg ttgtcatgat gcttttgaca tc                        342


<210> SEQ ID NO 18
<211> LENGTH: 114
<212> TYPE: PRT
<213> ORGANISM: Artificial
<220> FEATURE:
<223> OTHER INFORMATION: SC08-017 VH PROTEIN

<400> SEQUENCE: 18

Glu Val Gln Leu Val Glu Thr Gly Gly Asp Leu Val Gln Pro Gly Gly
1               5                   10                  15

Ser Leu Arg Leu Ser Cys Ser Ala Ser Glu Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Met Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
```

```
                85                  90                  95

Ala Arg Gly Ser Cys Asp Asp Ser Trp Thr Gly Cys His Asp Ala Phe
            100                 105                 110

Asp Ile


<210> SEQ ID NO 19
<211> LENGTH: 294
<212> TYPE: DNA
<213> ORGANISM: Artificial
<220> FEATURE:
<223> OTHER INFORMATION: SC08-017 VL DNA

<400> SEQUENCE: 19

tcttctgagc tgactcagga ccctgctgtg tctgtggcct tgggacagac agtcaggatc     60

acatgccaag gagacagcct cagaagctat tatgcaagct ggtaccagca gaagccagga    120

caggcccctg tacttgtcat ctatgctaaa accaaccggc cctcagggat cccagaccga    180

ttctctggct ccacctcagg aaacactgct tccttgacca tcactggggc tcaggcggag    240

gatgaggctg actattactg taactcccgg gacagcagtg gtaaccatgt ggta          294


<210> SEQ ID NO 20
<211> LENGTH: 98
<212> TYPE: PRT
<213> ORGANISM: Artificial
<220> FEATURE:
<223> OTHER INFORMATION: SC08-017 VL PROTEIN

<400> SEQUENCE: 20

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Ala Lys Thr Asn Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val


<210> SEQ ID NO 21
<211> LENGTH: 342
<212> TYPE: DNA
<213> ORGANISM: Artificial
<220> FEATURE:
<223> OTHER INFORMATION: SC08-018 VH DNA

<400> SEQUENCE: 21

gaggtgcagc tggtggagac tgggggagac ttggtccagc ctggggggtc cctgagactc     60

tcctgttcag cctctgaatt cagcttcagt agttattgga tgagctgggt ccgccaggct    120

ccagggaaag ggctggagtg ggtggccaac atgaagcaag atggaagtga gaagtactat    180

gtggactctg tgaagggccg gttcaccatc tccagagaca acgccaagaa ctcattatat    240

ctgcaaatga acagcctgag aggcgaggac acggctgtgt attactgtgc gaggggttcc    300

tgtgacgatt cttggactgg ttgtcatgat gcttttgata tc                       342
```

```
<210> SEQ ID NO 22
<211> LENGTH: 114
<212> TYPE: PRT
<213> ORGANISM: Artificial
<220> FEATURE:
<223> OTHER INFORMATION: SC08-018 VH PROTEIN

<400> SEQUENCE: 22

Glu Val Gln Leu Val Glu Thr Gly Gly Asp Leu Val Gln Pro Gly Gly
1               5                   10                  15

Ser Leu Arg Leu Ser Cys Ser Ala Ser Glu Phe Ser Phe Ser Ser Tyr
            20                  25                  30

Trp Met Ser Trp Val Arg Gln Ala Pro Gly Lys Gly Leu Glu Trp Val
        35                  40                  45

Ala Asn Met Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Gly Ser Cys Asp Asp Ser Trp Thr Gly Cys His Asp Ala Phe
            100                 105                 110

Asp Ile


<210> SEQ ID NO 23
<211> LENGTH: 303
<212> TYPE: DNA
<213> ORGANISM: Artificial
<220> FEATURE:
<223> OTHER INFORMATION: SC08-018 VL DNA

<400> SEQUENCE: 23

cagtctgccc tgactcagcc tgcctccgtg tctgggtctc ctggacagtc gatcaccatc     60

tcctgcactg gaaccagcag tgacgttggt ggttataact atgtctcctg gtaccaacaa    120

cacccaggca aagcccccaa actcatgatt tatgaggtca gtcatcggcc ctcaggggtt    180

tctaatcgct tctctggctc caagtctggc agcacggcct ccctgaccat ctctggcctc    240

cagtctgagg acgaggctga ttattactgc agctcttata caggtgaagg cccccctagga    300

gtg                                                                  303


<210> SEQ ID NO 24
<211> LENGTH: 101
<212> TYPE: PRT
<213> ORGANISM: Artificial
<220> FEATURE:
<223> OTHER INFORMATION: SC08-018 VL PROTEIN

<400> SEQUENCE: 24

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser His Arg Pro Ser Gly Val Ser Asn Arg Phe
    50                  55                  60

Ser Gly Ser Lys Ser Gly Ser Thr Ala Ser Leu Thr Ile Ser Gly Leu
65                  70                  75                  80
```

```
Gln Ser Glu Asp Glu Ala Asp Tyr Tyr Cys Ser Ser Tyr Thr Gly Glu
                85                  90                  95

Gly Pro Leu Gly Val
            100


<210> SEQ ID NO 25
<211> LENGTH: 357
<212> TYPE: DNA
<213> ORGANISM: Artificial
<220> FEATURE:
<223> OTHER INFORMATION: SC08-019 VH DNA

<400> SEQUENCE: 25

gaggtgcagc tggtggagtc tgggggaggc ttggtacagc ctgggggtc cctgagactc      60

tcctgtggag cctctggaat cagcgttagc acttctgcca tgagctgggt ccgccaggtt     120

ccagggaagg ggctggagtg ggtctcaggt attagtggta gtggtgctac cacatactac     180

gcaggctccg tgaagggtcg attcaccatc tccagagaca aatccaagaa cacactgcat     240

ctgcaaatga gcagactgag agccgaggac acggccattt actactgtgc gaaagatacc     300

tccttgtttg agtatgatac aagtggtttt acggctcccg gcaatgcttt tgatatc        357


<210> SEQ ID NO 26
<211> LENGTH: 119
<212> TYPE: PRT
<213> ORGANISM: Artificial
<220> FEATURE:
<223> OTHER INFORMATION: SC08-019 VH PROTEIN

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Gly Ala Ser Gly Ile Ser Val Ser Thr Ser
            20                  25                  30

Ala Met Ser Trp Val Arg Gln Val Pro Gly Lys Gly Leu Glu Trp Val
        35                  40                  45

Ser Gly Ile Ser Gly Ser Gly Ala Thr Thr Tyr Tyr Ala Gly Ser Val
    50                  55                  60

Lys Gly Arg Phe Thr Ile Ser Arg Asp Lys Ser Lys Asn Thr Leu His
65                  70                  75                  80

Leu Gln Met Ser Arg Leu Arg Ala Glu Asp Thr Ala Ile Tyr Tyr Cys
                85                  90                  95

Ala Lys Asp Thr Ser Leu Phe Glu Tyr Asp Thr Ser Gly Phe Thr Ala
            100                 105                 110

Pro Gly Asn Ala Phe Asp Ile
        115


<210> SEQ ID NO 27
<211> LENGTH: 294
<212> TYPE: DNA
<213> ORGANISM: Artificial
<220> FEATURE:
<223> OTHER INFORMATION: SC08-019 VL DNA

<400> SEQUENCE: 27

gacatccagw tgacccagtc tccatcctcc ctgtctgcat ctgtagatga cagagtcacc      60

atcacttgcc gggcaagtca gagcattagc ggctatttaa attggtatca acagaaacca     120

gggaaagccc ctaacctcct gatctatggt gcatccactt tgcagagtgg ggtcccatca     180
```

```
aggttcagtg gcagtggatc tgggacagat ttcactctca ccatcaccag tctgcaacct    240

gaagactatg caacttacta ctgtcaacag acttacacct cccctccgta cgct          294


<210> SEQ ID NO 28
<211> LENGTH: 98
<212> TYPE: PRT
<213> ORGANISM: Artificial
<220> FEATURE:
<223> OTHER INFORMATION: SC08-019 VL PROTEIN
<220> FEATURE:
<221> NAME/KEY: misc_feature
<222> LOCATION: (4)..(4)
<223> OTHER INFORMATION: Xaa can be any naturally occurring amino acid

<400> SEQUENCE: 28

Asp Ile Gln Xaa Thr Gln Ser Pro Ser Ser Leu Ser Ala Ser Val Asp
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Asn Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Tyr Ala Thr Tyr Tyr Cys Gln Gln Thr Tyr Thr Ser Pro Pro
                85                  90                  95

Tyr Ala


<210> SEQ ID NO 29
<211> LENGTH: 333
<212> TYPE: DNA
<213> ORGANISM: Artificial
<220> FEATURE:
<223> OTHER INFORMATION: SC08-020 VH DNA

<400> SEQUENCE: 29

caggtacagc tgcagcagtc aggagctgag gtgaagaccc ctggggcctc agtgaaggtc     60

tcctgcaagg cctctggata cacctttacc aggtttggtg tcagctggat acgacaggcc    120

cctggacaag ggcttgagtg gattggatgg atcagcgctt acaatggtga cacatactat    180

gcacagaagt tccaggccag agtcaccatg accacagaca catccacgac cacagcctac    240

atggagatga ggagcctgag atctgacgac acggccgtgt attactgtgc gagagaaccc    300

cccctttttt acagcagctg gtctcttgac aac                                 333


<210> SEQ ID NO 30
<211> LENGTH: 111
<212> TYPE: PRT
<213> ORGANISM: Artificial
<220> FEATURE:
<223> OTHER INFORMATION: SC08-020 VH PROTEIN

<400> SEQUENCE: 30

Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Arg Phe
            20                  25                  30

Gly Val Ser Trp Ile Arg Gln Ala Pro Gly Gln Gly Leu Glu Trp Ile
        35                  40                  45
```

```
Gly Trp Ile Ser Ala Tyr Asn Gly Asp Thr Tyr Tyr Ala Gln Lys Phe
    50                  55                  60

Gln Ala Arg Val Thr Met Thr Thr Asp Thr Ser Thr Thr Thr Ala Tyr
65                  70                  75                  80

Met Glu Met Arg Ser Leu Arg Ser Asp Asp Thr Ala Val Tyr Tyr Cys
                85                  90                  95

Ala Arg Glu Pro Pro Leu Phe Tyr Ser Ser Trp Ser Leu Asp Asn
            100                 105                 110


<210> SEQ ID NO 31
<211> LENGTH: 294
<212> TYPE: DNA
<213> ORGANISM: Artificial
<220> FEATURE:
<223> OTHER INFORMATION: SC08-020 VL DNA

<400> SEQUENCE: 31

gaaattgtgw tgacrcagtc tccaggcacc ctgtctttgt ctccagggga aagagccacc      60

ctctcctgca gggccagtca gagtgttagc atgaactact tagcctggtt ccagcagaaa     120

cctggccagg ctcccaggct cctcatctat ggtgcgtccc gcagggccac tggcatcccc     180

gacaggatca gtggcagtgg gtctgggaca gacttcactc tcaccatcag cagactggag     240

cctgcagatt ttgcagtgta ttactgtcag cagtatggta cctcacctcg gacg           294


<210> SEQ ID NO 32
<211> LENGTH: 98
<212> TYPE: PRT
<213> ORGANISM: Artificial
<220> FEATURE:
<223> OTHER INFORMATION: SC08-020 VL PROTEIN
<220> FEATURE:
<221> NAME/KEY: misc_feature
<222> LOCATION: (4)..(4)
<223> OTHER INFORMATION: Xaa can be any naturally occurring amino acid

<400> SEQUENCE: 32

Glu Ile Val Xaa Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Asn
            20                  25                  30

Tyr Leu Ala Trp Phe Gln Gln Lys Pro Gly Gln Ala Pro Arg Leu Leu
        35                  40                  45

Ile Tyr Gly Ala Ser Arg Arg Ala Thr Gly Ile Pro Asp Arg Ile Ser
    50                  55                  60

Gly Ser Gly Ser Gly Thr Asp Phe Thr Leu Thr Ile Ser Arg Leu Glu
65                  70                  75                  80

Pro Ala Asp Phe Ala Val Tyr Tyr Cys Gln Gln Tyr Gly Thr Ser Pro
                85                  90                  95

Arg Thr


<210> SEQ ID NO 33
<211> LENGTH: 330
<212> TYPE: DNA
<213> ORGANISM: Artificial
<220> FEATURE:
<223> OTHER INFORMATION: SC08-021 VH DNA

<400> SEQUENCE: 33

gaggtgcagc tggtggagtc tgggggaggc ttgatacagc ctggggggtc cctgagactc      60

tcctgtgcag cctctggatt cacctttagc gcctatgcca tgaactgggt ccgccaggct     120
```

```
ccagggaagg ggctggagtg ggtctcagct attggtggta gtggcggtag cacatactac    180

gcagactccg tgaagggccg gttcaccatc tccagagaca actccaagaa gatcctgtat    240

ctgcaaatga acggcctgag agccgaggac acggccatat attactgtgc gaaaggccgg    300

gattggactg gggttactt ctttgactcc                                      330


<210> SEQ ID NO 34
<211> LENGTH: 110
<212> TYPE: PRT
<213> ORGANISM: Artificial
<220> FEATURE:
<223> OTHER INFORMATION: SC08-021 VH PROTEIN

<400> SEQUENCE: 34

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Lys Ile Leu Tyr
65                  70                  75                  80

Leu Gln Met Asn Gly Leu Arg Ala Glu Asp Thr Ala Ile Tyr Tyr Cys
                85                  90                  95

Ala Lys Gly Arg Asp Trp Thr Gly Gly Tyr Phe Phe Asp Ser
            100                 105                 110


<210> SEQ ID NO 35
<211> LENGTH: 309
<212> TYPE: DNA
<213> ORGANISM: Artificial
<220> FEATURE:
<223> OTHER INFORMATION: SC08-021 VL DNA

<400> SEQUENCE: 35

gacatccagw tgacccagtc tccagactcc ctggctgtgt ctctgggcga gagggccacc     60

atcaactgca agtccagcca gagtattttc tacagctcca acaataagaa ctacttaact    120

tggtaccagc agaaaccagg acagcctcct aagctgctca tttactgggc atctacccgg    180

gaatccggag tccctgaccg attcagtggc agcgggtctg ggacagattt cactctcacc    240

atcagcagcc tgcaggctga agatgtggca gtttattact gtcagcaata ctatagtatt    300

ccctacact                                                            309


<210> SEQ ID NO 36
<211> LENGTH: 103
<212> TYPE: PRT
<213> ORGANISM: Artificial
<220> FEATURE:
<223> OTHER INFORMATION: SC08-021 VL PROTEIN
<220> FEATURE:
<221> NAME/KEY: misc_feature
<222> LOCATION: (4)..(4)
<223> OTHER INFORMATION: Xaa can be any naturally occurring amino acid

<400> SEQUENCE: 36

Asp Ile Gln Xaa Thr Gln Ser Pro Asp Ser Leu Ala Val Ser Leu Gly
1               5                   10                  15
```

```
Glu Arg Ala Thr Ile Asn Cys Lys Ser Ser Gln Ser Ile Phe Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Tyr Thr
            100


<210> SEQ ID NO 37
<211> LENGTH: 330
<212> TYPE: DNA
<213> ORGANISM: Artificial
<220> FEATURE:
<223> OTHER INFORMATION: SC08-038 VH DNA

<400> SEQUENCE: 37

gaggtgcagc tggtggactc tgggggaggc ttggtacagc cggggggtc cctgagactc      60

tcctgtgcag cctctggatt cgcctttagc ggctatgcca tgagctgggt ccgccaggct    120

ccagggaagg ggctggagtg ggtctcagat attggtggta gtggtggtgg cacatactac    180

gcagactccg tgaagggccg gttcaccatc tccagagaca atgccaagaa cacgctgtat    240

ctgcaaatga atagcctgag agccgaggac acggccgtat attactgtgc gaaaagcagt    300

agctgggacc gggcctactt ctttgactcc                                      330


<210> SEQ ID NO 38
<211> LENGTH: 109
<212> TYPE: PRT
<213> ORGANISM: Artificial
<220> FEATURE:
<223> OTHER INFORMATION: SC08-038 VH PROTEIN

<400> SEQUENCE: 38

Val Gln Leu Val Asp Ser Gly Gly Gly Leu Val Gln Pro Gly Gly Ser
1               5                   10                  15

Leu Arg Leu Ser Cys Ala Ala Ser Gly Phe Ala Phe Ser Gly Tyr Ala
            20                  25                  30

Met Ser Trp Val Arg Gln Ala Pro Gly Lys Gly Leu Glu Trp Val Ser
        35                  40                  45

Asp Ile Gly Gly Ser Gly Gly Gly Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Ser Ser Trp Asp Arg Ala Tyr Phe Phe Asp Ser
            100                 105


<210> SEQ ID NO 39
<211> LENGTH: 309
<212> TYPE: DNA
<213> ORGANISM: Artificial
<220> FEATURE:
<223> OTHER INFORMATION: SC08-038 VL DNA
```

<400> SEQUENCE: 39

```
gatattgtga tgacccagac tccagactcc ctggctgtgt ctctgggcga gagggccacc     60

atcaactgca agtccagcca gagtgtttta tacagctcca tccataagaa ctacttagcc    120

tggtaccagc aaaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcaata ttatagatct    300

cctccaact                                                             309
```

<210> SEQ ID NO 40
<211> LENGTH: 103
<212> TYPE: PRT
<213> ORGANISM: Artificial
<220> FEATURE:
<223> OTHER INFORMATION: SC08-038 VL PROTEIN

<400> SEQUENCE: 40

```
Asp Ile Val Met Thr Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile His Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Ser Pro Pro Thr
            100
```

<210> SEQ ID NO 41
<211> LENGTH: 336
<212> TYPE: DNA
<213> ORGANISM: Artificial
<220> FEATURE:
<223> OTHER INFORMATION: SC08-039 VH DNA

<400> SEQUENCE: 41

```
cagctgcagc tgcaggagtc gggcccagga ctggtgaagc cttcggagac cctgtccctc     60

acgtgcactg tctctggcgg ctccatcggt agttactact ggagctggat acggcagccc    120

ccagggaagg gactggagtg gattggatat atctattacc gtgggggtac cagttacaac    180

ccctccctca agagtcgagt caccatatca gtcgacacgt ccaagagcca gttcaccttg    240

aagctgaact ctgtgaccgc tgcggacacg gccgtgtatt actgtgcgag aaaggactgg    300

ggatcagcgg ccggaagtgt ctggtacttc gatctc                              336
```

<210> SEQ ID NO 42
<211> LENGTH: 112
<212> TYPE: PRT
<213> ORGANISM: Artificial
<220> FEATURE:
<223> OTHER INFORMATION: SC08-039 VH PROTEIN

<400> SEQUENCE: 42

```
Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Gly Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Arg Gly Gly Thr Ser Tyr Asn Pro Ser Leu Lys
    50                  55                  60

Ser Arg Val Thr Ile Ser Val Asp Thr Ser Lys Ser Gln Phe Thr Leu
65                  70                  75                  80

Lys Leu Asn Ser Val Thr Ala Ala Asp Thr Ala Val Tyr Tyr Cys Ala
                85                  90                  95

Arg Lys Asp Trp Gly Ser Ala Ala Gly Ser Val Trp Tyr Phe Asp Leu
            100                 105                 110


<210> SEQ ID NO 43
<211> LENGTH: 300
<212> TYPE: DNA
<213> ORGANISM: Artificial
<220> FEATURE:
<223> OTHER INFORMATION: SC08-039 VL DNA

<400> SEQUENCE: 43

cagtctgccc tgactcagcc tccctccgcg tccgggtctc ctggacagtc agtcaccatc     60

tcctgcactg gaaccagcag tgacgttggt ggttataatt atgtctcctg gtaccaacaa    120

cacccaggca aagcccccaa actcatgatt cgtgaggtca gtaagcggcc ctcaggggtc    180

cctgatcgct tctctggttc caagtctggc aacacggcct ccctgaccgt ctctgggctc    240

caggctgagg atgaggctga atactactgc agctcgtatg caggcagcaa caatctgata    300


<210> SEQ ID NO 44
<211> LENGTH: 100
<212> TYPE: PRT
<213> ORGANISM: Artificial
<220> FEATURE:
<223> OTHER INFORMATION: SC08-039 VL PROTEIN

<400> SEQUENCE: 44

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Arg Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Ala Gly Ser
                85                  90                  95

Asn Asn Leu Ile
            100


<210> SEQ ID NO 45
<211> LENGTH: 333
<212> TYPE: DNA
<213> ORGANISM: Artificial
<220> FEATURE:
<223> OTHER INFORMATION: SC08-040 VH DNA

<400> SEQUENCE: 45
```

```
gaggtgcagc tggtggagtc agggggaggc gtggtccagc ctgggaggtc cctgagactc     60

tcctgtgcag cgtctggatt cgctttcagt agctatggca tgcactgggt ccgccaggct    120

ccaggcaagg gactggagtg ggtgaccttt atatggtatg atggaagtaa taaacactat    180

gcagactcca tgaagggccg attcaccatc tccagagaca attccaagaa cacgctgtat    240

ctgcaaatga gcagcctgag agccgaggac acggctgttt attactgtgc gagagatggg    300

ggatatagca cctgggaatg gtacttcgat ctc                                 333


<210> SEQ ID NO 46
<211> LENGTH: 111
<212> TYPE: PRT
<213> ORGANISM: Artificial
<220> FEATURE:
<223> OTHER INFORMATION: SC08-040 VH PROTEIN

<400> SEQUENCE: 46

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Thr Phe Ile Trp Tyr Asp Gly Ser Asn Lys His Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Gly Gly Tyr Ser Thr Trp Glu Trp Tyr Phe Asp Leu
            100                 105                 110


<210> SEQ ID NO 47
<211> LENGTH: 291
<212> TYPE: DNA
<213> ORGANISM: Artificial
<220> FEATURE:
<223> OTHER INFORMATION: SC08-040 VL DNA

<400> SEQUENCE: 47

gaaattgtgc tgactcagtc tccggacttt cagtctgtga ctccaaagga gagagtcacc     60

atcacctgcc gggccagtca gggcattggc agtaacttac actggtacca gcagaaacca    120

gatcagtctc caaagctcct catcaagtat gcttcccagt ccatcacagg ggtcccctcg    180

aggttcagtg gcaggggatc tgggacagat ttcaccctca ccatcaatag cctggaagtt    240

gaagatgctg cagtgtatta ctgtcatcag agtagtagtt taccgctcac t             291


<210> SEQ ID NO 48
<211> LENGTH: 97
<212> TYPE: PRT
<213> ORGANISM: Artificial
<220> FEATURE:
<223> OTHER INFORMATION: SC08-040 VL PROTEIN

<400> SEQUENCE: 48

Glu Ile Val Leu Thr Gln Ser Pro Asp Phe Gln Ser Val Thr Pro Lys
1               5                   10                  15

Glu Arg Val Thr Ile Thr Cys Arg Ala Ser Gln Gly Ile Gly Ser Asn
            20                  25                  30
```

```
Leu His Trp Tyr Gln Gln Lys Pro Asp Gln Ser Pro Lys Leu Leu Ile
        35                  40                  45

Lys Tyr Ala Ser Gln Ser Ile Thr Gly Val Pro Ser Arg Phe Ser Gly
    50                  55                  60

Arg Gly Ser Gly Thr Asp Phe Thr Leu Thr Ile Asn Ser Leu Glu Val
65                  70                  75                  80

Glu Asp Ala Ala Val Tyr Tyr Cys His Gln Ser Ser Ser Leu Pro Leu
                85                  90                  95

Thr
```

<210> SEQ ID NO 49
<211> LENGTH: 333
<212> TYPE: DNA
<213> ORGANISM: Artificial
<220> FEATURE:
<223> OTHER INFORMATION: SC08-041 VH DNA

<400> SEQUENCE: 49

```
caggtgcagc tggtgcagtc tggcgctgag gtgaagaagc ctggggcctc agtgaaggtc     60

tcctgccagg cttcgggtta cacctttacc tcctttggtc tcagctgggt gcgacaggcc    120

cctggacaag ggcctgagtg gatgggatgg atcagcgctt acaatggtga aataaagtat    180

gcacagaagt tccagggcag agtctccatg accacagaca catcaacgag gacagcctac    240

atggaggtgc ggagcctcag acctgacgac acggccgtat actactgtgc gagagagccc    300

cccctgtatt tcagtagctg gtctctcgac ttc                                  333
```

<210> SEQ ID NO 50
<211> LENGTH: 111
<212> TYPE: PRT
<213> ORGANISM: Artificial
<220> FEATURE:
<223> OTHER INFORMATION: SC08-041 VH PROTEIN

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Ser Phe
            20                  25                  30

Gly Leu Ser Trp Val Arg Gln Ala Pro Gly Gln Gly Pro Glu Trp Met
        35                  40                  45

Gly Trp Ile Ser Ala Tyr Asn Gly Glu Ile Lys Tyr Ala Gln Lys Phe
    50                  55                  60

Gln Gly Arg Val Ser Met Thr Thr Asp Thr Ser Thr Arg Thr Ala Tyr
65                  70                  75                  80

Met Glu Val Arg Ser Leu Arg Pro Asp Asp Thr Ala Val Tyr Tyr Cys
                85                  90                  95

Ala Arg Glu Pro Pro Leu Tyr Phe Ser Ser Trp Ser Leu Asp Phe
            100                 105                 110
```

<210> SEQ ID NO 51
<211> LENGTH: 294
<212> TYPE: DNA
<213> ORGANISM: Artificial
<220> FEATURE:
<223> OTHER INFORMATION: SC08-041 VL DNA

<400> SEQUENCE: 51

```
gaaattgtgt tgacgcagtc tccaggcacc ctgtctttgt ctccagggga aagagccacc     60
```

ctctcctgca gggccagtca gagtgttagc agcaactact tagcctggtt ccagcagaaa 120
cctggccagg ctcccaggct cctcatctat ggtgcatcaa ggagggccac tggcatccca 180
gacaggttca gtggcagtgg gtctgggaca gacttcactc tcaccatcag cagactggag 240
cctgaagatt ttgcagtgta ttactgtcag cagtatgata gctcacctcg gacg 294

<210> SEQ ID NO 52
<211> LENGTH: 98
<212> TYPE: PRT
<213> ORGANISM: Artificial
<220> FEATURE:
<223> OTHER INFORMATION: SC08-041 VL PROTEIN

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Phe Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Arg Thr

<210> SEQ ID NO 53
<211> LENGTH: 330
<212> TYPE: DNA
<213> ORGANISM: Artificial
<220> FEATURE:
<223> OTHER INFORMATION: SC08-043 VH DNA

<400> SEQUENCE: 53
caggtgcagc tggtgcagtc tggggctgag gtgaagaagc ctggggcctc agtgaagctt 60
tcctgcaagg cttctggata caccttcact gcctattcta tgcattgggt gcgccaggcc 120
cccggacaaa gccttgagtg gttgggatgg atcaacactg ccatcggtaa cacacaatat 180
tcacagaagt tccaggacag agtcaccatt accagggaca catctgcgcg cacatcgtac 240
atggaactga gcagcctgag atctggagac acggctgtct atttctgtgc gagaggggcc 300
tcttgggacg cccgtgggtg gtctggctac 330

<210> SEQ ID NO 54
<211> LENGTH: 110
<212> TYPE: PRT
<213> ORGANISM: Artificial
<220> FEATURE:
<223> OTHER INFORMATION: SC08-043 VH PROTEIN

<400> SEQUENCE: 54

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ala Tyr
            20                  25                  30

Ser Met His Trp Val Arg Gln Ala Pro Gly Gln Ser Leu Glu Trp Leu
        35                  40                  45

```
Gly Trp Ile Asn Thr Ala Ile Gly Asn Thr Gln Tyr Ser Gln Lys Phe
    50                  55                  60

Gln Asp Arg Val Thr Ile Thr Arg Asp Thr Ser Ala Arg Thr Ser Tyr
65                  70                  75                  80

Met Glu Leu Ser Ser Leu Arg Ser Gly Asp Thr Ala Val Tyr Phe Cys
                85                  90                  95

Ala Arg Gly Ala Ser Trp Asp Ala Arg Gly Trp Ser Gly Tyr
            100                 105                 110


<210> SEQ ID NO 55
<211> LENGTH: 309
<212> TYPE: DNA
<213> ORGANISM: Artificial
<220> FEATURE:
<223> OTHER INFORMATION: SC08-043 VL DNA

<400> SEQUENCE: 55

gacatccagw tgacccagtc tccagactcc ctggctgtgt ctctgggcga gagggccacc      60

atcaactgca agtccagcca gagtgttttt tccagctcca ccaataagaa ctacttagct     120

tggtaccagc agaaaccagg acagcctcct aaggtgctaa tttactggtc atctacccgg     180

gaatccgggg tccctgaccg attcagtgcc agcgggtctg ggacagattt cactctcacc     240

atcagcagcc tgcaggctgc agatgtggca gtttattact gtcaccaata ttatactgct     300

ccgtggacg                                                             309


<210> SEQ ID NO 56
<211> LENGTH: 103
<212> TYPE: PRT
<213> ORGANISM: Artificial
<220> FEATURE:
<223> OTHER INFORMATION: SC08-043 VL PROTEIN
<220> FEATURE:
<221> NAME/KEY: misc_feature
<222> LOCATION: (4)..(4)
<223> OTHER INFORMATION: Xaa can be any naturally occurring amino acid

<400> SEQUENCE: 56

Asp Ile Gln Xaa Thr Gln Ser Pro Asp Ser Leu Ala Val Ser Leu Gly
1               5                   10                  15

Glu Arg Ala Thr Ile Asn Cys Lys Ser Ser Gln Ser Val Phe Ser Ser
            20                  25                  30

Ser Thr Asn Lys Asn Tyr Leu Ala Trp Tyr Gln Gln Lys Pro Gly Gln
        35                  40                  45

Pro Pro Lys Val Leu Ile Tyr Trp Ser Ser Thr Arg Glu Ser Gly Val
    50                  55                  60

Pro Asp Arg Phe Ser Ala Ser Gly Ser Gly Thr Asp Phe Thr Leu Thr
65                  70                  75                  80

Ile Ser Ser Leu Gln Ala Ala Asp Val Ala Val Tyr Tyr Cys His Gln
                85                  90                  95

Tyr Tyr Thr Ala Pro Trp Thr
            100


<210> SEQ ID NO 57
<211> LENGTH: 345
<212> TYPE: DNA
<213> ORGANISM: Artificial
<220> FEATURE:
<223> OTHER INFORMATION: SC08-049 VH DNA

<400> SEQUENCE: 57
```

```
caggtcacct tgaaggagtc tggtcctgta ctggtgaagc ccaaagagac cctcacgctg     60

acctgcaccg tctctgggtt ctcactcagc aacactagaa tgggtgtgag ttggatccgt    120

cagcccccag ggaaggccct ggagtggctt gcgcacatct tttcgaacga cgaaacatcc    180

tacaggacat ctctgaagag gaggctcacc atctcccagg acatctccaa aagtcaggtg    240

gtcctttcta tgaccaacgt ggaccctgca gacacagcca catatttttg tgcacggatc    300

gggtctggct atgagagtag tgcttactcc acctggctcg acccc                   345


<210> SEQ ID NO 58
<211> LENGTH: 115
<212> TYPE: PRT
<213> ORGANISM: Artificial
<220> FEATURE:
<223> OTHER INFORMATION: SC08-049 VH PROTEIN

<400> SEQUENCE: 58

Gln Val Thr Leu Lys Glu Ser Gly Pro Val Leu Val Lys Pro Lys Glu
1               5                   10                  15

Thr Leu Thr Leu Thr Cys Thr Val Ser Gly Phe Ser Leu Ser Asn Thr
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Thr Ser Tyr Arg Thr Ser
    50                  55                  60

Leu Lys Arg Arg Leu Thr Ile Ser Gln Asp Ile Ser Lys Ser Gln Val
65                  70                  75                  80

Val Leu Ser Met Thr Asn Val Asp Pro Ala Asp Thr Ala Thr Tyr Phe
                85                  90                  95

Cys Ala Arg Ile Gly Ser Gly Tyr Glu Ser Ser Ala Tyr Ser Thr Trp
            100                 105                 110

Leu Asp Pro
        115


<210> SEQ ID NO 59
<211> LENGTH: 98
<212> TYPE: PRT
<213> ORGANISM: Artificial
<220> FEATURE:
<223> OTHER INFORMATION: SC08-049 VL PROTEIN

<400> SEQUENCE: 59

Gln Ser Val Leu Thr Gln Pro Pro Ser Val Ser Val Ala Pro Gly Gln
1               5                   10                  15

Thr Ala Arg Leu Thr Cys Glu Gly Asp Thr Ile Gly Ser Lys Ser Val
            20                  25                  30

His Trp Tyr Gln Gln Arg Pro Gly Gln Ala Pro Val Leu Val Val Tyr
        35                  40                  45

Asn Asp Arg Asp Arg Pro Ser Gly Ile Pro Glu Arg Phe Ser Gly Ser
    50                  55                  60

Asn Ser Gly Arg Thr Ala Thr Leu Thr Ile Ser Arg Val Glu Ala Gly
65                  70                  75                  80

Asp Glu Ala Asp Tyr Phe Cys Gln Val Trp Glu Ser Gly Gly Asp Gln
                85                  90                  95

Thr Val


<210> SEQ ID NO 60
```

<211> LENGTH: 339
<212> TYPE: DNA
<213> ORGANISM: Artificial
<220> FEATURE:
<223> OTHER INFORMATION: SC08-050 VH DNA

<400> SEQUENCE: 60

```
caggtgcagc tacagcagtg gggcgcagga ctattgaagc cttcggagac cctgtccctc     60

acctgcgctg tgtatggtgg gtcgttcact gatcactact ggagctggat ccgccagtcc    120

ccagggaagg ggctggagtg gattggtgaa gtcgttcata gtggagacac caactacacc    180

ccgtccctca gaaatcgagt ttccatatcg gtcgactcgt ccaagaatca gttctccctg    240

aggctggggt ctgtgaccgc cgcggacacg gctgtctatt actgtgcgag aggcaggaat    300

gttgcggtag ttggtgctat tcagaggcac tatgactac                           339
```

<210> SEQ ID NO 61
<211> LENGTH: 113
<212> TYPE: PRT
<213> ORGANISM: Artificial
<220> FEATURE:
<223> OTHER INFORMATION: SC08-050 VH PROTEIN

<400> SEQUENCE: 61

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Thr Asp His
            20                  25                  30

Tyr Trp Ser Trp Ile Arg Gln Ser Pro Gly Lys Gly Leu Glu Trp Ile
        35                  40                  45

Gly Glu Val Val His Ser Gly Asp Thr Asn Tyr Thr Pro Ser Leu Arg
    50                  55                  60

Asn Arg Val Ser Ile Ser Val Asp Ser Ser Lys Asn Gln Phe Ser Leu
65                  70                  75                  80

Arg Leu Gly Ser Val Thr Ala Ala Asp Thr Ala Val Tyr Tyr Cys Ala
                85                  90                  95

Arg Gly Arg Asn Val Ala Val Val Gly Ala Ile Gln Arg His Tyr Asp
            100                 105                 110

Tyr
```

<210> SEQ ID NO 62
<211> LENGTH: 294
<212> TYPE: DNA
<213> ORGANISM: Artificial
<220> FEATURE:
<223> OTHER INFORMATION: SC08-050 VL DNA

<400> SEQUENCE: 62

```
gaaattgtga tgacgcagtc tccaggcacc ctgtctttgt ctccagggga aagagccacc     60

ctctcctgca gggccagtca gagtgttagc agaaactact tagcctggta ccagcagaag    120

cctggcctgg ctcccaggct cctcatctct ggtgcatcga gcagggccac tggcgtccca    180

gacaggttca gtggcagggg gtctgacaca gacttcactc tcaccatcag cagactggag    240

cctgaagatt ttgccgtgta ttactgtcag cactatggtt cggtccttgt agct          294
```

<210> SEQ ID NO 63
<211> LENGTH: 98
<212> TYPE: PRT
<213> ORGANISM: Artificial
<220> FEATURE:

<223> OTHER INFORMATION: SC08-050 VL PROTEIN

<400> SEQUENCE: 63

Glu Ile Val Met Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Asn
20 25 30

Tyr Leu Ala Trp Tyr Gln Gln Lys Pro Gly Leu Ala Pro Arg Leu Leu
35 40 45

Ile Ser Gly Ala Ser Ser Arg Ala Thr Gly Val Pro Asp Arg Phe Ser
50 55 60

Gly Arg Gly Ser Asp Thr Asp Phe Thr Leu Thr Ile Ser Arg Leu Glu
65 70 75 80

Pro Glu Asp Phe Ala Val Tyr Tyr Cys Gln His Tyr Gly Ser Val Leu
85 90 95

Val Ala

<210> SEQ ID NO 64
<211> LENGTH: 357
<212> TYPE: DNA
<213> ORGANISM: Artificial
<220> FEATURE:
<223> OTHER INFORMATION: SC08-052 VH DNA

<400> SEQUENCE: 64
caggtgcagc tgcaggagtc gggcccagga ctggtgaagc cttcggagac cctgtccctc 60
acctgcactg tctctggtgg ctccgtcagc agtggtactt actactggag ctggatccgg 120
cagcccccag ggaagggact ggagtggatt ggggatatct cttacagtgg gagcaccaac 180
tacaacccct ccctcaagag tcgagtcacc atttctagag acacgtccaa gaacctggtc 240
tccctgaagc tgacctctgt gaccgctgcg gacacggccg tgcattactg tgcgagagcg 300
atggcggctt ataattatga caggggtggt tataacgact actactacat ggacgtc 357

<210> SEQ ID NO 65
<211> LENGTH: 119
<212> TYPE: PRT
<213> ORGANISM: Artificial
<220> FEATURE:
<223> OTHER INFORMATION: SC08-052 VH PROTEIN

<400> SEQUENCE: 65

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Thr Tyr Tyr Trp Ser Trp Ile Arg Gln Pro Pro Gly Lys Gly Leu Glu
35 40 45

Trp Ile Gly Asp Ile Ser Tyr Ser Gly Ser Thr Asn Tyr Asn Pro Ser
50 55 60

Leu Lys Ser Arg Val Thr Ile Ser Arg Asp Thr Ser Lys Asn Leu Val
65 70 75 80

Ser Leu Lys Leu Thr Ser Val Thr Ala Ala Asp Thr Ala Val His Tyr
85 90 95

Cys Ala Arg Ala Met Ala Ala Tyr Asn Tyr Asp Arg Gly Gly Tyr Asn
100 105 110

Asp Tyr Tyr Tyr Met Asp Val
115

<210> SEQ ID NO 66
<211> LENGTH: 291
<212> TYPE: DNA
<213> ORGANISM: Artificial
<220> FEATURE:
<223> OTHER INFORMATION: SC08-052 VL DNA

<400> SEQUENCE: 66
gacatccagt tgacccagtc tccatcctcc ctgtctgcat ctgtcggaga cagagtcacc 60
atcacttgcc gggcaagtca gggcattaac acctatttaa attggtatca gcaaaaacca 120
gggaaggccc ctaaggtcct gatctttgct gcatccactt tgcaaagtgg agtcccatca 180
aggttcagtg gcagtggttc tgggacagaa ttcactctca acatcaacaa tctgcaacct 240
gaagattttg caacttacta ctgtcaacag agttacagta ctgcgatcac t 291

<210> SEQ ID NO 67
<211> LENGTH: 97
<212> TYPE: PRT
<213> ORGANISM: Artificial
<220> FEATURE:
<223> OTHER INFORMATION: SC08-052 VL PROTEIN

<400> SEQUENCE: 67

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Asn Thr Tyr
20 25 30

Leu Asn Trp Tyr Gln Gln Lys Pro Gly Lys Ala Pro Lys Val Leu Ile
35 40 45

Phe Ala Ala Ser Thr Leu Gln Ser Gly Val Pro Ser Arg Phe Ser Gly
50 55 60

Ser Gly Ser Gly Thr Glu Phe Thr Leu Asn Ile Asn Asn Leu Gln Pro
65 70 75 80

Glu Asp Phe Ala Thr Tyr Tyr Cys Gln Gln Ser Tyr Ser Thr Ala Ile
85 90 95

Thr

<210> SEQ ID NO 68
<211> LENGTH: 333
<212> TYPE: DNA
<213> ORGANISM: Artificial
<220> FEATURE:
<223> OTHER INFORMATION: SC08-055 VH DNA

<400> SEQUENCE: 68
gaggtgcagc tggtggagtc tgggggaggc gtggtccagc ctgggaggtc cctgagactc 60
tcctgtgcgg cgtctggatt cagcttcacc acctatggca tgcactgggt ccgccaggct 120
ccaggcaagg ggctggagtg ggtggccttt atttggtatg atggaagtaa caaacactat 180
caagactccg tgaagggccg attcaccatc tccaaggaca attccaacaa catgttgtat 240
ctgcaaatgg acagcctgag agtcgccgac acggctgttt attactgtgt gagagatggg 300
ggatatagca cctgggaatg gtacttcgat ctc 333

<210> SEQ ID NO 69
<211> LENGTH: 111
<212> TYPE: PRT
<213> ORGANISM: Artificial
<220> FEATURE:

<223> OTHER INFORMATION: SC08-055 VH PROTEIN

<400> SEQUENCE: 69

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Thr Thr Tyr
            20                  25                  30

Gly Met His Trp Val Arg Gln Ala Pro Gly Lys Gly Leu Glu Trp Val
        35                  40                  45

Ala Phe Ile Trp Tyr Asp Gly Ser Asn Lys His Tyr Gln Asp Ser Val
    50                  55                  60

Lys Gly Arg Phe Thr Ile Ser Lys Asp Asn Ser Asn Asn Met Leu Tyr
65                  70                  75                  80

Leu Gln Met Asp Ser Leu Arg Val Ala Asp Thr Ala Val Tyr Tyr Cys
                85                  90                  95

Val Arg Asp Gly Gly Tyr Ser Thr Trp Glu Trp Tyr Phe Asp Leu
            100                 105                 110
```

<210> SEQ ID NO 70
<211> LENGTH: 291
<212> TYPE: DNA
<213> ORGANISM: Artificial
<220> FEATURE:
<223> OTHER INFORMATION: SC08-055 VL DNA

<400> SEQUENCE: 70

```
gaaattgtgc tgactcagtc tccagacttt cagtctgtgg ctccaaagga gaaagtcacc     60

atcacctgcc gggccagtcg gagcattggt agtgacttgc actggtttca gcagaggcca    120

gatcagtctc caaagctcct catcaagttt gcttcccagt ccatgtcagg ggtcccctcg    180

aggttcagtg gcagtgggtc tgggagagat ttcaccctca ccatcagtag cctggaggct    240

gaagatgctg ctacgtatta ctgtcatcag agtagtagtt taccgctcac t             291
```

<210> SEQ ID NO 71
<211> LENGTH: 97
<212> TYPE: PRT
<213> ORGANISM: Artificial
<220> FEATURE:
<223> OTHER INFORMATION: SC08-055 VL PROTEIN

<400> SEQUENCE: 71

```
Glu Ile Val Leu Thr Gln Ser Pro Asp Phe Gln Ser Val Ala Pro Lys
1               5                   10                  15

Glu Lys Val Thr Ile Thr Cys Arg Ala Ser Arg Ser Ile Gly Ser Asp
            20                  25                  30

Leu His Trp Phe Gln Gln Arg Pro Asp Gln Ser Pro Lys Leu Leu Ile
        35                  40                  45

Lys Phe Ala Ser Gln Ser Met Ser Gly Val Pro Ser Arg Phe Ser Gly
    50                  55                  60

Ser Gly Ser Gly Arg Asp Phe Thr Leu Thr Ile Ser Ser Leu Glu Ala
65                  70                  75                  80

Glu Asp Ala Ala Thr Tyr Tyr Cys His Gln Ser Ser Ser Leu Pro Leu
                85                  90                  95

Thr
```

<210> SEQ ID NO 72
<211> LENGTH: 348
<212> TYPE: DNA

```
<213> ORGANISM: Artificial
<220> FEATURE:
<223> OTHER INFORMATION: SC08-057 VH DNA

<400> SEQUENCE: 72

gaggtgcagc tggtggagtc tggaggaggc ttggtccaac ctggggggtc cctgagactc     60

tcctgtgcag cctctgggtt caccgacagt gtcatcttca tgagttgggt ccgccaggct    120

ccagggaagg ggctggagtg tgtctcaatt atttatatcg atgattccac atactacgca    180

gactccgtga agggccgatt caccatctcc agacacaatt ccatgggcac agtgtttctt    240

gaaatgaaca gcctgagacc tgacgacacg gccgtctatt actgtgcgac agagagcgga    300

gactttggtg accaaacggg tccctatcat tactacgcta tggacgtc                 348


<210> SEQ ID NO 73
<211> LENGTH: 116
<212> TYPE: PRT
<213> ORGANISM: Artificial
<220> FEATURE:
<223> OTHER INFORMATION: SC08-057 VH PROTEIN (

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Ser Val Ile
            20                  25                  30

Phe Met Ser Trp Val Arg Gln Ala Pro Gly Lys Gly Leu Glu Cys Val
        35                  40                  45

Ser Ile Ile Tyr Ile Asp Asp Ser Thr Tyr Tyr Ala Asp Ser Val Lys
    50                  55                  60

Gly Arg Phe Thr Ile Ser Arg His Asn Ser Met Gly Thr Val Phe Leu
65                  70                  75                  80

Glu Met Asn Ser Leu Arg Pro Asp Asp Thr Ala Val Tyr Tyr Cys Ala
                85                  90                  95

Thr Glu Ser Gly Asp Phe Gly Asp Gln Thr Gly Pro Tyr His Tyr Tyr
            100                 105                 110

Ala Met Asp Val
        115


<210> SEQ ID NO 74
<211> LENGTH: 300
<212> TYPE: DNA
<213> ORGANISM: Artificial
<220> FEATURE:
<223> OTHER INFORMATION: SC08-057 VL DNA

<400> SEQUENCE: 74

cagtctgccc tgactcagcc tgcctccgtg tctgggtctc ctggacagtc gatcaccatc     60

tcctgcactg gaagcagcgg tgacattggt ggttataacg ctgtctcctg gtaccaacac    120

cacccaggca aagcccccaa actgatgatt tatgaggtca ctagtcggcc ctcaggggtt    180

tccgatcgct tctctgcgtc caggtctggc gacacggcct ccctgactgt ctctggtctc    240

caggctgagg acgaggctca ctattactgc tgctcatttg cagacagcaa cattttgatt    300


<210> SEQ ID NO 75
<211> LENGTH: 100
<212> TYPE: PRT
<213> ORGANISM: Artificial
<220> FEATURE:
<223> OTHER INFORMATION: SC08-057 VL PROTEIN
```

<400> SEQUENCE: 75

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Gly Asp Ile Gly Gly Tyr
            20                  25                  30

Asn Ala Val Ser Trp Tyr Gln His His Pro Gly Lys Ala Pro Lys Leu
        35                  40                  45

Met Ile Tyr Glu Val Thr Ser Arg Pro Ser Gly Val Ser Asp Arg Phe
    50                  55                  60

Ser Ala Ser Arg Ser Gly Asp Thr Ala Ser Leu Thr Val Ser Gly Leu
65                  70                  75                  80

Gln Ala Glu Asp Glu Ala His Tyr Tyr Cys Cys Ser Phe Ala Asp Ser
                85                  90                  95

Asn Ile Leu Ile
            100
```

<210> SEQ ID NO 76
<211> LENGTH: 336
<212> TYPE: DNA
<213> ORGANISM: Artificial
<220> FEATURE:
<223> OTHER INFORMATION: SC08-069 VH DNA

<400> SEQUENCE: 76

```
gaggtgcagc tggtggagac tgggggagtc gtggtacagc ctgggggtc cctgagactc     60

tcctgtgcag cctctggctt cacgtttgag gattatacca tgcactgggt ccgtcaagtt    120

ccggggaagg gtctggagtg ggtcgcgctc attagttggg atggcggtat gtcaaactat    180

gcagactctg tgaagggccg attcaccatc tccagagaca acagcaaaaa ctctctgtat    240

ctgcaagtga gcagtctgag aagtgaagac accgccctgt attactgtgc aaaagatata    300

cgaccccgta tgccagctcg tcactttatg gacgtc                              336
```

<210> SEQ ID NO 77
<211> LENGTH: 112
<212> TYPE: PRT
<213> ORGANISM: Artificial
<220> FEATURE:
<223> OTHER INFORMATION: SC08-069 VH PROTEIN

<400> SEQUENCE: 77

```
Glu Val Gln Leu Val Glu Thr Gly Gly Val Val Val Gln Pro Gly Gly
1               5                   10                  15

Ser Leu Arg Leu Ser Cys Ala Ala Ser Gly Phe Thr Phe Glu Asp Tyr
            20                  25                  30

Thr Met His Trp Val Arg Gln Val Pro Gly Lys Gly Leu Glu Trp Val
        35                  40                  45

Ala Leu Ile Ser Trp Asp Gly Gly Met Ser Asn Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Val Ser Ser Leu Arg Ser Glu Asp Thr Ala Leu Tyr Tyr Cys
                85                  90                  95

Ala Lys Asp Ile Arg Pro Arg Met Pro Ala Arg His Phe Met Asp Val
            100                 105                 110
```

<210> SEQ ID NO 78

```
<211> LENGTH: 297
<212> TYPE: DNA
<213> ORGANISM: Artificial
<220> FEATURE:
<223> OTHER INFORMATION: SC08-069 VL DNA

<400> SEQUENCE: 78

gaaattgtgt tgacgcagtc tccagccacc ctgtctgtgt ctccggggga aagagccacc     60

ctctcctgca gggccagtca gaatgtcaac tacaacttag cctggtacca gcagaaacct    120

ggccaggctc ccaggctcct catctatgtt gcatccacca gggccactgg tatcccagac    180

aggttcagtg gcagtgggtc tgggacagag ttcactctca ccatcagcag tctgcagtct    240

gaagattttg cagtttatta ctgtcagcag tataataact ggcctccggc gatcact       297


<210> SEQ ID NO 79
<211> LENGTH: 99
<212> TYPE: PRT
<213> ORGANISM: Artificial
<220> FEATURE:
<223> OTHER INFORMATION: SC08-069 VL PROTEIN

<400> SEQUENCE: 79

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Val Asn Tyr Asn
            20                  25                  30

Leu Ala Trp Tyr Gln Gln Lys Pro Gly Gln Ala Pro Arg Leu Leu Ile
        35                  40                  45

Tyr Val Ala Ser Thr Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Ile Thr


<210> SEQ ID NO 80
<211> LENGTH: 5
<212> TYPE: PRT
<213> ORGANISM: Artificial
<220> FEATURE:
<223> OTHER INFORMATION: HCDR1

<400> SEQUENCE: 80

Ser Asn Tyr Val Ser
1               5


<210> SEQ ID NO 81
<211> LENGTH: 16
<212> TYPE: PRT
<213> ORGANISM: Artificial
<220> FEATURE:
<223> OTHER INFORMATION: HCDR2

<400> SEQUENCE: 81

Leu Ile Tyr Thr Gly Gly Thr Thr Tyr Tyr Ala Asp Ser Val Lys Gly
1               5                   10                  15


<210> SEQ ID NO 82
<211> LENGTH: 16
<212> TYPE: PRT
<213> ORGANISM: Artificial
```

<220> FEATURE:
<223> OTHER INFORMATION: HCDR3

<400> SEQUENCE: 82

Val Ser Ala Leu Arg Phe Leu Gln Trp Pro Asn Tyr Ala Met Asp Val
1 5 10 15

<210> SEQ ID NO 83
<211> LENGTH: 14
<212> TYPE: PRT
<213> ORGANISM: Artificial
<220> FEATURE:
<223> OTHER INFORMATION: LCDR1

<400> SEQUENCE: 83

Ser Gly Thr Arg Ser Asp Val Gly Gly His Asn Tyr Val Ser
1 5 10

<210> SEQ ID NO 84
<211> LENGTH: 7
<212> TYPE: PRT
<213> ORGANISM: Artificial
<220> FEATURE:
<223> OTHER INFORMATION: LCDR2

<400> SEQUENCE: 84

Glu Val Ser His Arg Pro Ser
1 5

<210> SEQ ID NO 85
<211> LENGTH: 11
<212> TYPE: PRT
<213> ORGANISM: Artificial
<220> FEATURE:
<223> OTHER INFORMATION: LCDR3

<400> SEQUENCE: 85

Ser Ser Tyr Thr Gly Glu Gly Pro Leu Gly Val
1 5 10

<210> SEQ ID NO 86
<211> LENGTH: 5
<212> TYPE: PRT
<213> ORGANISM: Artificial
<220> FEATURE:
<223> OTHER INFORMATION: HCDR1

<400> SEQUENCE: 86

Ser Tyr Trp Met Ser
1 5

<210> SEQ ID NO 87
<211> LENGTH: 17
<212> TYPE: PRT
<213> ORGANISM: Artificial
<220> FEATURE:
<223> OTHER INFORMATION: HCDR2

<400> SEQUENCE: 87

Asn Met Lys Gln Asp Gly Ser Glu Lys Tyr Tyr Val Asp Ser Val Lys
1 5 10 15

Gly

<210> SEQ ID NO 88
<211> LENGTH: 16
<212> TYPE: PRT

<213> ORGANISM: Artificial
<220> FEATURE:
<223> OTHER INFORMATION: HCDR3

<400> SEQUENCE: 88

Gly Ser Cys Asp Asp Ser Trp Thr Gly Cys His Asp Ala Phe Asp Ile
1 5 10 15

<210> SEQ ID NO 89
<211> LENGTH: 11
<212> TYPE: PRT
<213> ORGANISM: Artificial
<220> FEATURE:
<223> OTHER INFORMATION: LCDR1

<400> SEQUENCE: 89

Gly Gly Asn Asn Ile Gly Ser Lys Ser Val His
1 5 10

<210> SEQ ID NO 90
<211> LENGTH: 6
<212> TYPE: PRT
<213> ORGANISM: Artificial
<220> FEATURE:
<223> OTHER INFORMATION: LCDR2

<400> SEQUENCE: 90

Asp Ser Ala Arg Pro Ser
1 5

<210> SEQ ID NO 91
<211> LENGTH: 12
<212> TYPE: PRT
<213> ORGANISM: Artificial
<220> FEATURE:
<223> OTHER INFORMATION: LCDR3

<400> SEQUENCE: 91

Gln Val Trp Glu Ser Gly Ser Asp Leu Arg Leu Leu
1 5 10

<210> SEQ ID NO 92
<211> LENGTH: 11
<212> TYPE: PRT
<213> ORGANISM: Artificial
<220> FEATURE:
<223> OTHER INFORMATION: LCDR1

<400> SEQUENCE: 92

Gly Gly Asp Asn Ile Gly Arg Lys Ser Val His
1 5 10

<210> SEQ ID NO 93
<211> LENGTH: 7
<212> TYPE: PRT
<213> ORGANISM: Artificial
<220> FEATURE:
<223> OTHER INFORMATION: LCDR2

<400> SEQUENCE: 93

Asp Asn Ser Asp Arg Pro Ser
1 5

<210> SEQ ID NO 94
<211> LENGTH: 11
<212> TYPE: PRT
<213> ORGANISM: Artificial

<220> FEATURE:
<223> OTHER INFORMATION: LCDR3

<400> SEQUENCE: 94

His Val Trp Gly Ser Ser Arg Asp His Tyr Val
1 5 10

<210> SEQ ID NO 95
<211> LENGTH: 14
<212> TYPE: PRT
<213> ORGANISM: Artificial
<220> FEATURE:
<223> OTHER INFORMATION: LCDR1

<400> SEQUENCE: 95

Thr Gly Ser Ser Ser Asn Ile Gly Ala Gly Tyr Asp Val His
1 5 10

<210> SEQ ID NO 96
<211> LENGTH: 7
<212> TYPE: PRT
<213> ORGANISM: Artificial
<220> FEATURE:
<223> OTHER INFORMATION: LCDR2

<400> SEQUENCE: 96

Gly Asn Asn Asn Arg Pro Ser
1 5

<210> SEQ ID NO 97
<211> LENGTH: 11
<212> TYPE: PRT
<213> ORGANISM: Artificial
<220> FEATURE:
<223> OTHER INFORMATION: LCDR3

<400> SEQUENCE: 97

Gln Ser Tyr Asp Ser Ser Leu Ser Val Tyr Val
1 5 10

<210> SEQ ID NO 98
<211> LENGTH: 11
<212> TYPE: PRT
<213> ORGANISM: Artificial
<220> FEATURE:
<223> OTHER INFORMATION: LCDR1

<400> SEQUENCE: 98

Gln Gly Asp Ser Leu Arg Ser Tyr Tyr Ala Ser
1 5 10

<210> SEQ ID NO 99
<211> LENGTH: 7
<212> TYPE: PRT
<213> ORGANISM: Artificial
<220> FEATURE:
<223> OTHER INFORMATION: LCDR2

<400> SEQUENCE: 99

Ala Lys Thr Asn Arg Pro Ser
1 5

<210> SEQ ID NO 100
<211> LENGTH: 11
<212> TYPE: PRT
<213> ORGANISM: Artificial
<220> FEATURE:

```
<223> OTHER INFORMATION: LCDR3

<400> SEQUENCE: 100

Asn Ser Arg Asp Ser Ser Gly Asn His Val Val
1               5                   10


<210> SEQ ID NO 101
<211> LENGTH: 14
<212> TYPE: PRT
<213> ORGANISM: Artificial
<220> FEATURE:
<223> OTHER INFORMATION: LCDR1

<400> SEQUENCE: 101

Thr Gly Thr Ser Ser Asp Val Gly Gly Tyr Asn Tyr Val Ser
1               5                   10


<210> SEQ ID NO 102
<211> LENGTH: 5
<212> TYPE: PRT
<213> ORGANISM: Artificial
<220> FEATURE:
<223> OTHER INFORMATION: HCDR1

<400> SEQUENCE: 102

Thr Ser Ala Met Ser
1               5


<210> SEQ ID NO 103
<211> LENGTH: 17
<212> TYPE: PRT
<213> ORGANISM: Artificial
<220> FEATURE:
<223> OTHER INFORMATION: HCDR2

<400> SEQUENCE: 103

Gly Ile Ser Gly Ser Gly Ala Thr Thr Tyr Tyr Ala Gly Ser Val Lys
1               5                   10                  15

Gly


<210> SEQ ID NO 104
<211> LENGTH: 21
<212> TYPE: PRT
<213> ORGANISM: Artificial
<220> FEATURE:
<223> OTHER INFORMATION: HCDR3

<400> SEQUENCE: 104

Asp Thr Ser Leu Phe Glu Tyr Asp Thr Ser Gly Phe Thr Ala Pro Gly
1               5                   10                  15

Asn Ala Phe Asp Ile
            20


<210> SEQ ID NO 105
<211> LENGTH: 11
<212> TYPE: PRT
<213> ORGANISM: Artificial
<220> FEATURE:
<223> OTHER INFORMATION: LCDR1

<400> SEQUENCE: 105

Arg Ala Ser Gln Ser Ile Ser Gly Tyr Leu Asn
1               5                   10


<210> SEQ ID NO 106
```

<211> LENGTH: 7
<212> TYPE: PRT
<213> ORGANISM: Artificial
<220> FEATURE:
<223> OTHER INFORMATION: LCDR2

<400> SEQUENCE: 106

Gly Ala Ser Thr Leu Gln Ser
1 5

<210> SEQ ID NO 107
<211> LENGTH: 10
<212> TYPE: PRT
<213> ORGANISM: Artificial
<220> FEATURE:
<223> OTHER INFORMATION: LCDR3

<400> SEQUENCE: 107

Gln Gln Thr Tyr Thr Ser Pro Pro Tyr Ala
1 5 10

<210> SEQ ID NO 108
<211> LENGTH: 5
<212> TYPE: PRT
<213> ORGANISM: Artificial
<220> FEATURE:
<223> OTHER INFORMATION: HCDR1

<400> SEQUENCE: 108

Arg Phe Gly Val Ser
1 5

<210> SEQ ID NO 109
<211> LENGTH: 17
<212> TYPE: PRT
<213> ORGANISM: Artificial
<220> FEATURE:
<223> OTHER INFORMATION: HCDR2

<400> SEQUENCE: 109

Trp Ile Ser Ala Tyr Asn Gly Asp Thr Tyr Tyr Ala Gln Lys Phe Gln
1 5 10 15

Ala

<210> SEQ ID NO 110
<211> LENGTH: 13
<212> TYPE: PRT
<213> ORGANISM: Artificial
<220> FEATURE:
<223> OTHER INFORMATION: HCDR3

<400> SEQUENCE: 110

Glu Pro Pro Leu Phe Tyr Ser Ser Trp Ser Leu Asp Asn
1 5 10

<210> SEQ ID NO 111
<211> LENGTH: 13
<212> TYPE: PRT
<213> ORGANISM: Artificial
<220> FEATURE:
<223> OTHER INFORMATION: LCDR1

<400> SEQUENCE: 111

Ala Arg Ala Ser Gln Ser Val Ser Met Asn Tyr Leu Ala
1 5 10

<210> SEQ ID NO 112
<211> LENGTH: 7
<212> TYPE: PRT
<213> ORGANISM: Artificial
<220> FEATURE:
<223> OTHER INFORMATION: LCDR2

<400> SEQUENCE: 112

```
Gly Ala Ser Arg Arg Ala Thr
1               5
```

<210> SEQ ID NO 113
<211> LENGTH: 9
<212> TYPE: PRT
<213> ORGANISM: Artificial
<220> FEATURE:
<223> OTHER INFORMATION: LCDR3

<400> SEQUENCE: 113

```
Gln Gln Tyr Gly Thr Ser Pro Arg Thr
1               5
```

<210> SEQ ID NO 114
<211> LENGTH: 5
<212> TYPE: PRT
<213> ORGANISM: Artificial
<220> FEATURE:
<223> OTHER INFORMATION: HCDR1

<400> SEQUENCE: 114

```
Ala Tyr Ala Met Asn
1               5
```

<210> SEQ ID NO 115
<211> LENGTH: 17
<212> TYPE: PRT
<213> ORGANISM: Artificial
<220> FEATURE:
<223> OTHER INFORMATION: HCDR2

<400> SEQUENCE: 115

```
Ala Ile Gly Gly Ser Gly Gly Ser Thr Tyr Tyr Ala Asp Ser Val Lys
1               5                   10                  15

Gly
```

<210> SEQ ID NO 116
<211> LENGTH: 12
<212> TYPE: PRT
<213> ORGANISM: Artificial
<220> FEATURE:
<223> OTHER INFORMATION: HCDR3

<400> SEQUENCE: 116

```
Gly Arg Asp Trp Thr Gly Gly Tyr Phe Phe Asp Ser
1               5                   10
```

<210> SEQ ID NO 117
<211> LENGTH: 17
<212> TYPE: PRT
<213> ORGANISM: Artificial
<220> FEATURE:
<223> OTHER INFORMATION: LCDR1

<400> SEQUENCE: 117

```
Lys Ser Ser Gln Ser Ile Phe Tyr Ser Ser Asn Asn Lys Asn Tyr Leu
1               5                   10                  15
```

Thr

<210> SEQ ID NO 118
<211> LENGTH: 7
<212> TYPE: PRT
<213> ORGANISM: Artificial
<220> FEATURE:
<223> OTHER INFORMATION: LCDR2

<400> SEQUENCE: 118

Trp Ala Ser Thr Arg Glu Ser
1 5

<210> SEQ ID NO 119
<211> LENGTH: 9
<212> TYPE: PRT
<213> ORGANISM: Artificial
<220> FEATURE:
<223> OTHER INFORMATION: LCDR3

<400> SEQUENCE: 119

Gln Gln Tyr Tyr Ser Ile Pro Tyr Thr
1 5

<210> SEQ ID NO 120
<211> LENGTH: 5
<212> TYPE: PRT
<213> ORGANISM: Artificial
<220> FEATURE:
<223> OTHER INFORMATION: HCDR1

<400> SEQUENCE: 120

Gly Tyr Ala Met Ser
1 5

<210> SEQ ID NO 121
<211> LENGTH: 17
<212> TYPE: PRT
<213> ORGANISM: Artificial
<220> FEATURE:
<223> OTHER INFORMATION: HCDR2

<400> SEQUENCE: 121

Asp Ile Gly Gly Ser Gly Gly Gly Thr Tyr Tyr Ala Asp Ser Val Lys
1 5 10 15

Gly

<210> SEQ ID NO 122
<211> LENGTH: 12
<212> TYPE: PRT
<213> ORGANISM: Artificial
<220> FEATURE:
<223> OTHER INFORMATION: HCDR3

<400> SEQUENCE: 122

Ser Ser Ser Trp Asp Arg Ala Tyr Phe Phe Asp Ser
1 5 10

<210> SEQ ID NO 123
<211> LENGTH: 17
<212> TYPE: PRT
<213> ORGANISM: Artificial
<220> FEATURE:
<223> OTHER INFORMATION: LCDR1

<400> SEQUENCE: 123

```
Lys Ser Ser Gln Ser Val Leu Tyr Ser Ser Ile His Lys Asn Tyr Leu
1               5                   10                  15

Ala


<210> SEQ ID NO 124
<211> LENGTH: 9
<212> TYPE: PRT
<213> ORGANISM: Artificial
<220> FEATURE:
<223> OTHER INFORMATION: LCDR3

<400> SEQUENCE: 124

Gln Gln Tyr Tyr Arg Ser Pro Pro Thr
1               5


<210> SEQ ID NO 125
<211> LENGTH: 5
<212> TYPE: PRT
<213> ORGANISM: Artificial
<220> FEATURE:
<223> OTHER INFORMATION: HCDR1

<400> SEQUENCE: 125

Ser Tyr Tyr Trp Ser
1               5


<210> SEQ ID NO 126
<211> LENGTH: 16
<212> TYPE: PRT
<213> ORGANISM: Artificial
<220> FEATURE:
<223> OTHER INFORMATION: HCDR2

<400> SEQUENCE: 126

Tyr Ile Tyr Tyr Arg Gly Gly Thr Ser Tyr Asn Pro Ser Leu Lys Ser
1               5                   10                  15


<210> SEQ ID NO 127
<211> LENGTH: 15
<212> TYPE: PRT
<213> ORGANISM: Artificial
<220> FEATURE:
<223> OTHER INFORMATION: HCDR3

<400> SEQUENCE: 127

Lys Asp Trp Gly Ser Ala Ala Gly Ser Val Trp Tyr Phe Asp Leu
1               5                   10                  15


<210> SEQ ID NO 128
<211> LENGTH: 14
<212> TYPE: PRT
<213> ORGANISM: Artificial
<220> FEATURE:
<223> OTHER INFORMATION: LCDR1

<400> SEQUENCE: 128

Thr Gly Thr Ser Ser Asp Val Gly Gly Tyr Asn Tyr Val Ser
1               5                   10


<210> SEQ ID NO 129
<211> LENGTH: 7
<212> TYPE: PRT
<213> ORGANISM: Artificial
<220> FEATURE:
<223> OTHER INFORMATION: LCDR2

<400> SEQUENCE: 129
```

Glu Val Ser Lys Arg Pro Ser
1 5

<210> SEQ ID NO 130
<211> LENGTH: 10
<212> TYPE: PRT
<213> ORGANISM: Artificial
<220> FEATURE:
<223> OTHER INFORMATION: LCDR3

<400> SEQUENCE: 130

Ser Ser Tyr Ala Gly Ser Asn Asn Leu Ile
1 5 10

<210> SEQ ID NO 131
<211> LENGTH: 5
<212> TYPE: PRT
<213> ORGANISM: Artificial
<220> FEATURE:
<223> OTHER INFORMATION: HCDR1

<400> SEQUENCE: 131

Ser Tyr Gly Met His
1 5

<210> SEQ ID NO 132
<211> LENGTH: 17
<212> TYPE: PRT
<213> ORGANISM: Artificial
<220> FEATURE:
<223> OTHER INFORMATION: HCDR2

<400> SEQUENCE: 132

Phe Ile Trp Tyr Asp Gly Ser Asn Lys His Tyr Ala Asp Ser Met Lys
1 5 10 15

Gly

<210> SEQ ID NO 133
<211> LENGTH: 13
<212> TYPE: PRT
<213> ORGANISM: Artificial
<220> FEATURE:
<223> OTHER INFORMATION: HCDR3

<400> SEQUENCE: 133

Asp Gly Gly Tyr Ser Thr Trp Glu Trp Tyr Phe Asp Leu
1 5 10

<210> SEQ ID NO 134
<211> LENGTH: 11
<212> TYPE: PRT
<213> ORGANISM: Artificial
<220> FEATURE:
<223> OTHER INFORMATION: LCDR1

<400> SEQUENCE: 134

Arg Ala Ser Gln Gly Ile Gly Ser Asn Leu His
1 5 10

<210> SEQ ID NO 135
<211> LENGTH: 7
<212> TYPE: PRT
<213> ORGANISM: Artificial
<220> FEATURE:
<223> OTHER INFORMATION: LCDR2

<400> SEQUENCE: 135

Tyr Ala Ser Gln Ser Ile Thr
1 5

<210> SEQ ID NO 136
<211> LENGTH: 9
<212> TYPE: PRT
<213> ORGANISM: Artificial
<220> FEATURE:
<223> OTHER INFORMATION: LCDR3

<400> SEQUENCE: 136

His Gln Ser Ser Ser Leu Pro Leu Thr
1 5

<210> SEQ ID NO 137
<211> LENGTH: 5
<212> TYPE: PRT
<213> ORGANISM: Artificial
<220> FEATURE:
<223> OTHER INFORMATION: HCDR1

<400> SEQUENCE: 137

Ser Phe Gly Leu Ser
1 5

<210> SEQ ID NO 138
<211> LENGTH: 17
<212> TYPE: PRT
<213> ORGANISM: Artificial
<220> FEATURE:
<223> OTHER INFORMATION: HCDR2

<400> SEQUENCE: 138

Trp Ile Ser Ala Tyr Asn Gly Glu Ile Lys Tyr Ala Gln Lys Phe Gln
1 5 10 15

Gly

<210> SEQ ID NO 139
<211> LENGTH: 13
<212> TYPE: PRT
<213> ORGANISM: Artificial
<220> FEATURE:
<223> OTHER INFORMATION: HCDR3

<400> SEQUENCE: 139

Glu Pro Pro Leu Tyr Phe Ser Ser Trp Ser Leu Asp Phe
1 5 10

<210> SEQ ID NO 140
<211> LENGTH: 13
<212> TYPE: PRT
<213> ORGANISM: Artificial
<220> FEATURE:
<223> OTHER INFORMATION: LCDR1

<400> SEQUENCE: 140

Ala Arg Ala Ser Gln Ser Val Ser Ser Asn Tyr Leu Ala
1 5 10

<210> SEQ ID NO 141
<211> LENGTH: 7
<212> TYPE: PRT
<213> ORGANISM: Artificial
<220> FEATURE:
<223> OTHER INFORMATION: LCDR2

<400> SEQUENCE: 141

Gly Ala Ser Arg Arg Ala Thr
1 5

<210> SEQ ID NO 142
<211> LENGTH: 9
<212> TYPE: PRT
<213> ORGANISM: Artificial
<220> FEATURE:
<223> OTHER INFORMATION: LCDR3

<400> SEQUENCE: 142

Gln Gln Tyr Asp Ser Ser Pro Arg Thr
1 5

<210> SEQ ID NO 143
<211> LENGTH: 5
<212> TYPE: PRT
<213> ORGANISM: Artificial
<220> FEATURE:
<223> OTHER INFORMATION: HCDR1

<400> SEQUENCE: 143

Ala Tyr Ser Met His
1 5

<210> SEQ ID NO 144
<211> LENGTH: 17
<212> TYPE: PRT
<213> ORGANISM: Artificial
<220> FEATURE:
<223> OTHER INFORMATION: HCDR2

<400> SEQUENCE: 144

Trp Ile Asn Thr Ala Ile Gly Asn Thr Gln Tyr Ser Gln Lys Phe Gln
1 5 10 15

Asp

<210> SEQ ID NO 145
<211> LENGTH: 12
<212> TYPE: PRT
<213> ORGANISM: Artificial
<220> FEATURE:
<223> OTHER INFORMATION: HCDR3

<400> SEQUENCE: 145

Gly Ala Ser Trp Asp Ala Arg Gly Trp Ser Gly Tyr
1 5 10

<210> SEQ ID NO 146
<211> LENGTH: 17
<212> TYPE: PRT
<213> ORGANISM: Artificial
<220> FEATURE:
<223> OTHER INFORMATION: LCDR1

<400> SEQUENCE: 146

Lys Ser Ser Gln Ser Val Phe Ser Ser Ser Thr Asn Lys Asn Tyr Leu
1 5 10 15

Ala

<210> SEQ ID NO 147
<211> LENGTH: 7
<212> TYPE: PRT

<213> ORGANISM: Artificial
<220> FEATURE:
<223> OTHER INFORMATION: LCDR2

<400> SEQUENCE: 147

Trp Ser Ser Thr Arg Glu Ser
1 5

<210> SEQ ID NO 148
<211> LENGTH: 9
<212> TYPE: PRT
<213> ORGANISM: Artificial
<220> FEATURE:
<223> OTHER INFORMATION: LCDR3

<400> SEQUENCE: 148

His Gln Tyr Tyr Thr Ala Pro Trp Thr
1 5

<210> SEQ ID NO 149
<211> LENGTH: 7
<212> TYPE: PRT
<213> ORGANISM: Artificial
<220> FEATURE:
<223> OTHER INFORMATION: HCDR1

<400> SEQUENCE: 149

Asn Thr Arg Met Gly Val Ser
1 5

<210> SEQ ID NO 150
<211> LENGTH: 16
<212> TYPE: PRT
<213> ORGANISM: Artificial
<220> FEATURE:
<223> OTHER INFORMATION: HCDR2

<400> SEQUENCE: 150

His Ile Phe Ser Asn Asp Glu Thr Ser Tyr Arg Thr Ser Leu Lys Arg
1 5 10 15

<210> SEQ ID NO 151
<211> LENGTH: 16
<212> TYPE: PRT
<213> ORGANISM: Artificial
<220> FEATURE:
<223> OTHER INFORMATION: HCDR3

<400> SEQUENCE: 151

Ile Gly Ser Gly Tyr Glu Ser Ser Ala Tyr Ser Thr Trp Leu Asp Pro
1 5 10 15

<210> SEQ ID NO 152
<211> LENGTH: 11
<212> TYPE: PRT
<213> ORGANISM: Artificial
<220> FEATURE:
<223> OTHER INFORMATION: LCDR1

<400> SEQUENCE: 152

Glu Gly Asp Thr Ile Gly Ser Lys Ser Val His
1 5 10

<210> SEQ ID NO 153
<211> LENGTH: 7
<212> TYPE: PRT
<213> ORGANISM: Artificial

```
<220> FEATURE:
<223> OTHER INFORMATION: LCDR2

<400> SEQUENCE: 153

Asn Asp Arg Asp Arg Pro Ser
1               5


<210> SEQ ID NO 154
<211> LENGTH: 11
<212> TYPE: PRT
<213> ORGANISM: Artificial
<220> FEATURE:
<223> OTHER INFORMATION: LCDR3

<400> SEQUENCE: 154

Gln Val Trp Glu Ser Gly Gly Asp Gln Thr Val
1               5                   10


<210> SEQ ID NO 155
<211> LENGTH: 5
<212> TYPE: PRT
<213> ORGANISM: Artificial
<220> FEATURE:
<223> OTHER INFORMATION: HCDR1

<400> SEQUENCE: 155

Asp His Tyr Trp Ser
1               5


<210> SEQ ID NO 156
<211> LENGTH: 16
<212> TYPE: PRT
<213> ORGANISM: Artificial
<220> FEATURE:
<223> OTHER INFORMATION: HCDR2

<400> SEQUENCE: 156

Glu Val Val His Ser Gly Asp Thr Asn Tyr Thr Pro Ser Leu Arg Asn
1               5                   10                  15


<210> SEQ ID NO 157
<211> LENGTH: 16
<212> TYPE: PRT
<213> ORGANISM: Artificial
<220> FEATURE:
<223> OTHER INFORMATION: HCDR3

<400> SEQUENCE: 157

Gly Arg Asn Val Ala Val Val Gly Ala Ile Gln Arg His Tyr Asp Tyr
1               5                   10                  15


<210> SEQ ID NO 158
<211> LENGTH: 12
<212> TYPE: PRT
<213> ORGANISM: Artificial
<220> FEATURE:
<223> OTHER INFORMATION: LCDR1

<400> SEQUENCE: 158

Arg Ala Ser Gln Ser Val Ser Arg Asn Tyr Leu Ala
1               5                   10


<210> SEQ ID NO 159
<211> LENGTH: 7
<212> TYPE: PRT
<213> ORGANISM: Artificial
<220> FEATURE:
```

<223> OTHER INFORMATION: LCDR2

<400> SEQUENCE: 159

Gly Ala Ser Ser Arg Ala Thr
1               5

<210> SEQ ID NO 160
<211> LENGTH: 9
<212> TYPE: PRT
<213> ORGANISM: Artificial
<220> FEATURE:
<223> OTHER INFORMATION: LCDR3

<400> SEQUENCE: 160

Gln His Tyr Gly Ser Val Leu Val Ala
1               5

<210> SEQ ID NO 161
<211> LENGTH: 7
<212> TYPE: PRT
<213> ORGANISM: Artificial
<220> FEATURE:
<223> OTHER INFORMATION: HCDR1

<400> SEQUENCE: 161

Ser Gly Thr Tyr Tyr Trp Ser
1               5

<210> SEQ ID NO 162
<211> LENGTH: 16
<212> TYPE: PRT
<213> ORGANISM: Artificial
<220> FEATURE:
<223> OTHER INFORMATION: HCDR2

<400> SEQUENCE: 162

Asp Ile Ser Tyr Ser Gly Ser Thr Asn Tyr Asn Pro Ser Leu Lys Ser
1               5                   10                  15

<210> SEQ ID NO 163
<211> LENGTH: 20
<212> TYPE: PRT
<213> ORGANISM: Artificial
<220> FEATURE:
<223> OTHER INFORMATION: HCDR3

<400> SEQUENCE: 163

Ala Met Ala Ala Tyr Asn Tyr Asp Arg Gly Gly Tyr Asn Asp Tyr Tyr
1               5                   10                  15

Tyr Met Asp Val
            20

<210> SEQ ID NO 164
<211> LENGTH: 11
<212> TYPE: PRT
<213> ORGANISM: Artificial
<220> FEATURE:
<223> OTHER INFORMATION: LCDR1

<400> SEQUENCE: 164

Arg Ala Ser Gln Gly Ile Asn Thr Tyr Leu Asn
1               5                   10

<210> SEQ ID NO 165
<211> LENGTH: 7
<212> TYPE: PRT

<213> ORGANISM: Artificial
<220> FEATURE:
<223> OTHER INFORMATION: LCDR2

<400> SEQUENCE: 165

Ala Ala Ser Thr Leu Gln Ser
1 5

<210> SEQ ID NO 166
<211> LENGTH: 9
<212> TYPE: PRT
<213> ORGANISM: Artificial
<220> FEATURE:
<223> OTHER INFORMATION: LCDR3

<400> SEQUENCE: 166

Gln Gln Ser Tyr Ser Thr Ala Ile Thr
1 5

<210> SEQ ID NO 167
<211> LENGTH: 5
<212> TYPE: PRT
<213> ORGANISM: Artificial
<220> FEATURE:
<223> OTHER INFORMATION: HCDR1

<400> SEQUENCE: 167

Thr Tyr Gly Met His
1 5

<210> SEQ ID NO 168
<211> LENGTH: 17
<212> TYPE: PRT
<213> ORGANISM: Artificial
<220> FEATURE:
<223> OTHER INFORMATION: HCDR2

<400> SEQUENCE: 168

Phe Ile Trp Tyr Asp Gly Ser Asn Lys His Tyr Gln Asp Ser Val Lys
1 5 10 15

Gly

<210> SEQ ID NO 169
<211> LENGTH: 13
<212> TYPE: PRT
<213> ORGANISM: Artificial
<220> FEATURE:
<223> OTHER INFORMATION: HCDR3

<400> SEQUENCE: 169

Asp Gly Gly Tyr Ser Thr Trp Glu Trp Tyr Phe Asp Leu
1 5 10

<210> SEQ ID NO 170
<211> LENGTH: 11
<212> TYPE: PRT
<213> ORGANISM: Artificial
<220> FEATURE:
<223> OTHER INFORMATION: LCDR1

<400> SEQUENCE: 170

Arg Ala Ser Arg Ser Ile Gly Ser Asp Leu His
1 5 10

<210> SEQ ID NO 171
<211> LENGTH: 7

<212> TYPE: PRT
<213> ORGANISM: Artificial
<220> FEATURE:
<223> OTHER INFORMATION: LCDR2

<400> SEQUENCE: 171

Phe Ala Ser Gln Ser Met Ser
1               5

<210> SEQ ID NO 172
<211> LENGTH: 5
<212> TYPE: PRT
<213> ORGANISM: Artificial
<220> FEATURE:
<223> OTHER INFORMATION: HCDR1

<400> SEQUENCE: 172

Val Ile Phe Met Ser
1               5

<210> SEQ ID NO 173
<211> LENGTH: 16
<212> TYPE: PRT
<213> ORGANISM: Artificial
<220> FEATURE:
<223> OTHER INFORMATION: HCDR2

<400> SEQUENCE: 173

Ile Ile Tyr Ile Asp Asp Ser Thr Tyr Tyr Ala Asp Ser Val Lys Gly
1               5                   10                  15

<210> SEQ ID NO 174
<211> LENGTH: 19
<212> TYPE: PRT
<213> ORGANISM: Artificial
<220> FEATURE:
<223> OTHER INFORMATION: HCDR3

<400> SEQUENCE: 174

Glu Ser Gly Asp Phe Gly Asp Gln Thr Gly Pro Tyr His Tyr Tyr Ala
1               5                   10                  15

Met Asp Val

<210> SEQ ID NO 175
<211> LENGTH: 14
<212> TYPE: PRT
<213> ORGANISM: Artificial
<220> FEATURE:
<223> OTHER INFORMATION: LCDR1

<400> SEQUENCE: 175

Thr Gly Ser Ser Gly Asp Ile Gly Gly Tyr Asn Ala Val Ser
1               5                   10

<210> SEQ ID NO 176
<211> LENGTH: 7
<212> TYPE: PRT
<213> ORGANISM: Artificial
<220> FEATURE:
<223> OTHER INFORMATION: LCDR2

<400> SEQUENCE: 176

Glu Val Thr Ser Arg Pro Ser
1               5

<210> SEQ ID NO 177

<211> LENGTH: 10
<212> TYPE: PRT
<213> ORGANISM: Artificial
<220> FEATURE:
<223> OTHER INFORMATION: LCDR3

<400> SEQUENCE: 177

Cys Ser Phe Ala Asp Ser Asn Ile Leu Ile
1               5                   10

<210> SEQ ID NO 178
<211> LENGTH: 5
<212> TYPE: PRT
<213> ORGANISM: Artificial
<220> FEATURE:
<223> OTHER INFORMATION: HCDR1

<400> SEQUENCE: 178

Asp Tyr Thr Met His
1               5

<210> SEQ ID NO 179
<211> LENGTH: 17
<212> TYPE: PRT
<213> ORGANISM: Artificial
<220> FEATURE:
<223> OTHER INFORMATION: HCDR2

<400> SEQUENCE: 179

Leu Ile Ser Trp Asp Gly Gly Met Ser Asn Tyr Ala Asp Ser Val Lys
1               5                   10                  15

Gly

<210> SEQ ID NO 180
<211> LENGTH: 14
<212> TYPE: PRT
<213> ORGANISM: Artificial
<220> FEATURE:
<223> OTHER INFORMATION: HCDR3

<400> SEQUENCE: 180

Asp Ile Arg Pro Arg Met Pro Ala Arg His Phe Met Asp Val
1               5                   10

<210> SEQ ID NO 181
<211> LENGTH: 11
<212> TYPE: PRT
<213> ORGANISM: Artificial
<220> FEATURE:
<223> OTHER INFORMATION: LCDR1

<400> SEQUENCE: 181

Arg Ala Ser Gln Asn Val Asn Tyr Asn Leu Ala
1               5                   10

<210> SEQ ID NO 182
<211> LENGTH: 7
<212> TYPE: PRT
<213> ORGANISM: Artificial
<220> FEATURE:
<223> OTHER INFORMATION: LCDR2

<400> SEQUENCE: 182

Val Ala Ser Thr Arg Ala Thr
1               5

<210> SEQ ID NO 183
<211> LENGTH: 11
<212> TYPE: PRT
<213> ORGANISM: Artificial
<220> FEATURE:
<223> OTHER INFORMATION: LCDR3

<400> SEQUENCE: 183

```
Gln Gln Tyr Asn Asn Trp Pro Pro Ala Ile Thr
1               5                   10
```

<210> SEQ ID NO 184
<211> LENGTH: 1353
<212> TYPE: DNA
<213> ORGANISM: Artificial
<220> FEATURE:
<223> OTHER INFORMATION: CR6261 HC DNA

<400> SEQUENCE: 184

```
gaggtgcagc tggtggagtc tggggctgag gtgaagaagc ctgggtcctc ggtgaaagtc     60
tcttgcaagg cttctggagg ccccttccgc agctatgcta tcagctgggt gcgacaggcc    120
cctggacaag ggcctgagtg gatgggaggg atcatcccta tttttggtac aacaaaatac    180
gcaccgaagt tccagggcag agtcacgatt accgcggacg atttcgcggg cacagtttac    240
atggagctga gcagcctgcg atctgaggac acggccatgt actactgtgc gaaacatatg    300
gggtaccagg tgcgcgaaac tatggacgtc tggggcaaag ggaccacggt caccgtctcg    360
agtgctagca ccaagggccc cagcgtgttc cccctggccc ccagcagcaa gagcaccagc    420
ggcggcacag ccgccctggg ctgcctggtg aaggactact tccccgagcc cgtgaccgtg    480
agctggaaca gcggcgcctt gaccagcggc gtgcacacct tccccgccgt gctgcagagc    540
agcggcctgt acagcctgag cagcgtggtg accgtgccca gcagcagcct gggcacccag    600
acctacatct gcaacgtgaa ccacaagccc agcaacacca aggtggacaa acgcgtggag    660
cccaagagct gcgacaagac ccacacctgc cccccctgcc ctgcccccga gctgctgggc    720
ggaccctccg tgttcctgtt cccccccaag cccaaggaca ccctcatgat cagccggacc    780
cccgaggtga cctgcgtggt ggtggacgtg agccacgagg accccgaggt gaagttcaac    840
tggtacgtgg acggcgtgga ggtgcacaac gccaagacca agccccggga ggagcagtac    900
aacagcacct accgggtggt gagcgtgctc accgtgctgc accaggactg gctgaacggc    960
aaggagtaca agtgcaaggt gagcaacaag gccctgcctg cccccatcga gaagaccatc   1020
agcaaggcca agggccagcc ccgggagccc caggtgtaca ccctgccccc cagccgggag   1080
gagatgacca agaaccaggt gtccctcacc tgtctggtga agggcttcta ccccagcgac   1140
atcgccgtgg agtgggagag caacggccag cccgagaaca actacaagac caccccccct   1200
gtgctggaca gcgacggcag cttcttcctg tacagcaagc tcaccgtgga caagagccgg   1260
tggcagcagg gcaacgtgtt cagctgcagc gtgatgcacg aggccctgca caaccactac   1320
acccagaaga gcctgagcct gagccccggc aag                                 1353
```

<210> SEQ ID NO 185
<211> LENGTH: 451
<212> TYPE: PRT
<213> ORGANISM: Artificial
<220> FEATURE:
<223> OTHER INFORMATION: CR6261 HC PROTEIN

<400> SEQUENCE: 185

```
Glu Val Gln Leu Val Glu Ser Gly Ala Glu Val Lys Lys Pro Gly Ser
```

```
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
        435                 440                 445

Pro Gly Lys
    450


<210> SEQ ID NO 186
<211> LENGTH: 663
<212> TYPE: DNA
<213> ORGANISM: Artificial
<220> FEATURE:
<223> OTHER INFORMATION: CR6261 LC DNA

<400> SEQUENCE: 186

cagtctgtgt tgacgcagcc gccctcagtg tctgcggccc caggacagaa ggtcaccatc      60

tcctgctctg gaagcagctc caacattggg aatgattatg tatcctggta ccagcagctc     120

ccaggaacag cccccaaact cctcatttat gacaataata agcgaccctc agggattcct     180

gaccgattct ctggctccaa gtctggcacg tcagccaccc tgggcatcac cggactccag     240

actggggacg aggccaacta ttactgcgca acatgggatc gccgcccgac tgcttatgtt     300

gtcttcggcg gagggaccaa gctgaccgtc ctaggtgcgg ccgcaggcca gcccaaggcc     360

gctcccagcg tgaccctgtt cccccctcc tccgaggagc tgcaggccaa caaggccacc      420

ctggtgtgcc tcatcagcga cttctaccct ggcgccgtga ccgtggcctg gaaggccgac     480

agcagccccg tgaaggccgg cgtggagacc accaccccca gcaagcagag caacaacaag     540

tacgccgcca gcagctacct gagcctcacc cccgagcagt ggaagagcca ccggagctac     600

agctgccagg tgacccacga gggcagcacc gtggagaaga ccgtggcccc caccgagtgc     660

agc                                                                   663


<210> SEQ ID NO 187
<211> LENGTH: 221
<212> TYPE: PRT
<213> ORGANISM: Artificial
<220> FEATURE:
<223> OTHER INFORMATION: CR6261 LC PROTEIN

<400> SEQUENCE: 187

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
            100                 105                 110

Ala Ala Ala Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
```

```
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220


<210> SEQ ID NO 188
<211> LENGTH: 10515
<212> TYPE: DNA
<213> ORGANISM: Artificial
<220> FEATURE:
<223> OTHER INFORMATION: Vector pIg-C911-HCgamma1

<400> SEQUENCE: 188

tcgacggatc gggagatctc ccgatcccct atggtgcact ctcagtacaa tctgctctga      60

tgccgcatag ttaagccagt atctgctccc tgcttgtgtg ttggaggtcg ctgagtagtg     120

cgcgagcaaa atttaagcta caacaaggca aggcttgacc gacaattgca tgaagaatct     180

gcttagggtt aggcgttttg cgctgcttcg ctaggtggtc aatattggcc attagccata     240

ttattcattg gttatatagc ataaatcaat attggctatt ggccattgca tacgttgtat     300

ccatatcata atatgtacat ttatattggc tcatgtccaa cattaccgcc atgttgacat     360

tgattattga ctagttatta atagtaatca attacggggt cattagttca tagcccatat     420

atggagttcc gcgttacata acttacggta aatggcccgc ctggctgacc gcccaacgac     480

ccccgcccat tgacgtcaat aatgacgtat gttcccatag taacgccaat agggactttc     540

cattgacgtc aatgggtgga gtatttacgg taaactgccc acttggcagt acatcaagtg     600

tatcatatgc caagtacgcc ccctattgac gtcaatgacg gtaaatggcc cgcctggcat     660

tatgcccagt acatgacctt atgggacttt cctacttggc agtacatcta cgtattagtc     720

atcgctatta ccatggtgat gcggttttgg cagtacatca atgggcgtgg atagcggttt     780

gactcacggg gatttccaag tctccacccc attgacgtca atgggagttt gttttggcac     840

caaaatcaac gggactttcc aaaatgtcgt aacaactccg ccccattgac gcaaatgggc     900

ggtaggcgtg tacggtggga ggtctatata agcagagctc gtttagtgaa ccgtcagatc     960

gcctggagac gccatccacg ctgttttgac ctccatagaa gacaccggga ccgatccagc    1020

ctccgcggcc gggaacggtg cattggaagc tggcctggat atcctgactc tcttaggtag    1080

ccttgcagaa gttggtcgtg aggcactggg caggtaagta tcaaggttac aagacaggtt    1140

taaggagatc aatagaaact gggcttgtcg agacagagaa gactcttgcg tttctgatag    1200

gcacctattg gtcttactga catccacttt gcctttctct ccacaggtgt ccactcccag    1260

ttcaattaca gctcgccacc atgggatgga gctgtatcat cctcttcttg gtactgctgc    1320

tggcccagcc ggccagtgac cttgaccggt gcaccacttt tgatgatgtt caagctccta    1380

attacactca acatacttca tctatgaggg gggtttacta tcctgatgaa atttttagat    1440

cggacactct ttatttaact caggatttat ttcttccatt ttattctaat gttacagggt    1500

ttcatactat taatcatacg tttggcaacc ctgtcatacc ttttaaggat ggtatttatt    1560

ttgctgccac agagaaatca aatgttgtcc gtggttgggt ttttggttct accatgaaca    1620

acaagtcaca gtcggtgatt attattaaca attctactaa tgttgttata cgagcatgta    1680
```

```
actttgaatt gtgtgacaac cctttctttg ctgtttctaa acccatgggt acacagacac   1740
atactatgat attcgataat gcatttaatt gcactttcga gtacatatct gatgcctttt   1800
cgcttgatgt ttcagaaaag tcaggtaatt ttaaacactt acgagagttt gtgtttaaaa   1860
ataaagatgg gtttctctat gtttataagg gctatcaacc tatagatgta gttcgtgatc   1920
taccttctgg ttttaacact ttgaaaccta tttttaagtt gcctcttggt attaacatta   1980
caaattttag agccattctt acagcctttt cacctgctca agacatttgg ggcacgtcag   2040
ctgcagccta ttttgttggc tatttaaagc caactacatt tatgctcaag tatgatgaaa   2100
atggtacaat cacagatgct gttgattgtt ctcaaaatcc acttgctgaa ctcaaatgct   2160
ctgttaagag ctttgagatt gacaaaggaa tttaccagac ctctaatttc agggttgttc   2220
cctcaggaga tgttgtgaga ttccctaata ttacaaactt gtgtcctttt ggagaggttt   2280
ttaatgctac taaattccct tctgtctatg catgggagag aaaaaaaatt tctaattgtg   2340
ttgctgatta ctctgtgctc tacaactcaa catttttttc aacctttaag tgctatggcg   2400
tttctgccac taagttgaat gatctttgct tctccaatgt ctatgcagat tcttttgtag   2460
tcaagggaga tgatgtaaga caaatagcgc caggacaaac tggtgttatt gctgattata   2520
attataaatt gccagatgat ttcatgggtt gtgtccttgc ttggaatact aggaacattg   2580
atgctacttc aactggtaat tataattata aatataggta tcttagacat ggcaagctta   2640
ggccctttga gagagacata tctaatgtgc ctttctcccc tgatggcaaa ccttgcaccc   2700
cacctgctct taattgttat tggccattaa atgattatgg tttttacacc actactggca   2760
ttggctacca accttacaga gttgtagtac tttcttttga acttttaaat gcaccggcca   2820
cggtttgtgg accaaaatta tccactgacc ttattaagaa ccagtgtgtc aattttaatt   2880
ttaatggact cactggtact ggtgtgttaa ctccttcttc aaagagattt caaccatttc   2940
aacaatttgg ccgtgatgtt tctgatttca ctgattccgt tcgagatcct aaaacatctg   3000
aaatattaga catttcacct tgctcttttg gggtgtaag tgtaattaca cctggaacaa   3060
atgcttcatc tgaagttgct gttctatatc aagatgttaa ctgcactgat gtttctacag   3120
caattcatgc agatcaactc acaccagctt ggcgcatata ttctactgga aacaatgtat   3180
tccagactca ggcaggctgt cttataggag ctgagcatgt cgacacttct tatgagtgcg   3240
acattcctat tggagctggc atttgtgcta gttaccatac agtttcttta ttacgtagta   3300
ctagccaaaa atctattgtg gcttatacta tgtctttagg tgctgatagt tcaattgctt   3360
actctaataa caccattgct atacctacta acttttcaat tagcattact acagaagtaa   3420
tgcctgtttc tatggctaaa acctccgtag attgtaatat gtacatctgc ggagattcta   3480
ctgaatgtgc taatttgctt ctccaatatg gtagcttttg cacacaacta aatcgtgcac   3540
tctcaggtat tgctgctgaa caggatcgca acacacgtga agtgttcgct caagtcaaac   3600
aaatgtacaa aaccccaact ttgaaatatt ttggtggttt taatttttca caaatattac   3660
ctgaccctct aaagccaact aagaggtctt ttattgagga cttgctcttt aataaggtga   3720
cactcgctga tgctggcttc atgaagcaat atggcgaatg cctaggtgat attaatgcta   3780
gagatctcat ttgtgcgcag aagttcaatg gacttacagt gttgccacct ctgctcactg   3840
atgatatgat tgctgcctac actgctgctc tagttagtgg tactgccact gctggatgga   3900
catttggtgc tggcgctgct cttcaaatac cttttgctat gcaaatggca tataggttca   3960
atggcattgg agttacccaa aatgttctct atgagaacca aaaacaaatc gccaaccaat   4020
```

-continued

```
ttaacaaggc gattagtcaa attcaagaat cacttacaac aacatcaact gcattgggca   4080
agctgcaaga cgttgttaac cagaatgctc aagcattaaa cacacttgtt aaacaactta   4140
gctctaattt tggtgcaatt tcaagtgtgc taaatgatat cctttcgcga cttgataaag   4200
tcgaggcgga ggtacaaatt gacaggttaa ttacaggcag acttcaaagc cttcaaacct   4260
atgtaacaca acaactaatc agggctgctg aaatcagggc ttctgctaat cttgctgcta   4320
ctaaaatgtc tgagtgtgtt cttggacaat caaaaagagt tgacttttgt ggaaagggct   4380
accaccttat gtccttccca caagcagccc cgcatggtgt tgtcttccta catgtcacgt   4440
atgtgccatc ccaggagagg aacttcacca cagcgccagc aatttgtcat gaaggcaaag   4500
catacttccc tcgtgaaggt gtttttgtgt ttaatggcac ttcttggttt attacacaga   4560
ggaacttctt ttctccacaa ataattacta cagacaatac atttgtctca ggaaattgtg   4620
atgtcgttat tggcatcatt aacaacacag tttatgatcc tctgcaacct gagcttgact   4680
cattcaaaga agagctggac aagtacttca aaaatcatac atcaccagat gttgattttg   4740
gcgacatttc aggcattaac gcttctgtcg tcaacattca aaaagaaatt gaccgcctca   4800
atgaggtcgc taaaaattta aatgaatcac tcattgacct tcaagaactg ggaaaatatg   4860
agcaatatat taaatggcct ctcgacgaac aaaaactcat ctcagaagag gatctgaatg   4920
ctgtgggcca ggacacgcag gaggtcatcg tggtgccaca ctccttgccc tttaaggtgg   4980
tggtgatctc agccatcctg gccctggtgg tgctcaccat catctccctt atcatcctca   5040
tcatgctttg gcagaagaag ccacgttagg cggccgctcg agtgctagca ccaagggccc   5100
cagcgtgttc cccctggccc ccagcagcaa gagcaccagc ggcggcacag ccgccctggg   5160
ctgcctggtg aaggactact tccccgagcc cgtgaccgtg agctggaaca gcggcgcctt   5220
gaccagcggc gtgcacacct tccccgccgt gctgcagagc agcggcctgt acagcctgag   5280
cagcgtggtg accgtgccca gcagcagcct gggcacccag acctacatct gcaacgtgaa   5340
ccacaagccc agcaacacca aggtggacaa acgcgtggag cccaagagct gcgacaagac   5400
ccacacctgc ccccccctgcc ctgcccccga gctgctgggc ggaccctccg tgttcctgtt   5460
ccccccccaag cccaaggaca ccctcatgat cagccggacc cccgaggtga cctgcgtggt   5520
ggtggacgtg agccacgagg accccgaggt gaagttcaac tggtacgtgg acggcgtgga   5580
ggtgcacaac gccaagacca agccccggga ggagcagtac aacagcacct accgggtggt   5640
gagcgtgctc accgtgctgc accaggactg gctgaacggc aaggagtaca agtgcaaggt   5700
gagcaacaag gccctgcctg cccccatcga gaagaccatc agcaaggcca agggccagcc   5760
ccgggagccc caggtgtaca ccctgccccc cagccgggag gagatgacca agaaccaggt   5820
gtccctcacc tgtctggtga agggcttcta ccccagcgac atcgccgtgg agtgggagag   5880
caacggccag cccgagaaca actacaagac caccccccct gtgctggaca gcgacggcag   5940
cttcttcctg tacagcaagc tcaccgtgga caagagccgg tggcagcagg gcaacgtgtt   6000
cagctgcagc gtgatgcacg aggccctgca caaccactac acccagaaga gcctgagcct   6060
gagccccggc aagtgataat ctagagggcc cgtttaaacc cgctgatcag cctcgactgt   6120
gccttctagt tgccagccat ctgttgtttg cccctccccc gtgccttcct tgaccctgga   6180
aggtgccact cccactgtcc tttcctaata aaatgaggaa attgcatcgc attgtctgag   6240
taggtgtcat tctattctgg ggggtggggt ggggcaggac agcaaggggg aggattggga   6300
agacaatagc aggcatgctg ggatgcggt gggctctatg gcttctgagg cggaaagaac   6360
cagctggggc tctagggggt atccccacgc gccctgtagc ggcgcattaa gcgcggcggg   6420
```

```
tgtggtggtt acgcgcagcg tgaccgctac acttgccagc gccctagcgc ccgctccttt   6480
cgctttcttc ccttcctttc tcgccacgtt cgccggcttt ccccgtcaag ctctaaatcg   6540
ggggctccct ttagggttcc gatttagtgc tttacggcac ctcgacccca aaaaacttga   6600
ttagggtgat ggttcacgta gtgggccatc gccctgatag acggtttttc gccctttgac   6660
gttggagtcc acgttcttta atagtggact cttgttccaa actggaacaa cactcaaccc   6720
tatctcggtc tattcttttg atttataagg gattttgccg atttcggcct attggttaaa   6780
aaatgagctg atttaacaaa aatttaacgc gaattaattc tgtggaatgt gtgtcagtta   6840
gggtgtggaa agtccccagg ctccccagca ggcagaagta tgcaaagcat gcatctcaat   6900
tagtcagcaa ccaggtgtgg aaagtcccca ggctccccag caggcagaag tatgcaaagc   6960
atgcatctca attagtcagc aaccatagtc ccgcccctaa ctccgcccat cccgccccta   7020
actccgccca gttccgccca ttctccgccc catggctgac taattttttt tatttatgca   7080
gaggccgagg ccgcctctgc ctctgagcta ttccagaagt agtgaggagg cttttttgga   7140
ggcctaggct tttgcaaaaa gctcccggga gcttgtatat ccattttcgg atctgatcaa   7200
gagacaggat gaggatcgtt tcgcatgatt gaacaagatg gattgcacgc aggttctccg   7260
gccgcttggg tggagaggct attcggctat gactgggcac aacagacaat cggctgctct   7320
gatgccgccg tgttccggct gtcagcgcag gggcgcccgg ttctttttgt caagaccgac   7380
ctgtccggtg ccctgaatga actgcaggac gaggcagcgc ggctatcgtg gctggccacg   7440
acgggcgttc cttgcgcagc tgtgctcgac gttgtcactg aagcgggaag ggactggctg   7500
ctattgggcg aagtgccggg gcaggatctc ctgtcatctc accttgctcc tgccgagaaa   7560
gtatccatca tggctgatgc aatgcggcgg ctgcatacgc ttgatccggc tacctgccca   7620
ttcgaccacc aagcgaaaca tcgcatcgag cgagcacgta ctcggatgga agccggtctt   7680
gtcgatcagg atgatctgga cgaagagcat caggggctcg cgccagccga actgttcgcc   7740
aggctcaagg cgcgcatgcc cgacggcgag gatctcgtcg tgacccatgg cgatgcctgc   7800
ttgccgaata tcatggtgga aaatggccgc ttttctggat tcatcgactg tggccggctg   7860
ggtgtggcgg accgctatca ggacatagcg ttggctaccc gtgatattgc tgaagagctt   7920
ggcggcgaat gggctgaccg cttcctcgtg ctttacggta tcgccgctcc cgattcgcag   7980
cgcatcgcct tctatcgcct tcttgacgag ttcttctgag cgggactctg gggttcgaaa   8040
tgaccgacca agcgacgccc aacctgccat cacgagattt cgattccacc gccgccttct   8100
atgaaaggtt gggcttcgga atcgttttcc gggacgccgg ctggatgatc ctccagcgcg   8160
gggatctcat gctggagttc ttcgcccacc ccaacttgtt tattgcagct tataatggtt   8220
acaaataaag caatagcatc acaaatttca caaataaagc atttttttca ctgcattcta   8280
gttgtggttt gtccaaactc atcaatgtat cttatcatgt ctgtataccg tcgacctcta   8340
gctagagctt ggcgtaatca tggtcatagc tgtttcctgt gtgaaattgt tatccgctca   8400
caattccaca caacatacga gccggaagca taaagtgtaa agcctggggt gcctaatgag   8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
```

```
cgtttttcca taggctccgc cccccctgacg agcatcacaa aaatcgacgc tcaagtcaga   8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc ccgttcagcc cgaccgctgc gccttatccg   9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaagaacag tatttggtat ctgcgctctg ctgaagccag   9240
ttaccttcgg aaaaagagtt ggtagctctt gatccggcaa acaaaccacc gctggtagcg   9300
gtttttttgt ttgcaagcag cagattacgc gcagaaaaaa aggatctcaa gaagatcctt   9360
tgatcttttc tacggggtct gacgctcagt ggaacgaaaa ctcacgttaa gggattttgg   9420
tcatgagatt atcaaaaagg atcttcacct agatcctttt aaattaaaaa tgaagtttta   9480
aatcaatcta aagtatatat gagtaaactt ggtctgacag ttaccaatgc ttaatcagtg   9540
aggcacctat ctcagcgatc tgtctatttc gttcatccat agttgcctga ctccccgtcg   9600
tgtagataac tacgatacgg gagggcttac catctggccc cagtgctgca atgataccgc   9660
gagacccacg ctcaccggct ccagatttat cagcaataaa ccagccagcc ggaagggccg   9720
agcgcagaag tggtcctgca actttatccg cctccatcca gtctattaat tgttgccggg   9780
aagctagagt aagtagttcg ccagttaata gtttgcgcaa cgttgttgcc attgctacag   9840
gcatcgtggt gtcacgctcg tcgtttggta tggcttcatt cagctccggt tcccaacgat   9900
caaggcgagt tacatgatcc cccatgttgt gcaaaaaagc ggttagctcc ttcggtcctc   9960
cgatcgttgt cagaagtaag ttggccgcag tgttatcact catggttatg gcagcactgc  10020
ataattctct tactgtcatg ccatccgtaa gatgcttttc tgtgactggt gagtactcaa  10080
ccaagtcatt ctgagaatag tgtatgcggc gaccgagttg ctcttgcccg gcgtcaatac  10140
gggataatac cgcgccacat agcagaactt taaaagtgct catcattgga aaacgttctt  10200
cggggcgaaa actctcaagg atcttaccgc tgttgagatc cagttcgatg taacccactc  10260
gtgcacccaa ctgatcttca gcatctttta ctttcaccag cgtttctggg tgagcaaaaa  10320
caggaaggca aaatgccgca aaaaagggaa taagggcgac acggaaatgt tgaatactca  10380
tactcttcct ttttcaatat tattgaagca tttatcaggg ttattgtctc atgagcggat  10440
acatatttga atgtatttag aaaaataaac aaataggggt tccgcgcaca tttccccgaa  10500
aagtgccacc tgacg                                                   10515
```

<210> SEQ ID NO 189
<211> LENGTH: 8777
<212> TYPE: DNA
<213> ORGANISM: Artificial
<220> FEATURE:
<223> OTHER INFORMATION: Vector pIg-C909-Ckappa

<400> SEQUENCE: 189

```
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgtt aattaacatg    180
aagaatctgc ttagggttag gcgttttgcg ctgcttcgct aggtggtcaa tattggccat    240
tagccatatt attcattggt tatatagcat aaatcaatat tggctattgg ccattgcata    300
```

```
cgttgtatcc atatcataat atgtacattt atattggctc atgtccaaca ttaccgccat    360
gttgacattg attattgact agttattaat agtaatcaat tacggggtca ttagttcata    420
gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca agtacgcccc ctattgacgt caatgacggt aaatggcccg    660
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggctgcccgc ccagctgctg ggccttctca tgctgtgggt   1320
gcccgcctcg agatctatcg atgcatgcca tggtaccaag cttgccacca tgagcagcag   1380
ctcttggctg ctgctgagcc tggtggccgt gacagccgcc cagagcacca tcgaggagca   1440
ggccaagacc ttcctggaca agttcaacca cgaggccgag gacctgttct accagagcag   1500
cctggccagc tggaactaca acaccaacat caccgaggag aacgtgcaga acatgaacaa   1560
cgccggcgac aagtggagcg ccttcctgaa ggagcagagc acactggccc agatgtaccc   1620
cctgcaggag atccagaacc tgaccgtgaa gctgcagctg caggccctgc agcagaacgg   1680
cagcagcgtg ctgagcgagg acaagagcaa gcggctgaac accatcctga acaccatgtc   1740
caccatctac agcaccggca aagtgtgcaa ccccgacaac ccccaggagt gcctgctgct   1800
ggagcccggc ctgaacgaga tcatggccaa cagcctggac tacaacgagc ggctgtgggc   1860
ctgggagagc tggcggagcg aagtgggcaa gcagctgcgg cccctgtacg aggagtacgt   1920
ggtgctgaag aacgagatgg ccagggccaa ccactacgag gactacggcg actactggag   1980
aggcgactac gaagtgaacg gcgtggacgg ctacgactac agcagaggcc agctgatcga   2040
ggacgtggag cacaccttcg aggagatcaa gcctctgtac gagcacctgc acgcctacgt   2100
gcgggccaag ctgatgaacg cctaccccag ctacatcagc cccatcggct gcctgcccgc   2160
ccacctgctg ggcgacatgt ggggccggtt ctggaccaac ctgtacagcc tgaccgtgcc   2220
cttcggccag aagcccaaca tcgacgtgac cgacgccatg gtggaccagg cctgggacgc   2280
ccagcggatc ttcaaggagg ccgagaagtt cttcgtgagc gtgggcctgc ccaacatgac   2340
ccagggcttt tgggagaaca gcatgctgac cgaccccggc aatgtgcaga aggccgtgtg   2400
ccaccccacc gcctgggacc tgggcaaggg cgacttccgg atcctgatgt gcaccaaagt   2460
gaccatggac gacttcctga ccgcccacca cgagatgggc cacatccagt acgacatggc   2520
ctacgccgcc cagcccttcc tgctgcggaa cggcgccaac gagggctttc acgaggccgt   2580
gggcgagatc atgagcctga gcgccgccac ccccaagcac ctgaagagca tcggcctgct   2640
```

```
gagccccgac ttccaggagg acaacgagac cgagatcaac ttcctgctga agcaggccct   2700

gaccatcgtg ggcaccctgc ccttcaccta catgctggag aagtggcggt ggatggtgtt   2760

taagggcgag atccccaagg accagtggat gaagaagtgg tgggagatga agcgggagat   2820

cgtgggcgtg gtggagcccg tgccccacga cgagacctac tgcgaccccg ccagcctgtt   2880

ccacgtgagc aacgactact ccttcatccg gtactacacc cggaccctgt accagttcca   2940

gttccaggag gccctgtgcc aggccgccaa gcacgagggc cccctgcaca agtgcgacat   3000

cagcaacagc accgaggccg gacagaaact gttcaacatg ctgcggctgg gcaagagcga   3060

gccctggacc ctggccctgg agaatgtggt gggcgccaag aacatgaatg tgcgccccct   3120

gctgaactac ttcgagcccc tgttcacctg gctgaaggac cagaacaaga acagcttcgt   3180

gggctggagc accgactgga gcccctacgc cgaccagagc atcaaagtgc ggatcagcct   3240

gaagagcgcc ctgggcgaca aggcctacga gtggaacgac aacgagatgt acctgttccg   3300

gagcagcgtg gcctatgcca tgcggcagta cttcctgaaa gtgaagaacc agatgatcct   3360

gttcggcgag gaggacgtga gagtggccaa cctgaagccc cggatcagct tcaacttctt   3420

cgtgaccgcc cccaagaacg tgagcgacat catccccccgg accgaagtgg agaaggccat   3480

ccggatgagc cggagccgga tcaacgacgc cttccggctg aacgacaact ccctggagtt   3540

cctgggcatc cagcccaccc tgggccctcc caaccagccc cccgtgagca tctggctgat   3600

cgtgtttggc gtggtgatgg gcgtgatcgt ggtgggaatc gtgatcctga tcttcaccgg   3660

catccgggac cggaagaaga agaacaaggc ccggagcggc gagaacccct acgccagcat   3720

cgatatcagc aagggcgaga acaaccccgg cttccagaac accgacgacg tgcagaccag   3780

cttctgataa tctagaacga gctcgaattc gaagcttctg cagacgcgtc gacgtcatat   3840

ggatccgata tcgccgtggc ggccgcaccc agcgtgttca tcttcccccc ctccgacgag   3900

cagctgaaga gcggcaccgc cagcgtggtg tgcctgctga acaacttcta cccccgggag   3960

gccaaggtgc agtggaaggt ggacaacgcc ctgcagagcg gcaacagcca ggagagcgtg   4020

accgagcagg acagcaagga ctccacctac agcctgagca gcaccctcac cctgagcaag   4080

gccgactacg agaagcacaa ggtgtacgcc tgcgaggtga cccaccaggg cctgagcagc   4140

cccgtgacca agagcttcaa ccggggcgag tgttaataga cttaagttta aaccgctgat   4200

cagcctcgac tgtgccttct agttgccagc catctgttgt ttgcccctcc cccgtgcctt   4260

ccttgaccct ggaaggtgcc actcccactg tcctttccta ataaaatgag gaaattgcat   4320

cgcattgtct gagtaggtgt cattctattc tggggggtgg ggtggggcag gacagcaagg   4380

gggaggattg ggaagacaat agcaggcatg ctggggatgc ggtgggctct atggcttctg   4440

aggcggaaag aaccagctgg ggctctaggg ggtatcccca cgcgccctgt agcggcgcat   4500

taagcgcggc gggtgtggtg gttacgcgca gcgtgaccgc tacacttgcc agcgccctag   4560

cgcccgctcc tttcgctttc ttcccttcct ttctcgccac gttcgccggc tttccccgtc   4620

aagctctaaa tcgggggctc cctttagggt tccgatttag tgctttacgg cacctcgacc   4680

ccaaaaaact tgattagggt gatggttcac gtagtgggcc atcgccctga tagacggttt   4740

ttcgcccttt gacgttggag tccacgttct ttaatagtgg actcttgttc caaactggaa   4800

caacactcaa ccctatctcg gtctattctt ttgatttata agggattttg gccatttcgg   4860

cctattggtt aaaaaatgag ctgatttaac aaaaatttaa cgcgaattaa ttctgtggaa   4920

tgtgtgtcag ttagggtgtg gaaagtcccc aggctcccca gcaggcagaa gtatgcaaag   4980

catgcatctc aattagtcag caaccaggtg tggaaagtcc ccaggctccc cagcaggcag   5040
```

```
aagtatgcaa agcatgcatc tcaattagtc agcaaccata gtcccgcccc taactccgcc   5100
catcccgccc ctaactccgc ccagttccgc ccattctccg ccccatggct gactaatttt   5160
ttttatttat gcagaggccg aggccgcctc tgcctctgag ctattccaga agtagtgagg   5220
aggctttttt ggaggcctag gcttttgcaa aaagctcccg ggagcttgta tatccatttt   5280
cggatctgat cagcacgtga tgaaaaagcc tgaactcacc gcgacgtctg tcgagaagtt   5340
tctgatcgaa aagttcgaca gcgtctccga cctgatgcag ctctcggagg gcgaagaatc   5400
tcgtgctttc agcttcgatg taggagggcg tggatatgtc ctgcgggtaa atagctgcgc   5460
cgatggtttc tacaaagatc gttatgttta tcggcacttt gcatcggccg cgctcccgat   5520
tccggaagtg cttgacattg gggaattcag cgagagcctg acctattgca tctcccgccg   5580
tgcacagggt gtcacgttgc aagacctgcc tgaaaccgaa ctgcccgctg ttctgcagcc   5640
ggtcgcggag gccatggatg cgatcgctgc ggccgatctt agccagacga gcgggttcgg   5700
cccattcgga ccacaaggaa tcggtcaata cactacatgg cgtgatttca tatgcgcgat   5760
tgctgatccc catgtgtatc actggcaaac tgtgatggac gacaccgtca gtgcgtccgt   5820
cgcgcaggct ctcgatgagc tgatgctttg ggccgaggac tgccccgaag tccggcacct   5880
cgtgcacgcg gatttcggct ccaacaatgt cctgacggac aatggccgca taacagcggt   5940
cattgactgg agcgaggcga tgttcgggga ttcccaatac gaggtcgcca acatcttctt   6000
ctggaggccg tggttggctt gtatggagca gcagacgcgc tacttcgagc ggaggcatcc   6060
ggagcttgca ggatcgccgc ggctccgggc gtatatgctc cgcattggtc ttgaccaact   6120
ctatcagagc ttggttgacg gcaatttcga tgatgcagct tgggcgcagg gtcgatgcga   6180
cgcaatcgtc cgatccggag ccgggactgt cgggcgtaca caaatcgccc gcagaagcgc   6240
ggccgtctgg accgatggct gtgtagaagt actcgccgat agtggaaacc gacgccccag   6300
cactcgtccg agggcaaagg aatagcacgt gctacgagat ttcgattcca ccgccgcctt   6360
ctatgaaagg ttgggcttcg gaatcgtttt ccgggacgcc ggctggatga tcctccagcg   6420
cggggatctc atgctggagt tcttcgccca ccccaacttg tttattgcag cttataatgg   6480
ttacaaataa agcaatagca tcacaaattt cacaaataaa gcattttttt cactgcattc   6540
tagttgtggt ttgtccaaac tcatcaatgt atcttatcat gtctgtatac cgtcgacctc   6600
tagctagagc ttggcgtaat catggtcata gctgtttcct gtgtgaaatt gttatccgct   6660
cacaattcca cacaacatac gagccggaag cataaagtgt aaagcctggg gtgcctaatg   6720
agtgagctaa ctcacattaa ttgcgttgcg ctcactgccc gctttccagt cgggaaacct   6780
gtcgtgccag ctgcattaat gaatcggcca acgcgcgggg agaggcggtt tgcgtattgg   6840
gcgctcttcc gcttcctcgc tcactgactc gctgcgctcg gtcgttcggc tgcggcgagc   6900
ggtatcagct cactcaaagg cggtaatacg gttatccaca gaatcagggg ataacgcagg   6960
aaagaacatg tgagcaaaag gccagcaaaa ggccaggaac cgtaaaaagg ccgcgttgct   7020
ggcgtttttc cataggctcc gcccccctga cgagcatcac aaaaatcgac gctcaagtca   7080
gaggtggcga aacccgacag gactataaag ataccaggcg tttccccctg gaagctccct   7140
cgtgcgctct cctgttccga ccctgccgct taccggatac ctgtccgcct ttctcccttc   7200
gggaagcgtg gcgctttctc atagctcacg ctgtaggtat ctcagttcgg tgtaggtcgt   7260
tcgctccaag ctgggctgtg tgcacgaacc ccccgttcag cccgaccgct gcgccttatc   7320
cggtaactat cgtcttgagt ccaacccggt aagacacgac ttatcgccac tggcagcagc   7380
```

```
cactggtaac aggattagca gagcgaggta tgtaggcggt gctacagagt tcttgaagtg   7440
gtggcctaac tacggctaca ctagaagaac agtatttggt atctgcgctc tgctgaagcc   7500
agttaccttc ggaaaaagag ttggtagctc ttgatccggc aaacaaacca ccgctggtag   7560
cggttttttt gtttgcaagc agcagattac gcgcagaaaa aaaggatctc aagaagatcc   7620
tttgatcttt tctacggggt ctgacgctca gtggaacgaa aactcacgtt aagggatttt   7680
ggtcatgaga ttatcaaaaa ggatcttcac ctagatcctt ttaaattaaa aatgaagttt   7740
taaatcaatc taaagtatat atgagtaaac ttggtctgac agttaccaat gcttaatcag   7800
tgaggcacct atctcagcga tctgtctatt tcgttcatcc atagttgcct gactccccgt   7860
cgtgtagata actacgatac gggagggctt accatctggc cccagtgctg caatgatacc   7920
gcgagaccca cgctcaccgg ctccagattt atcagcaata aaccagccag ccggaagggc   7980
cgagcgcaga agtggtcctg caactttatc cgcctccatc cagtctatta attgttgccg   8040
ggaagctaga gtaagtagtt cgccagttaa tagtttgcgc aacgttgttg ccattgctac   8100
aggcatcgtg gtgtcacgct cgtcgtttgg tatggcttca ttcagctccg gttcccaacg   8160
atcaaggcga gttacatgat cccccatgtt gtgcaaaaaa gcggttagct ccttcggtcc   8220
tccgatcgtt gtcagaagta agttggccgc agtgttatca ctcatggtta tggcagcact   8280
gcataattct cttactgtca tgccatccgt aagatgcttt tctgtgactg gtgagtactc   8340
aaccaagtca ttctgagaat agtgtatgcg gcgaccgagt tgctcttgcc cggcgtcaat   8400
acgggataat accgcgccac atagcagaac tttaaaagtg ctcatcattg gaaaacgttc   8460
ttcggggcga aaactctcaa ggatcttacc gctgttgaga tccagttcga tgtaacccac   8520
tcgtgcaccc aactgatctt cagcatcttt tactttcacc agcgtttctg ggtgagcaaa   8580
aacaggaagg caaaatgccg caaaaaaggg aataagggcg acacggaaat gttgaatact   8640
catactcttc ctttttcaat attattgaag catttatcag ggttattgtc tcatgagcgg   8700
atacatattt gaatgtattt agaaaaataa acaaataggg gttccgcgca catttccccg   8760
aaaagtgcca cctgacg                                                  8777
```

<210> SEQ ID NO 190
<211> LENGTH: 8792
<212> TYPE: DNA
<213> ORGANISM: Artificial
<220> FEATURE:
<223> OTHER INFORMATION: Vector pIg-C910-Clambda

<400> SEQUENCE: 190

```
tcgacggatc gggagatctc ccgatcccct atggtgcact ctcagtacaa tctgctctga     60
tgccgcatag ttaagccagt atctgctccc tgcttgtgtg ttggaggtcg ctgagtagtg    120
cgcgagcaaa atttaagcta caacaaggca aggcttgacc gacaattgtt aattaacatg    180
aagaatctgc ttagggttag gcgttttgcg ctgcttcgct aggtggtcaa tattggccat    240
tagccatatt attcattggt tatatagcat aaatcaatat tggctattgg ccattgcata    300
cgttgtatcc atatcataat atgtacattt atattggctc atgtccaaca ttaccgccat    360
gttgacattg attattgact agttattaat agtaatcaat tacggggtca ttagttcata    420
gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca agtacgcccc ctattgacgt caatgacggt aaatggcccg    660
```

```
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggttctccgc tcagctgctg ggccttctgg tgctgtggat   1320
tcccggcgtc tcgagatcta tcgatgcatg ccatggtacc aagcttgcca ccatgagcag   1380
cagctcttgg ctgctgctga gcctggtggc cgtgacagcc gcccagagca ccatcgagga   1440
gcaggccaag accttcctgg acaagttcaa ccacgaggcc gaggacctgt tctaccagag   1500
cagcctggcc agctggaact acaacaccaa catcaccgag gagaacgtgc agaacatgaa   1560
caacgccggc gacaagtgga gcgccttcct gaaggagcag agcacactgg cccagatgta   1620
cccccctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caaccccgac aacccccagg agtgcctgct   1800
gctggagccc ggcctgaacg agatcatggc caacagcctg gactacaacg agcggctgtg   1860
ggcctgggag agctggcgga gcgaagtggg caagcagctg cggcccctgt acgaggagta   1920
cgtggtgctg aagaacgaga tggccagggc caaccactac gaggactacg gcgactactg   1980
gagaggcgac tacgaagtga acggcgtgga cggctacgac tacagcagag gccagctgat   2040
cgaggacgtg gagcacacct tcgaggagat caagcctctg tacgagcacc tgcacgccta   2100
cgtgcgggcc aagctgatga acgcctaccc cagctacatc agccccatcg gctgcctgcc   2160
cgcccacctg ctgggcgaca tgtggggccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc ttttgggaga acagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct tcctgctgcg gaacggcgcc aacgagggct ttcacgaggc   2580
cgtgggcgag atcatgagcc tgagcgccgc cacccccaag cacctgaaga gcatcggcct   2640
gctgagcccc gacttccagg aggacaacga gaccgagatc aacttcctgc tgaagcaggc   2700
cctgaccatc gtgggcaccc tgcccttcac ctacatgctg gagaagtggc ggtggatggt   2760
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccccctgc acaagtgcga   3000
```

```
catcagcaac agcaccgagg ccggacagaa actgttcaac atgctgcggc tgggcaagag   3060
cgagccctgg accctggccc tggagaatgt ggtgggcgcc aagaacatga atgtgcgccc   3120
cctgctgaac tacttcgagc ccctgttcac ctggctgaag gaccagaaca agaacagctt   3180
cgtgggctgg agcaccgact ggagcccta cgccgaccag agcatcaaag tgcggatcag    3240
cctgaagagc gccctgggcg acaaggccta cgagtggaac gacaacgaga tgtacctgtt   3300
ccggagcagc gtggcctatg ccatgcggca gtacttcctg aaagtgaaga accagatgat   3360
cctgttcggc gaggaggacg tgagagtggc caacctgaag ccccggatca gcttcaactt   3420
cttcgtgacc gcccccaaga acgtgagcga catcatcccc cggaccgaag tggagaaggc   3480
catccggatg agccggagcc ggatcaacga cgccttccgg ctgaacgaca actccctgga   3540
gttcctgggc atccagccca ccctgggccc tcccaaccag ccccccgtga gcatctggct   3600
gatcgtgttt ggcgtggtga tgggcgtgat cgtggtggga atcgtgatcc tgatcttcac   3660
cggcatccgg gaccggaaga agaagaacaa ggcccggagc ggcgagaacc cctacgccag   3720
catcgatatc agcaagggcg agaacaaccc cggcttccag aacaccgacg acgtgcagac   3780
cagcttctga taatctagaa cgagctcgaa ttcgaagctt ctgcagacgc gtcgacgtca   3840
tatggatccg atatcgccgt ggcggccgca ggccagccca aggccgctcc cagcgtgacc   3900
ctgttccccc cctcctccga ggagctgcag gccaacaagg ccaccctggt gtgcctcatc   3960
agcgacttct accctggcgc cgtgaccgtg gcctggaagg ccgacagcag ccccgtgaag   4020
gccggcgtgg agaccaccac ccccagcaag cagagcaaca acaagtacgc cgccagcagc   4080
tacctgagcc tcacccccga gcagtggaag agccaccgga gctacagctg ccaggtgacc   4140
cacgagggca gcaccgtgga gaagaccgtg gcccccaccg agtgcagcta atagacttaa   4200
gtttaaaccg ctgatcagcc tcgactgtgc cttctagttg ccagccatct gttgtttgcc   4260
cctcccccgt gccttccttg accctggaag gtgccactcc cactgtcctt tcctaataaa   4320
atgaggaaat tgcatcgcat tgtctgagta ggtgtcattc tattctgggg ggtggggtgg   4380
ggcaggacag caagggggag gattgggaag acaatagcag gcatgctggg gatgcggtgg   4440
gctctatggc ttctgaggcg gaaagaacca gctggggctc tagggggtat ccccacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
ccggctttcc ccgtcaagct ctaaatcggg ggctcccttt agggttccga tttagtgctt   4680
tacggcacct cgaccccaaa aaacttgatt agggtgatgg ttcacgtagt gggccatcgc   4740
cctgatagac ggtttttcgc cctttgacgt tggagtccac gttctttaat agtggactct   4800
tgttccaaac tggaacaaca ctcaacccta tctcggtcta ttcttttgat ttataaggga   4860
ttttggccat ttcggcctat tggttaaaaa atgagctgat ttaacaaaaa tttaacgcga   4920
attaattctg tggaatgtgt gtcagttagg gtgtggaaag tccccaggct ccccagcagg   4980
cagaagtatg caaagcatgc atctcaatta gtcagcaacc aggtgtggaa agtccccagg   5040
ctccccagca ggcagaagta tgcaaagcat gcatctcaat tagtcagcaa ccatagtccc   5100
gcccctaact ccgcccatcc cgcccctaac tccgcccagt tccgcccatt ctccgcccca   5160
tggctgacta atttttttta tttatgcaga ggccgaggcc gcctctgcct ctgagctatt   5220
ccagaagtag tgaggaggct tttttggagg cctaggcttt tgcaaaaagc tcccgggagc   5280
ttgtatatcc attttcggat ctgatcagca cgtgatgaaa aagcctgaac tcaccgcgac   5340
gtctgtcgag aagtttctga tcgaaaagtt cgacagcgtc tccgacctga tgcagctctc   5400
```

```
ggagggcgaa gaatctcgtg ctttcagctt cgatgtagga gggcgtggat atgtcctgcg   5460
ggtaaatagc tgcgccgatg gtttctacaa agatcgttat gtttatcggc actttgcatc   5520
ggccgcgctc ccgattccgg aagtgcttga cattggggaa ttcagcgaga gcctgaccta   5580
ttgcatctcc cgccgtgcac agggtgtcac gttgcaagac ctgcctgaaa ccgaactgcc   5640
cgctgttctg cagccggtcg cggaggccat ggatgcgatc gctgcggccg atcttagcca   5700
gacgagcggg ttcggcccat tcggaccgca aggaatcggt caatacacta catggcgtga   5760
tttcatatgc gcgattgctg atccccatgt gtatcactgg caaactgtga tggacgacac   5820
cgtcagtgcg tccgtcgcgc aggctctcga tgagctgatg ctttgggccg aggactgccc   5880
cgaagtccgg cacctcgtgc acgcggattt cggctccaac aatgtcctga cggacaatgg   5940
ccgcataaca gcggtcattg actggagcga ggcgatgttc ggggattccc aatacgaggt   6000
cgccaacatc ttcttctgga ggccgtggtt ggcttgtatg gagcagcaga cgcgctactt   6060
cgagcggagg catccggagc ttgcaggatc gccgcggctc cgggcgtata tgctccgcat   6120
tggtcttgac caactctatc agagcttggt tgacggcaat ttcgatgatg cagcttgggc   6180
gcagggtcga tgcgacgcaa tcgtccgatc cggagccggg actgtcgggc gtacacaaat   6240
cgcccgcaga agcgcggccg tctggaccga tggctgtgta gaagtactcg ccgatagtgg   6300
aaaccgacgc cccagcactc gtccgagggc aaaggaatag cacgtgctac gagatttcga   6360
ttccaccgcc gccttctatg aaaggttggg cttcggaatc gttttccggg acgccggctg   6420
gatgatcctc cagcgcgggg atctcatgct ggagttcttc gcccacccca acttgtttat   6480
tgcagcttat aatggttaca aataaagcaa tagcatcaca aatttcacaa ataaagcatt   6540
tttttcactg cattctagtt gtggtttgtc caaactcatc aatgtatctt atcatgtctg   6600
tataccgtcg acctctagct agagcttggc gtaatcatgg tcatagctgt ttcctgtgtg   6660
aaattgttat ccgctcacaa ttccacacaa catacgagcc ggaagcataa agtgtaaagc   6720
ctggggtgcc taatgagtga gctaactcac attaattgcg ttgcgctcac tgcccgcttt   6780
ccagtcggga aacctgtcgt gccagctgca ttaatgaatc ggccaacgcg cggggagagg   6840
cggtttgcgt attgggcgct cttccgcttc ctcgctcact gactcgctgc gctcggtcgt   6900
tcggctgcgg cgagcggtat cagctcactc aaaggcggta atacggttat ccacagaatc   6960
aggggataac gcaggaaaga acatgtgagc aaaaggccag caaaaggcca ggaaccgtaa   7020
aaaggccgcg ttgctggcgt ttttccatag gctccgcccc cctgacgagc atcacaaaaa   7080
tcgacgctca agtcagaggt ggcgaaaccc gacaggacta taaagatacc aggcgtttcc   7140
ccctggaagc tccctcgtgc gctctcctgt tccgaccctg ccgcttaccg gatacctgtc   7200
cgcctttctc ccttcgggaa gcgtggcgct ttctcatagc tcacgctgta ggtatctcag   7260
ttcggtgtag gtcgttcgct ccaagctggg ctgtgtgcac gaaccccccg ttcagcccga   7320
ccgctgcgcc ttatccggta actatcgtct tgagtccaac ccggtaagac acgacttatc   7380
gccactggca gcagccactg gtaacaggat tagcagagcg aggtatgtag gcggtgctac   7440
agagttcttg aagtggtggc ctaactacgg ctacactaga agaacagtat ttggtatctg   7500
cgctctgctg aagccagtta ccttcggaaa aagagttggt agctcttgat ccggcaaaca   7560
aaccaccgct ggtagcggtt tttttgtttg caagcagcag attacgcgca gaaaaaaagg   7620
atctcaagaa gatcctttga tcttttctac ggggtctgac gctcagtgga acgaaaactc   7680
acgttaaggg attttggtca tgagattatc aaaaaggatc ttcacctaga tccttttaaa   7740
```

-continued

```
ttaaaaatga agttttaaat caatctaaag tatatatgag taaacttggt ctgacagtta   7800

ccaatgctta atcagtgagg cacctatctc agcgatctgt ctatttcgtt catccatagt   7860

tgcctgactc cccgtcgtgt agataactac gatacgggag ggcttaccat ctggccccag   7920

tgctgcaatg ataccgcgag acccacgctc accggctcca gatttatcag caataaacca   7980

gccagccgga agggccgagc gcagaagtgg tcctgcaact ttatccgcct ccatccagtc   8040

tattaattgt tgccgggaag ctagagtaag tagttcgcca gttaatagtt tgcgcaacgt   8100

tgttgccatt gctacaggca tcgtggtgtc acgctcgtcg tttggtatgg cttcattcag   8160

ctccggttcc caacgatcaa ggcgagttac atgatccccc atgttgtgca aaaaagcggt   8220

tagctccttc ggtcctccga tcgttgtcag aagtaagttg gccgcagtgt tatcactcat   8280

ggttatggca gcactgcata attctcttac tgtcatgcca tccgtaagat gcttttctgt   8340

gactggtgag tactcaacca agtcattctg agaatagtgt atgcggcgac cgagttgctc   8400

ttgcccggcg tcaatacggg ataataccgc gccacatagc agaactttaa aagtgctcat   8460

cattggaaaa cgttcttcgg ggcgaaaact ctcaaggatc ttaccgctgt tgagatccag   8520

ttcgatgtaa cccactcgtg cacccaactg atcttcagca tcttttactt tcaccagcgt   8580

ttctgggtga gcaaaaacag gaaggcaaaa tgccgcaaaa aagggaataa gggcgacacg   8640

gaaatgttga atactcatac tcttcctttt tcaatattat tgaagcattt atcagggtta   8700

ttgtctcatg agcggataca tatttgaatg tatttagaaa aataaacaaa taggggttcc   8760

gcgcacattt ccccgaaaag tgccacctga cg                                 8792
```

<210> SEQ ID NO 191
<211> LENGTH: 23
<212> TYPE: DNA
<213> ORGANISM: Artificial
<220> FEATURE:
<223> OTHER INFORMATION: OK1 (HuVK1B)

<400> SEQUENCE: 191

```
gacatccagw tgacccagtc tcc                                             23
```

<210> SEQ ID NO 192
<211> LENGTH: 23
<212> TYPE: DNA
<213> ORGANISM: Artificial
<220> FEATURE:
<223> OTHER INFORMATION: OK2 (HuVK2)

<400> SEQUENCE: 192

```
gatgttgtga tgactcagtc tcc                                             23
```

<210> SEQ ID NO 193
<211> LENGTH: 23
<212> TYPE: DNA
<213> ORGANISM: Artificial
<220> FEATURE:
<223> OTHER INFORMATION: OK3 (HuVK2B2)

<400> SEQUENCE: 193

```
gatattgtga tgacccagac tcc                                             23
```

<210> SEQ ID NO 194
<211> LENGTH: 23
<212> TYPE: DNA
<213> ORGANISM: Artificial
<220> FEATURE:
<223> OTHER INFORMATION: OK4 (HuVK3B)

<400> SEQUENCE: 194
gaaattgtgw tgacrcagtc tcc 23

<210> SEQ ID NO 195
<211> LENGTH: 23
<212> TYPE: DNA
<213> ORGANISM: Artificial
<220> FEATURE:
<223> OTHER INFORMATION: OK5 (HuVK5)

<400> SEQUENCE: 195
gaaacgacac tcacgcagtc tcc 23

<210> SEQ ID NO 196
<211> LENGTH: 23
<212> TYPE: DNA
<213> ORGANISM: Artificial
<220> FEATURE:
<223> OTHER INFORMATION: OK6 (HuVK6)

<400> SEQUENCE: 196
gaaattgtgc tgactcagtc tcc 23

<210> SEQ ID NO 197
<211> LENGTH: 24
<212> TYPE: DNA
<213> ORGANISM: Artificial
<220> FEATURE:
<223> OTHER INFORMATION: OCK (HuCK)

<400> SEQUENCE: 197
acactctccc ctgttgaagc tctt 24

<210> SEQ ID NO 198
<211> LENGTH: 23
<212> TYPE: DNA
<213> ORGANISM: Artificial
<220> FEATURE:
<223> OTHER INFORMATION: OL1 (HuVL1A)*

<400> SEQUENCE: 198
cagtctgtgc tgactcagcc acc 23

<210> SEQ ID NO 199
<211> LENGTH: 23
<212> TYPE: DNA
<213> ORGANISM: Artificial
<220> FEATURE:
<223> OTHER INFORMATION: OL1 (HuVL1B)*

<400> SEQUENCE: 199
cagtctgtgy tgacgcagcc gcc 23

<210> SEQ ID NO 200
<211> LENGTH: 23
<212> TYPE: DNA
<213> ORGANISM: Artificial
<220> FEATURE:
<223> OTHER INFORMATION: OL1 (HuVL1C)*

<400> SEQUENCE: 200
cagtctgtcg tgacgcagcc gcc 23

<210> SEQ ID NO 201

<211> LENGTH: 20
<212> TYPE: DNA
<213> ORGANISM: Artificial
<220> FEATURE:
<223> OTHER INFORMATION: OL2 (HuVL2B)

<400> SEQUENCE: 201
cagtctgccc tgactcagcc 20

<210> SEQ ID NO 202
<211> LENGTH: 23
<212> TYPE: DNA
<213> ORGANISM: Artificial
<220> FEATURE:
<223> OTHER INFORMATION: OL3 (HuVL3A)

<400> SEQUENCE: 202
tcctatgwgc tgactcagcc acc 23

<210> SEQ ID NO 203
<211> LENGTH: 23
<212> TYPE: DNA
<213> ORGANISM: Artificial
<220> FEATURE:
<223> OTHER INFORMATION: OL4 (HuVL3B)

<400> SEQUENCE: 203
tcttctgagc tgactcagga ccc 23

<210> SEQ ID NO 204
<211> LENGTH: 20
<212> TYPE: DNA
<213> ORGANISM: Artificial
<220> FEATURE:
<223> OTHER INFORMATION: OL5 (HuVL4B)

<400> SEQUENCE: 204
cagcytgtgc tgactcaatc 20

<210> SEQ ID NO 205
<211> LENGTH: 23
<212> TYPE: DNA
<213> ORGANISM: Artificial
<220> FEATURE:
<223> OTHER INFORMATION: OL6 (HuVL5)

<400> SEQUENCE: 205
caggctgtgc tgactcagcc gtc 23

<210> SEQ ID NO 206
<211> LENGTH: 23
<212> TYPE: DNA
<213> ORGANISM: Artificial
<220> FEATURE:
<223> OTHER INFORMATION: OL7 (HuVL6)

<400> SEQUENCE: 206
aattttatgc tgactcagcc cca 23

<210> SEQ ID NO 207
<211> LENGTH: 23
<212> TYPE: DNA
<213> ORGANISM: Artificial
<220> FEATURE:
<223> OTHER INFORMATION: OL8 (HuVL7/8)

<400> SEQUENCE: 207
cwgcctgtgc tgactcagcc mcc 23

<210> SEQ ID NO 208
<211> LENGTH: 23
<212> TYPE: DNA
<213> ORGANISM: Artificial
<220> FEATURE:
<223> OTHER INFORMATION: OL9 (HuVL9)#

<400> SEQUENCE: 208
cwgcctgtgc tgactcagcc mcc 23

<210> SEQ ID NO 209
<211> LENGTH: 18
<212> TYPE: DNA
<213> ORGANISM: Artificial
<220> FEATURE:
<223> OTHER INFORMATION: OL9 (HuVL10)#

<400> SEQUENCE: 209
caggcagggc tgactcag 18

<210> SEQ ID NO 210
<211> LENGTH: 23
<212> TYPE: DNA
<213> ORGANISM: Artificial
<220> FEATURE:
<223> OTHER INFORMATION: OCL (HuCL2)X

<400> SEQUENCE: 210
tgaacattct gtaggggcca ctg 23

<210> SEQ ID NO 211
<211> LENGTH: 23
<212> TYPE: DNA
<213> ORGANISM: Artificial
<220> FEATURE:
<223> OTHER INFORMATION: OCL (HuCL7)X

<400> SEQUENCE: 211
agagcattct gcaggggcca ctg 23

<210> SEQ ID NO 212
<211> LENGTH: 23
<212> TYPE: DNA
<213> ORGANISM: Artificial
<220> FEATURE:
<223> OTHER INFORMATION: OH1(HuVH1B7A)+

<400> SEQUENCE: 212
cagrtgcagc tggtgcartc tgg 23

<210> SEQ ID NO 213
<211> LENGTH: 23
<212> TYPE: DNA
<213> ORGANISM: Artificial
<220> FEATURE:
<223> OTHER INFORMATION: OH1 (HuVH1C)+

<400> SEQUENCE: 213
saggtccagc tggtrcagtc tgg 23

<210> SEQ ID NO 214
<211> LENGTH: 23
<212> TYPE: DNA

<213> ORGANISM: Artificial
<220> FEATURE:
<223> OTHER INFORMATION: OH2 (HuVH2B)

<400> SEQUENCE: 214
cagrtcacct tgaaggagtc tgg 23

<210> SEQ ID NO 215
<211> LENGTH: 18
<212> TYPE: DNA
<213> ORGANISM: Artificial
<220> FEATURE:
<223> OTHER INFORMATION: OH3 (HuVH3A)

<400> SEQUENCE: 215
gaggtgcagc tggtggag 18

<210> SEQ ID NO 216
<211> LENGTH: 23
<212> TYPE: DNA
<213> ORGANISM: Artificial
<220> FEATURE:
<223> OTHER INFORMATION: OH4 (HuVH3C)

<400> SEQUENCE: 216
gaggtgcagc tggtggagwc ygg 23

<210> SEQ ID NO 217
<211> LENGTH: 23
<212> TYPE: DNA
<213> ORGANISM: Artificial
<220> FEATURE:
<223> OTHER INFORMATION: OH5 (HuVH4B)

<400> SEQUENCE: 217
caggtgcagc tacagcagtg ggg 23

<210> SEQ ID NO 218
<211> LENGTH: 23
<212> TYPE: DNA
<213> ORGANISM: Artificial
<220> FEATURE:
<223> OTHER INFORMATION: OH6 (HuVH4C)

<400> SEQUENCE: 218
cagstgcagc tgcaggagtc sgg 23

<210> SEQ ID NO 219
<211> LENGTH: 23
<212> TYPE: DNA
<213> ORGANISM: Artificial
<220> FEATURE:
<223> OTHER INFORMATION: OH7 (HuVH6A)

<400> SEQUENCE: 219
caggtacagc tgcagcagtc agg 23

<210> SEQ ID NO 220
<211> LENGTH: 24
<212> TYPE: DNA
<213> ORGANISM: Artificial
<220> FEATURE:
<223> OTHER INFORMATION: OCM (HuCIgM)

<400> SEQUENCE: 220
tggaagaggc acgttctttt cttt 24

<210> SEQ ID NO 221
<211> LENGTH: 41
<212> TYPE: DNA
<213> ORGANISM: Artificial
<220> FEATURE:
<223> OTHER INFORMATION: OK1S (HuVK1B-SAL)

<400> SEQUENCE: 221
tgagcacaca ggtcgacgga catccagwtg acccagtctc c 41

<210> SEQ ID NO 222
<211> LENGTH: 41
<212> TYPE: DNA
<213> ORGANISM: Artificial
<220> FEATURE:
<223> OTHER INFORMATION: OK2S (HuVK2-SAL)

<400> SEQUENCE: 222
tgagcacaca ggtcgacgga tgttgtgatg actcagtctc c 41

<210> SEQ ID NO 223
<211> LENGTH: 41
<212> TYPE: DNA
<213> ORGANISM: Artificial
<220> FEATURE:
<223> OTHER INFORMATION: OK3S (HuVK2B2-SAL)

<400> SEQUENCE: 223
tgagcacaca ggtcgacgga tattgtgatg acccagactc c 41

<210> SEQ ID NO 224
<211> LENGTH: 41
<212> TYPE: DNA
<213> ORGANISM: Artificial
<220> FEATURE:
<223> OTHER INFORMATION: OK4S (HuVK3B-SAL)

<400> SEQUENCE: 224
tgagcacaca ggtcgacgga aattgtgwtg acrcagtctc c 41

<210> SEQ ID NO 225
<211> LENGTH: 41
<212> TYPE: DNA
<213> ORGANISM: Artificial
<220> FEATURE:
<223> OTHER INFORMATION: OK5S (HuVK5-SAL)

<400> SEQUENCE: 225
tgagcacaca ggtcgacgga aacgacactc acgcagtctc c 41

<210> SEQ ID NO 226
<211> LENGTH: 41
<212> TYPE: DNA
<213> ORGANISM: Artificial
<220> FEATURE:
<223> OTHER INFORMATION: OK6S (HuVK6-SAL)

<400> SEQUENCE: 226
tgagcacaca ggtcgacgga aattgtgctg actcagtctc c 41

<210> SEQ ID NO 227
<211> LENGTH: 48
<212> TYPE: DNA
<213> ORGANISM: Artificial
<220> FEATURE:

<223> OTHER INFORMATION: OJK1 (HuJK1-NOT)

<400> SEQUENCE: 227
gagtcattct cgacttgcgg ccgcacgttt gatttccacc ttggtccc 48

<210> SEQ ID NO 228
<211> LENGTH: 48
<212> TYPE: DNA
<213> ORGANISM: Artificial
<220> FEATURE:
<223> OTHER INFORMATION: OJK2 (HuJK2-NOT)

<400> SEQUENCE: 228
gagtcattct cgacttgcgg ccgcacgttt gatctccagc ttggtccc 48

<210> SEQ ID NO 229
<211> LENGTH: 48
<212> TYPE: DNA
<213> ORGANISM: Artificial
<220> FEATURE:
<223> OTHER INFORMATION: OJK3 (HuJK3-NOT)

<400> SEQUENCE: 229
gagtcattct cgacttgcgg ccgcacgttt gatatccact ttggtccc 48

<210> SEQ ID NO 230
<211> LENGTH: 48
<212> TYPE: DNA
<213> ORGANISM: Artificial
<220> FEATURE:
<223> OTHER INFORMATION: OJK4 (HuJK4-NOT)

<400> SEQUENCE: 230
gagtcattct cgacttgcgg ccgcacgttt gatctccacc ttggtccc 48

<210> SEQ ID NO 231
<211> LENGTH: 48
<212> TYPE: DNA
<213> ORGANISM: Artificial
<220> FEATURE:
<223> OTHER INFORMATION: OJK5 (HuJK5-NOT)

<400> SEQUENCE: 231
gagtcattct cgacttgcgg ccgcacgttt aatctccagt cgtgtccc 48

<210> SEQ ID NO 232
<211> LENGTH: 41
<212> TYPE: DNA
<213> ORGANISM: Artificial
<220> FEATURE:
<223> OTHER INFORMATION: OL1S (HuVL1A-SAL)*

<400> SEQUENCE: 232
tgagcacaca ggtcgacgca gtctgtgctg actcagccac c 41

<210> SEQ ID NO 233
<211> LENGTH: 41
<212> TYPE: DNA
<213> ORGANISM: Artificial
<220> FEATURE:
<223> OTHER INFORMATION: OL1S (HuVL1B-SAL)*

<400> SEQUENCE: 233
tgagcacaca ggtcgacgca gtctgtgytg acgcagccgc c 41

<210> SEQ ID NO 234
<211> LENGTH: 41
<212> TYPE: DNA
<213> ORGANISM: Artificial
<220> FEATURE:
<223> OTHER INFORMATION: OL1S (HuVL1C-SAL)*

<400> SEQUENCE: 234
tgagcacaca ggtcgacgca gtctgtcgtg acgcagccgc c 41

<210> SEQ ID NO 235
<211> LENGTH: 38
<212> TYPE: DNA
<213> ORGANISM: Artificial
<220> FEATURE:
<223> OTHER INFORMATION: OL2S (HuVL2B-SAL)

<400> SEQUENCE: 235
tgagcacaca ggtcgacgca gtctgccctg actcagcc 38

<210> SEQ ID NO 236
<211> LENGTH: 41
<212> TYPE: DNA
<213> ORGANISM: Artificial
<220> FEATURE:
<223> OTHER INFORMATION: OL3S (HuVL3A-SAL)

<400> SEQUENCE: 236
tgagcacaca ggtcgacgtc ctatgwgctg actcagccac c 41

<210> SEQ ID NO 237
<211> LENGTH: 41
<212> TYPE: DNA
<213> ORGANISM: Artificial
<220> FEATURE:
<223> OTHER INFORMATION: OL4S (HuVL3B-SAL)

<400> SEQUENCE: 237
tgagcacaca ggtcgacgtc ttctgagctg actcaggacc c 41

<210> SEQ ID NO 238
<211> LENGTH: 38
<212> TYPE: DNA
<213> ORGANISM: Artificial
<220> FEATURE:
<223> OTHER INFORMATION: OL5S (HuVL4B-SAL)

<400> SEQUENCE: 238
tgagcacaca ggtcgacgca gcytgtgctg actcaatc 38

<210> SEQ ID NO 239
<211> LENGTH: 41
<212> TYPE: DNA
<213> ORGANISM: Artificial
<220> FEATURE:
<223> OTHER INFORMATION: OL6S (HuVL5-SAL)

<400> SEQUENCE: 239
tgagcacaca ggtcgacgca ggctgtgctg actcagccgt c 41

<210> SEQ ID NO 240
<211> LENGTH: 41
<212> TYPE: DNA
<213> ORGANISM: Artificial
<220> FEATURE:
<223> OTHER INFORMATION: OL7S (HuVL6-SAL)

<400> SEQUENCE: 240
tgagcacaca ggtcgacgaa ttttatgctg actcagcccc a 41

<210> SEQ ID NO 241
<211> LENGTH: 41
<212> TYPE: DNA
<213> ORGANISM: Artificial
<220> FEATURE:
<223> OTHER INFORMATION: OL8S (HuVL7/8-SAL)

<400> SEQUENCE: 241
tgagcacaca ggtcgacgca grctgtggtg acycaggagc c 41

<210> SEQ ID NO 242
<211> LENGTH: 41
<212> TYPE: DNA
<213> ORGANISM: Artificial
<220> FEATURE:
<223> OTHER INFORMATION: OL9S (HuVL9-SAL)#

<400> SEQUENCE: 242
tgagcacaca ggtcgacgcw gcctgtgctg actcagccmc c 41

<210> SEQ ID NO 243
<211> LENGTH: 36
<212> TYPE: DNA
<213> ORGANISM: Artificial
<220> FEATURE:
<223> OTHER INFORMATION: OL9S (HuVL10-SAL)#

<400> SEQUENCE: 243
tgagcacaca ggtcgacgca ggcagggctg actcag 36

<210> SEQ ID NO 244
<211> LENGTH: 48
<212> TYPE: DNA
<213> ORGANISM: Artificial
<220> FEATURE:
<223> OTHER INFORMATION: OJL1 (HuJL1-NOT)

<400> SEQUENCE: 244
gagtcattct cgacttgcgg ccgcacctag gacggtgacc ttggtccc 48

<210> SEQ ID NO 245
<211> LENGTH: 48
<212> TYPE: DNA
<213> ORGANISM: Artificial
<220> FEATURE:
<223> OTHER INFORMATION: OJL2 (HuJL2/3-NOT)

<400> SEQUENCE: 245
gagtcattct cgacttgcgg ccgcacctag gacggtcagc ttggtccc 48

<210> SEQ ID NO 246
<211> LENGTH: 48
<212> TYPE: DNA
<213> ORGANISM: Artificial
<220> FEATURE:
<223> OTHER INFORMATION: OJL3 (HuJL7-NOT)

<400> SEQUENCE: 246
gagtcattct cgacttgcgg ccgcaccgag gacggtcagc tgggtgcc 48

<210> SEQ ID NO 247
<211> LENGTH: 56

<212> TYPE: DNA
<213> ORGANISM: Artificial
<220> FEATURE:
<223> OTHER INFORMATION: OH1S (HuVH1B-SFI)+

<400> SEQUENCE: 247
gtcctcgcaa ctgcggccca gccggccatg gcccagrtgc agctggtgca rtctgg 56

<210> SEQ ID NO 248
<211> LENGTH: 56
<212> TYPE: DNA
<213> ORGANISM: Artificial
<220> FEATURE:
<223> OTHER INFORMATION: OH1S (HuVH1C-SFI)+

<400> SEQUENCE: 248
gtcctcgcaa ctgcggccca gccggccatg gccsaggtcc agctggtrca gtctgg 56

<210> SEQ ID NO 249
<211> LENGTH: 56
<212> TYPE: DNA
<213> ORGANISM: Artificial
<220> FEATURE:
<223> OTHER INFORMATION: OH2S (HuVH2B-SFI)

<400> SEQUENCE: 249
gtcctcgcaa ctgcggccca gccggccatg gcccagrtca ccttgaagga gtctgg 56

<210> SEQ ID NO 250
<211> LENGTH: 51
<212> TYPE: DNA
<213> ORGANISM: Artificial
<220> FEATURE:
<223> OTHER INFORMATION: OH3S (HuVH3A-SFI)

<400> SEQUENCE: 250
gtcctcgcaa ctgcggccca gccggccatg gccgaggtgc agctggtgga g 51

<210> SEQ ID NO 251
<211> LENGTH: 56
<212> TYPE: DNA
<213> ORGANISM: Artificial
<220> FEATURE:
<223> OTHER INFORMATION: OH4S (HuVH3C-SFI)

<400> SEQUENCE: 251
gtcctcgcaa ctgcggccca gccggccatg gccgaggtgc agctggtgga gwcygg 56

<210> SEQ ID NO 252
<211> LENGTH: 56
<212> TYPE: DNA
<213> ORGANISM: Artificial
<220> FEATURE:
<223> OTHER INFORMATION: OH5S (HuVH4B-SFI)

<400> SEQUENCE: 252
gtcctcgcaa ctgcggccca gccggccatg gcccaggtgc agctacagca gtgggg 56

<210> SEQ ID NO 253
<211> LENGTH: 56
<212> TYPE: DNA
<213> ORGANISM: Artificial
<220> FEATURE:
<223> OTHER INFORMATION: OH6S (HuVH4C-SFI)

<400> SEQUENCE: 253

-continued

```
gtcctcgcaa ctgcggccca gccggccatg gcccagstgc agctgcagga gtcsgg        56


<210> SEQ ID NO 254
<211> LENGTH: 56
<212> TYPE: DNA
<213> ORGANISM: Artificial
<220> FEATURE:
<223> OTHER INFORMATION: OH7S (HuVH6A-SFI)

<400> SEQUENCE: 254

gtcctcgcaa ctgcggccca gccggccatg gcccaggtac agctgcagca gtcagg        56


<210> SEQ ID NO 255
<211> LENGTH: 36
<212> TYPE: DNA
<213> ORGANISM: Artificial
<220> FEATURE:
<223> OTHER INFORMATION: OJH1 (HuJH1/2-XHO)

<400> SEQUENCE: 255

gagtcattct cgactcgaga crgtgaccag ggtgcc                              36


<210> SEQ ID NO 256
<211> LENGTH: 36
<212> TYPE: DNA
<213> ORGANISM: Artificial
<220> FEATURE:
<223> OTHER INFORMATION: OJH2 (HuJH3-XHO)

<400> SEQUENCE: 256

gagtcattct cgactcgaga cggtgaccat tgtccc                              36


<210> SEQ ID NO 257
<211> LENGTH: 36
<212> TYPE: DNA
<213> ORGANISM: Artificial
<220> FEATURE:
<223> OTHER INFORMATION: OJH3 (HuJH4/5-XHO)

<400> SEQUENCE: 257

gagtcattct cgactcgaga cggtgaccag ggttcc                              36


<210> SEQ ID NO 258
<211> LENGTH: 36
<212> TYPE: DNA
<213> ORGANISM: Artificial
<220> FEATURE:
<223> OTHER INFORMATION: OJH4 (HuJH6-XHO)

<400> SEQUENCE: 258

gagtcattct cgactcgaga cggtgaccgt ggtccc                              36
```

HUMAN BINDING MOLECULES CAPABLE OF NEUTRALIZING INFLUENZA VIRUS H3N2 AND USES THEREOF

CROSS-REFERENCE TO RELATED APPLICATIONS

This application is a continuation of co-pending U.S. patent application Ser. No. 13/138,941, filed Oct. 27, 2011, which application is a national phase entry under 35 U.S.C. §371 of International Patent Application PCT/EP2010/056217, filed May 6, 2010, published in English as International Patent Publication WO 2010/130636 A1 on Nov. 18, 2010, which claims the benefit under Article 8 of the Patent Cooperation Treaty to EP Application Serial No. 10151155.8, filed Jan. 20, 2010, which itself claims priority under Article 8 of the PCT to European Patent Application Serial No. 09159947.2 filed May 11, 2009, and also under 35 U.S.C. §119(e) to U.S. Provisional Patent Application 61/215,890, filed May 11, 2009, each of which is incorporated herein by this reference.

STATEMENT ACCORDING TO 37 C.F.R. §1.821(c) or (e)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the prior application.

TECHNICAL FIELD

The disclosure relates to biotechnology and medicine, particularly, to human binding molecules able to neutralize various influenza A subtypes, including neutralizing binding molecules against influenza viruses comprising HA of the H3 subtype, such as influenza virus H3N2. In particular, it relates to the diagnosis, prophylaxis and/or treatment of an infection by an influenza virus comprising HA of the H3 subtype, in particular influenza virus H3N2.

BACKGROUND

Influenza viruses are RNA orthomyxoviruses and consist of three types, A, B and C. Whereas influenza viruses of types B and C are predominantly human pathogens, influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A subtypes, such as H5N1, also exist that cause systemic infections in poultry in which mortality may reach 100%. Several subtypes of influenza A viruses also may cause severe illness in man.

Influenza A viruses can be classified into subtypes based on allelic variations in antigenic regions of two genes that encode surface glycoproteins, namely, hemagglutinin (HA) and neuraminidase (NA), which are required for viral attachment and cellular release. Other major viral proteins include the nucleoprotein, the nucleocapsid structural protein, membrane proteins (M1 and M2), polymerases (PA, PB and PB2)

and non-structural proteins (NS1 and NS2). Currently, sixteen subtypes of HA (H1-H16) and nine NA (N1-N9) antigenic variants are known in influenza A virus. Influenza virus subtypes can further be classified by reference to their phylogenetic group. Phylogenetic analysis (Fouchier et al., 2005) has demonstrated a subdivision of HAs that falls into two main groups (Air, 1981): inter alia the H1, H2, H5 and H9 subtypes in phylogenetic group 1 and inter alia the H3, H4 and H7 subtypes in phylogenetic group 2 (FIG. 1).

Only some of the influenza A subtypes (i.e., H1N1, H1N2 and H3N2) circulate among people, but all combinations of the 16 HA and 9 NA subtypes have been identified in avian species Animals infected with influenza A often act as a reservoir for the influenza viruses and certain subtypes have been shown to cross the species barrier to humans, such as the highly pathogenic influenza A strain H5N1.

Influenza infection is one of the most common diseases known to man, causing between three and five million cases of severe illness and between 250,000 and 500,000 deaths every year around the world. Influenza rapidly spreads in seasonal epidemics affecting 5-15% of the population and the burden on health care costs and lost productivity are extensive (World Healthcare Organization (WHO)). Hospitalization and deaths mainly occur in high-risk groups (elderly, chronically ill).

Annual epidemics of influenza occur when the antigenic properties of the viral surface protein HA and NA are altered. The mechanism of altered antigenicity is twofold: antigenic shift, caused by genetic rearrangement between human and animal viruses after double infection of host cells, which can cause a pandemic; and antigenic drift, caused by small changes in the HA and NA proteins on the virus surface, which can cause influenza epidemics. The emergence of variant virus strains by these two mechanisms is the cause of influenza epidemics. Three times in the last century, the influenza A viruses have undergone major genetic changes, mainly in their HA-component, resulting in global pandemics and large tolls in terms of both disease and deaths. The most infamous pandemic was “Spanish Flu,” caused by influenza virus H1N1, which affected large parts of the world population and is thought to have killed at least 40 million people in 1918-1919. More recently, two other influenza A pandemics occurred, in 1957 (“Asian influenza,” caused by influenza virus H2N2) and 1968 (“Hong Kong influenza,” caused by influenza virus H3N2), and caused significant morbidity and mortality globally. In contrast to current seasonal influenza epidemics, these pandemics were associated with severe outcomes also among healthy younger persons.

Current approaches to dealing with annual influenza epidemics include annual vaccination, preferably generating heterotypic cross-protection. However, as indicated above, circulating influenza viruses in humans are subject to permanent antigenic changes, which require annual adaptation of the influenza vaccine formulation to ensure the closest possible match between the influenza vaccine strains and the circulating influenza strains.

Although yearly vaccination with the flu vaccine is the best way to prevent the flu, antiviral drugs, such as oseltamivir (TAMIFLU®), can be effective for prevention and treatment of the flu. However, the number of influenza virus strains showing resistance against such oseltamivir is increasing.

An alternative approach is the development of antibody-based prophylactic or therapeutic means to neutralize various seasonal influenza viruses. The primary target of neutralizing antibodies that protect against influenza virus infection is the globular head (HA1 part) of the viral HA protein, which contains the receptor binding site, but is subject to continuing genetic evolution with amino acid substitutions in antibody-binding sites (antigenic drift). Cross-neutralizing antibodies recognizing the more conserved stem-region of HA of influenza A viruses of phylogenetic group 1 (e.g., H1 and H5) have recently been identified (e.g., WO2008/028946). There has, however, been limited success in identifying antibodies that neutralize one or more influenza A virus subtypes of phylogenetic group 2, such as H3 viruses, and their breadth of neutralization is narrow and their potency low.

Antibodies specifically recognizing H3N2 influenza virus strains have been described. Thus, a human monoclonal antibody, C28, capable of binding to and neutralizing several H3N2 influenza virus strains from the years between 1968 and 1980 has been described by Östberg and Pursch (1983). Wang et al. (2010) have described an anti-HA2 murine antibody neutralizing H3 viruses spanning several decades, but which was shown not to neutralize any non-H3 subtype viruses.

Cross-reactive anti-HA2 murine antibodies recognizing HA of the H3 subtype, as well as of the H4 and H7 subtype, and capable of in vitro reducing influenza virus replication of H3 and H4 influenza viruses have been described by Stropkovská et al. (2009). It was demonstrated that the accessibility of the HA2 epitopes to these antibodies in the native virus was low, and that the antibodies have a higher reactivity with HA after its trypsin cleavage and pH 5 treatment (Varečková et al., 2003a), which may explain the observation that the in vitro inhibition of virus replication (Varečková et al., 2003b), as well as in vivo potency of these antibodies was relatively low (Gocník et al., 2007).

In WO2009/115972, a human monoclonal antibody, Fab28, is disclosed that recognizes an epitope on the stem region of HA and displays a neutralizing activity against H1N1, but less neutralizing activity against H3N2.

SUMMARY

In view of the severity of the respiratory illness caused by certain influenza A viruses, and the always existing threat of a potential pandemic, as well has the high economic impact of the seasonal epidemics, an ongoing need exists for effective means for preventing and treating the various influenza A subtypes. Thus, a need exist for binding molecules, such as broadly neutralizing human binding molecules, able to neutralize seasonal influenza virus subtypes, including influenza viruses comprising HA of the H3 subtype, e.g., H3N2, and that have little or none of the drawbacks of the antibodies known in the prior art.

Provided are binding molecules that can be used in medicine, in particular, for diagnosis, prevention, and/or treatment of infection with influenza virus comprising HA of the H3 subtype, such as H3N2 infections. Some of the binding molecules described herein are unique in their breadth of neutralizing activity within the H3 subtype. Thus, some of the binding molecules identified herein are able to neutralize several, including at least one or more recent, strains within the H3N2 subtype and may be used as a universal prophylactic and/or treatment agent for seasonal influenza, irrespective of the causative influenza H3N2 strain. At least some of the binding molecules are able to prevent in vitro the cleavage of the HA precursor molecule HA0 by trypsin. Furthermore, at least some of the binding molecules hereof are able to prevent the conformational change of the HA protein, thought to be involved in membrane fusion of the influenza viral membrane and the endosomal membrane of an infected cell. Furthermore, at least some binding molecules hereof are unique in that they are also able to cross-neutralizing influenza viruses of at least one other subtype, including influenza viruses comprising HA of the H7 and/or H10 subtypes, and thus can be used as a universal prophylactic, diagnostic and/or treatment agent for influenza viruses, even irrespective of the causative influenza subtype.

DETAILED DESCRIPTION

Figure 1:
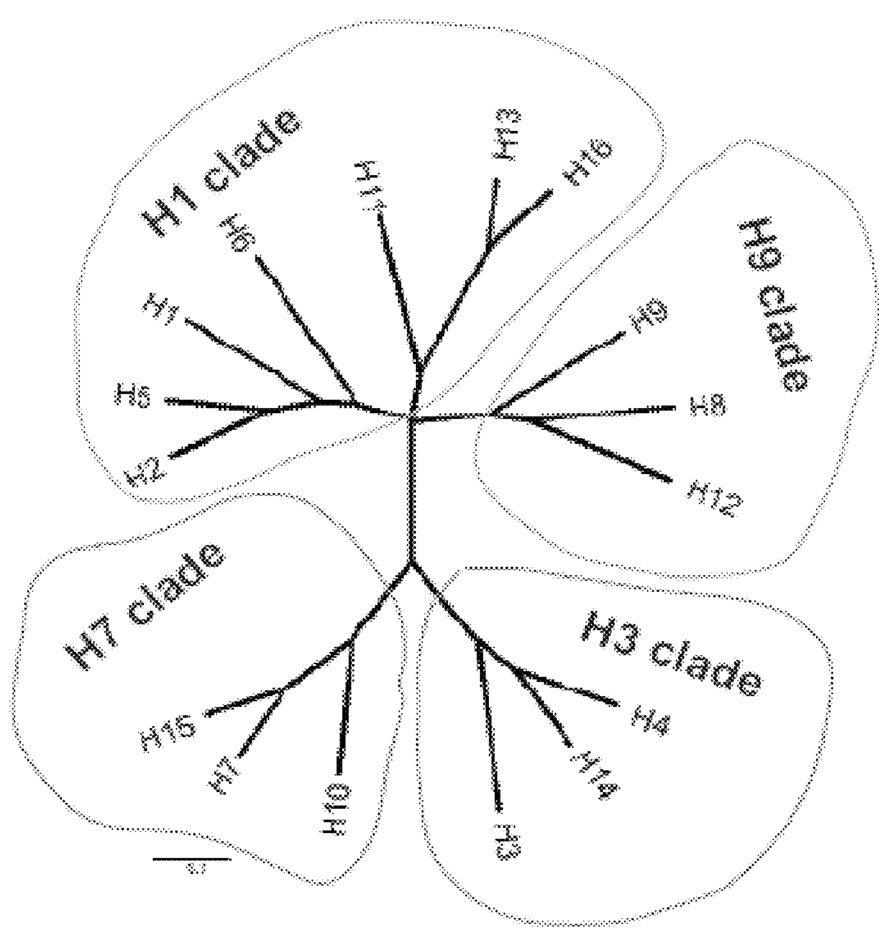
FIG. 1 shows a phylogenetic tree of amino acid sequences at the subtype level. Division of subtypes by group is indicated. The H1 clade, comprising inter alia the H1 subtypes, and the H9 clade, comprising the H9 subtypes, form phylogenetic group 1, and the H7, comprising inter alia the H7 subtypes, and the H3 clade, comprising inter alia the H3 subtypes, form phylogenetic group 2.

Unless another usage is indicated, the term "included" or "including" as used herein is deemed to be followed by the words "without limitation."

As used herein, the term "binding molecule" refers to an intact immunoglobulin including monoclonal antibodies, such as chimeric, humanized or human monoclonal antibodies, or to an antigen-binding and/or variable domain-comprising fragment of an immunoglobulin that competes with the intact immunoglobulin for specific binding to the binding partner of the immunoglobulin, e.g., H3. Regardless of structure, the antigen-binding fragment binds with the same antigen that is recognized by the intact immunoglobulin. An antigen-binding fragment can comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the binding molecule.

The term "binding molecule," as used herein, includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')2, Fv, dAb, Fd, complementarity-determining region (CDR) fragments, single-chain antibodies (scFv), bivalent single-chain antibodies, single-chain phage antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule, but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, or an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term "naked or unconjugated binding molecule" does not exclude the ability of the binding molecule to form functional associations with effector cells and/or molecules after administration to the body, as some of such interactions are necessary in order to exert a biological effect. The lack of associated effector group or tag is, therefore, applied in definition to the naked or unconjugated binding molecule in vitro, not in vivo.

As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

The term "complementarity-determining regions" (CDR) as used herein means sequences within the variable regions of binding molecules, such as immunoglobulins, that usually contribute to a large extent to the antigen binding site, which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

The term "deletion," as used herein, denotes a change in either amino acid or nucleotide sequence in which one or more amino acid or nucleotide residues, respectively, are absent as compared to the reference, often the naturally occurring, molecule.

The term "expression-regulating nucleic acid sequence (or polynucleotide)" as used herein refers to polynucleotides necessary for and/or affecting the expression of an operably linked coding sequence in a particular host organism. The expression-regulating polynucletides, such as inter alia appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and, when desired, sequences that enhance protein secretion, can be any nucleic acid sequence showing activity in the host organism of choice and can be derived from genes encoding proteins, which are either homologous or heterologous to the host organism. The identification and employment of expression-regulating sequences is routine to the person skilled in the art.

The term "functional variant," as used herein, refers to a binding molecule that comprises a nucleotide and/or amino acid sequence that is altered by one or more nucleotides and/or amino acids compared to the nucleotide and/or amino acid sequences of the reference binding molecule and that is still capable of competing for binding to the binding partner, e.g., H3N2, with the reference binding molecule. In other words, the modifications in the amino acid and/or nucleotide sequence of the reference binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), non-polar side chains (e.g., glycine, alanine, valine, leucine, isoleucine, proline, phenylalanine, methionine), beta-branched side chains (e.g., threonine, valine, isoleucine) and aromatic side chains (e.g., tyrosine, phenylalanine, tryptophan). It will be clear to the skilled artisan that other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a polynucleotide can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

The term "influenza virus subtype" as used herein refers to influenza A virus variants that are characterized by various combinations of the hemagglutinin (H) and neuramidase (N) viral surface proteins. Hereof, influenza virus subtypes may be referred to by their H number, such as, for example, "influenza virus comprising HA of the H3 subtype," or "H3 influenza," or by a combination of an H number and an N number, such as, for example, "influenza virus subtype H3N2" or "H3N2." The term "subtype" specifically includes all individual "strains" within each subtype, which usually result from mutations and show different pathogenic profiles. Such strains may also be referred to as various "isolates" of a viral subtype. Accordingly, as used herein, the terms "strains" and "isolates" may be used interchangeably. The current nomenclature for human influenza virus strains or isolates includes the geographical location of the first isolation, strain number and year of isolation, usually with the antigenic description of HA and NA given in brackets, e.g., A/Moscow/10/00 (H3N2). Non-human strains also include the host of origin in the nomenclature.

The influenza virus subtypes can further be classified by reference to their phylogenetic group. Phylogenetic analysis (Fouchier et al., 2005) has demonstrated a subdivision of HAs that falls into two main groups (Air, 1981): inter alia the H1, H2, H5 and H9 subtypes in phylogenetic group 1 and inter alia the H3, H4 and H7 subtypes in phylogenetic group 2 (FIG. 1).

The term "neutralizing" as used herein in relation to the binding molecules hereof refers to binding molecules that inhibit an influenza virus from replicatively infecting a target cell, regardless of the mechanism by which neutralization is achieved. Thus, neutralization can, e.g., be achieved by inhibiting the attachment or adhesion of the virus to the cell surface, or by inhibition of the fusion of viral and cellular membranes following attachment of the virus to the target cell, and the like.

The term "cross-neutralizing" or "cross-neutralization" as used herein in relation to binding molecules refers to the ability of the binding molecules hereof to neutralize influenza A viruses of different subtypes, such as, for example, influenza viruses comprising HA of the H3, H7 and/or H10 subtype.

The term "host," is intended to refer to an organism or a cell into which a vector such as a cloning vector or an expression vector has been introduced. The organism or cell can be prokaryotic or eukaryotic. The hosts may be isolated host cells, e.g., host cells in culture. The term "host cells" merely signifies that the cells are modified for the (over)-expression of the binding molecules hereof and include B-cells that originally express these binding molecules and which cells have been modified to over-express the binding molecule by immortalization, amplification, enhancement of expression, etc. It should be understood that the term "host" is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term "human," when applied to binding molecules, is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo). "Based on" as used herein refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

The term "insertion," also known as the term "addition," denotes a change in an amino acid or nucleotide sequence resulting in the addition of one or more amino acid or nucleotide residues, respectively, as compared to the parent sequence.

The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they may be substantially free of culture medium components and, when the binding molecules are produced by chemical synthesis, they may be substantially free of chemical precursors or other chemicals, i.e., they are separated from chemical precursors or other chemicals that are involved in the synthesis of the protein. The term "isolated" when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than H5N1. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material or culture medium when produced by recombinant techniques, or substantially free of chemical precursors or other chemicals when chemically synthesized.

The term "monoclonal antibody" as used herein refers to a preparation of antibody molecules of single specificity. A monoclonal antibody displays a single binding specificity and affinity for a particular epitope. Accordingly, the term "human monoclonal antibody" refers to an antibody displaying a single binding specificity that has variable and constant regions derived from or based on human germline immunoglobulin sequences or derived from completely synthetic sequences. The method of preparing the monoclonal antibody is not relevant for the binding specificity.

The term "naturally occurring" as used herein as applied to an object refers to the fact that an object can be found in nature. For example, a polypeptide or polynucleotide sequence that is present in an organism that can be isolated from a source in nature and that has not been intentionally modified by man in the laboratory is naturally occurring.

The term "nucleic acid molecule" as used herein refers to a polymeric form of nucleotides and includes both sense and anti-sense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed, and is compatible with other ingredients of the formulation comprising the drug, agent or binding molecule. Pharmaceutically acceptable excipients are widely applied in the art.

The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigenic determinant or epitope and not immunospecifically binding to other antigenic determinants or epitopes. A binding molecule that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding molecules or fragments thereof that immunospecifically bind to an antigen may be cross-reactive with related antigens, carrying the same epitope. In certain embodiments, binding molecules or fragments thereof that immunospecifically bind to an antigen do not cross-react with other antigens.

A "substitution," as used herein, denotes the replacement of one or more amino acids or nucleotides by different amino acids or nucleotides, respectively.

The term "therapeutically effective amount" refers to an amount of the binding molecule as defined herein that is effective for preventing, ameliorating and/or treating a condition resulting from infection with influenza of the H3 subtype. "Amelioration" as used herein may refer to the reduction of visible or perceptible disease symptoms, viremia, or any other measurable manifestation of influenza infection.

The term "treatment" or "treating" refers to therapeutic treatment as well as prophylactic or preventative measures to cure or halt or at least retard disease progress. Those in need of treatment include those already inflicted with a condition resulting from infection with influenza virus comprising HA of the H3 subtype as well as those in which infection with influenza virus comprising HA of the H3 subtype is to be prevented. Subjects partially or totally recovered from infection with H3 influenza might also be in need of treatment. Prevention encompasses inhibiting or reducing the spread of influenza virus comprising HA of the H3 subtype or inhibiting or reducing the onset, development or progression of one or more of the symptoms associated with infection with H3 influenza.

The term "vector" denotes a nucleic acid molecule into which a second nucleic acid molecule can be inserted for introduction into a host where it will be replicated, and in some cases, expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

Provided are human binding molecules able to specifically bind to influenza virus strains comprising HA of the H3 subtype, including H3N2, and exhibiting neutralizing activity against such influenza virus. In certain embodiments, the binding molecules hereof are unique in that they are able to neutralize several, including at least one or more recent, strains, such as all known strains, of influenza virus subtype H3, the most common epidemic subtype in humans, with high potency. In certain embodiments, the binding molecules bind to a conserved epitope in the stem region of the H3 HA protein. In certain embodiments, the binding molecules have hemagglutination-inhibiting activity. In certain embodiments, the binding molecules are able to prevent in vitro cleavage of the HA precursor molecule HA0. In certain embodiments, the binding molecules hereof are able to prevent the conformational change of the HA protein required for fusion of the influenza viral membrane with the endosomal membrane of an infected cell.

Also provided are binding molecules that bind to an epitope in the hemagglutinin protein that is shared between influenza subtypes within the phylogenetic group 2 to which H3 subtypes belong and, therefore, relates to binding molecules that cross-react between H3-, H7-, and/or H10 influenza-based subtypes, and other influenza subtypes that contain the HA protein with these particular epitopes, such as all subtypes of phylogenetic group 2. Several binding molecules hereof are thus unique in that they possess cross-neutralizing activity against one or more other influenza virus A subtypes, such as influenza viruses comprising HA of the H7 and/or the H10 subtype. The binding molecules hereof may be able to cross-neutralize all influenza virus subtypes of phylogenetic group 2, encompassing the H3, H7 and H10 subtypes, and thus can be used as a universal prophylactic, diagnostic and/or treatment agent for influenza viruses belonging to phylogenetic group 2, irrespective of the causative influenza subtype within that phylogenetic group.

It is surmised that these binding molecules bind to hitherto unknown conserved epitopes that are not or much less prone to antigenic drift or shift. Hence, it is also encompassed to use the binding molecules hereof to identify and/or characterize these epitopes. Also described are nucleic acid molecules encoding at least the binding region of the human binding molecules. Further described is the use of the human binding molecules hereof in the prophylaxis and/or treatment of a subject having, or at risk of developing, an H3 influenza infection, such as a H3N2 influenza infection. Furthermore, disclosed is the use of the human binding molecules hereof in the diagnosis/detection of such influenza infection.

Provided are binding molecules that specifically bind to and have neutralizing activity against influenza virus A, particularly influenza virus A comprising HA of the H3 subtype, in particular, H3N2. The binding molecules may be human binding molecules. In certain embodiments, the binding molecules hereof are able to specifically bind to and/or have neutralizing activity against several influenza virus H3N2 strains, preferably two or more different H3N2 strains, more preferably three or more, more preferably four or more, more preferably five or more, different H3N2 strains. The strains may be obtained from both humans or from non-human animals, e.g., birds. In certain embodiments, the binding molecules bind to and neutralize at least one or more of the recent H3N2 strains selected from the group consisting of A/Wisconsin/67/2005, A/Hiroshima/52/2005, A/Panama/2007/99, and A/Johannesburg/33/94. In another embodiment, the binding molecules also bind to and neutralize the H3N2 strain A/Hong Kong/1/68. Most preferably, the binding molecules bind to and have neutralizing activity against all influenza H3N2 strains from the years between 1968 and 2005. The binding molecules may have neutralizing activity against at least all naturally occurring isolates of influenza virus H3N2 known before Jan. 20, 2010.

The binding molecules hereof may be able to specifically bind to the HA0, HA1 and/or HA2 subunit of the HA protein. They may be able to specifically bind to linear or structural and/or conformational epitopes on the HA0, HA1 and/or HA2 subunit of the HA protein. The HA molecule may be purified from viruses or recombinantly produced and optionally isolated before use. Alternatively, HA may be expressed on the surface of cells. In certain embodiments, the binding molecules hereof bind to an epitope comprising one or more of the amino acids at positions 19, 25, 27, 33 and 34 of the HA2 polypeptide of the H3 HA protein. In certain embodiments, the binding molecules bind to the epitope on HA2, when the amino acid on position 19 is aspartic acid (D), the amino acid on position 25 is glutamine (Q), the amino acid on position 27 is glycine (G), the amino acid at position 33 is glycine (G) and/or the amino acid at position 34 is glutamine (numbering of HA2 starting at position 1 just following the Arginine residue that constitutes the cleavage site between HA1 and HA2). In certain embodiments, the binding molecules do not bind to the epitope on HA2 when one or more of the amino acids have changed.

In another aspect, also described are binding molecules that are capable of, at least in vitro, preventing the trypsin cleavage of the H3 HA precursor molecule HA0 in HA1 and HA2.

In another aspect, described are binding molecules that are able to prevent the conformational change of the H3 HA protein, required for membrane fusion of the influenza viral membrane and the endosomal membrane of an infected cell, at least in vitro.

In another aspect, the binding molecules have some or all of the properties listed above, i.e., cross-neutralizing activity, binding to a conserved epitope on the stem region of HA2, inhibiting in vitro trypsin cleavage of HA0, and/or inhibiting conformational change.

In certain embodiments, the binding molecules hereof have all or some of the properties above and, in addition, are not capable of binding to and/or neutralizing influenza virus A comprising HA of the H1 subtype, such as H1N1.

The binding molecules hereof may be able to specifically bind to, e.g., influenza virus H3N2 that are viable, living and/or infective or that are in inactivated/attenuated form. Methods for inactivating/attenuating virus, e.g., influenza virus H3N2, are well known in the art and include, but are not limited to, treatment with formalin, β-propiolactone (BPL), merthiolate, and/or ultraviolet light.

The binding molecules hereof may also be able to specifically bind to one or more fragments of the influenza viruses, such as inter alia a preparation of one or more proteins and/or (poly)peptides derived from subtype H3N2 or one or more recombinantly produced proteins and/or polypeptides of H3N2. For methods of treatment and/or prevention of H3N2 infections, the binding molecules are preferably able to specifically bind to surface accessible proteins of H3N2 such as the surface glycoproteins, hemagglutinin (HA), which is required for viral attachment and cellular release.

The nucleotide and/or amino acid sequence of proteins of various H3N2 strains can be found in the GenBank-database, NCBI Influenza Virus Sequence Database, Influenza Sequence Database (ISD), EMBL-database and/or other databases. It is well within the reach of the skilled person to find such sequences in the respective databases.

In another embodiment, the binding molecules hereof are able to specifically bind to a fragment of the above-mentioned proteins and/or polypeptides, wherein the fragment at least comprises an epitope recognized by the binding molecules hereof. An "epitope" as used herein is a moiety that is capable of binding to a binding molecule hereof with sufficiently high affinity to form a detectable antigen-binding molecule complex.

The binding molecules hereof may or may not be able to specifically bind to the extracellular part of HA (also called herein soluble HA (sHA)).

The binding molecules hereof can be intact immunoglobulin molecules, such as polyclonal or monoclonal antibodies, or the binding molecules can be antigen-binding fragments including, but not limited to, Fab, F(ab'), $F(ab')_2$, Fv, dAb, Fd, complementarity-determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to influenza virus H3N2 strains or a fragment thereof. In a preferred embodiment, the binding molecules hereof are human monoclonal antibodies.

The binding molecules hereof can be used in non-isolated or isolated form. Furthermore, the binding molecules hereof can be used alone or in a mixture comprising at least one binding molecule (or variant or fragment thereof) hereof. In other words, the binding molecules can be used in combination, e.g., as a pharmaceutical composition comprising two or more binding molecules hereof, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. Optionally, the mixture further comprises at least one other therapeutic agent. In certain embodiments, the therapeutic agent such as, e.g., M2 inhibitors (e.g., amantidine, rimantadine) and/or neuraminidase inhibitors (e.g., zanamivir, oseltamivir) is useful in the prophylaxis and/or treatment of an influenza virus H3N2 infection.

Typically, binding molecules described herein can bind to their binding partners, i.e., influenza virus H3N2 or fragments thereof, with an affinity constant ($K_d$-value) that is lower than $0.2\times10^{-4}$ M, $1.0\times10^{-5}$ M, $1.0\times10^{-6}$ M, $1.0\times10^{-7}$ M, preferably lower than $1.0\times10^{-8}$ M, more preferably lower than $1.0\times10^{-9}$ M, more preferably lower than $1.0\times10^{-1o}$ M, even more preferably lower than $1.0\times10^{-11}$ M, and, in particular, lower than $1.0\times10^{-12}$ M. The affinity constants can vary for antibody isotypes. For example, affinity binding for an IgM isotype refers to a binding affinity of at least about $1.0\times10^{-7}$ M. Affinity constants can, for instance, be measured using surface plasmon resonance, for example, using the BIACORE system (Pharmacia Biosensor AB, Uppsala, Sweden).

Typically, the binding molecules hereof have a neutralizing activity of 10 μg/ml or less, preferably 5 μg/ml or less, more preferably 2 μg/ml or less, even more preferably 1 μg/ml or less, as determined in an in vitro virus neutralization assay (VNA) as described in Example 6.

The binding molecules hereof may bind to influenza virus H3N2 or a fragment thereof in soluble form, such as, for instance, in a sample or in suspension or may bind to influenza virus H3N2 or a fragment thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to influenza virus H3N2 in purified/isolated or non-purified/non-isolated form.

The binding molecules hereof exhibit neutralizing activity. Neutralizing activity can, for instance, be measured as described herein. Alternative assays measuring neutralizing activity are described in, for instance, *WHO Manual on Animal Influenza Diagnosis and Surveillance*, Geneva: World Health Organisation, 2005, version 2002.5.

Described is an isolated human binding molecule that is able to recognize and bind to an epitope in the influenza hemagglutinin protein (HA), characterized in that the binding molecule has neutralizing activity against an influenza virus A, comprising HA of the H3 subtype. An example of an influenza subtype that contains HA of the H3 subtype is H3N2. Particularly preferred are binding molecules that neutralize the H3N2 influenza subtype. In certain embodiments, the binding molecules neutralize at least one or more of the recent H3N2 strains. In certain embodiments, the binding molecules thus at least bind to and neutralize one or more H3N2 strains selected from the group consisting of A/Wisconsin/67/2005, A/Hiroshima/52/2005, A/Panama/2007/99, and A/Johannesburg/33/94. In another embodiment, the binding molecules also bind to and neutralize the H3N2 strain A/Hong Kong/1/68. Most preferably, the binding molecules bind to and have neutralizing activity against all influenza H3N2 strains from the years between 1968 and 2005, preferably all known strains of the influenza virus subtype.

In another embodiment, the binding molecules hereof also have neutralizing activity against influenza viruses of other influenza virus A subtypes, preferably at least influenza viruses comprising HA of the H7 subtype, such as the strain A/Mallard/Netherlands/12/2000, and/or H10 subtype, such as the strain A/chick/Germany/N/49. It thus has been shown that some of the binding molecules described herein cross-neutralize these influenza subtypes. Also provided are binding molecules that bind to an epitope in the hemagglutinin protein that is shared and conserved between influenza subtypes and, therefore, relates to binding molecules that cross-react between H3-, H7-, and/or H10 influenza-based subtypes, and other influenza subtypes that contain the HA protein with these particular epitopes, preferably all influenza viruses of phylogenetic group 2. The cross-neutralizing binding molecules preferably bind to and neutralize several strains of the H3-, H7, and/or H10-subtypes. In certain embodiments, these cross-neutralizing binding molecules bind to and neutralize at least one or more of the recent H3N2 strains selected from the group consisting of A/Wisconsin/67/2005, A/Hiroshima/52/2005, A/Johannesburg/33/94, and A/Panama/2007/99. In another embodiment, the binding molecules also bind to and neutralize the H3N2 strain A/Hong Kong/1/68. Most preferably, the binding molecules bind to and have neutralizing activity against all influenza H3N2 strains from the years between 1968 and 2005, preferably all known and, In certain embodiments, also future H3N2 strains. In a further embodiment, the binding molecules neutralize substantially all isolates of the other influenza virus subtypes.

In certain embodiments, the binding molecules bind to and neutralize all influenza virus subtypes of phylogenetic group 2.

The skilled person, based on what has been disclosed herein, can determine whether an antibody indeed crossreacts with HA proteins from different subtypes and also determine whether they are able to neutralize influenza viruses of different subtypes in vivo.

Figure 4:
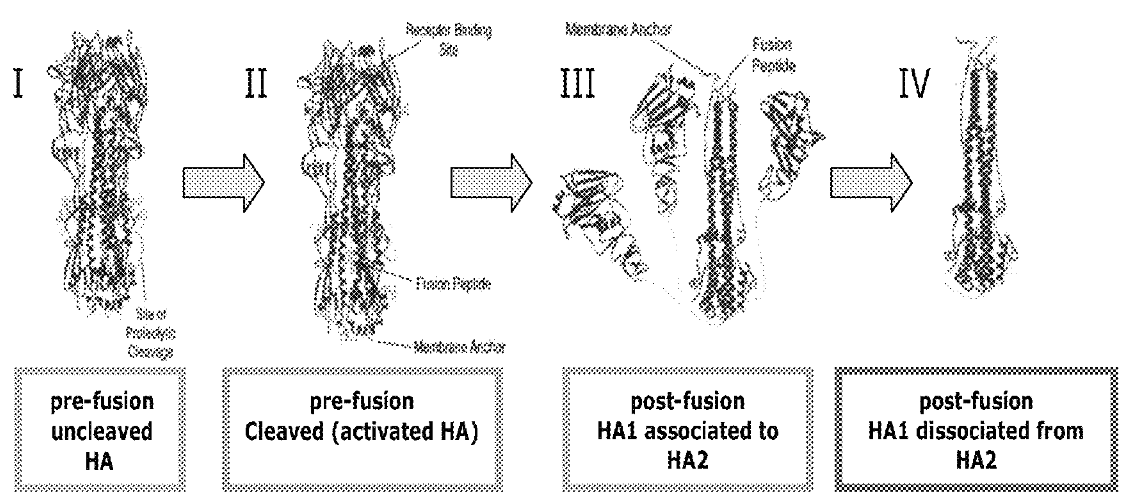
FIG. 4 is a schematic representation of the different conformations of the HA protein during the infection process.

Influenza viruses infect cells by binding to sialic acid residues on the cell surface of target cells, and following transfer into endosomes, by fusing their membranes with the endosomal membranes and releasing the genome-transcriptase complex into the cell. Both receptor binding and membrane fusion processes are mediated by the HA glycoprotein. The HA of influenza virus A comprises two structurally distinct regions, i.e., a globular head region, which contains a receptor binding site that is responsible for virus attachment to the target cell, and is involved in the hemagglutination activity of HA, and a stem region, containing a fusion peptide, which is necessary for membrane fusion between the viral envelope and the endosomal membrane of the cell. The HA protein is a trimer in which each monomer consists of two disulphide-linked glycopolypeptides, HA1 and HA2, that are produced during infection by proteolytic cleavage of a precursor (HA0). Cleavage is necessary for virus infectivity since it is required to prime the HA for membrane fusion to allow conformational change. Activation of the primed molecule occurs at low pH in endosomes, between pH5 and pH6, and requires extensive changes in HA structure. The three-dimensional structure of the pre-fusion uncleaved (I), pre-fusion cleaved (II) and post-fusion HA (III) conformations are schematically shown in FIG. 4. Each of the stages in the priming and activation of HA for its participation in the membrane fusion process presents a different target for inhibition, e.g., by monoclonal antibodies.

In certain embodiments, the binding molecules are at least able to prevent the cleavage of the HA precursor molecule HA0 in an in vitro assay, e.g., an assay as described below in the Examples. As explained above, cleavage of the HA precursor molecule HA0 into HA1 and HA2 by host proteases is required to activate virus infectivity. The prevention of cleavage of the HA precursor molecule HA0 by the binding molecules hereof thus may prevent infection by the influenza virus.

In certain embodiments, the binding molecules bind to an epitope comprising the amino acid at position 19, 25, 27, 33 and/or 34 of the HA2 polypeptide of the H3 HA protein. In certain embodiments, the binding molecules bind to the epitope on HA2, when the amino acid on position 19 is aspartic acid (D), the amino acid on position 25 is glutamine (Q), the amino acid on position 27 is glycine (G), the amino acid at position 33 is glycine (G) and/or the amino acid at position 34 is glutamine. In certain embodiments, the binding molecules do not bind to the epitope on HA2 when one or more of the amino acids have changed. The numbering of the amino acids is based on the hemagglutinin sequence from Uniprot database number Q91MA7 (SEQ ID NO:193 of the incorporated herein SEQUENCE LISTING). Q91MA7 gives the full-length sequence of immature HA from A/Hong Kong/1/1968. The HA2 sequence starts at G346 of the uncleaved HA immature protein. In the numbering above, the G346 is G1 in HA2 sequence.

Preferred is a binding molecule that is selected from the group consisting of:

a) a binding molecule comprising a heavy chain CDR1 region of SEQ ID NO:81, a heavy chain CDR2 region of SEQ ID NO:82, and a heavy chain CDR3 region of SEQ ID NO:83, b) a binding molecule comprising a heavy chain CDR1 region of SEQ ID NO:87, a heavy chain CDR2 region of SEQ ID NO:88, and a heavy chain CDR3 region of SEQ ID NO:89, c) a binding molecule comprising a heavy chain CDR1 region of SEQ ID NO:103, a heavy chain CDR2 region of SEQ ID NO:104, and a heavy chain CDR3 region of SEQ ID NO:105, d) a binding molecule comprising a heavy chain CDR1 region of SEQ ID NO:109, a heavy chain CDR2 region of SEQ ID NO:110, and a heavy chain CDR3 region of SEQ ID NO:111, e) a binding molecule comprising a heavy chain CDR1 region of SEQ ID NO:115, a heavy chain CDR2 region of SEQ ID NO:116, and a heavy chain CDR3 region of SEQ ID NO:117, f) a binding molecule comprising a heavy chain CDR1 region of SEQ ID NO:121, a heavy chain CDR2 region of SEQ ID NO:122, and a heavy chain CDR3 region of SEQ ID NO:123, g) a binding molecule comprising a heavy chain CDR1 region of SEQ ID NO:126, a heavy chain CDR2 region of SEQ ID NO:127, and a heavy chain CDR3 region of SEQ ID NO:128, h) a binding molecule comprising a heavy chain CDR1 region of SEQ ID NO:132, a heavy chain CDR2 region of SEQ ID NO:133, and a heavy chain CDR3 region of SEQ ID NO:134, i) a binding molecule comprising a heavy chain CDR1 region of SEQ ID NO:138, a heavy chain CDR2 region of SEQ ID NO:139, and a heavy chain CDR3 region of SEQ ID NO:140, j) a binding molecule comprising a heavy chain CDR1 region of SEQ ID NO:144, a heavy chain CDR2 region of SEQ ID NO:145, and a heavy chain CDR3 region of SEQ ID NO:146, k) a binding molecule comprising a heavy chain CDR1 region of SEQ ID NO:150, a heavy chain CDR2 region of SEQ ID NO:151, and a heavy chain CDR3 region of SEQ ID NO:152, l) a binding molecule comprising a heavy chain CDR1 region of SEQ ID NO:156, a heavy chain CDR2 region of SEQ ID NO:157, and a heavy chain CDR3 region of SEQ ID NO:158, m) a binding molecule comprising a heavy chain CDR1 region of SEQ ID NO:162, a heavy chain CDR2 region of SEQ ID NO:163, and a heavy chain CDR3 region of SEQ ID NO:164, n) a binding molecule comprising a heavy chain CDR1 region of SEQ ID NO:168, a heavy chain CDR2 region of SEQ ID NO:169, and a heavy chain CDR3 region of SEQ ID NO:170, o) a binding molecule comprising a heavy chain CDR1 region of SEQ ID NO:173, a heavy chain CDR2 region of SEQ ID NO:174, and a heavy chain CDR3 region of SEQ ID NO:175, and p) a binding molecule comprising a heavy chain CDR1 region of SEQ ID NO:179, a heavy chain CDR2 region of SEQ ID NO:180, and a heavy chain CDR3 region of SEQ ID NO:181.

In a preferred embodiment, the binding molecule is for a use as a medicament and preferably for the diagnostic, therapeutic and/or prophylactic treatment of influenza infection. In certain embodiments, the influenza virus that causes the influenza infection and that can be treated by the binding molecules hereof, is influenza virus subtype H3N2. Also described is a pharmaceutical composition comprising a binding molecule hereof, and a pharmaceutically acceptable excipient.

In yet another embodiment, also described is the use of a binding molecule hereof in the preparation of a medicament for the diagnosis, prophylaxis, and/or treatment of an influenza virus infection. Such infections can occur in small populations, but can also spread around the world in seasonal epidemics or, worse, in global pandemics where millions of individuals are at risk. Provided are binding molecules that can neutralize the infection of influenza strains that cause such seasonal epidemics, as well as potential pandemics. Importantly, protection and treatment can be envisioned now with the binding molecules hereof in relation to various influenza subtypes as it has been disclosed that the binding molecules hereof are able to cross-neutralizing various influenza subtypes of phylogenetic group 2, encompassing subtypes H3, H7 and H10.

In a preferred embodiment, the human binding molecules hereof are characterized in that the human binding molecules are selected from the group consisting of:

a) a binding molecule comprising a heavy chain CDR1 region of SEQ ID NO:81, a heavy chain CDR2 region of SEQ ID NO:82, and a heavy chain CDR3 region of SEQ ID NO:83, a light chain CDR1 region comprising the peptide of SEQ ID NO:84, a light chain CDR2 region comprising the peptide of SEQ ID NO:85, and a light chain CDR3 region comprising the peptide of SEQ ID NO:86, b) a binding molecule comprising a heavy chain CDR1 region of SEQ ID NO:87, a heavy chain CDR2 region of SEQ ID NO:88, and a heavy chain CDR3 region of SEQ ID NO:89, a light chain CDR1 region comprising the peptide of SEQ ID NO:90, a light chain CDR2 region comprising the peptide of SEQ ID NO:91, and a light chain CDR3 region comprising the peptide of SEQ ID NO:92, c) a binding molecule comprising a heavy chain CDR1 region of SEQ ID NO:87, a heavy chain CDR2 region of SEQ ID NO:88, and a heavy chain CDR3 region of SEQ ID NO:89, a light chain CDR1 region comprising the peptide of SEQ ID NO:93, a light chain CDR2 region comprising the peptide of SEQ ID NO:94, and a light chain CDR3 region comprising the peptide of SEQ ID NO:95, d) a binding molecule comprising a heavy chain CDR1 region of SEQ ID NO:87, a heavy chain CDR2 region of SEQ ID NO:88, and a heavy chain CDR3 region of SEQ ID NO:89, a light chain CDR1 region comprising the peptide of SEQ ID NO:96, a light chain CDR2 region comprising the peptide of SEQ ID NO:97, and a light chain CDR3 region comprising the peptide of SEQ ID NO:98, e) a binding molecule comprising a heavy chain CDR1 region of SEQ ID NO:87, a heavy chain CDR2 region of SEQ ID NO:88, and a heavy chain CDR3 region of SEQ ID NO:89, a light chain CDR1 region comprising the peptide of SEQ ID NO:99, a light chain CDR2 region comprising the peptide of SEQ ID NO:100, and a light chain CDR3 region comprising the peptide of SEQ ID NO:101, f) a binding molecule comprising a heavy chain CDR1 region of SEQ ID NO:87, a heavy chain CDR2 region of SEQ ID NO:88, and a heavy chain CDR3 region of SEQ ID NO:89, a light chain CDR1 region comprising the peptide of SEQ ID NO:102, a light chain CDR2 region comprising the peptide of SEQ ID NO:85, and a light chain CDR3 region comprising the peptide of SEQ ID NO:86, g) a binding molecule comprising a heavy chain CDR1 region of SEQ ID NO:103, a heavy chain CDR2 region of SEQ ID NO:104, and a heavy chain CDR3 region of SEQ ID NO:105, a light chain CDR1 region comprising the peptide of SEQ ID NO:106, a light chain CDR2 region comprising the peptide of SEQ ID NO:107, and a light chain CDR3 region comprising the peptide of SEQ ID NO:108, h) a binding molecule comprising a heavy chain CDR1 region of SEQ ID NO:109, a heavy chain CDR2 region of SEQ ID NO:110, and a heavy chain CDR3 region of SEQ ID NO:111, a light chain CDR1 region comprising the peptide of SEQ ID NO:112, a light chain CDR2 region comprising the peptide of SEQ ID NO:113, and a light chain CDR3 region comprising the peptide of SEQ ID NO:114, i) a binding molecule comprising a heavy chain CDR1 region of SEQ ID NO:115, a heavy chain CDR2 region of SEQ ID NO:116, and a heavy chain CDR3 region of SEQ ID NO:117, a light chain CDR1 region comprising the peptide of SEQ ID NO:118, a light chain CDR2 region comprising the peptide of SEQ ID NO:119, and a light chain CDR3 region comprising the peptide of SEQ ID NO:120, j) a binding molecule comprising a heavy chain CDR1 region of SEQ ID NO:121, a heavy chain CDR2 region of SEQ ID NO:122, and a heavy chain CDR3 region of SEQ ID NO:123, a light chain CDR1 region comprising the peptide of SEQ ID NO:124, a light chain CDR2 region comprising the peptide of SEQ ID NO:119, and a light chain CDR3 region comprising the peptide of SEQ ID NO:125, k) a binding molecule comprising a heavy chain CDR1 region of SEQ ID NO:126, a heavy chain CDR2 region of SEQ ID NO:127, and a heavy chain CDR3 region of SEQ ID NO:128, a light chain CDR1 region comprising the peptide of SEQ ID NO:129, a light chain CDR2 region comprising the peptide of SEQ ID NO:130, and a light chain CDR3 region comprising the peptide of SEQ ID NO:131, l) a binding molecule comprising a heavy chain CDR1 region of SEQ ID NO:132, a heavy chain CDR2 region of SEQ ID NO:133, and a heavy chain CDR3 region of SEQ ID NO:134, a light chain CDR1 region comprising the peptide of SEQ ID NO:135, a light chain CDR2 region comprising the peptide of SEQ ID NO:136, and a light chain CDR3 region comprising the peptide of SEQ ID NO:137, m) a binding molecule comprising a heavy chain CDR1 region of SEQ ID NO:138, a heavy chain CDR2 region of SEQ ID NO:139, and a heavy chain CDR3 region of SEQ ID NO:140, a light chain CDR1 region comprising the peptide of SEQ ID NO:141, a light chain CDR2 region comprising the peptide of SEQ ID NO:142, and a light chain CDR3 region comprising the peptide of SEQ ID NO:143, n) a binding molecule comprising a heavy chain CDR1 region of SEQ ID NO:144, a heavy chain CDR2 region of SEQ ID NO:145, and a heavy chain CDR3 region of SEQ ID NO:146, a light chain CDR1 region comprising the peptide of SEQ ID NO:147, a light chain CDR2 region comprising the peptide of SEQ ID NO:148, and a light chain CDR3 region comprising the peptide of SEQ ID NO:149, o) a binding molecule comprising a heavy chain CDR1 region of SEQ ID NO:150, a heavy chain CDR2 region of SEQ ID NO:151, and a heavy chain CDR3 region of SEQ ID NO:152, a light chain CDR1 region comprising the peptide of SEQ ID NO:153, a light chain CDR2 region comprising the peptide of SEQ ID NO:154, and a light chain CDR3 region comprising the peptide of SEQ ID NO:155, p) a binding molecule comprising a heavy chain CDR1 region of SEQ ID NO:156, a heavy chain CDR2 region of SEQ ID NO:157, and a heavy chain CDR3 region of SEQ ID NO:158, a light chain CDR1 region comprising the peptide of SEQ ID NO:159, a light chain CDR2 region comprising the peptide of SEQ ID NO:160, and a light chain CDR3 region comprising the peptide of SEQ ID NO:161, q) a binding molecule comprising a heavy chain CDR1 region of SEQ ID NO:162, a heavy chain CDR2 region of SEQ ID NO:163, and a heavy chain CDR3 region of SEQ ID NO:164, a light chain CDR1 region comprising the peptide of SEQ ID NO:165, a light chain CDR2 region comprising the peptide of SEQ ID NO:166, and a light chain CDR3 region comprising the peptide of SEQ ID NO:167, r) a binding molecule comprising a heavy chain CDR1 region of SEQ ID NO:168, a heavy chain CDR2 region of SEQ ID NO:169, and a heavy chain CDR3 region of SEQ ID NO:170, a light chain CDR1 region comprising the peptide of SEQ ID NO:171, a light chain CDR2 region comprising the peptide of SEQ ID NO:172, and a light chain CDR3 region comprising the peptide of SEQ ID NO:137, s) a binding molecule comprising a heavy chain CDR1 region of SEQ ID NO:173, a heavy chain CDR2 region of SEQ ID NO:174, and a heavy chain CDR3 region of SEQ ID NO:175, a light chain CDR1 region comprising the peptide of SEQ ID NO:176, a light chain CDR2 region comprising the peptide of SEQ ID NO:177, and a light chain CDR3 region comprising the peptide of SEQ ID NO:178, and t) a binding molecule comprising a heavy chain CDR1 region of SEQ ID NO:179, a heavy chain CDR2 region of SEQ ID NO:180, and a heavy chain CDR3 region of SEQ ID NO:181, a light chain CDR1 region comprising the peptide of SEQ ID NO:182, a light chain CDR2 region comprising the peptide of SEQ ID NO:183, and a light chain CDR3 region comprising the peptide of SEQ ID NO:184.

In a specific embodiment, the binding molecules are selected from the group consisting of a binding molecule comprising a heavy chain CDR1 region comprising the peptide of SEQ ID NO:81, a heavy chain CDR2 region comprising the peptide of SEQ ID NO:82 and a heavy chain CDR3 region comprising the peptide of SEQ ID NO:83; a binding molecule comprising a heavy chain CDR1 region comprising the peptide of SEQ ID NO:109, a heavy chain CDR2 region comprising the peptide of SEQ ID NO:110 and a heavy chain CDR3 region comprising the peptide of SEQ ID NO:111; a binding molecule comprising a heavy chain CDR1 region comprising the peptide of SEQ ID NO:138, a heavy chain CDR2 region comprising the peptide of SEQ ID NO:139 and a heavy chain CDR3 region comprising the peptide of SEQ ID NO:140; a binding molecule comprising a heavy chain CDR1 region comprising the peptide of SEQ ID NO:144, a heavy chain CDR2 region comprising the peptide of SEQ ID NO:145 and a heavy chain CDR3 region comprising the peptide of SEQ ID NO:146; and a binding molecule comprising a heavy chain CDR1 region comprising the peptide of SEQ ID NO:173, a heavy chain CDR2 region comprising the peptide of SEQ ID NO:174 and a heavy chain CDR3 region comprising the peptide of SEQ ID NO:175.

The CDR regions of the binding molecules are shown in Table 1. CDR regions are according to Kabat et al. (1991) as described in *Sequences of Proteins of Immunological Interest*. The binding molecules may comprise one, two, three, four, five or all six CDR regions as disclosed herein. In certain embodiments, a binding molecule comprises at least two of the CDRs disclosed herein.

In yet another embodiment, the binding molecules comprise a heavy chain variable region comprising an amino acid sequence selected from the group consisting of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, SEQ ID NO:62, SEQ ID NO:66, SEQ ID NO:70, SEQ ID NO:74, and SEQ ID NO:78. In a further embodiment, the binding molecules comprise a light chain variable region comprising an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, and SEQ ID NO:80.

Another aspect includes functional variants of the binding molecules as defined herein. Molecules are considered to be functional variants of a binding molecule hereof, if the variants are capable of competing for specifically binding to influenza virus H3N2 or a fragment thereof with the "parental" or "reference" binding molecules; in other words, when the functional variants are still capable of binding to the same or overlapping epitope of the influenza virus H3N2 or a fragment thereof. For the sake of this application, "parental" and "reference" will be used as synonyms meaning that the information of the reference or parental molecule, or the physical molecule itself may form the basis for the variation. In certain embodiments, the functional variants are capable of competing for specifically binding to at least two (or more) different influenza virus H3N2 strains or fragments thereof that are specifically bound by the reference binding molecules.

Furthermore, molecules are considered to be functional variants of a binding molecule hereof, if they have neutralizing activity against influenza virus H3N2, preferably against the at least two (or more) influenza virus H3N2 strains against which the parental binding molecule exhibits neutralizing activity. Functional variants include, but are not limited to, derivatives that are substantially similar in primary structural sequence, including those that have modifications in the Fc receptor or other regions involved with effector functions, and/or which contain, e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules as defined herein comprising an amino acid sequence containing substitutions, insertions, deletions or combinations thereof of one or more amino acids compared to the amino acid sequences of the parental binding molecules. Furthermore, functional variants can comprise truncations of the amino acid sequence at either or both the amino or carboxyl termini. Functional variants may have the same or different, either higher or lower, binding affinities compared to the parental binding molecule, but are still capable of binding to influenza virus H3N2 or a fragment thereof. For instance, functional variants hereof may have increased or decreased binding affinities for influenza virus H3N2 or a fragment thereof compared to the parental binding molecules. In certain embodiments, the amino acid sequences of the variable regions, including, but not limited to, framework regions, hypervariable regions, in particular, the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the disclosure have at least about 50% to about 99%, preferably at least about 60% to about 99%, more preferably at least about 70% to about 99%, even more preferably at least about 80% to about 99%, most preferably at least about 90% to about 99%, in particular, at least about 95% to about 99%, and, in particular, at least about 97% to about 99% amino acid sequence homology with the parental binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parental binding molecules or parts thereof by general molecular biology methods known in the art including, but not limited to, error-prone PCR, oligonucleotide-directed mutagenesis, site-directed mutagenesis and heavy and/or light chain shuffling. In certain embodiments, the functional variants hereof have neutralizing activity against influenza virus H3N2. The neutralizing activity may either be identical, or be higher or lower compared to the parental binding molecules. Henceforth, when the term (human) binding molecule is used, this also encompasses functional variants of the (human) binding molecule.

In yet a further aspect, described are immunoconjugates, i.e., molecules comprising at least one binding molecule as defined herein and further comprising at least one tag, such as inter alia a detectable moiety/agent. Also contemplated are mixtures of immunoconjugates hereof or mixtures of at least one immunoconjugate hereof and another molecule, such as a therapeutic agent or another binding molecule or immunoconjugate. In a further embodiment, the immunoconjugates may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates hereof may be therapeutic agents, but they can also be detectable moieties/agents. Tags suitable in therapy and/or prevention may be toxins or functional parts thereof, antibiotics, enzymes, or other binding molecules that enhance phagocytosis or immune stimulation. Immunoconjugates comprising a detectable agent can be used diagnostically to, for example, assess if a subject has been infected with an influenza virus H3N2 strain or monitor the development or progression of an influenza virus H3N2 infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron-emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

The human binding molecules or immunoconjugates hereof can also be attached to solid supports, which are particularly useful for in vitro immunoassays or purification of influenza virus H3N2 or a fragment thereof. Such solid supports might be porous or nonporous, planar or non-planar. The binding molecules hereof can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect, the binding molecules hereof may be conjugated/attached to one or more antigens. In certain embodiments, these antigens are antigens that are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules hereof will bind to influenza virus H3N2 and the antigens attached to the binding molecules will initiate a powerful T-cell attack on the conjugate, which will eventually lead to the destruction of the influenza virus H3N2.

Next to producing immunoconjugates chemically by conjugating, directly or indirectly, via, for instance, a linker, the immunoconjugates can be produced as fusion proteins comprising the binding molecules hereof and a suitable tag. Fusion proteins can be produced by methods known in the art such as, e.g., recombinantly by constructing nucleic acid molecules comprising nucleotide sequences encoding the binding molecules in frame with nucleotide sequences encoding the suitable tag(s) and then expressing the nucleic acid molecules.

Also provided is a polynucleotide encoding at least a binding molecule, functional variant or immunoconjugate hereof. Such nucleic acid molecules can be used as intermediates for cloning purposes, e.g., in the process of affinity maturation as described above. In a preferred embodiment, the nucleic acid molecules are isolated or purified.

The skilled person will appreciate that functional variants of these nucleic acid molecules are also intended to be a part of the disclosure. Functional variants are polynucletides that can be directly translated, using the standard genetic code, to provide an amino acid sequence identical to that translated from the parental nucleic acid molecules.

In certain embodiments, the polynucleotides encode binding molecules comprising the CDR regions as described above. In a further embodiment, polynucleotides encode binding molecules comprising two, three, four, five or even all six CDR regions of the binding molecules hereof.

In another embodiment, the polynucleotides encode binding molecules comprising a heavy chain comprising the variable heavy chain sequences as described above. In another embodiment, the polynucleotides encode binding molecules comprising a light chain comprising the variable light chain sequences as described above. The nucleotide sequences and the amino acid sequences of the heavy and light chain variable regions of the binding molecules hereof are given below.

Also provided are vectors, i.e., nucleic acid constructs, comprising one or more nucleic acid molecules hereof. Vectors can be derived from plasmids such as inter alia F, R1, RP1, Col, pBR322, TOL, Ti, etc.; cosmids; phages such as lambda, lambdoid, M13, Mu, P1, P22, Qβ, T-even, T-odd, T2, T4, T7, etc.; and plant viruses. Vectors can be used for cloning and/or for expression of the binding molecules hereof and might even be used for gene therapy purposes. Vectors comprising one or more nucleic acid molecules hereof operably linked to one or more expression-regulating nucleic acid molecules are also covered by the disclosure. The choice of the vector is dependent on the recombinant procedures followed and the host used. Introduction of vectors in host cells can be effected by inter alia calcium phosphate transfection, virus infection, DEAE-dextran-mediated transfection, lipofectamin transfection or electroporation. Vectors may be autonomously replicating or may replicate together with the chromosome into which they have been integrated. In certain embodiments, the vectors contain one or more selection markers. The choice of the markers may depend on the host cells of choice, although this is not critical to the disclosure as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr) Vectors comprising one or more nucleic acid molecules encoding the human binding molecules as described above operably linked to one or more nucleic acid molecules encoding proteins or peptides that can be used to isolate the human binding molecules are also covered. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject hereof. The hosts may be host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells, preferably, yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells, NSO cells or Bowes melanoma cells are preferred herein. Mammalian cells provide expressed proteins with post-translational modifications that are most similar to natural molecules of mammalian origin. Since the disclosure deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B. V.) For the purposes of this application "PER.C6® cells" refers to cells deposited under number 96022940 or ancestors, passages upstream or downstream, as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

Binding molecules can be prepared by various means. A method of producing a binding molecule hereof is an additional part of the disclosure. The method comprises the steps of a) culturing a host hereof under conditions conducive to the expression of the binding molecule, and b) optionally, recovering the expressed binding molecule. The expressed binding molecules can be recovered from the cell-free extract, but preferably they are recovered from the culture medium. The above method of producing can also be used to make functional variants of the binding molecules and/or immunoconjugates hereof. Methods to recover proteins, such as binding molecules, from cell-free extracts or culture medium are well known to the man skilled in the art. Binding molecules, functional variants and/or immunoconjugates as obtainable by the above-described method are also a part hereof.

Alternatively, next to the expression in hosts, such as host cells, the binding molecules and immunoconjugates hereof can be produced synthetically by conventional peptide synthesizers or in cell-free translation systems using RNA nucleic acid derived from DNA molecules hereof. Binding molecules and immunoconjugates as obtainable by the above-described synthetic production methods or cell-free translation systems are also a part hereof.

In certain embodiments, binding molecules can also be produced in transgenic, non-human, mammals such as inter alia rabbits, goats or cows, and secreted into, for instance, the milk thereof.

In yet another alternative embodiment, binding molecules hereof, preferably human binding molecules specifically binding to influenza virus H3N2 or a fragment thereof, may be generated by transgenic non-human mammals, such as, for instance, transgenic mice or rabbits, that express human immunoglobulin genes. In certain embodiments, the transgenic non-human mammals have a genome comprising a human heavy chain transgene and a human light chain transgene encoding all or a portion of the human binding molecules as described above. The transgenic non-human mammals can be immunized with a purified or enriched preparation of influenza virus H3N2 or a fragment thereof. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, N.Y., and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B-cells, plasma and/or memory cells derived from the transgenic animals. In yet another embodiment, the human binding molecules are produced by hybridomas, which are prepared by fusion of B-cells obtained from the above-described transgenic non-human mammals to immortalized cells. B-cells, plasma cells and hybridomas as obtainable from the above-described transgenic non-human mammals and human binding molecules as obtainable from the above-described transgenic non-human mammals, B-cells, plasma and/or memory cells and hybridomas are also a part hereof.

In a further aspect, provided is a method of identifying a binding molecule, such as a human binding molecule, e.g., a human monoclonal antibody or fragment thereof, specifically binding to influenza virus H3N2 or nucleic acid molecules encoding such binding molecules and comprises the steps of: (a) contacting a collection of binding molecules on the surface of replicable genetic packages with influenza virus H3N2 or a fragment thereof under conditions conducive to binding, (b) selecting at least once for a replicable genetic package binding to influenza virus H3N2 or a fragment thereof, (c) separating and recovering the replicable genetic package binding to influenza virus H3N2 or a fragment thereof from replicable genetic packages that do not bind to influenza virus H3N2 or a fragment thereof. A replicable genetic package as used herein can be prokaryotic or eukaryotic and includes cells, spores, yeasts, bacteria, viruses, (bacterio)phage, ribosomes and polysomes. A preferred replicable genetic package is a phage. The binding molecules, such as, for instance, single chain Fvs, are displayed on the replicable genetic package, i.e., they are attached to a group or molecule located at an exterior surface of the replicable genetic package. The replicable genetic package is a screenable unit comprising a binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of binding molecules is formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

The selection step(s) in the methods hereof can be performed with influenza H3N2 viruses that are live and still infective or inactivated. Inactivation of influenza virus H3N2 may be performed by viral inactivation methods well known to the skilled artisan such as inter alia treatment with formalin, β-propiolactone (BPL), merthiolate, and/or ultraviolet light. Methods to test, if influenza virus H3N2 is still alive, infective and/or viable or partly or completely inactivated, are well known to the person skilled in the art. The influenza virus H3N2 used in the above method does not need to be in purified form and, e.g., may be present in serum and/or blood of an infected individual. The influenza virus H3N2 used may also be isolated from cell culture in a suitable medium.

In certain embodiments, the influenza virus H3N2 is in suspension when contacted with the replicable genetic packages. Alternatively, they may also be coupled to a carrier when contact takes place. In certain embodiments, a first and further selection may take place against one influenza virus H3N2 strain. Alternatively, first and further selection rounds may be performed against different influenza virus H3N2 strains. Alternatively, the selection step(s) may be performed in the presence of a fragment of influenza virus H3N2 such as, e.g., cell membrane preparations, recombinant H3N2 proteins or polypeptides, fusion proteins comprising H3N2 proteins or polypeptides, cells expressing recombinant H3N2 proteins or polypeptides, and the like. Extracellularly exposed parts of these proteins or polypeptides can also be used as selection material. The fragments of influenza virus H3N2 may be immobilized to a suitable material before use or may be used in suspension. In certain embodiments, the selection can be performed on different fragments of influenza virus H3N2 or fragments of different influenza virus H3N2 strains. Finding suitable selection combinations are well within the reach of the skilled artisan. Selections may be performed by ELISA or FACS.

In yet a further aspect, provided is a method of obtaining a binding molecule specifically binding to an influenza virus H3N2 strain or fragment thereof or a nucleic acid molecule encoding such a binding molecule, wherein the method comprises the steps of a) performing the above-described method of identifying binding molecules, and b) isolating from the recovered replicable genetic package the binding molecule and/or the nucleic acid molecule encoding the binding molecule. The collection of binding molecules on the surface of replicable genetic packages can be a collection of scFvs or Fabs. Once a new scFv or Fab has been established or identified with the above-mentioned method of identifying binding molecules or nucleic acid molecules encoding the binding molecules, the DNA encoding the scFv or Fab can be isolated from the bacteria or phages and combined with standard molecular biological techniques to make constructs encoding scFvs, bivalent scFvs, Fabs or complete human immunoglobulins of a desired specificity (e.g., IgG, IgA or IgM). These constructs can be transfected into suitable cell lines and complete human monoclonal antibodies can eventually be produced (see Huls et al., 1999; Boel et al., 2000).

As mentioned before, the preferred replicable genetic package is a phage. Phage display methods for identifying and obtaining (human) binding molecules, e.g., (human) monoclonal antibodies, are by now well-established methods known by the person skilled in the art. They are, e.g., described in U.S. Pat. No. 5,696,108; Burton and Barbas, 1994; de Kruif et al., 1995b; and *Phage Display: A Laboratory Manual*, edited by C. F. Barbas, D. R. Burton, J. K. Scott and G. J. Silverman (2001), Cold Spring Harbor Laboratory Press, Cold Spring Harbor, N.Y. All these references are herewith incorporated herein in their entirety. For the construction of phage display libraries, collections of human monoclonal antibody heavy and light chain variable region genes are expressed on the surface of bacteriophage, preferably filamentous bacteriophage, particles, in, for example, single-chain Fv (scFv) or in Fab format (see de Kruif et al., 1995b). Large libraries of antibody fragment-expressing phages typically contain more than $1.0\times10^9$ antibody specificities and may be assembled from the immunoglobulin V-regions expressed in the B-lymphocytes of immunized or non-immunized individuals. In a specific embodiment hereof, the phage library of binding molecules, preferably scFv phage library, is prepared from RNA isolated from cells obtained from a subject that has been vaccinated against influenza virus, recently vaccinated against an unrelated pathogen, recently suffered from an influenza virus H3N2 infection or from a healthy individual. RNA can be isolated from inter alia bone marrow or peripheral blood, preferably peripheral blood lymphocytes or isolated B-cells or even subpopulations of B-cells such as memory B-cells, identified as CD24+/CD27+ B-cells. The subject can be an animal, preferably a human. In a preferred embodiment, the libraries may be assembled from the immunoglobulin V-regions expressed by IgM memory B-cells, identified as IgM+/CD24+/CD27+ cells.

Alternatively, phage display libraries may be constructed from immunoglobulin variable regions that have been partially assembled in vitro to introduce additional antibody diversity in the library (semi-synthetic libraries). For example, in vitro-assembled variable regions contain stretches of synthetically produced, randomized or partially randomized DNA in those regions of the molecules that are important for antibody specificity, e.g., CDR regions. Phage antibodies specific for influenza virus H3N2 can be selected from the library by exposing the virus or fragment thereof to a phage library to allow binding of phages expressing antibody fragments specific for the virus or fragment thereof. Non-bound phages are removed by washing and bound phages eluted for infection of *E. coli* bacteria and subsequent propagation. Multiple rounds of selection and propagation are usually required to sufficiently enrich for phages binding specifically to the virus or fragment thereof. If desired, before exposing the phage library to the virus or fragment thereof, the phage library can first be subtracted by exposing the phage library to non-target material such as viruses or fragments thereof of a different strain, i.e., non-H3N2 influenza viruses. These subtractor viruses or fragments thereof can be bound to a solid phase or can be in suspension. Phages may also be selected for binding to complex antigens such as complex mixtures of H3N2 proteins or (poly)peptides optionally supplemented with other material. Host cells expressing one or more proteins or (poly)peptides of influenza virus H3N2 may also be used for selection purposes. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules. Of course, the subtraction may be performed before, during or after the screening with virus or fragments thereof. The process is referred to as the MABSTRACT® process (MABSTRACT® is a registered trademark of Crucell Holland B. V., see also, U.S. Pat. No. 6,265,150, which is incorporated herein by reference).

In yet another aspect, provided is a method of obtaining a binding molecule potentially having neutralizing activity against influenza virus H3N2, wherein the method comprises the steps of (a) performing the method of obtaining a binding molecule specifically binding to influenza virus H3N2 or a fragment thereof or a nucleic acid molecule encoding such a binding molecule as described above, and (b) verifying if the binding molecule isolated has neutralizing activity against the virus, preferably against at least one or more influenza virus H3N2 strains selected from the group consisting of A/Hong Kong/1/68, A/Johannesburg/33/94, A/Panama/2007/99, A/Wisconsin/67/2005 and A/Hiroshima/52/2005, preferably all strains of H3N2, in particular, all known and future H3N2 strains. Assays for verifying if a binding molecule has neutralizing activity are well known in the art (see *WHO Manual on Animal Influenza Diagnosis and Surveillance*, Geneva: World Health Organisation, 2005 version 2002.5).

In a further aspect, provided is a human binding molecule having neutralizing activity against at least influenza virus A comprising HA of the H3 subtype, obtainable by one of the methods as described above.

In yet a further aspect, provided are compositions comprising at least a binding molecule, such as a human monoclonal antibody, at least a functional variant thereof, at least an immunoconjugate hereof and/or a combination thereof. In addition to that, the compositions may comprise inter alia stabilizing molecules, such as albumin or polyethylene glycol, or salts. In certain embodiments, the salts used are salts that retain the desired biological activity of the binding molecules and do not impart any undesired toxicological effects. If necessary, the human binding molecules may be coated in or on a material to protect them from the action of acids or other natural or non-natural conditions that may inactivate the binding molecules.

In yet a further aspect, provided are compositions comprising at least a polynucleotide as defined herein. The compositions may comprise aqueous solutions such as aqueous solutions containing salts (e.g., NaCl or salts as described above), detergents (e.g., SDS) and/or other suitable components.

Furthermore, also described are pharmaceutical compositions comprising at least a binding molecule such as a human monoclonal antibody hereof (or functional fragment or variant thereof), at least an immunoconjugate hereof, at least a composition hereof, or combinations thereof. The pharmaceutical composition further comprises at least one pharmaceutically acceptable excipient. Pharmaceutically acceptable excipients are well known to the skilled person. The pharmaceutical composition may further comprise at least one other therapeutic agent. Suitable agents are also well known to the skilled artisan.

In a preferred embodiment, such pharmaceutical composition comprises at least one additional binding molecule, i.e., the pharmaceutical composition can be a cocktail or mixture of binding molecules. The pharmaceutical composition may comprise at least two binding molecules hereof, or at least one binding molecule hereof and at least one further influenza virus binding and/or neutralizing molecule.

In another embodiment, the additional binding molecule may be formulated for simultaneous separate or sequential administration.

In certain embodiments, the pharmaceutical compositions may comprise two or more binding molecules that have neutralizing activity against influenza virus A comprising HA of the H3 subtype, such as H3N2. In certain embodiments, the binding molecules exhibit synergistic neutralizing activity when used in combination. In other words, the compositions may comprise at least two binding molecules having neutralizing activity, characterized in that the binding molecules act synergistically in neutralizing influenza virus H3N2. As used herein, the term "synergistic" means that the combined effect of the binding molecules when used in combination is greater than their additive effects when used individually. The synergistically acting binding molecules may bind to different structures on the same or distinct fragments of influenza virus H3N2. A way of calculating synergy is by means of the combination index. The concept of the combination index (CI) has been described by Chou and Talalay (1984). The compositions may, e.g., comprise one binding molecule having neutralizing activity and one non-neutralizing H3N2-specific binding molecule. The non-neutralizing and neutralizing H3N2-specific binding molecules may also act synergistically in neutralizing influenza virus H3N2.

In certain embodiments, the pharmaceutical composition may comprise at least two influenza virus neutralizing binding molecules, wherein at least one binding molecule is able to neutralize one or more influenza virus subtypes of phylogenetic group 1 and wherein at least one binding molecule is able to neutralize one or more influenza virus subtypes of phylogenetic group 2.

In certain embodiments, the pharmaceutical composition may comprise at least one binding molecule hereof and at least one further influenza virus neutralizing binding molecule.

In another embodiment, the further influenza virus neutralizing binding molecule preferably is capable of binding to and neutralizing an influenza virus of a different subtype, preferably an influenza virus comprising HA of the H1, such as H1N1, and/or HA of the H5 subtype, such as H5N1, such as the binding molecules as disclosed in WO 2008/028946. In certain embodiments, the further binding molecule is a cross-neutralizing binding molecule against (all) influenza virus subtypes of phylogenetic group 1, including H1, H2, H5, H9. In a preferred embodiment, the further binding molecule is the binding molecule identified as CR6261 in WO 2008/028946, comprising a heavy chain variable region comprising amino acids 1-121 of amino acid sequence of SEQ ID NO:186, or a functional variant thereof, and/or a light chain variable region comprising amino acids 1-112 of SEQ ID NO:188. In yet another embodiment, the binding molecule comprises a heavy and light chain comprising the amino acid sequences of SEQ ID NO:186 and SEQ ID NO:188, respectively. The binding molecules in the pharmaceutical composition thus preferably are capable of reacting with influenza viruses of different subtypes. The binding molecules should be of high affinity and should have a broad specificity. In certain embodiments, both binding molecules are cross-neutralizing molecules in that they each neutralize influenza viruses of different subtypes. In addition, they preferably neutralize as many strains of each of the different influenza virus subtypes as possible.

A pharmaceutical composition hereof can further comprise at least one other therapeutic, prophylactic and/or diagnostic agent. The pharmaceutical composition may comprise at least one other prophylactic and/or therapeutic agent. The further therapeutic and/or prophylactic agents may be agents able to prevent and/or treat an influenza virus H3N2 infection and/or a condition resulting from such an infection. Therapeutic and/or prophylactic agents include, but are not limited to, anti-viral agents. Such agents can be binding molecules, small molecules, organic or inorganic compounds, enzymes, polynucleotide sequences, anti-viral peptides, etc. Other agents that are currently used to treat patients infected with influenza virus H3N2 are M2 inhibitors (e.g., amantidine, rimantadine) and/or neuraminidase inhibitors (e.g., zanamivir, oseltamivir). These can be used in combination with the binding molecules hereof. "In combination" herein means simultaneously, as separate formulations, or as one single combined formulation, or according to a sequential administration regimen as separate formulations, in any order. Agents able to prevent and/or treating an infection with influenza virus H3N2 and/or a condition resulting from such an infection that are in the experimental phase might also be used as other therapeutic and/or prophylactic agents useful herein.

The binding molecules or pharmaceutical compositions can be tested in suitable animal model systems prior to use in humans. Such animal model systems include, but are not limited to, mouse, ferret, and monkey.

Typically, pharmaceutical compositions must be sterile and stable under the conditions of manufacture and storage. The binding molecules, immunoconjugates, nucleic acid molecules or compositions can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions can be in solution and the appropriate pharmaceutically acceptable excipient can be added and/or mixed before or at the time of delivery to provide a unit dosage injectable form. In certain embodiments, the pharmaceutically acceptable excipient used herein is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration, such as intravenous or by inhalation.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutical excipients including, but not limited to, inert diluents, granulating and disintegrating agents, binding agents, lubricating agents, preservatives, coloring, flavoring or sweetening agents, vegetable or mineral oils, wetting agents, and thickening agents.

The pharmaceutical compositions can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity- or solubility-increasing agents, water-soluble antioxidants, oil-soluble antioxidants and metal chelating agents.

In a further aspect, the binding molecules, such as human monoclonal antibodies, (functional fragments and variants thereof), immunoconjugates, compositions, or pharmaceutical compositions hereof can be used as a medicament. So, a method of diagnosis, treatment and/or prevention of an influenza virus H3N2 infection using the binding molecules, immunoconjugates, compositions, or pharmaceutical compositions hereof is another part hereof. The above-mentioned molecules can inter alia be used in the diagnosis, prophylaxis, treatment, or combination thereof, of an influenza virus H3N2 infection. They are suitable for treatment of yet untreated patients suffering from an influenza virus H3N2 infection and patients who have been or are treated for an influenza virus H3N2 infection.

The above-mentioned molecules or compositions may be employed in conjunction with other molecules useful in diagnosis, prophylaxis and/or treatment. They can be used in vitro, ex vivo or in vivo. For instance, the binding molecules such as human monoclonal antibodies (or functional variants thereof), immunoconjugates, compositions or pharmaceutical compositions hereof can be co-administered with a vaccine against influenza virus H3N2 (if available). Alternatively, the vaccine may also be administered before or after administration of the molecules hereof. Instead of a vaccine, anti-viral agents can also be employed in conjunction with the binding molecules hereof. Suitable anti-viral agents are mentioned above.

The molecules are typically formulated in the compositions and pharmaceutical compositions hereof in a therapeutically or diagnostically effective amount. Alternatively, they may be formulated and administered separately. For instance, the other molecules, such as the anti-viral agents, may be applied systemically, while the binding molecules hereof may be applied intravenously.

Treatment may be targeted at patient groups that are susceptible to H3N2 infection. Such patient groups include, but are not limited to, e.g., the elderly (e.g., ≥50 years old, ≥60 years old, and preferably ≥65 years old), the young (e.g., ≤5 years old, ≤1 year old), hospitalized patients and patients who have been treated with an antiviral compound, but have shown an inadequate antiviral response.

Dosage regimens can be adjusted to provide the optimum desired response (e.g., a therapeutic response). A suitable dosage range may, for instance, be 0.1-100 mg/kg body weight, preferably 1-50 mg/kg body weight, preferably 0.5-15 mg/kg body weight. For example, a single bolus may be administered, several divided doses may be administered over time or the dose may be proportionally reduced or increased as indicated by the exigencies of the therapeutic situation. The molecules and compositions hereof are preferably sterile. Methods to render these molecules and compositions sterile are well known in the art. The other molecules useful in diagnosis, prophylaxis and/or treatment can be administered in a similar dosage regimen as proposed for the binding molecules hereof. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions hereof. The exact dosing regimen is usually sorted out during clinical trials in human patients.

Human binding molecules and pharmaceutical compositions comprising the human binding molecules are particularly useful, and often preferred, when they are to be administered to human beings as in vivo therapeutic agents, since recipient immune response to the administered antibody will often be substantially less than that occasioned by administration of a monoclonal murine, chimeric or humanized binding molecule.

In another aspect, described is the use of the binding molecules such as neutralizing human monoclonal antibodies (functional fragments and variants thereof), immunoconjugates, nucleic acid molecules, compositions or pharmaceutical compositions hereof in the preparation of a medicament for the diagnosis, prophylaxis, treatment, or combination thereof, of an influenza virus H3N2 infection.

Next to that, kits comprising at least a binding molecule such as a neutralizing human monoclonal antibody (functional fragments and variants thereof), at least an immunoconjugate, at least a nucleic acid molecule, at least a composition, at least a pharmaceutical composition, at least a vector, at least a host hereof or a combination thereof are also a part hereof. Optionally, the above-described components of the kits hereof are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper to be pierced by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products that contain information about, for example, the indications, usage, dosage, manufacture, administration, contra-indications and/or warnings concerning the use of such therapeutic, prophylactic or diagnostic products.

The binding molecules can also be advantageously used as a diagnostic agent in an in vitro method for the detection of phylogenetic group 2 subtype influenza virus. Thus also disclosed is a method of detecting influenza virus phylogenetic group 2 subtype influenza virus in a sample, wherein the method comprises the steps of (a) contacting a sample with a diagnostically effective amount of a binding molecule (functional fragments and variants thereof) or an immunoconjugate hereof, and (b) determining whether the binding molecule or immunoconjugate specifically binds to a molecule of the sample. The sample may be a biological sample including, but not limited to blood, serum, stool, sputum, nasopharyngeal aspirates, bronchial lavages, urine, tissue or other biological material from (potentially) infected subjects, or a non-biological sample such as water, drink, etc. The (potentially) infected subjects may be human subjects, but also animals that are suspected as carriers of influenza virus phylogenetic group 2 subtype influenza virus might be tested for the presence of the virus using the human binding molecules or immunoconjugates hereof. The sample may first be manipulated to make it more suitable for the method of detection. Manipulation means inter alia treating the sample suspected to contain and/or containing the virus in such a way that the virus will disintegrate into antigenic components such as proteins, (poly)peptides or other antigenic fragments. In certain embodiments, the human binding molecules or immunoconjugates hereof are contacted with the sample under conditions that allow the formation of an immunological complex between the human binding molecules and the virus or antigenic components thereof that may be present in the sample. The formation of an immunological complex, if any, indicating the presence of the virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates hereof are conveniently bonded to the inside surface of microtiter wells. The binding molecules or immunoconjugates hereof may be directly bonded to the microtiter well. However, maximum binding of the binding molecules or immunoconjugates hereof to the wells might be accomplished by pre-treating the wells with polylysine prior to the addition of the binding molecules or immunoconjugates hereof. Furthermore, the binding molecules or immunoconjugates hereof may be covalently attached by known means to the wells. Generally, the binding molecules or immunoconjugates are used between 0.01 to 100 μg/ml for coating, although higher as well as lower amounts may also be used. Samples are then added to the wells coated with the binding molecules or immunoconjugates hereof.

Furthermore, binding molecules hereof can be used to identify specific binding structures of influenza virus H3N2. The binding structures can be epitopes on proteins and/or polypeptides. They can be linear, but also structural and/or conformational. In one embodiment, the binding structures can be analyzed by means of PEPSCAN analysis (see inter alia WO 84/03564, WO 93/09872, Slootstra et al., 1996). Alternatively, a random peptide library comprising peptides from a protein of influenza virus H3N2 can be screened for peptides capable of binding to the binding molecules hereof. The binding structures/peptides/epitopes found can be used as vaccines and for the diagnosis of influenza virus H3N2 infections. In case fragments other than proteins and/or polypeptides are bound by the binding molecules, binding structures can be identified by mass spectrometry, high performance liquid chromatography and nuclear magnetic resonance.

In a further aspect, provided is a method of screening a binding molecule (or a functional fragment or variant thereof) for specific binding to the same epitope of influenza virus H3N2, as the epitope bound by a human binding molecule hereof, wherein the method comprises the steps of (a) contacting a binding molecule to be screened, a binding molecule hereof and influenza virus H3N2 or a fragment thereof, (b) measure if the binding molecule to be screened is capable of competing for specifically binding to influenza virus H3N2 or a fragment thereof with the binding molecule hereof. In a further step, it may be determined if the screened binding molecules that are capable of competing for specifically binding to influenza virus H3N2 or a fragment thereof have neutralizing activity. A binding molecule that is capable of competing for specifically binding to influenza virus H3N2 or a fragment thereof with the binding molecule hereof is another part hereof. In the above-described screening method, "specifically binding to the same epitope" also contemplates specific binding to substantially or essentially the same epitope as the epitope bound by the binding molecule hereof. The capacity to block, or compete with, the binding of the binding molecules hereof to influenza virus H3N2 typically indicates that a binding molecule to be screened binds to an epitope or binding site on influenza virus H3N2 that structurally overlaps with the binding site on influenza virus H3N2 that is immunospecifically recognized by the binding molecules hereof. Alternatively, this can indicate that a binding molecule to be screened binds to an epitope or binding site that is sufficiently proximal to the binding site immunospecifically recognized by the binding molecules hereof to sterically or otherwise inhibit binding of the binding molecules hereof to influenza virus H3N2.

In general, competitive inhibition is measured by means of an assay, wherein an antigen composition, i.e., a composition comprising influenza virus H3N2 or fragments thereof, is admixed with reference binding molecules, i.e., the binding molecules hereof, and binding molecules to be screened. Usually, the binding molecules to be screened are present in excess. Protocols based upon ELISAs and Western blotting are suitable for use in such simple competition studies. By using species or isotype secondary antibodies, one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such as, e.g., biotin, an enzymatic, a radioactive or other label to enable subsequent identification. Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule hereof, as well as antibodies, antibody fragments and other binding agents that bind to an epitope or binding site sufficiently proximal to an epitope bound by the reference binding molecule for competitive binding between the binding molecules to be screened and the reference binding molecule to occur. In certain embodiments, competitive binding molecules hereof will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules hereof is a straightforward technical matter. As the identification of competitive binding molecules is determined in comparison to a reference binding molecule, i.e., a binding molecule hereof, it will be understood that actually determining the epitope to which the reference binding molecule and the competitive binding molecule bind is not in any way required in order to identify a competitive binding molecule that binds to the same or substantially the same epitope as the reference binding molecule. The disclosure is further illustrated in the following Examples and figures. The Examples are not intended to limit the scope hereof in any way.

EXAMPLES

Example 1

Construction of scFv Phage Display Libraries Using RNA Extracted from Memory B Cells Peripheral blood was collected from normal healthy donors by venapuncture in EDTA anti-coagulation sample tubes. scFv phage display libraries were obtained as described in WO 2008/028946, which is incorporated by reference herein. Memory B cells (CD24+/CD27+) were separated from naive B cells (CD24+/CD27−) and memory T cells (CD24−/CD27+) and in a next step, IgM memory B cells (IgM+) were separated from switch memory B cells (IgM−) using IgM expression. RNA was isolated from the IgM memory B cells and cDNA prepared.

A two-round PCR amplification approach was applied using the primer sets shown in Tables 1 and 2 to isolate the immunoglobulin VH and VL regions from the respective donor repertoire.

First-round amplification on the respective cDNA using the primer sets mentioned in Table 1 yielded seven, six and nine products of about 650 base pairs for, respectively, VH, Vkappa and Vlambda regions. For IgM memory B cell VH region amplification, the OCM constant primer was used in combination with OH1 to OH7. The thermal cycling program for first-round amplifications was: 2 minutes 96° C. (denaturation step), 30 cycles of 30 seconds 96° C./30 seconds 55° C./60 seconds 72° C., 10 minutes 72° C. final elongation and 4° C. refrigeration. The products were loaded on and isolated from a 1% agarose gel using gel-extraction columns (Qiagen) and eluted in 50 μl 1 mM Tris-HCl pH 8.0. Ten percent of first-round products (5 μl) was subjected to second-round amplification using the primers mentioned in Table 2. These primers were extended with restriction sites enabling the directional cloning of the respective VL and VH regions into phage display vector PDV-006. The PCR program for second-round amplifications was as follows: 2 minutes 96° C. (denaturation step), 30 cycles of 30 seconds 96° C./30 seconds 60° C./60 seconds 72° C., 10 minutes 72° C. final elongation and 4° C. refrigeration. The second-round products (~350 base pairs) were first pooled according to natural occurrence of J segments found in immunoglobulin gene products, resulting in seven, six and nine pools for, respectively, the VH, Vkappa and Vlambda variable regions (see Tables 3 and 4).

To obtain a normalized distribution of immunoglobulin sequences in the immune library, the six Vkappa and nine Vlambda light chain pools were mixed according to the percentages mentioned in Table 3. This single final VL pool (3 μg) was digested overnight with SalI and NotI restriction enzymes, loaded on and isolated from a 1.5% agarose gel (~350 base pairs) using Qiagen gel-extraction columns and ligated in SalI-NotI cut PDV-006 vector (~5000 base pairs) as follows: 10 μl PDV-006 vector (50 ng/μl), 7 μl VL insert (10 ng/μl), 5 μl 10× ligation buffer (NEB), 2.5 T4 DNA Ligase (400 U/μl) (NEB), 25.5 μl ultrapure water (vector to insert ratio was 1:2). Ligation was performed overnight in a water bath of 16° C. Next, the volume was doubled with water, extracted with an equal volume of phenol-chloroform-isoamylalcohol (75:24:1) (Invitrogen) followed by chloroform (Merck) extraction and precipitated with 1 μl Pellet Paint (Novogen), 10 μl sodium acetate (3 M pH 5.0) and 100 μl isopropanol for two hours at −20° C.

The obtained sample was subsequently centrifuged at 20,000×g for 30 minutes at 4° C. The obtained precipitate was washed with 70% ethanol and centrifuged for 10 minutes at 20,000×g at room temperature. Ethanol was removed by vacuum aspiration and the pellet was air dried for several minutes and then dissolved in 50 μl buffer containing 10 mM Tris-HCl, pH 8.0. One μl ligation mixture was used for the transformation of 40 μl TG-1 electro-competent cells (Stratagene) in a chilled 0.1 cm electroporation cuvette (Biorad) using a Genepulser II apparatus (Biorad) set at 1.7 kV, 200 Ohm, 25 μF (time constant ~4.5 msec). Directly after pulse, the bacteria were flushed from the cuvette with 1000 μl SOC medium (Invitrogen) containing 5% (w/v) glucose (Sigma) at 37° C. and transferred to a 15 ml round bottom culture tube. Another 500 μl SOC/glucose was used to flush residual bacteria from the cuvette and was added to the culture tube. Bacteria were recovered by culturing for exactly one hour at 37° C. in a shaker incubator at 220 rpm. The transformed bacteria were plated over large 240 mm square petri dishes (NUNC) containing 200 ml 2TY agar (16 g/l bacto-tryptone, 10 g/l bacto-yeast extract, 5 g/l NaCl, 15 g/l agar, pH 7.0) supplemented with 50 μg/ml ampicillin and 5% (w/v) glucose (Sigma). A 1 to 1000 dilution was plated for counting purposes on 15 cm petri dishes containing the same medium.

This transformation procedure was repeated sequentially twenty times and the complete library was plated over a total of thirty large square petri dishes and grown overnight in a 37° C. culture stove. Typically, around $1\times10^7$ cfu were obtained using the above protocol. The intermediate VL light chain library was harvested from the plates by mildly scraping the bacteria into 10 ml 2TY medium per plate. The cell mass was determined by OD600 measurement and two times 500 OD of bacteria was used for maxi plasmid DNA preparation using two P500 maxiprep columns (Qiagen) according to manufacturer's instructions.

Analogous to the VL variable regions, the second round VH-JH products were first mixed together to obtain the normal J segment usage distribution (see Table 4), resulting in seven VH subpools called PH1 to PH7. The pools were mixed to acquire a normalized sequence distribution using the percentages depicted in Table 4, obtaining one VH fraction that was digested with SfiI and XhoI restriction enzymes and ligated in SfiI-XhoI cut PDV-VL intermediate library obtained as described above. The ligation set-up, purification method, subsequent transformation of TG1 and harvest of bacteria was exactly as described for the VL intermediate library (see above). The final library (approximately $5\times10^6$ cfu) was checked for insert frequency with a colony PCR using a primer set flanking the inserted VH-VL regions. More than 95% of the colonies showed a correct length insert (see Table 5). The colony PCR products were used for subsequent DNA sequence analysis to check sequence variation and to assess the percentage of colonies showing a complete ORF. This was typically above 70% (see Table 5). The frequency of mutations in the V genes was also analyzed. Out of 50 sequences, 47 (94%) were not in germline configuration indicative of a maturation process and consistent with the memory phenotype of the B cells used as an RNA source for the library. Finally, the library was rescued and amplified by using CT helper phages (see WO 02/103012) and was used for phage antibody selection by panning methods as described below.

Example 2

Selection of Phages Carrying Single Chain Fv Fragments Against Influenza A Subtypes H3 and H7 and Influenza B Antibody fragments were selected using antibody phage display libraries constructed essentially as described above and general phage display technology and MABSTRACT® technology essentially as described in U.S. Pat. No. 6,265,150 and in WO 98/15833 (both of which are incorporated by reference herein). Furthermore, the methods and helper phages as described in WO 02/103012 (which is incorporated by reference herein) were used herein.

Selection was performed against recombinant hemagglutinin (HA) of influenza A subtype H3 (A/Wisconsin/67/2005) and H7 (A/Netherlands/219/2003) or influenza B (B/Ohio/01/2005). HA antigens were diluted in PBS (5.0 μg/ml), added to MaxiSorp™ Nunc-Immuno Tubes (Nunc) and incubated overnight at 4° C. on a rotating wheel. The immunotubes were emptied and washed three times in block buffer (2% non-fat dry milk (ELK) in PBS). Subsequently, the immunotubes were filled completely with block buffer and incubated for one to two hours at room temperature. Aliquots of phage display library (500-1000 μl, $0.5\times10^{13}$-$1\times10^{13}$ cfu, amplified using CT helper phage (see WO 02/103012)) were blocked in blocking buffer supplemented with 10% non-heat inactivated fetal bovine serum and 2% mouse serum for one to two hours at room temperature. The blocked phage library was added to the immunotubes, incubated for two hours at room temperature, and washed with wash buffer (0.05% (v/v) TWEEN®-20 in PBS) to remove unbound phages. Bound phages were eluted from the respective antigen by incubation with 1 ml of 100 mM triethylamine (TEA) for 10 minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for 10 minutes at 3000×g at room temperature and the bacterial pellet was resuspended in 0.5 ml 2-trypton yeast extract (2TY) medium. The obtained bacterial suspension was divided over two 2TY agar plates supplemented with tetracycline, ampicillin and glucose.

After incubation overnight of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection. The second round of selection is performed either on the same HA subtype or on HA of a different subtype.

Two consecutive rounds of selections were performed before isolation of individual single-chain phage antibodies. After the second round of selection, individual *E. coli* colonies were used to prepare monoclonal phage antibodies. Essentially, individual colonies were grown to log-phase in 96-well plate format and infected with VCS-M13 helper phages, after which phage antibody production was allowed to proceed overnight. The supernatants containing phage antibodies were used directly in ELISA for binding to HA antigens. Alternatively, phage antibodies were PEG/NaCl-precipitated and filter-sterilized for both elisa and flow cytometry analysis.

Example 3

Validation of the HA Specific Single-Chain Phage Antibodies

Selected supernatants containing single-chain phage antibodies that were obtained in the screenings described above were validated in ELISA for specificity, i.e., binding to different HA antigens. For this purpose, baculovirus-expressed recombinant H3 (A/Wisconsin/67/2005), H7 (A/Netherlands/219/2003) and B (B/Ohio/01/2005) HAs (Protein Sciences, CT, USA) were coated to Maxisorp™ ELISA plates. After coating, the plates were washed three times with PBS containing 0.1% v/v TWEEN®-20 and blocked in PBS containing 3% BSA or 2% ELK for one hour at room temperature. The selected single-chain phage antibodies were incubated for one hour in an equal volume of PBS containing 4% ELK to obtain blocked phage antibodies. The plates were emptied, washed three times with PBS/0.1% TWEEN®-20 and the blocked single-chain phage antibodies were added to the wells. Incubation was allowed to proceed for one hour, the plates were washed with PBS/0.1% TWEEN®-20 and bound phage antibodies were detected (using OD 492 nm measurement) using an anti-M13 antibody conjugated to peroxidase. As a control, the procedure was performed simultaneously without single-chain phage antibody and with an unrelated negative control single-chain phage antibody. From the selections on the different HA antigens with the IgM memory B cell libraries, six unique single-chain phage antibodies specific for both recombinant H3 HA and H7 HA were obtained (SC08-001, SC08-003, SC08-006, SC08-014, SC08-017 and SC08-018). In addition, two unique single-chain phage antibodies specific for recombinant H3 HA (SC08-015 and SC08-016)

and five for recombinant H7 HA (SC08-007, SC08-009, SC08-010, SC08-011 and SC08-013) were isolated. See, Table 6.

Alternatively, PEG/NaCl-precipitated and filter-sterilized phage antibodies were used to validate elisa binding and specificity. For this purpose, baculovirus-expressed recombinant influenza A H1 (A/New Caledonia/20/1999), H3 (A/Wisconsin/67/2005), H5 (A/Vietnam/1203/2004), H7 (A/Netherlands/219/2003) and influenza B (B/Ohio/01/2005, B/Malaysia/2506/2004, B/Jilin/219/2003) HAs (Protein Sciences, CT, USA) were coated to Maxisorp™ ELISA plates. After coating, the plates were washed three times with PBS containing 0.1% v/v TWEEN®-20 and blocked in PBS containing 3% BSA or 2% ELK for one hour at room temperature. The selected single-chain phage antibodies were incubated for one hour in an equal volume of PBS containing 4% ELK to obtain blocked phage antibodies. The plates were emptied, washed three times with PBS/0.1% TWEEN®-20 and the blocked single-chain phage antibodies were added to the wells. Incubation was allowed to proceed for one hour, the plates were washed with PBS/0.1% TWEEN®-20 and bound phage antibodies were detected (using OD 492 nm measurement) using an anti-M13 antibody conjugated to peroxidase. As a control, the procedure was performed simultaneously without single-chain phage antibody and with a negative control single-chain phage antibody. From the selections on the different HA antigens with the IgM memory B cell libraries, two unique single-chain phage antibodies specific for recombinant H1, H3 and H7 HA were obtained (SC08-001 and SC08-014). In addition, six unique single-chain phage antibodies specific for recombinant H3 HA (SC08-003, SC08-006, SC08-015, SC08-016, SC08-017 and SC08-018), and five for recombinant H7 HA (SC08-007, SC08-009, SC08-010, SC08-011 and SC08-013) were isolated. See, Table 7.

Alternatively, PEG/NaCl-precipitated and filter-sterilized phage antibodies were used to validate binding and specificity by FACS analysis. For this purpose, full-length recombinant influenza A subtypes H1 (A/New Caledonia/20/1999), H3 (A/Wisconsin/67/2005), H5(TV), H7 (A/Netherlands/219/2003) and influenza B (B/Ohio/o1/2005) HAs were expressed on the surface of PER.C6® cells. The cells were incubated with single-chain phage antibodies for one hour followed by three wash steps with PBS+0.1% BSA. Bound phages were detected using FITC-conjugated M13-antibody. From the selections on the different HA antigens with the IgM memory B cell libraries, one single-chain phage antibody specific for influenza A subtypes H1, H3 and H7 HA was isolated (SC08-001). In addition, six unique single-chain phage antibodies specific for H3 HA (SC08-003, SC08-006, SC08-015, SC08-016, SC08-017 and SC08-018), four unique single-chain phage antibodies specific for H7 HA (SC08-007, SC08-010, SC08-011 and SC08-013) were isolated. See Table 8. Of these, six phage antibodies (SC08-001, SC08-003, SC08-015, SC08-016, SC08-017, SC08-018) were used for construction of fully human immunoglobulins for further characterization (see Example 5).

Example 4

Selection and Validation of Influenza A (H3N2) HA Specific Immortalized B-Cell Clones In addition to phage display, the binding molecules hereof can also be isolated by other methods, for example, using immortalized B cells, as described in, e.g., WO 2007067046. Immortalized IgM memory cells (CD19+/CD27+, IgD+), derived from vaccinated donors, were stained with APC-labeled H3 HA and single cells sorted into limiting dilution culture. After recovery and cell expansion, the supernatants of the H3 HA sorted cells were measured by solid phase ELISA for H1, H3 and H7 immunoreactivity.

Subsequently, the target-specific B cells were characterized for binding activity and neutralization. The B cells were cloned by limiting dilution to yield single clones. The clones were seeded into culture plates and the cells cultured for 14 days. Supernatants of the clones were screened for production of anti-HA monoclonal antibodies that bind to HA-transfected 293 cells expressing H1, H3, H5 and H7 derived HA. As a control for a specific or background staining, untransfected 293 cells were used.

In order to determine whether the selected B-cell clone supernatants containing either IgM or IgG antibodies that were obtained in the screenings described above were capable of blocking influenza A (H3N2) infection, an in vitro virus neutralization assay (VNA) was performed. The VNA was performed on MDCK cells (ATCC CCL-34). MDCK cells were cultured in MDCK cell culture medium (MEM medium supplemented with antibiotics, 20 mM Hepes and 0.15% (w/v) sodium bicarbonate (complete MEM medium), supplemented with 10% (v/v) fetal bovine serum). The H3N2 (A/Wisconsin/67/2005) strain that was used in the assay was diluted to a titer of $5.7\times10^3$ TCID50/ml (50% tissue culture infective dose per ml), with the titer calculated according to the method of Spearman and Karber. The IgG or IgM preparations were serially two-fold diluted (1:2-1:64) in complete MEM medium in quadruplicate wells. 25 μl of the respective IgG dilution was mixed with 25 μl of virus suspension (100 TCID50/25 μl) and incubated for one hour at 37° C. The suspension was then transferred in quadruplicate onto 96-well plates containing confluent MDCK cultures in 50 μl complete MEM medium. Prior to use, MDCK cells were seeded at $3\times10^4$ cells per well in MDCK cell culture medium, grown until cells had reached confluence, washed with 300-350 μl PBS, pH 7.4 and finally 50 μl complete MEM medium was added to each well. The inoculated cells were cultured for three to four days at 37° C. and observed daily for the development of cytopathogenic effect (CPE). CPE was compared to the positive control.

Of the 187 IgG supernatants tested, 43 were found to neutralize the H3N2 (A/Wisconsin/67/2005) strain used in this assay. Of these, 14 were used for construction of human IgG immunoglobulins as described in Example 5.

Example 5

Construction of Fully Human Immunoglobulin Molecules (Human Monoclonal Antibodies) from the Selected Single Chain Fvs and B-Cell Clones From the selected specific single-chain phage antibody (scFv) clones, plasmid DNA was obtained and nucleotide and amino acid sequences were determined according to standard techniques. Heavy and light chain variable regions of the scFvs were cloned directly by restriction digest for expression in the IgG expression vectors pIg-C911-HCgamma1 (see SEQ ID NO:189), pIG-C909-Ckappa (see SEQ ID NO:190), or pIg-C910-Clambda (see SEQ ID NO:191). Heavy and light chain variable regions of the B-cell clones were PCR-amplified and cloned directly by restriction digest for expression in the IgG expression vectors pIg-C911-HCgamma1 (see SEQ ID NO:190), pIG- C909-Ckappa (see SEQ ID NO:191), or pIg-C910-Clambda (see SEQ ID NO:192). The VH and VL gene identity (see I. M. Tomlinson et al., V-BASE Sequence Directory, Cambridge United Kingdom: MRC Centre for Protein Engineering (1997)) of the scFvs were determined (see Table 9).

Nucleotide sequences for all constructs were verified according to standard techniques known to the skilled artisan. The resulting expression constructs encoding the human IgG1 heavy and light chains were transiently expressed in combination in 293T cells and supernatants containing human IgG1 antibodies were obtained and produced using standard purification procedures. The human IgG1 antibodies were titrated in a concentration range of between 10 and 0.003 μg/ml against H3, H7 or B antigen (data not shown). An unrelated antibody was included as a control antibody.

The amino acid sequence of the CDRs of the heavy and light chains of the selected immunoglobulin molecules is given in Table 9. The nucleotide sequence and amino acid sequence of the heavy and light chain variable regions are given below. The immunoglobulins comprise the heavy and light chain constant region of CR6261, as given below.

Example 6

In Vitro Neutralization of Influenza Virus by H3N2 Binding IgGs (Virus Neutralization Assay)

In order to determine whether the selected IgGs were capable of blocking influenza A (H3N2) infection, an in vitro virus neutralization assay (VNA) was performed. The VNA was performed on MDCK cells (ATCC CCL-34). MDCK cells were cultured in MDCK cell culture medium (MEM medium supplemented with antibiotics, 20 mM Hepes and 0.15% (w/v) sodium bicarbonate (complete MEM medium), supplemented with 10% (v/v) fetal bovine serum). The H3N2 (A/Wisconsin/67/2005) strain that was used in the assay was diluted to a titer of $5.7\times10^3$ TCID50/ml (50% tissue culture infective dose per ml), with the titer calculated according to the method of Spearman and Karber. The IgG preparations (200 μg/ml) were serially two-fold diluted (1:2-1:512) in complete MEM medium in quadruplicate wells. 25 μl of the respective IgG dilution was mixed with 25 μl of virus suspension (100 TCID50/25 μl) and incubated for one hour at 37° C. The suspension was then transferred in quadruplicate onto 96-well plates containing confluent MDCK cultures in 50 μl complete MEM medium. Prior to use, MDCK cells were seeded at $3\times10^4$ cells per well in MDCK cell culture medium, grown until cells had reached confluence, washed with 300-350 μl PBS, pH 7.4 and finally 50 μl complete MEM medium was added to each well. The inoculated cells were cultured for three to four days at 37° C. and observed daily for the development of cytopathogenic effect (CPE). CPE was compared to the positive control.

The human anti-H3 HA and/or anti-H7 HA antibodies of Example 5 were subjected to the above-described VNA. Of these antibodies, all antibodies, except CR8040, CR8052 and CR8069, neutralized the A/Wisconsin/67/2005 H3N2 strain. The concentrations (in μg/ml) at which these antibodies protect MDCK cultures against CPE are given in Table 11.

Example 7

Cross-Binding Reactivity of Anti-H3N2 IgGs

The H3N2 neutralizing IgG antibodies described above were validated in ELISA for binding specificity, i.e., binding to different HA antigens. For this purpose, baculovirus-expressed recombinant H1 (A/New Caledonia/20/1999), H3 (A/Wisconsin/67/2005, A/New York/55/2004, A/Wyoming/3/2003) and H7 (A/Netherlands/219/2003) HAs (Protein Sciences, CT, USA) were coated to Maxisorp™ ELISA plates. After coating, the plates were washed three times with PBS containing 0.1% v/v TWEEN®-20 and blocked in PBS containing 3% BSA or 2% ELK for one hour at room temperature. The plates were emptied, washed three times with PBS/0.1% TWEEN®-20 and the IgG antibodies were added to the wells. Incubation was allowed to proceed for one hour, the plates were washed with PBS/0.1% TWEEN®-20 and bound antibodies were detected (using OD 492 nm measurement) using an anti-human IgG antibody conjugated to peroxidase. As a control, an unrelated IgG CR4098 was used.

From the selected H3N2 neutralizing antibodies, CR8001 shows heterosubtypic cross-binding to all the recombinant HAs tested, CR8020, CR8021, CR8041, CR8043 and CR8057 show heterosubtypic cross-binding to all three tested H3 HAs, as well as the H7 HA. CR8003, CR8015, CR8016, CR8017, CR8018, CR8038, CR8039, CR8040, CR8049, CR8050, CR8052 and CR8069 show cross-binding to all three tested H3 HAs. One antibody, CR8019, shows binding to only two of the H3 HAs. See Table 12.

Additionally, the selected H3N2-neutralizing antibodies were used to test heterosubtypic binding by FACS analysis. For this purpose, full-length recombinant influenza A subtypes H1 (A/New Caledonia/20/1999), H3 (A/Wisconsin/67/2005) and H7 (A/Netherlands/219/2003) HAs were expressed on the surface of PER.C6® cells. The cells were incubated with IgG antibodies for one hour followed by three wash steps with PBS+0.1% BSA. Bound antibodies were detected using PE-conjugated anti-human antibody. As a control, untransfected PER.C6® cells were used.

From the H3N2-neutralizing antibodies, CR8001 shows cross-binding activity to influenza A subtypes H1, H3 and H7 HA, but not wild-type PER.C6® cells. In addition, CR8020 and CR8041 show strong binding to both H3 and H7 HA. CR8043 and CR8057 show strong binding to H3 HA and weak binding to H7 HA. CR8055 showed low levels of background staining on PER.C6® cells. The remaining 13 antibodies show binding to H3 transfected cells only. See Table 12.

Example 8

Cross-Neutralizing Activity of Anti-H3N2 IgGs

In order to determine whether the selected IgGs were capable of blocking multiple influenza A strains, additional in vitro virus neutralization assays (VNA) were performed. The VNA were performed on MDCK cells (ATCC CCL-34). MDCK cells were cultured in MDCK cell culture medium (MEM medium supplemented with antibiotics, 20 mM Hepes and 0.15% (w/v) sodium bicarbonate (complete MEM medium), supplemented with 10% (v/v) fetal bovine serum). The H1N1 (A/New Caledonia/20/1999 A/Brisbane/59/2007 and A/Solomon Islands/IVR-145), H3N2 (A/Hong Kong/1/68, A/Johannesburg/33/94, A/Panama/2000/1999, A/Hiroshima/52/2005 and A/Wisconsin/67/2005), H7N3 (A/Mallard/Netherlands/12/2000) and H10 (A/Chick/Germany/N/49) strains that were used in the assay were all diluted to a titer of $5.7\times10^3$ TCID50/ml (50% tissue culture infective dose per ml), with the titer calculated according to the method of Spearman and Karber. The IgG preparations (80 μg/ml) were serially two-fold diluted (1:2-1:512) in complete MEM medium in quadruplicate wells. 25 μl of the respective IgG dilution was mixed with 25 μl of virus suspension (100 TCID50/25 μl) and incubated for one hour at 37° C. The suspension was then transferred in quadruplicate onto 96-well plates containing confluent MDCK cultures in 50 μl complete MEM medium. Prior to use, MDCK cells were seeded at $3\times10^4$ cells per well in MDCK cell culture medium, grown until cells had reached confluence, washed with 300-350 μl PBS, pH 7.4 and finally 50 μl complete MEM medium was added to each well. The inoculated cells were cultured for three to four days at 37° C. and observed daily for the development of cytopathogenic effect (CPE). CPE was compared to the positive control.

From the panel of H3N2-neutralizing antibodies, CR8020 and CR8041 show heterosubtypic cross-neutralizing activity to all tested influenza A subtypes H3, H7 and H10 viruses, but not H1 viruses. In addition, CR8043 shows cross-neutralization to all tested H3 and H10 virus strains. CR8039, CR8041, CR8043 and CR8057 show cross-neutralization of all tested H3 virus strains. An additional 13 antibodies show cross-neutralization to more than one of the tested H3 virus strains. See Table 13.

Example 9

Anti-H3N2 Antibodies Bind to the Pre-Fusion Conformation of HA

In order to determine whether the selected IgGs were capable of binding the pre- or post-fusion conformation of the HA molecule, an in vitro pH-shift experiment was performed.

Figure 2:
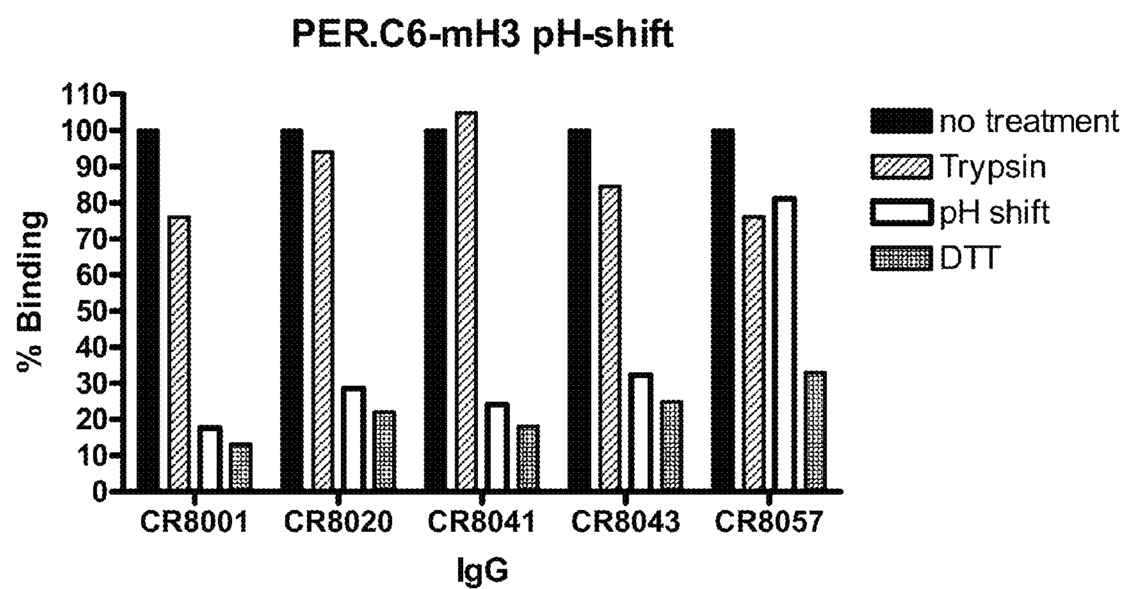
FIG. 2 is a bar diagram showing binding of IgG1 to surface-expressed H3 rHA, measured by FACS analysis, after sequential treatment with trypsin (striped bars), pH 4.9 buffered medium (solid white bars) and DTT (crossed bars) and expressed as percentage binding to untreated rHA (solid black bars).

For this purpose, full-length recombinant influenza A subtype H3 (A/Wisconsin/67/2005) HA was expressed on the surface of PER.C6® cells. To assay for specific reactivity at different structural HA conformations, $3\times10^5$ cells were treated with 10 μg/ml trypsin-EDTA in DMEM for 30 minutes at RT, washed and incubated for 5 minutes in acidified PBS (pH 4.9), washed and then incubated for 20 minutes in the presence of 20 mM DTT at RT. Cells were split at each step and untreated adherent cells were resuspended in 0.05% EDTA. Cell fractions of each treatment were incubated with anti-H3N2 IgGs CR8001, CR8020, CR8041, CR8043 and CR8057 for 30 minutes. Cells were then incubated for 30 minutes with phycoerythrin-conjugated anti-IgG (Southern Biotech). Stained cells were analyzed using a FACS Calibur with CELLQuest Pro software (Becton Dickinson). FACS binding of IgG1 to surface-expressed H3 rHA was measured after sequential treatment with trypsin (striped bars), pH 4.9 buffered medium (solid white bars) and DTT (crossed bars) and expressed as percentage binding to untreated rHA (solid black bars). See FIG. 2.

Antibodies CR8001, CR8020, CR8041 and CR8043 all show a marked decrease in binding after pH-shift indicating specificity for an epitope present only before the low PH-induced conformational change of the HA molecule. Antibody CR8057 showed a decrease in binding only after DTT treatment indicating specificity for a conformation-independent epitope available only when HA1 is present.

Example 10

Anti-H3N2 Antibody CR8041 Prevents Cleavage of HA0

In order to determine whether the selected IgGs were capable of protecting the HA molecule from protease cleavage, an in vitro protease susceptibility assay was performed.

Figure 3:
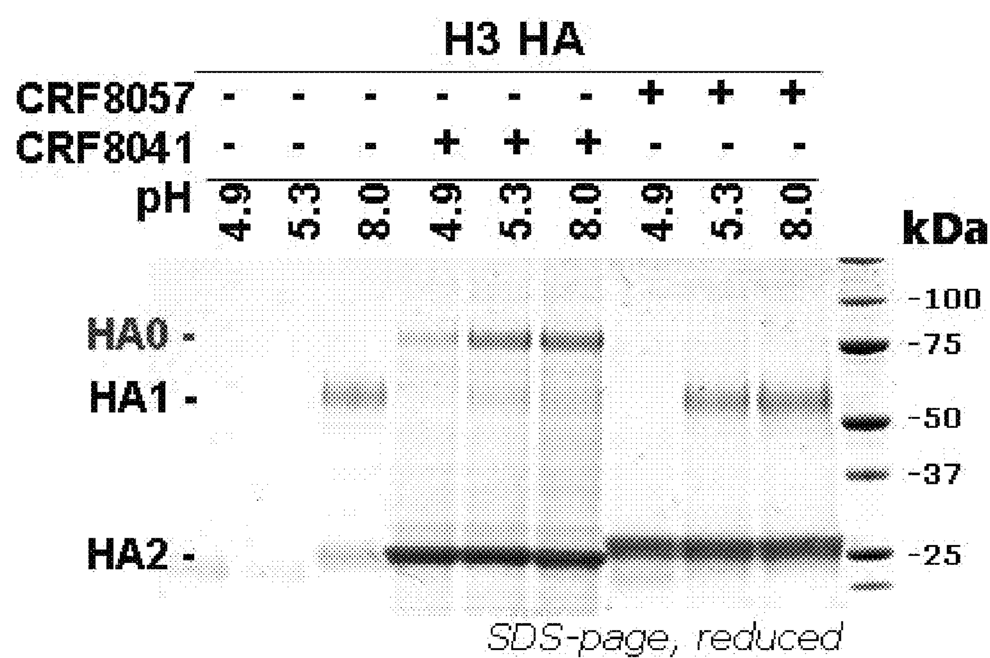
FIG. 3 shows the results of an in vitro protease susceptibility assay. Samples were run on a 4-12% BisTris gel in 1×MOPS buffer. Protein bands were visualized by colloidal blue staining.

For this purpose, 7.5 μg recombinant soluble influenza A subtype H3 (A/Wisconsin/67/2005) HA (Protein Sciences, CT, USA) was subjected to different pH (4.9, 5.3 and 8.0) treatments for one hour at 37° C. After incubation, reactions were neutralized. The samples were digested overnight with 0.5 μg trypsin in the presence and absence of 7.5 μg CR8041 or CR8057 Fab fragments. Reactions were quenched by addition of SDS loading buffer. Three μl Nupage reducing agent (Invitrogen) was added to each sample. Samples were run on a 4-12% BisTris gel in 1×MOPS buffer. Protein bands were visualized by colloidal blue staining (see FIG. 3). In the absence of Fab fragments, the H3 HA molecule is readily converted to its protease-susceptible post-fusion form at pH 4.9 or 5.3, but not at pH 8.0. In the presence of Fab fragment CR8057, the degradation of H3 HA and thus the conformational change at pH 4.9 is not inhibited. In contrast, the presence of Fab CR8041 not only prevents H3 HA conformational change and degradation at low pH, but also the pH-independent cleavage of HA0 into HA1 and HA2. These results point towards an epitope for CR8041 on, or close to, the cleavage site. Competition experiments (results not shown) with the anti-H3N2 antibody panel indicate an overlapping epitope and a similar working mechanism for the CR8001, CR8020 and CR8043 antibodies.

Example 11

Mechanism of Action of the Binding Molecules

The HA glycoprotein is a trimer in which each monomer consists of two disulphide-linked glycopolypeptides (named HA1 and HA2) that are produced during infection by proteolytic cleavage of a precursor (HA0). Cleavage is necessary for virus infectivity since it is required to prime the HA for membrane fusion, to allow conformational change.

Activation of the primed molecule occurs at low pH in endosomes, between pH5 and pH6, and requires extensive changes in HA structure. The three-dimensional structure of the pre-fusion uncleaved (I), pre-fusion cleaved (II) and post-fusion HA (III) conformations are schematically shown in FIG. 4.

In vitro, the conformational changes of the HA molecule can be mimicked using HA surface-expressed mammalian cells. First, the proteolytic cleavage can be triggered by adding trypsin to the cells. Second, the pre- to post-fusion conformational change can be achieved by lowering the pH. Additionally, the HA1 part of the molecule can be removed by adding a reducing agent like DTT. In this way and by addition of the antibodies at specific stages, it is possible to investigate at what stage the antibody interferes with the infection process. Hereto, PER.C6® cells were transfected with an H3 HA expression construct harboring HA from A/Wisconsin/67/2005 and subjected to different treatments as described in Example 10.

For this experiment, cells were first incubated with anti-H3 mAbs before trypsin cleavage and subsequently treated as described above (see FIG. 5).

Figure 5:
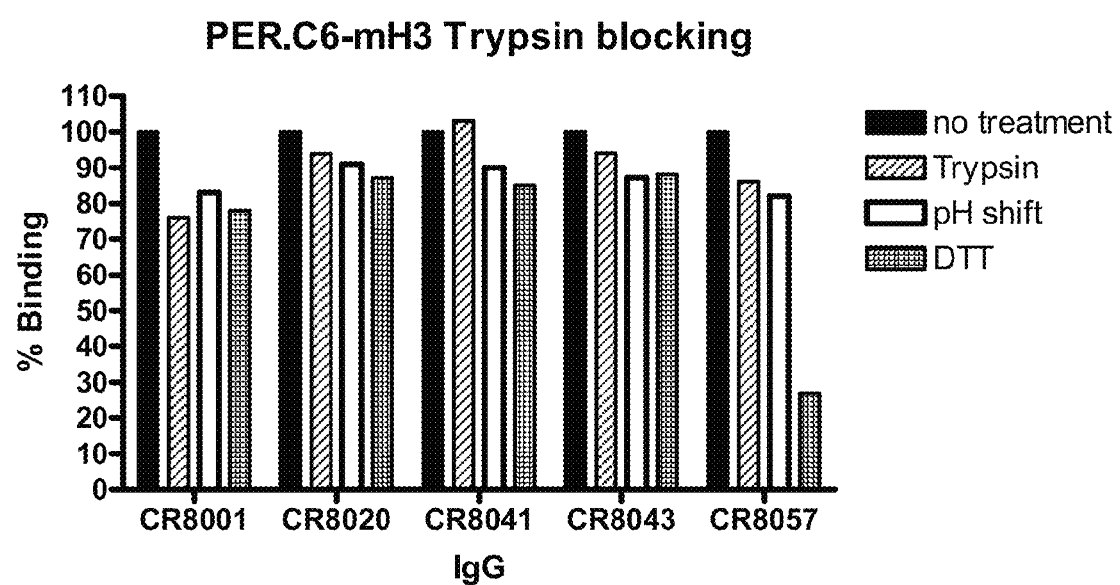
FIG. 5 is a bar diagram showing binding of the H3 mAbs to HA-expressing cells after different treatments measured by FACS analysis, after sequential treatment with trypsin (striped bars), pH 4.9 buffered medium (solid white bars) and DTT (crossed bars) and expressed as percentage binding to untreated rHA (solid black bars).

Binding of anti-H3 mAbs was detected with PE-conjugated anti-human antibody according to standard protocols. Fluorescence signals were measured by FACS analysis. "Cells only" means the signal obtained after mAb binding to untreated cells and was set at 100%. As can be seen in FIG. 5, the mAbs are still bound to HA following the different treatments. Since it was shown in Example 10 above that the H3 mAbs CR8020, CR8041 and CR8043 only bind to the pre-fusion state (i.e., before the conformational shift due to lower pH), it was concluded that binding of the antibody in fact inhibits the trypsin cleavage (see also Example 10), at least in vitro, and thus also the subsequent steps leading to the conformational change and fusion. Antibody CR8057, which binds the HA1 part of the HA molecule near the receptor attachment site is capable of binding to HA after conformational shift and, as expected, is lost when the HA1 part is removed following disruption of the disulphide bonds between HA1 and HA2 domains by DTT treatment.

Figure 6:
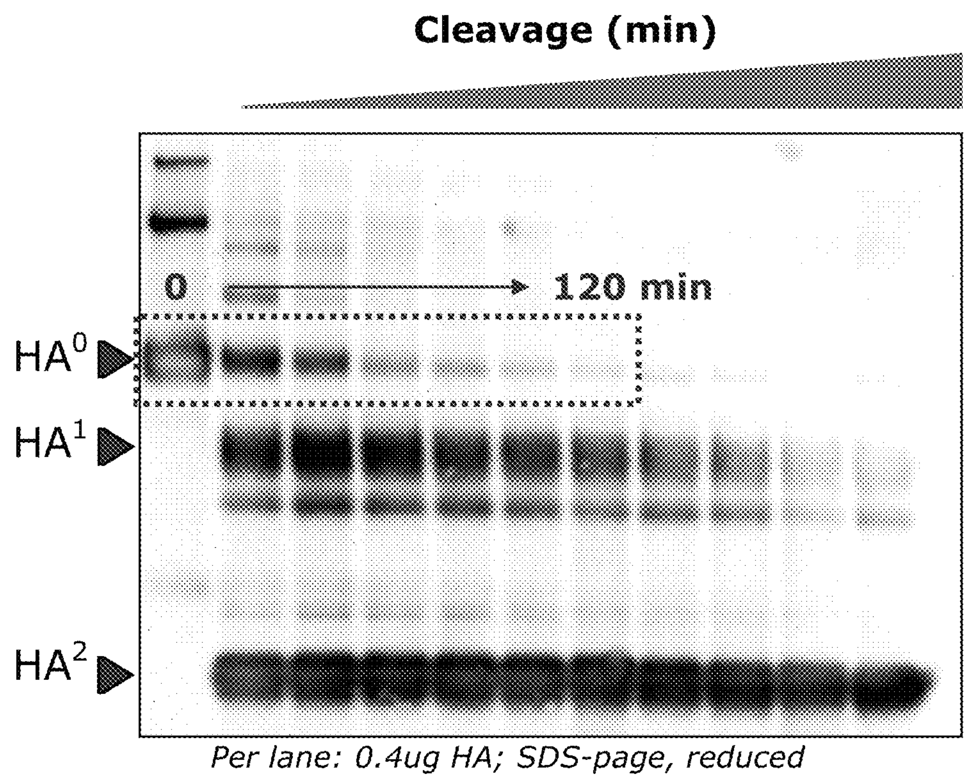
FIG. 6 shows the result of the time course experiment described in Example 11 to determine the incubation time of HA with trypsin to achieve cleavage of H3 HA.
Figure 7:
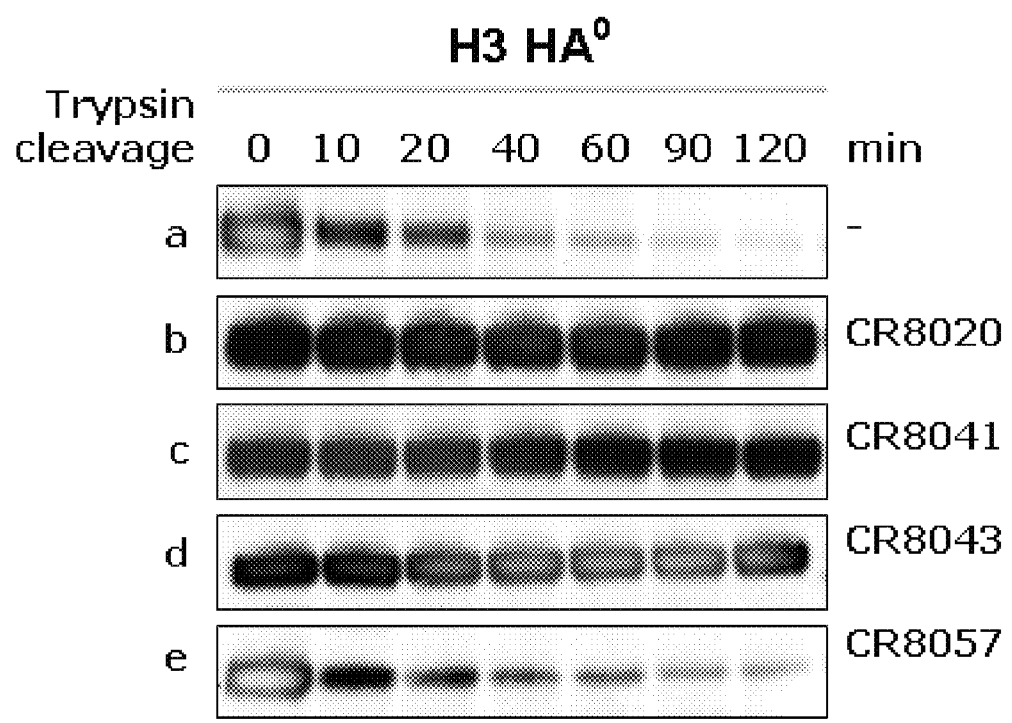
FIG. 7 shows the results of trypsin digestion of H3 HA samples pre-incubated with mAbs, as described in Example 11.

The inhibition of trypsin cleavage was subsequently confirmed in a different in vitro experiment. First, a time course experiment was done to determine how long H3 HA should be incubated with trypsin to achieve proper cleavage of HA0 in HA1 and HA2. Hereto, recombinant soluble H3 HA (A/Wisconsin/67/2005; Protein Sciences, CT, USA) was incubated in 4 mM Tris.HCl buffer at pH 8.0 containing 6.7 μg/ml Trypsin and 1% N-dodecyl-β-demaltosid. Trypsin digestion was stopped at several time points by addition of 1% BSA. Samples were run on SDS-page gel (reduced) and blotted according to standard methods. HA0, HA1 and HA2 bands were detected using a rabbit anti-H3HA polyclonal antibody (Protein Sciences, CT, USA). FIG. 6 shows that two hours' incubation is enough for near complete cleavage evidenced by appearance of the HA1 and HA2 bands on the reducing gel. Next, recombinant soluble H3 HA was incubated with either CR8020, CR8041, CR8043 or CR8057 and subsequently subjected to trypsin cleavage at pH 8.0. Trypsin digestion was again stopped at several time points by adding 1% BSA. Samples were run on SDS-page (reduced) and blotted. HA0, HA1 and HA2 bands were detected using an anti-H3 polyclonal antibody. The results show that all three mAbs CR8020, CR8041 and CR8043 prevent trypsin cleavage in vitro since incubation of the H3 HA bound to the antibody with trypsin results in protection of the HA0 form of HA on the gel (FIG. 7). In contrast, incubation of H3 HA with a control mAb (CR8057) at the same conditions results in disappearance of the HA0 band. This experiment confirms the data discussed in Example 10 for CR8041 and extends this observation to CR8020 and CR8043 antibodies. The binding molecules hereof thus prevent at least trypsin cleavage of the HA0 molecule, at least in vitro. It is, however, noted that this does not exclude that additional inhibitory effects are also mediated by the CR8020, CR8041 and CR8043 mAbs that are more downstream in the process of infection and result in interference with the pH-induced conformational shift and/or fusion process.

Figure 8:
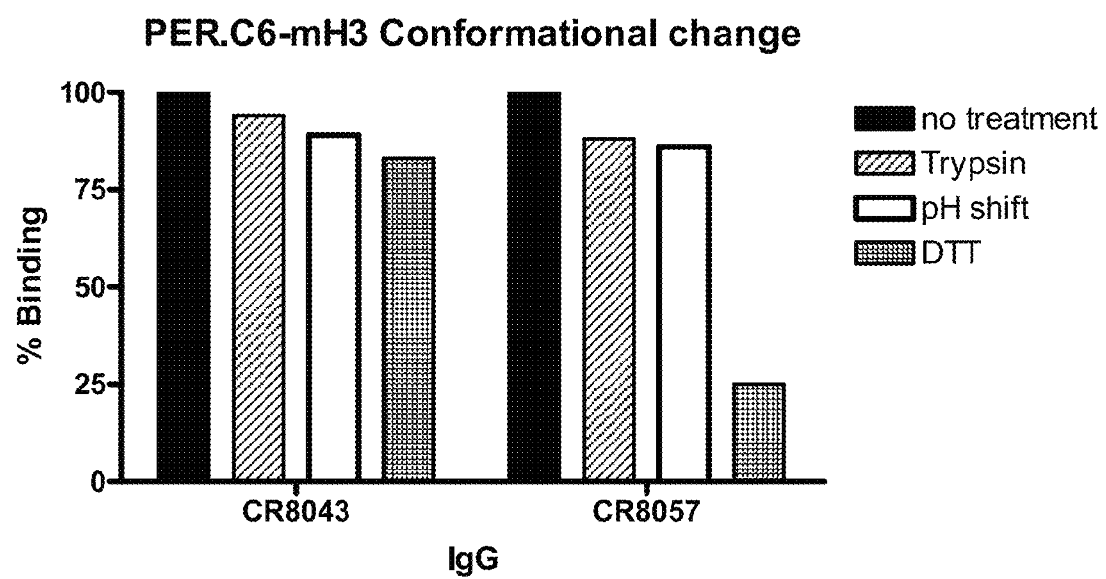
FIG. 8 is a bar diagram demonstrating that CR8043 inhibits pH-induced conformational change in H3 HA.

To investigate whether this could be the case, the experiment discussed above was repeated, but now the antibody CR8043, or the antibody CR8057 as a control, was added to the cells expressing H3 HA only after trypsin cleavage. Following incubation, the cells were subsequently incubated in low pH buffer as described in Example 10 and treated with DTT as described. If the mechanism of action would be restricted to inhibition of trypsin cleavage, it is expected that the mAb CR8043 loses binding after pH treatment since we have established in Example 10 that the antibodies do not bind to the post-fusion conformation of HA. In contrast, as can be seen from FIG. 8, mAb CR8043 binding is still detected after exposure to low pH and subsequent DTT treatment indicating that the pH-induced conformational shift is also inhibited by CR8043, at least in vitro. CR8057, which has been shown to bind to the HA1 region of HA, behaves as expected and is no longer detectable when the HA1 part is lost following DTT treatment.

To investigate whether antibodies CR8020 and CR8041 are also capable of blocking the pH-induced conformational change of HA, the experiments discussed above were repeated. Now the antibodies CR8020, CR8041 and CR8043, or the antibody CR8057 as a control, were added to cells expressing either A/Hong Kong/1/1968, A/Hong Kong/24/1985 or A/Wisconsin/67/2005 subtype H3 HA, either after all treatments described in above, before low pH incubation or before trypsin cleavage.

Figure 9:
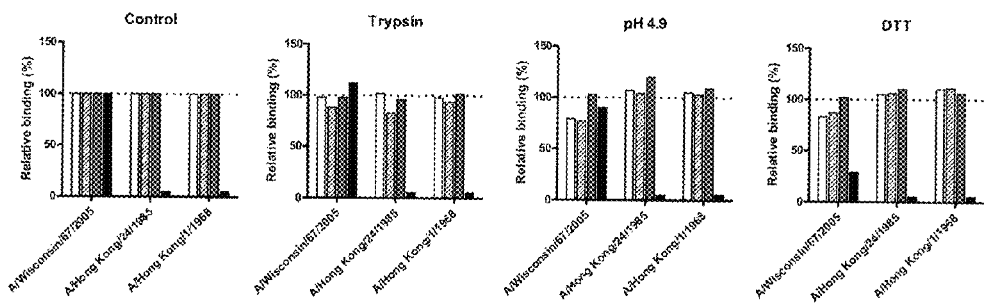
FIG. 9 shows that CR8020 and CR8041 are also capable of blocking the pH-induced conformational change of HA: Panel A. mAbs added before Trypsin cleavage; Panel B. mAbs added after trypsin cleavage; Panel C. mAbs added after all treatments.
Figure 9:
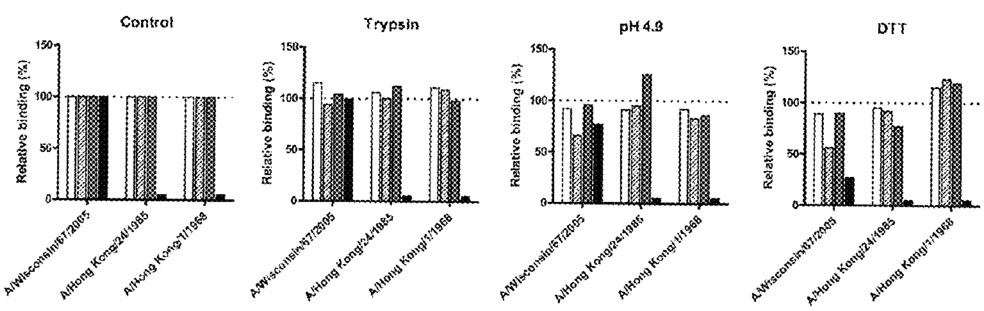
Figure 9:
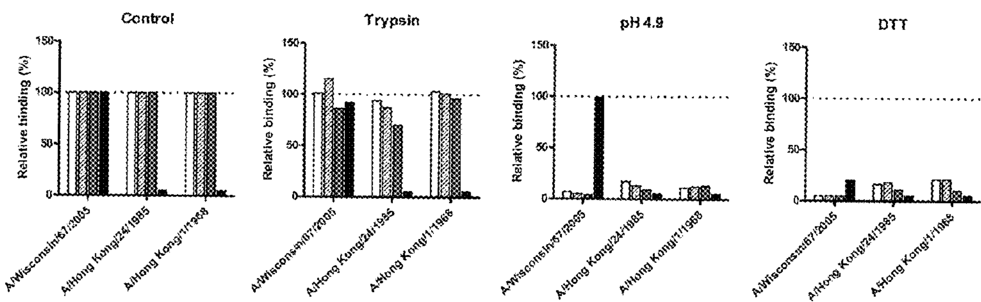

As shown earlier for A/Wisconsin/67/2005 H3 HA, the CR8020, CR8041 and CR8043 antibodies recognize an epitope present only before low pH treatment. This epitope is conserved in the three HAs used in this experiment as can be seen in FIG. 9, Panel C.

If the mechanism of action would be restricted to inhibition of trypsin cleavage, it is expected that the mAbs CR8020, CR8041 and CR8043 lose binding of already cleaved HA after pH treatment since we have established in Example 10 that the antibodies do not bind to the post-fusion conformation of HA. In contrast, as can be seen from FIG. 9, Panel B, mAb binding is still detected after exposure to low pH and subsequent DTT treatment on all three different H3 HAs indicating that the pH-induced conformational shift is also inhibited by CR8020, CR8041 and CR8043, at least in vitro. CR8057, which has been shown to bind to the highly variable HA1 region of HA, shows no binding to A/Hong Kong/1/1968 and A/Hong Kong/24/1985 HAs.

Example 12

In Vitro-Generated Escape Mutants Indicate that the Position of the Epitope Coincides with a Conserved Sequence in H3 HA To investigate to which region in HA CR8020, CR8041 and CR8043 binds, it was attempted to generate escape mutants in in vitro cultures. A/Hong Kong/1/1968 viruses were passaged in MDCK cell cultures in the presence of limiting amounts of monoclonal antibodies. First, it was determined what concentration of antibody resulted in a 3 log reduction of virus infection following inoculation of MDCK cells with 100 TCID50 units mixed with different amounts of monoclonal antibody and incubation for three days. This concentration of antibody was added to the inoculum in serial passages and after each passage, the virus was plaque titrated in the absence and presence of different amounts of antibody to determine whether the viruses are still sensitive to antibody-mediated neutralization. This procedure was followed for each of the mAbs CR8020, CR8041 and CR8043. From each culture, escape viruses could be isolated by plaque assay and, of two isolates of each, viral RNA was extracted and used to determine the HA sequence. The observed mutated amino acids were as follows:

CR8020: D19N and Q27L in both analyzed plaques;
CR8041: G33E in two plaques;
CR8043: R25M in one and Q34R in the other plaque.

All three monoclonal antibodies show escape mutations in a similar domain in the HA2 part of the HA stem region adjacent to the fusion peptide. Comparison of amino acid sequences of H3N2 viruses present in the NCBI influenza database (on the World Wide Web at ncbi.nlm.nih.gov/genomes/FLU/Database/select.cgi) in this region reveals a striking conservation of the sequence. Table 14 depicts the sequence variation in the HA2 region between amino acids W14 and K39 with the observed escape mutations highlighted. N=number of strains having a specific sequence. In addition, the year of isolation (years) is indicated as well as the strains tested positive in neutralization experiments with the H3 antibodies (Pa=A/Panama/2000/1999; Wis=A/Wisconsin/67/2005; Hs=A/Hiroshima/52/2005; HK=A/Hong-Kong/1/1968). Of the 1363 H3 viruses present in the database that contained the mentioned HA2 sequence, the majority (81%) had sequences that are present in virus strains that were shown to be neutralized. Of the remaining sequences, most have amino acids that can be considered conserved changes. For the other mutations, a functional neutralization test will be needed to establish whether the change affects the functionality of the antibody. Importantly, three amino acid changes that came up in the escape virus experiment (R25, G33 and Q34) do not occur in natural influenza sequences and the other two mutations appeared only in combination (D19 and Q27), a combination that is also not present in the natural sequences. This could mean that the mutations have a negative effect on the virus fitness. Altogether, it is concluded that the antibodies interact with an epitope on HA2 that is highly conserved between H3 subtype viruses confirming the broad neutralization capability of the monoclonal antibodies.

Example 13

Preparation of Monoclonal Antibodies for In Vivo Experiments

To enable characterization and the subsequent validation of the IgGs as potential therapeutic antibodies in vivo, they need to be manufactured and purified in sufficient quantities. The IgGs were produced in PER.C6® cells in a 25 L Wave-bag and the culture was harvested. From the clarified harvest, IgG was purified using Protein A affinity chromatography and a buffer exchange step. The monomer content of the purified buffer exchanged IgG is ~99% both before and after 0.2 μm sterile filtration. Additional in vitro virus neutralization assays (VNA) were performed with the different antibody preparations obtained, as described above. The results are shown in Table 15.

Example 14

Prophylactic Activity of Human IgG Monoclonal Antibodies Against Lethal H3N2 Challenge In Vivo MAbs CR8020, CR8041 and CR8043 were tested for prophylactic efficacy in a mouse lethal challenge model with influenza A/HK/1/68-MA20 (H3N2) virus in female 129X1/SvJ mice (Jackson Labs) (MA=mouse adapted). A/HK/1/68-MA20 virus was obtained from Prof. E. G. Brown, University of Ottawa, Ottawa, Ontario, Canada; E. G. Brown et al. (2001). The virus was passaged once in embryonated chicken eggs before use in the mice experiments. All mice were acclimatized and maintained for a period of at least four days prior to the start of the experiment.

MAbs were intravenously dosed at 30, 10, 3 and 1 mg/kg in the tail vein (vena coccygeus) at day −1 before challenge, assuming an average weight of 18 g per mouse and a fixed dose volume of 0.2 mL. The mice (n=8 per group) were then challenged at day 0 with 25 LD50 A/HK/1/68-MA20 (H3N2) virus by intranasal inoculation. The actual dose of the virus administered was estimated by titrating a few replicate samples from the inoculum remaining after inoculation of the animals was completed. Virus titers (TCID50/mL) of the inoculum were determined on MDCK cells. The results showed that no inactivation of virus had unintentionally occurred during preparation or administration of the inoculum. Clinical signs and body weights were determined daily from day −1 before challenge until the end of the study at day 21. Clinical signs were scored with a scoring system (0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back). At a score of 4, the animal was euthanized. To analyze mAb plasma levels at day 0 and determine the presence of hemagglutination-inhibiting (HI) antibodies at day 21, blood samples were drawn from all mice on D0, just before challenge, and on D21 post-infection.

The mAbs were tested in two separate experiments. In each experiment, a negative control antibody (CR3014) group was taken along, dosed at 30 mg/kg. MAb CR8020 was tested in the first experiment; mAbs CR8041 and CR8043 in the second.

Figure 10:
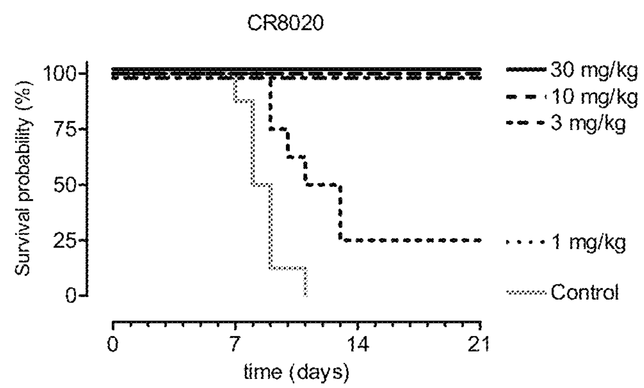
FIG. 10 shows the Kaplan-Meier survival probability curves. Antibody was administered intravenously at day −1 before challenge using a dose range from 30 down to 1 mg/kg. Control Ab was administered at 30 mg/kg (grey), followed by a lethal challenge at day 0 with 25 LD50 A/HK/1/68-MA20 (H3N2). CR8020 (A) was tested in a separate study from CR8041 (B) and CR8043 (C), which were evaluated in one experiment. Therefore, the same control antibody group is used for B and C.
Figure 10:
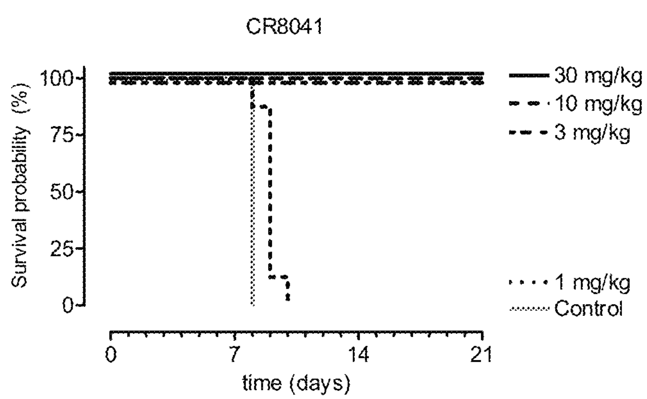
Figure 10:
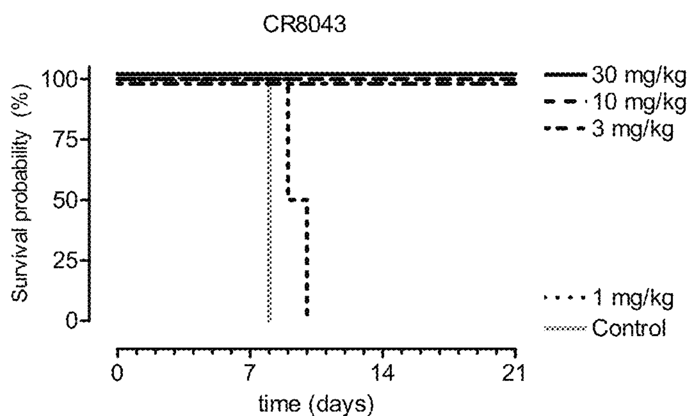

All mice were active and appeared healthy without showing signs of disease during the acclimatization period. FIG. 10 shows the survival rates of the mice following mAb administration. A clear dose-response relationship was observed, with all groups dosed with CR8020, CR8041 or CR8043 at 30, 10 or 3 mg/kg showing 100% survival, whereas at 1 mg/kg CR8020, 25% of the mice survived and none of the mice survived in the 1 mg/kg CR8041 and CR8043 groups. The two control mAb groups showed 0% survival. In the first experiment, administration of mAb CR8020 resulted in a statistically significant difference in survival time at all four concentrations tested, compared to the control group ($p<0.005$; Log Rank Test). In the second experiment, administration of mAbs CR8041 and CR8043 also resulted in a statistically significant difference in survival time at all four concentrations tested, compared to the control group ($p<0.001$ for both mAbs; Log Rank Test).

Figure 11:
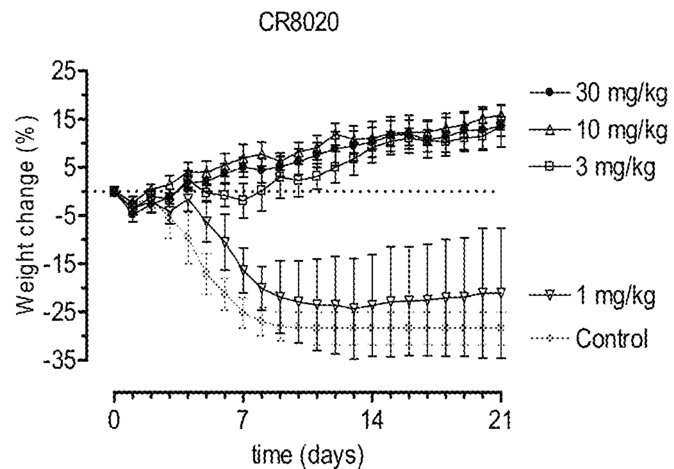
FIG. 11 shows the mean body weight change (%) relative to day 0. Antibody was administered intravenously at day −1 before challenge using a dose range from 30 down to 1 mg/kg. Control Ab was administered at 30 mg/kg (grey), followed by a lethal challenge at day 0 with 25 LD50 A/HK/1/68-MA20 (H3N2). Bars represent the 95% CI of the mean. If a mouse died or was euthanized during follow-up of the study, the last observed body weight was carried forward. CR8020 (A) was tested in a separate study from CR8041 (B) and CR8043 (C), which were evaluated in one experiment. Therefore, the same control antibody group is used for B and C.
Figure 11:
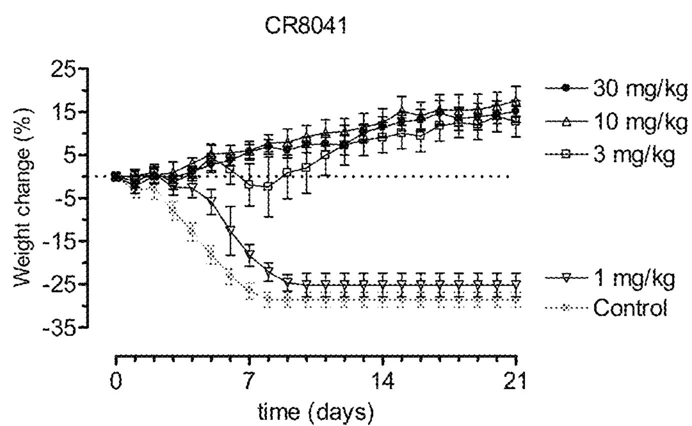
Figure 11:
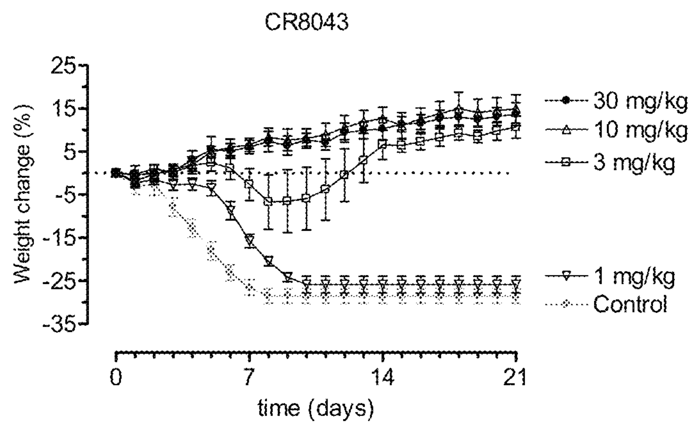

In FIG. 11, the mean body weight change of the mice during the 21-day study period following mAb administration is shown. Like with the survival rates, there is a clear inverse relationship between the weight loss and dose of antibody used. When the concentration of antibody was increased, the weight loss decreased: mice in groups dosed with CR8020, CR8041 or CR8043 at 30, 10 or 3 mg/kg showed an increase in mean body weight of approximately 10-15% from day 0 to day 21, consistent with age-related weight gain, whereas in the 1-mg/kg groups and in the control mAb groups, the mean body weight of the mice declined in the study period.

Body weight changes were analyzed in more detail with Area under the Curve (AUC) analysis. For the purpose of this analysis, the last observed body weight was carried forward to day 21 if a mouse died or was euthanized during follow-up of the study. Briefly, the weight per mouse at day 0 was used as baseline value and weight change from day 0 to day 21 was determined relative to baseline. The AUC was defined as the summation of the area above and the area below the baseline. Mean AUC values of the mAb dose groups were compared with the respective control groups using analysis of variance with Dunnet's adjustment for multiple comparisons (Table 16).

The analysis showed that the mean AUC of the 3-, 10- and 30-mg/kg groups from CR8020, CR8041 and CR8043 differed statistically significantly ($P<0.001$) from that of the corresponding control groups (Table 16). Both for the CR8041 as well as for the CR8043 1-mg/kg dose groups, a statistically significant difference was found when compared to the control group ($p=0.004$ and $p<0.001$ respectively). However, due to the two surviving mice in the CR8020 1-mg/kg dose groups, an increase in variation of body weight was observed and, therefore, no statistical significant difference could be demonstrated when compared to the control group.

Additional analysis was performed to investigate a dose response in the reduction of weight loss by comparing mean AUC values per antibody concentration for each antibody using analysis of variance with Tukey's adjustment for multiple comparisons (Table 16). Both for mAbs CR8020 and CR8041, the body weight loss in the 1-mg/kg groups is statistically significantly higher ($p<0.001$) than in the respective 3-mg/kg groups, whereas there is no statistically significant difference between the 3-, 10- and 30-mg/kg groups ($p>0.05$). For mAb CR8043, both the weight loss in the 1-mg/kg group was statistically significantly higher than in the 3-mg/kg group ($p<0.001$) and that of the 3-mg/kg group was significantly higher than that of the 10-mg/kg group ($p<0.001$). The mean AUC of the 10- and 30-mg/kg groups of CR8043 did not significantly differ ($p=0.997$).

Figure 12:
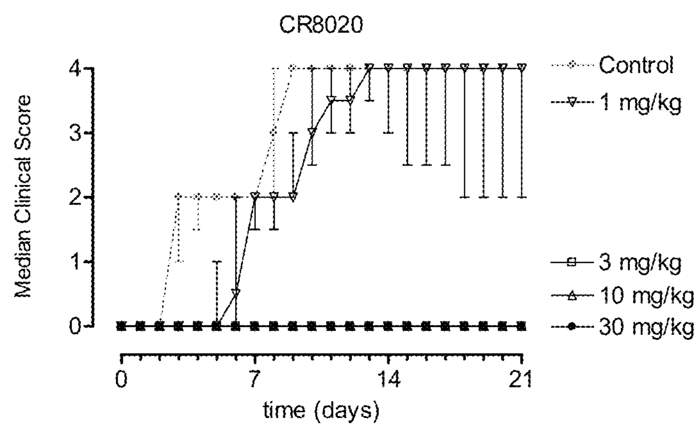
FIG. 12 shows the median clinical score. Antibody was administered intravenously at day −1 before challenge using a dose range from 30 down to 1 mg/kg. Control Ab was administered at 30 mg/kg (grey), followed by a lethal challenge at day 0 with 25 LD50 A/HK1/68-MA20 (H3N2). Bars represent interquartile ranges. CR8020 (A) was tested in a separate study from CR8041 (B) and CR8043 (C), which were evaluated in one experiment. Therefore, the same control antibody group is used for B and C. Clinical score explanation: 0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back. Mice observed with clinical score 4 were euthanized on the same day.
Figure 12:
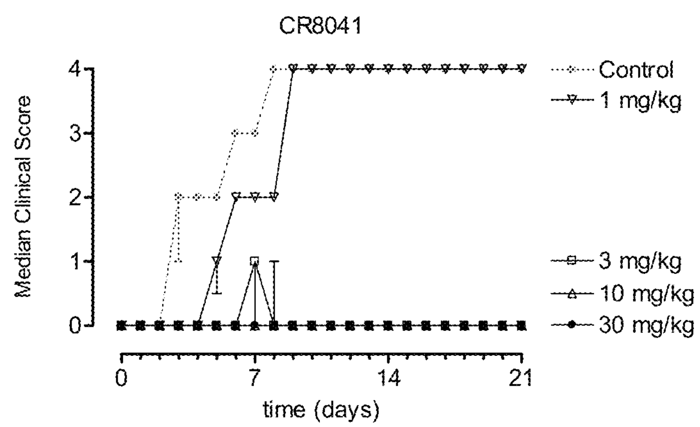
Figure 12:
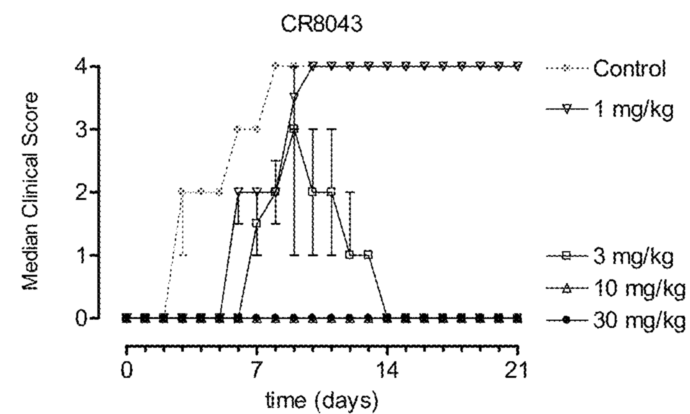

Median clinical scores of the mice are depicted in FIG. 12. The mice dosed with CR8020, CR8041 or CR8043 at 30 and 10 mg/kg did not show any clinical signs, as indicated by a median clinical score of 0 throughout the 21-day study period of the two studies. MAb 8020 also showed no clinical score in the 3-mg/kg dose group, whereas in the 3-mg/kg dose groups of mAb 8041 and 8043, increases in clinical score were observed to a median score of 1 and 3, respectively. In the 1-mg/kg dose groups of all three mAbs, clinical scores were increased reaching a median score of 4 in all groups. Mice observed with clinical score 4 were euthanized on the same day. The two surviving mice in the CR8020 1-mg/kg dose group became ill at day 7 of the study and showed a maximum clinical score of 1 and 3, respectively. Both mice recovered completely. Of the CR8041 and CR8043 3-mg/kg dose groups, the body weight loss profile shows a similar pattern as the clinical score profile.

These results show that at least three human anti-H3N2 antibodies, identified and developed as disclosed herein (CR8020, CR8041 and CR8043), are each separately able to provide protection against a lethal dose of influenza H3N2 in vivo. A clear dose-response relationship between the amount of each antibody administered and survival rate was observed. The results show that anti-H3N2 IgG antibody CR8041 and 8043 were able to prevent clinical manifestation of H3N2 infection in mice when administered one day prior to infection at a dose of 10 mg/kg or higher. MAb CR8020 was able to prevent clinical manifestation of H3N2 infection in mice when administered one day prior to infection at a dose of 3 mg/kg or higher.

Example 15

Protective and Therapeutic Activity of Human IgG Monoclonal Antibodies Against Lethal H3N2 Challenge In Vivo A study was performed to test the therapeutic effect of the monoclonal antibodies as disclosed herein, exemplified by CR8020, in a post-infection model, against a lethal H3N2 A/HK/1/68-MA20 influenza virus challenge in vivo.

Mice (n=10 per group) were intravenously dosed with mAb CR8020 at 15 mg/kg in the tail vein (vena coccygeus) at day −1 before challenge (group 1; prophylaxis positive control) or at day 1, 2, 3, 4, 5 or 6 after challenge (groups 2-7), assuming an average weight of 18 g per mouse and a fixed dose volume of 0.2 mL. Group 8 received negative control mAb CR3014 (15 mg/kg) at day 1 after challenge. The mice were challenged at day 0 with 25 LD50 (2.8 log TCID50) A/HK/1/68-MA20 (H3N2) virus by intranasal inoculation. The virus batch, type, and age of mice were the same as used in Example 14. Clinical signs and body weights were determined daily from day −1 before challenge until the end of the study at day 21.

Figure 13:
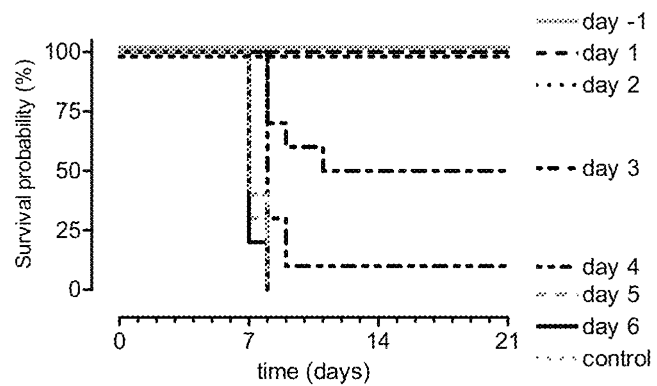
FIG. 13 demonstrates the therapeutic efficacy of mAb CR8020 in the mouse lethal challenge model with influenza A/HK/1/68-MA20 (H3N2). A single dose of mAb CR8020 (15 mg/kg) was administered intravenously either at day −1 pre-challenge or at day 1, 2, 3, 4, 5, or 6 post-challenge in 129X1/SvJ mice (n=10/group). Control mAb (15 mg/kg) was administered at day 1 post-challenge. Mice were challenged at day 0 with 25 LD50 A/HK/1/68-MA20 (H3N2) and monitored for 21 days. Panel A: Kaplan-Meier survival probability curves. Panel B: Mean body weight change (%) relative to day 0. Bars represent the 95% CI of the mean. If a mouse died or was euthanized during follow-up of the study, the last observed body weight was carried forward. Panel C: Median clinical score. Bars represent interquartile ranges. 0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back. Mice observed with clinical score 4 were euthanized on the same day.
Figure 13:
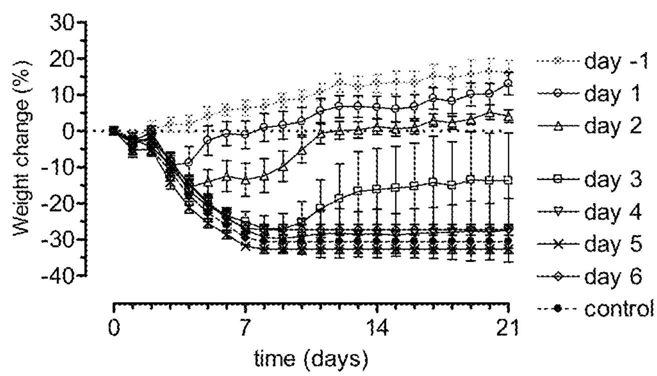
Figure 13:
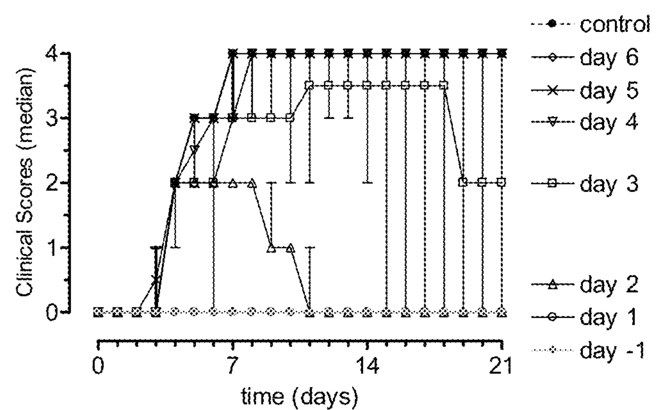

FIG. 13, Panel A, shows the survival rates of the mice following intravenous administration of mAb CR8020 (15 mg/kg in all groups) or control mAb (15 mg/kg). When 15 mg/kg mAb CR8020 was administered at day −1 pre-challenge or day 1 or 2 post-challenge, all animals survived the viral challenge, whereas the survival rate in the control mAb group was 0%. When 15 mg/kg mAb CR8020 was administered at day 3 or 4 after challenge, 50% and 10% survival was observed, respectively. The survival time of each of these groups was statistically significantly different compared to the control group (day 3 group, $p<0.001$, and day 4 group, $p=0.002$; Log Rank Test). Groups treated with 15 mg/kg CR8020 at day 5 or 6 showed a survival rate of 0%. There was no statistically significant difference in survival time of the day 5 or 6 treated groups compared to the control group ($p=0.648$ and $p=0.342$, respectively; Log Rank Test).

In FIG. 13, Panel B, the mean body weight change relative to day 0 of the mice during the 21-day study period is shown. Like with the survival rates, there is a clear relationship between weight loss and time of 15 mg/kg mAb CR8020 administration; when treatment with 15 mg/kg mAb CR8020 is administered at later time points, the weight loss increased.

Body weight changes were statistically analyzed in more detail using Area under the Curve (AUC) analysis (Table 17). For area under the curve analysis, the last observed body weight was carried forward to day 21 if a mouse died or was euthanized during follow-up of the study. Briefly, the weight per mouse at day 0 was used as baseline value and weight change from day 0 to day 21 was determined relative to baseline. The AUC was defined as the summation of the area above and the area below the baseline.

Median clinical scores of the mice are depicted in FIG. 13, Panel C. Of the mice treated with 15 mg/kg CR8020 at day −1 pre-challenge, all survived and none showed any clinical signs during the observation period. Mice treated with 15 mg/kg CR8020 at day 1 post-challenge showed a 100% survival, however, four out of ten animals showed clinical signs, reaching a maximum clinical score between 1 and 3. Of the animals treated with 15 mg/kg CR8020 at day 2 post-challenge, all survived. However, nine out of ten animals showed clinical signs reaching a maximum clinical score of 2 or 3. Animals treated with 15 mg/kg CR8020 at day 3 post-challenge showed a 50% survival. Of the survivors (n=5), all animals showed clinical signs with a maximum clinical score of 3. Of the animals treated with 15 mg/kg CR8020 at day 4 post-challenge, all, but one mouse died. The surviving mouse showed clinical signs reaching a maximum clinical score of 2. All mice that survived across the treatment arms were free from symptoms at day 21.

Clinical scores were analyzed using the GENMOD procedure (SAS) to fit a model for repeated measures with mice as subjects and data measured on an ordinal scale (Table 18). Since the curves do have different patterns, the variable "day" was entered as a class variable in this model. From the groups treated with 15 mg/kg mAb CR8020 at day −1 before challenge and days 1 and 2 post-challenge in which 100% of the mice survived, the median clinical score was significantly different from the control mAb group during most of the study period of 21 days ($p\leq0.001$ for all three groups). From the groups treated with 15 mg/kg mAb CR8020 at day 3 or day 4 post-challenge in which, respectively, 50% and 10% of the mice survived, the median clinical score was also significantly different from the control mAb group during most of the study period of 21 days ($p<0.05$ for both groups). From the groups treated with 15 mg/kg mAb CR8020 at day 5 or day 6 post-challenge, the median clinical score was significantly different from the control mAb group at day 3 only ($p\leq 0.001$). This difference, although statistically significant, is not considered relevant.

In conclusion, therapy with 15 mg/kg of mAb CR8020 provides 100% protection up to day 2 after challenge in a lethal H3N2 mouse model. When administered at day 3 or day 4 after challenge, treatment with 15 mg/kg mAb CR8020 provides partial protection. When administered at day 5 or day 6 after challenge, no protective effect of 15 mg/kg mAb CR8020 was observed in the lethal H3N2 mouse model.

These results show that a post-infection treatment with a monoclonal antibody directed against H3N2 influenza virus, as disclosed herein and exemplified by antibody CR8020, can rescue mammalian subjects, as showed herein in mice, after challenge with a lethal dose of H3N2 influenza virus. Even at a late stage, i.e., four days post-infection, the antibody is able to partially protect mice from lethal infection with influenza H3N2 virus. Strikingly, at day 21 post-infection, all surviving antibody-treated animals reached normal body weight levels and did not show any remaining clinical signs.

Example 16

Prophylactic Activity of Human IgG Monoclonal Antibodies Against Lethal H7N7 Challenge in Vivo A study was performed to test the prophylactic effect of the monoclonal antibodies as disclosed herein, exemplified by CR8020, against a lethal challenge with H7N7 influenza virus in vivo. MAb CR8020 was tested for prophylactic efficacy in a mouse lethal challenge model with mouse-adapted influenza A/Chicken/Netherlands/621557/2003 (H7N7) virus (Central Veterinary Institute (CVI), Lelystad, The Netherlands). The A/CH/NL/621557/03 (H7N7) virus was adapted to mice after three lung-to-lung passages. The mouse-adapted H7N7 Passage 3 virus was propagated in embryonated chicken eggs in CVI's laboratory. All mice (Balb/c, female, age six to eight weeks, n=8 per group) were acclimatized and maintained for a period of at least four days prior to the start of the experiment. MAb CR8020 was intravenously dosed at 30, 10, 3 or 1 mg/kg in the tail vein (vena coccygeus) at day −1 before challenge, assuming an average weight of 18 g per mouse and a fixed dose volume of 0.2 mL. A control group was taken along and dosed with 30 mg/kg negative control mAb CR3014. The mice were then challenged at day 0 with 25 $LD_{50}$ A/CH/NL/621557/03 (H7N7) virus by intranasal inoculation. The actual dose of the virus administered was estimated by titrating a few replicate samples from the inoculum remaining after inoculation of the animals was completed. Virus titers ($TCID_{50}$/mL) of the inoculum were determined on MDCK cells. Clinical signs and body weights were determined daily from day −1 before challenge until the end of the study at day 21 in the same manner as described in Example 14. To analyze mAb plasma levels at day 0 and determine the presence of hemagglutination-inhibiting (HI) antibodies at day 21, blood samples were drawn from all mice on D0, just before challenge, and on D21 post-infection.

Figure 14:
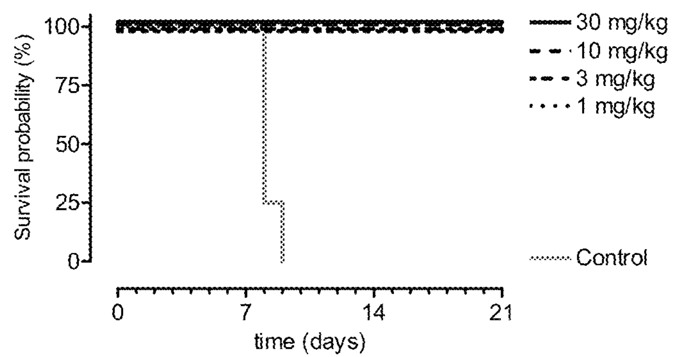
FIG. 14 shows the prophylactic efficacy of mAb CR8020 in the mouse lethal challenge model with mouse-adapted influenza A/CH/NL/621557/03 (H7N7). Panel A: Kaplan-Meier survival probability curves. Panel B: Mean body weight change (%) relative to day 0. Bars represent the 95% CI of the mean. If a mouse died or was euthanized during follow-up of the study, the last observed body weight was carried forward. Panel C: Median clinical score. Bars represent interquartile ranges. 0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back. Mice observed with clinical score 4 were euthanized on the same day.
Figure 14:
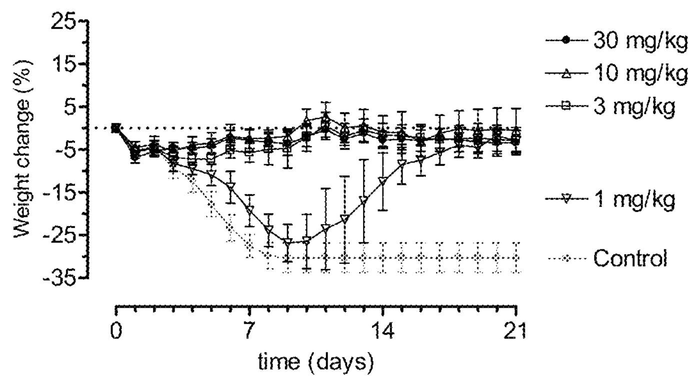
Figure 14:
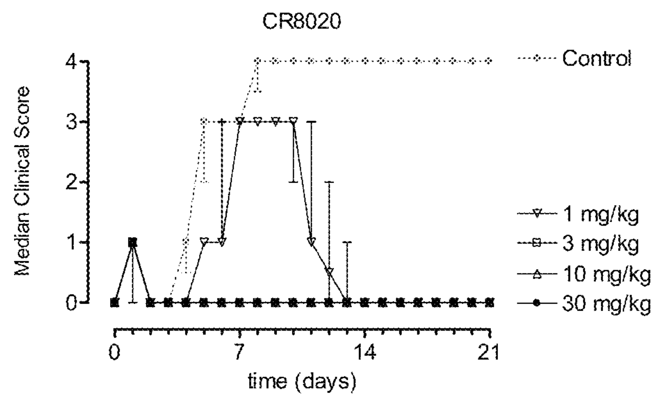

All mice were active and appeared healthy without showing signs of disease during the acclimatization period. FIG. 14, Panel A, shows the survival rates of the mice, following mAb administration. Mice dosed with 1 mg/kg mAb CR8020 or more showed a survival rate of 100%, whereas in the control mAb group, 0% survived.

In FIG. 14, Panel B, the mean body weight change of the mice during the 21-day study period following mAb administration is shown. In the mAb CR8020 3-, 10- and 30-mg/kg groups, the mice did not lose weight over the 21-day study period, whereas in the mAb CR8020 1-mg/kg and control mAb groups, weight loss was observed, with the mean body weight of the mice in the mAb CR8020 1-mg/kg group recovering to baseline level at day 21. Body weight changes were analyzed in more detail with Area under the Curve (AUC) analysis (Table 19). For area under the curve analysis, the last observed body weight was carried forward to day 21 if a mouse died or was euthanized during follow-up of the study. Briefly, the weight per mouse at day 0 was used as baseline value and weight change from day 0 to day 21 was determined relative to baseline. The AUC was defined as the summation of the area above and the area below the baseline.

There is a clear inverse relationship between the weight loss and dose of antibody used. When the concentration of antibody was increased, the weight loss decreased. The mean difference in weight loss, as compared to the control mAb, was 47.44, 79.75, 86.71 and 80.48 g*day in the mAb CR8020 1-, 3-, 10- and 30-mg/kg groups, respectively. All differences were statistically significant ($p<0.001$).

Median clinical scores of the mice are depicted in FIG. 14, Panel C. All, except one or two, animals within each group showed clinical signs (score=1) at day 1 post-challenge. This is probably not related to the viral challenge, since a non-challenged group taken along in the study showed a similar effect at day 1 (data not shown).

Of the mice treated with 3, 10 or 30 mg/kg mAb CR8020 at day −1 pre-challenge, all survived and none of the animals showed any clinical signs during the observation period (from day 2 to day 21 post-infection). Mice treated with 1 mg/kg mAb CR8020 at day −1 pre-challenge, showed a 100% survival rate, but all eight mice showed clinical signs reaching a maximum clinical score of 3.

These results show that human anti-H3N2 antibody CR8020, identified and developed as disclosed herein (CR8020), is able to provide heterosubtypic protection against a lethal dose of influenza H7N7 in vivo. When administered one day prior to infection at a dose of 3 mg/kg or higher, mAb CR8020 was able to completely prevent clinical manifestation of H7N7 infection in mice. At a dose of 1 mg/kg CR8020 administered one day prior to infection, all mice survived the lethal challenge, and the body weight loss and clinical signs observed fully resolved at the end of the 21-day study period.

A second study was performed to assess and compare the prophylactic efficacy of mAb CR8020, CR8041 and CR8043 in the H7N7 mouse model. MAb CR8020, CR8041 and CR8043 (produced in PER.C6® cells) were tested for prophylactic efficacy in the mouse lethal challenge model with mouse-adapted influenza A/Chicken/Netherlands/621557/2003 (H7N7) virus (Central Veterinary Institute (CVI), Lelystad, The Netherlands). Briefly, all mice (Balb/c, female, age six to eight weeks, n=8 per group) were acclimatized and maintained for a period of at least four days prior to the start of the experiment. MAb CR8020 was intravenously dosed at 10, 3 or 1 mg/kg in the tail vein (vena coccygeus) at day −1 before challenge, assuming an average weight of 18 g per mouse and a fixed dose volume of 0.2 mL. Mabs CR8041 and CR8043 were dosed in the same manner at 30, 10, 3 or 1 mg/kg. A control group was taken along and dosed with 30 mg/kg negative control mAb CR3014. After mAb administration, the mice were challenged at day 0 with 25 $LD_{50}$ mouse-adapted A/CH/NL/621557/03 (H7N7) virus by intranasal inoculation. Clinical signs and body weights were determined daily from day −1 before challenge until the end of the study at day 21.

Figure 15:
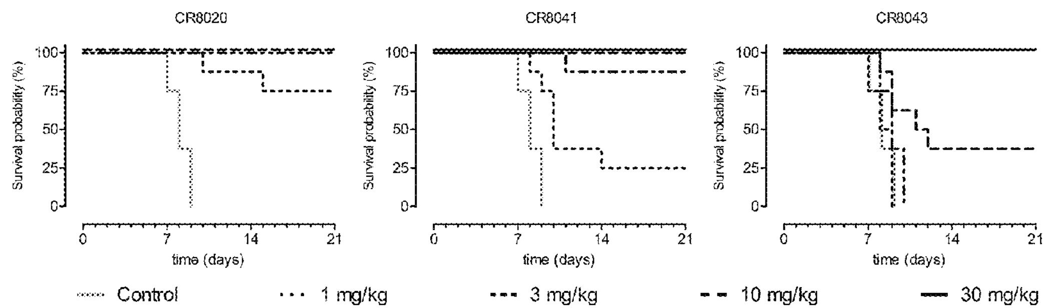
FIG. 15 shows the prophylactic efficacy of mAbs CR8020, CR8041 and CR8043 in the mouse lethal challenge model with mouse-adapted influenza A/CH/NL/621557/03 (H7N7). MAbs were administered intravenously at day −1 before challenge in female Balb/c mice (n=8/group) using a dose range from 10 down to 1 mg/kg (CR8020) or 30 down to 1 mg/kg (CR8041 and CR8043). Control mAb was administered at day −1 at 30 mg/kg (grey). At day 0, a lethal challenge was given by intranasal inoculation with 25 $LD_{50}$ mouse-adapted A/CH/NL/621557/03 (H7N7) and the mice were subsequently monitored for 21 days. Panel A: Kaplan-Meier survival probability curves. Panel B: Mean body weight change (%) relative to day 0. Bars represent the 95% CI of the mean. If a mouse died or was euthanized during follow-up of the study, the last observed body weight was carried forward. Panel C: Median Clinical score. Bars represent interquartile ranges. 0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back. Mice observed with clinical score 4 were euthanized on the same day.
Figure 15:
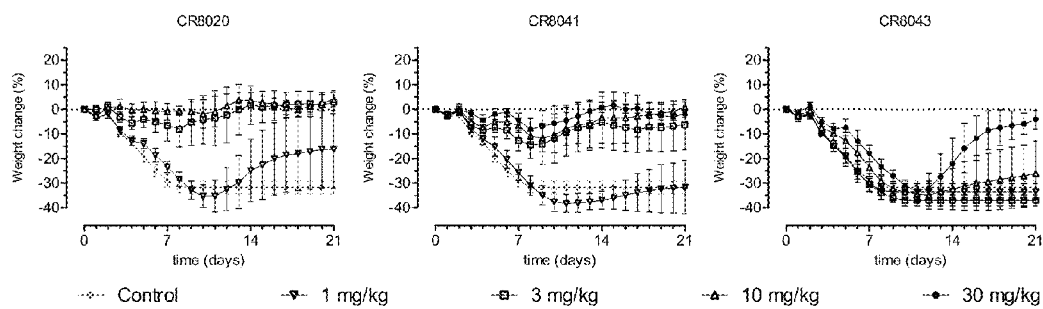
Figure 15:
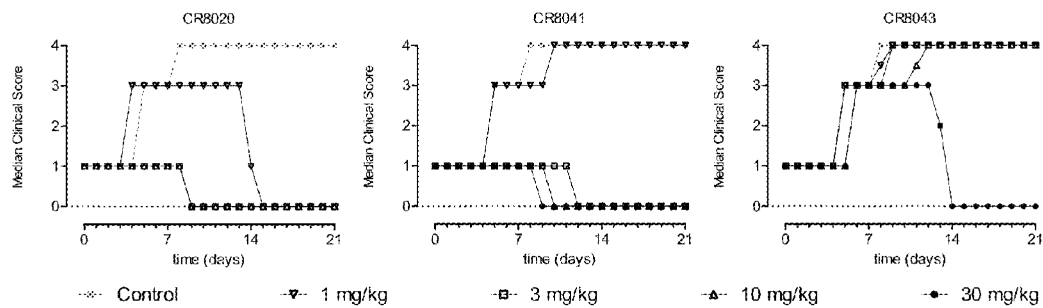

In FIG. 15, the survival rates, the percentage of body weight change and the clinical scores of the mice are depicted, following prophylactic administration of the mAbs. As shown in FIG. 15, Panel A, 100% survival was observed in the groups receiving 3 or 10 mg/kg CR8020, 10 or 30 mg/kg CR8041 and in the group receiving 30 mg/kg CR8043. In the control mAb group, the survival rate was 0%. Prophylactic administration of CR8020 at all three dose levels and CR8041 at all four dose levels provided a statistically significant improvement of survival time, compared to the control mAb group (log-rank, $p<0.002$). Prophylactic administration of 1 mg/kg of CR8043 did not result in a statistically significant improvement of survival time, compared to the control mAb group (log-rank, $p=0.692$). Increasing the CR8043 dose to 3 mg/kg or more, resulted in a statistically significant improvement of survival time, compared to the control mAb group (log-rank, $p\leq 0.034$).

In a post-hoc analysis, the survival times were compared of the lowest dose groups of mAbs CR8020, CR8041 and CR8043. Prophylactic administration of 1 mg/kg CR8020 resulted in a statistically significant improvement of survival time, compared to 1 mg/kg of CR8041 and 1 mg/kg of CR8043 (log-rank, respectively $p=0.029$ and $p<0.001$). In addition, prophylactic administration of 1 mg/kg CR8041 resulted in a statistically significant improvement of survival time when compared to 1 mg/kg CR8043 (log-rank, $p=0.004$).

In FIG. 15, Panel B, the mean body weight change of the mice during the 21-day study period following prophylactic administration of the mAbs is shown. In the mAb CR8020 and mAb CR8041 1-mg/kg groups, severe weight loss was observed comparable to that of the control mAb group. In the higher dose groups of mAb CR8020 and CR8041, weight loss during the 21-day study was limited or absent. In the groups dosed with mAb CR8043, severe weight loss was observed in all groups, with the mean body weight of the group dosed at 30 mg/kg recovering almost to the baseline level at day 21. Body weight changes were analyzed in more detail with Area under the Curve (AUC) analysis (Table 21). There is a clear inverse relationship between the weight loss and dose of antibody used. When the concentration of antibody was increased, the weight loss decreased. With 1 mg/kg of CR8020, there was no statistically significant reduction in weight loss compared to the control group ($p=0.356$). Increasing the dosing to 3 or 10 mg/kg resulted in a statistically significant reduction in weight loss, compared to the control group ($p<0.001$ in both cases). With 1 mg/kg of CR8041, there was no statistically significant reduction in weight loss compared to the control group ($p=1$).

Increasing the dosing to 3, 10 or 30 mg/kg CR8041 resulted in a statistically significant reduction in weight loss, compared to the control group ($p<0.001$ in all three cases). With 1, 3 or 10 mg/kg of CR8043, there was no statistically significant reduction in weight loss compared to the control group ($p=0.997$, 0.510 and 0.992, respectively). Increasing the dosing to 30 mg/kg resulted in a statistically significant reduction in weight loss, compared to the control group ($p<0.001$). In an additional analysis of the mean AUC of body weight change data, mAbs CR8020, CR8041 and CR8043 were compared using a univariate analysis of variance with antibody and doses included in the model as fixed factors. Since a dose of 30 mg/kg of CR8020 was not included in the study, the comparison was limited to antibody doses of 1, 3 and 10 mg/kg. Differences between antibodies were estimated by using marginal means with Sidak adjustment for multiple comparisons. Over the three doses of antibody considered, treatment with CR8020 resulted in a statistically significant improved reduction of weight loss compared to CR8041 and CR8043 (mean difference in marginal means of 23.73 and 68.29 g*day, respectively, $p=0.013$ and $p<0.001$). In addition, treatment with CR8041 resulted in a statistically significant improved reduction of weight loss when compared to CR8043 (difference in marginal means of 44.56 g*day, $p<0.001$).

Median clinical scores of the mice are depicted in FIG. 15, Panel C. All mice, except one at day 0 (3-mg/kg CR8020 group), showed clinical signs (score=1, rough coat)) from day 0-day 3. This increase was not observed in the acclimatization period and at day −1. The cause of this increased clinical score is not precisely clear. Of the groups treated with 3 or 10 mg/kg mAb CR8020 at day −1 pre-challenge, the median clinical score returned to 0 at day 9 post-challenge, whereas in the control group, the median clinical score reached 4 at day 8, with all mice dead or euthanized at day 9. The CR8020 1-mg/kg group showed a median clinical score of 3 from days 4-13, returning to score 0 at day 15. Of the groups treated with 3, 10 or 30 mg/kg mAb CR8041 at day −1 pre-challenge, the median clinical score returned to 0 at day 9, 10 or 12 post-challenge, respectively. The CR8041 1-mg/kg group reached a median clinical score of 4 at day 10 after challenge. Of the groups treated with 1, 3 or 10 mg/kg CR8043, the median clinical score reached 4 at day 9, 9 or 12, respectively, whereas the median clinical score of the 30-mg/kg CR8043 group reached 3 from days 6 to 13 and returned to 0 at day 14.

The above results clearly show that human anti-H3N2 antibodies CR8020, CR8041 and CR8043 are able to provide heterosubtypic protection against a lethal dose of influenza H7N7 in vivo. Mab CR8020 was found to be the most potent of the three mAbs against the mouse-adapted influenza A/CH/NL/621557/03 (H7N7) virus, based on the outcome of the post-hoc analyses of survival times and body weight change. At a dose of 3 or 10 mg/kg mAb CR8020 administered one day prior to infection, 100% of the mice survived the lethal challenge and clinical manifestation of the H7N7 infection was strongly reduced. At a dose of 1 mg/kg CR8020 administered one day prior to infection, 75% of the mice survived the lethal challenge in this experiment, and the clinical signs of the surviving mice resolved completely at day 15 of the 21-day study period.

Example 17

Therapeutic Activity of Human IgG Monoclonal Antibodies Against Lethal H7N7 Challenge in Vivo This study was performed to assess the therapeutic efficacy and window of mAb CR8020 in the H7N7 model. MAb CR8020 (produced in PER.C6® cells) was tested for therapeutic efficacy in the mouse lethal challenge model with mouse-adapted influenza A/Chicken/Netherlands/621557/2003 (H7N7) virus (Central Veterinary Institute (CVI), Lelystad, The Netherlands). Briefly, all mice (Balb/c, female, age six to eight weeks, n=8 per group) were acclimatized and maintained for a period of at least four days prior to the start of the experiment. MAb CR8020 was intravenously dosed at 15 mg/kg in the tail vein (vena coccygeus) at day −1 before challenge, (group 1; prophylaxis positive control) or at day 1, 2, 3, 4, 5 or 6 after challenge (groups 2-7), assuming an average weight of 18 g per mouse and a fixed dose volume of 0.2 mL. Group 8 received negative control mAb CR3014 (15 mg/kg) at day 1 after challenge. The mice were challenged at day 0 with 25 $LD_{50}$ mouse-adapted A/CH/NL/621557/03 (H7N7) virus by intranasal inoculation. Clinical signs and body weights were determined daily from day −1 before challenge until the end of the study at day 21.

Figure 16:
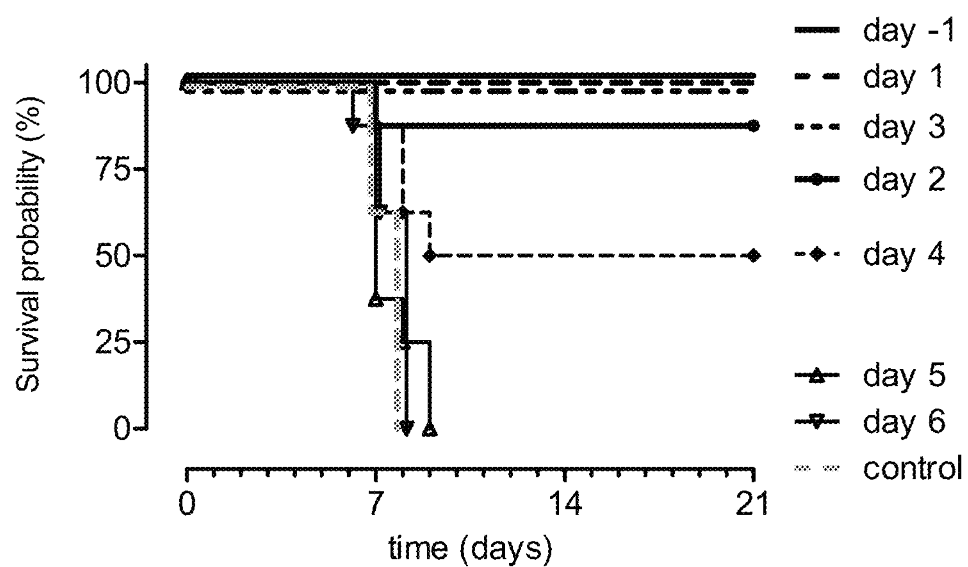
FIG. 16 shows the therapeutic efficacy of mAb CR8020 in the mouse lethal challenge model with mouse-adapted influenza A/CH/NL/621557/03 (H7N7). A single dose of mAb CR8020 (15 mg/kg) was administered intravenously either at day −1 pre-challenge or at day 1, 2, 3, 4, 5, or 6 post-challenge in female Balb/c mice (n=8/group). Control mAb (15 mg/kg) was administered at day 1 post-challenge. Mice were challenged at day 0 with 25 $LD_{50}$ mouse-adapted A/CH/NL/621557/03 (H7N7) and monitored for 21 days. Panel A: Kaplan-Meier survival probability curves. Panel B: Mean body weight change (%) relative to day 0. Bars represent the 95% CI of the mean. If a mouse died or was euthanized during follow-up of the study, the last observed body weight was carried forward. Panel C: Median clinical score. Bars represent interquartile ranges. 0=no clinical signs; 1=rough coat; 2=rough coat, less reactive, passive during handling; 3=rough coat, rolled up, labored breathing, passive during handling; 4=rough coat, rolled up, labored breathing, does not roll back on stomach when laid down on its back. Mice observed with clinical score 4 were euthanized on the same day.
Figure 16:
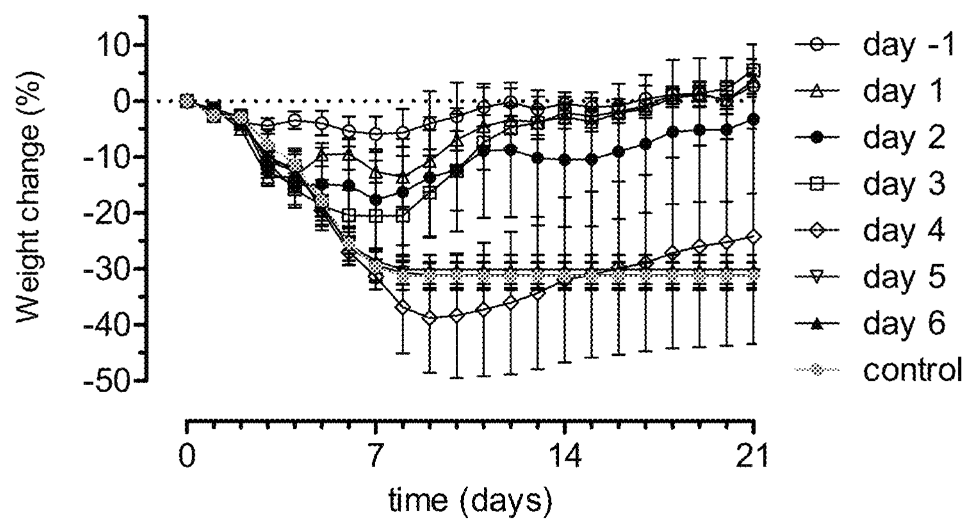
Figure 16:
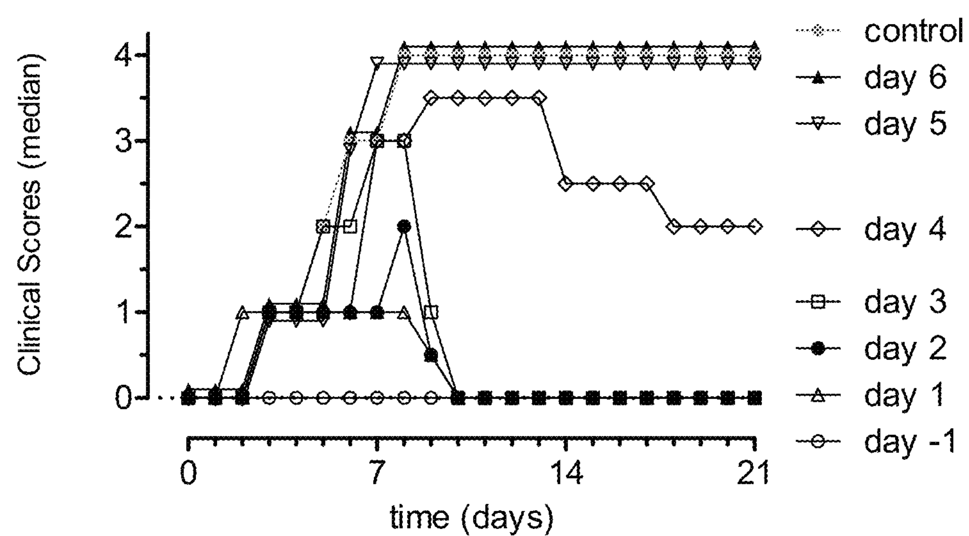

FIG. 16, Panel A, shows the survival rates of the mice, following intravenous administration of mAb CR8020 (15 mg/kg in all groups) or control mAb (15 mg/kg). When 15 mg/kg mAb CR8020 was administered at day 1 pre-challenge or day 1 or 3 post-challenge, all animals survived the viral challenge, whereas in the control mAb group, the survival rate was 0%. When 15 mg/kg mAb CR8020 was administered at days 2 and 4, respectively, 87.5% and 50% survival was observed. The survival time of these groups was statistically significantly different from that of the control mAb group (p=0.002 and p=0.014, respectively). Groups treated with 15 mg/kg CR8020 at days 5 and 6 experienced a survival rate of 0% and there was no statistically significant difference in survival time of these groups compared to the control mAb group (p=0.837 and p=0.876, respectively).

In FIG. 16, Panel B, the mean body weight change relative to day 0 of the mice during the 21-day study period is shown. In general, mean body weight loss increases when mAb CR8020 is administered at later time points following challenge. However, the mean body weight curves of the mAb CR8020 day-2 and -3 treatment groups cross at day 10, due to the single non-surviving mouse in the day-2 treatment group. Area under the curve analysis of the body weight changes shows a sharp transition in the mean weight loss between the treatments at day −1 to day 3 compared to treatment at days 4 to 6 (Table 22). Treatment with 15 mg/kg of CR8020 at day −1 pre-challenge or day 1, 2 or 3 post-challenge resulted in a statistically significant reduction in weight loss compared to the control group (p<0.001 for all four groups). Treatment with 15 mg/kg of CR8020 at days 4, 5 or day 6 did not result in a statistically significant reduction in weight loss compared to the control group (p=0.566, p=0.979 and p=0.858, respectively).

Median clinical scores of the mice are depicted in FIG. 16, Panel C. Of the animals treated with 15 mg/kg CR8020 at day −1 pre-challenge, all survived and none of the animals showed any clinical signs during the observation period. Animals treated at day 1 post-challenge showed a 100% survival, however, seven out of eight animals showed clinical signs reaching a maximum clinical score of 1. The eighth animal reached a maximum clinical score of 3. Of the animals treated at day 2 post-challenge, all, but one animal survived. The surviving animals (seven out of eight) showed clinical signs reaching a maximum clinical score of 1 (n=4) or 3 (n=3) Animals treated at day 3 post-challenge showed a 100% survival and all animals showed clinical signs with a maximum clinical score of 3. Of the animals treated at day 4 post-challenge, 50% survived the lethal challenge. The surviving animals showed clinical signs reaching a maximum clinical score of 3. Animals treated at day 5 or 6 post-challenge did not survive. Clinical scores were analyzed using the GENMOD procedure (SAS) to fit a model to repeated measures with mice as subjects and data measured on an ordinal scale (Table 23). From the groups treated with 15 mg/kg mAb CR8020 at day −1 before challenge and day 1, 2, 3 or 4 post-challenge, the median clinical score was statistically significantly different from the control mAb group during most of the study period of 21 days (days 8-21; p≤0.038 for all four groups). From the group treated with 15 mg/kg mAb CR8020 at day 5 post-challenge, the median clinical score was significantly different from the control mAb group at day 8 only (p≤0.001). This difference, although statistically significant, is not considered relevant. The median clinical score of the 15-mg/kg mAb CR8020 day 6 treatment group was not statistically different from the control group.

This study clearly shows that therapy with 15 mg/kg of mAb CR8020 provides 87.5%-100% protection when administered up to day 3 after challenge in a lethal H7N7 mouse model. When administered at day 4 after challenge, treatment with 15 mg/kg mAb CR8020 provides partial protection. When administered at day 5 or day 6 after challenge, no protective effect of 15 mg/kg mAb CR8020 was observed in the lethal H7N7 mouse model. In other words, when administered four days or more before death, CR8020 provided protection in this lethal mouse model.

Example 18

Cocktail of Monoclonal Antibodies that Efficiently Neutralizes Multiple Influenza Subtypes from Phylogenetic Groups 1 and 2

The seasonal influenza vaccine each year consists of two different preparations inducing immunity to influenza A strains, a representative for the circulating H1 subtype and a representative for the circulating H3 strain. The underlying reason for this is that influenza strains from the H1 and H3 subtypes are so much different that the vaccines prepared from either type does not induce protection against the other subtype. Ideally, a broadly protective monoclonal antibody preparation to treat influenza would be effective against influenza strains from both the phylogenetic group 1 (H1) and group 2 (H3). However, again due to the sequence differences between the HA molecules, such a single antibody is hard to find. For example, the Fab28 antibody described in WO 2009/115972 binds and neutralizes H1 subtypes much better than H3 subtype viruses, probably due to the lesser conservation of the epitope between the group 1 and group 2 viruses compared to viruses within a phylogenetic group. To reach the goal of a single product effective against multiple influenza subtypes from both phylogenetic groups, one may thus have to combine two or more different antibodies in a cocktail. In order to be successful, such preparation should consist of antibodies that do not interfere with each other.

Antibodies that efficiently neutralize viruses from H1, H5 and H9 subtypes have been described in WO2008/028946, with antibodies CR6261 and CR6323 as typical examples. The binding region (epitope) of CR6261 has been elucidated in detail using co-crystallization of H1 or H5 HA molecules and CR6261 (see also PDB database entries 3GBM and 3GBM at http://www.pdb.org and Ekiert et al., 2009). To investigate whether the monoclonal antibodies hereof can be used in combination with the previously described CR6261 antibodies, it was tested whether the antibodies were able to bind to subtypes from both phylogenetic groups 1 and 2. Hereto, ELISA and FACS binding experiments were done as described in Example 7 using HA molecules of H1 and H5 subtypes, as well as H3 and H7 subtypes with CR6261, CR6323, CR8001, CR8020, CR8041 and CR8043. The results are summarized in Table 20 and show that the antibodies that broadly neutralize viruses of group 1 do not bind to viruses of group 2 and vice versa. Since the antibodies do not interfere with each other, it can be expected that the neutralizing potency of the antibodies against the respective subtypes will be maintained, resulting in efficient neutralization of both group 1 and 2 subtypes.

Therefore, a cocktail comprising CR6261 and/or CR6323 on the one hand and CR8020, CR8041, and/or CR8043 on the other hand will be active against viruses of at least both subtypes H1 and H3. Thus, efficient protection is possible to influenza subtypes from phylogenetic groups 1 and 2 using one preparation.

Example 19

Binding Kinetics of the Binding Molecules

The affinities of papain-cleaved Fab fragments of CR8020 and CR8043 were measured using the Octet RED system and streptavidin biosensors from ForteBio. Influenza hemagglutinin antigens of the H3 subtypes A/Wisconsin/67/2005 (Protein Science) and A/Brisbane/10/2007 (Protein Science) were biotinylated for immobilization to streptavidin biosensors (ForteBio). Fab binding experiments were repeated five times using a concentration range between 2.3-150 nM and 0.16-30 nM for CR8020 and CR8043, respectively, in kinetic buffer (ForteBio, 18.5032). The experimental set-up for affinity measurements on the Octet was as follows: Immobilization of the biotinylated hemagglutinin to streptavidin biosensors for 1800 seconds, followed by association of the serial diluted Fabs CR8020 and CR8043 for 1200 seconds, and subsequent dissociation in kinetic buffer for 1800 seconds. Binding data were analyzed with Octet Analysis software using the 1:1 model.

The affinity constant ($K_d$-value) of the binding molecules for HA of the H3 subtype are shown in Table 24.

TABLE 1

First round Vkappa, Vlambda and VH amplifications

| Primer name | Primer nucleotide sequence | SEQ ID NO: |
|---|---|---|
| OK1 (HuVK1B) | GAC ATC CAG WTG ACC CAG TCT CC | 192 |
| OK2 (HuVK2) | GAT GTT GTG ATG ACT CAG TCT CC | 193 |
| OK3 (HuVK2B2) | GAT ATT GTG ATG ACC CAG ACT CC | 194 |
| OK4 (HuVK3B) | GAA ATT GTG WTG ACR CAG TCT CC | 195 |
| OK5 (HuVK5) | GAA ACG ACA CTC ACG CAG TCT CC | 196 |
| OK6 (HuVK6) | GAA ATT GTG CTG ACT CAG TCT CC | 197 |
| OCK (HuCK) | ACA CTC TCC CCT GTT GAA GCT CTT | 198 |
| OL1 (HuVL1A) * | CAG TCT GTG CTG ACT CAG CCA CC | 199 |
| OL1 (HuVL1B) * | CAG TCT GTG YTG ACG CAG CCG CC | 200 |
| OL1 (HuVL1C) * | CAG TCT GTC GTG ACG CAG CCG CC | 201 |
| OL2 (HuVL2B) | CAG TCT GCC CTG ACT CAG CC | 202 |
| OL3 (HuVL3A) | TCC TAT GWG CTG ACT CAG CCA CC | 203 |
| OL4 (HuVL3B) | TCT TCT GAG CTG ACT CAG GAC CC | 204 |
| OL5 (HuVL4B) | CAG CYT GTG CTG ACT CAA TC | 205 |
| OL6 (HuVL5) | CAG GCT GTG CTG ACT CAG CCG TC | 206 |
| OL7 (HuVL6) | AAT TTT ATG CTG ACT CAG CCC CA | 207 |
| OL8 (HuVL7/8) | CAG RCT GTG GTG ACY CAG GAG CC | 208 |
| OL9 (HuVL9) # | CWG CCT GTG CTG ACT CAG CCM CC | 209 |
| OL9 (HuVL10) # | CAG GCA GGG CTG ACT CAG | 210 |
| OCL (HuCL2) X | TGA ACA TTC TGT AGG GGC CAC TG | 211 |
| OCL (HuCL7) X | AGA GCA TTC TGC AGG GGC CAC TG | 212 |
| OH1 (HuVH1B7A) + | CAG RTG CAG CTG GTG CAR TCT GG | 213 |
| OH1 (HuVH1C) + | SAG GTC CAG CTG GTR CAG TCT GG | 214 |
| OH2 (HuVH2B) | CAG RTC ACC TTG AAG GAG TCT GG | 215 |
| OH3 (HuVH3A) | GAG GTG CAG CTG GTG GAG | 216 |

TABLE 1 -continued

| First round Vkappa, Vlambda and VH amplifications | | |
|---|---|---|
| Primer name | Primer nucleotide sequence | SEQ ID NO: |
| OH4 (HuVH3C) | GAG GTG CAG CTG GTG GAG WCY GG | 217 |
| OH5 (HuVH4B) | CAG GTG CAG CTA CAG CAG TGG GG | 218 |
| OH6 (HuVH4C) | CAG STG CAG CTG CAG GAG TCS GG | 219 |
| OH7 (HuVH6A) | CAG GTA CAG CTG CAG CAG TCA GG | 220 |
| OCM (HuCIgM) | TGG AAG AGG CAC GTT CTT TTC TTT | 221 |

* Mix in 1:1:1 ratio
Mix in 1:1 ratio
X Mix in 1:1 ratio
+ Mix in 1:1 ratio

TABLE 2

| Second round Vkappa, Vlambda and VH amplifications | | |
|---|---|---|
| Primer name | Primer nucleotide sequence | SEQ ID NO |
| OK1S (HuVK1B-SAL) | TGA GCA CAC AGG TCG ACG GAC ATC CAG WTG ACC CAG TCT CC | 222 |
| OK2S (HuVK2-SAL) | TGA GCA CAC AGG TCG ACG GAT GTT GTG ATG ACT CAG TCT CC | 223 |
| OK3S (HuVK2B2-SAL) | TGA GCA CAC AGG TCG ACG GAT ATT GTG ATG ACC CAG ACT CC | 224 |
| OK4S (HuVK3B-SAL) | TGA GCA CAC AGG TCG ACG GAA ATT GTG WTG ACR CAG TCT CC | 225 |
| OK5S (HuVK5-SAL) | TGA GCA CAC AGG TCG ACG GAA ACG ACA CTC ACG CAG TCT CC | 226 |
| OK6S (HuVK6-SAL) | TGA GCA CAC AGG TCG ACG GAA ATT GTG CTG ACT CAG TCT CC | 227 |
| OJK1 (HuJK1-NOT) | GAG TCA TTC TCG ACT TGC GGC CGC ACG TTT GAT TTC CAC CTT GGT CCC | 228 |
| OJK2 (HuJK2-NOT) | GAG TCA TTC TCG ACT TGC GGC CGC ACG TTT GAT CTC CAG CTT GGT CCC | 229 |
| OJK3 (HuJK3-NOT) | GAG TCA TTC TCG ACT TGC GGC CGC ACG TTT GAT ATC CAC TTT GGT CCC | 230 |
| OJK4 (HuJK4-NOT) | GAG TCA TTC TCG ACT TGC GGC CGC ACG TTT GAT CTC CAC CTT GGT CCC | 231 |
| OJK5 (HuJK5-NOT) | GAG TCA TTC TCG ACT TGC GGC CGC ACG TTT AAT CTC CAG TCG TGT CCC | 232 |
| OL1S (HuVL1A-SAL) * | TGA GCA CAC AGG TCG ACG CAG TCT GTG CTG ACT CAG CCA CC | 233 |
| OL1S (HuVL1B-SAL) * | TGA GCA CAC AGG TCG ACG CAG TCT GTG YTG ACG CAG CCG CC | 234 |
| OL1S (HuVL1C-SAL) * | TGA GCA CAC AGG TCG ACG CAG TCT GTC GTG ACG CAG CCG CC | 235 |
| OL2S (HuVL2B-SAL) | TGA GCA CAC AGG TCG ACG CAG TCT GCC CTG ACT CAG CC | 236 |
| OL3S (HuVL3A-SAL) | TGA GCA CAC AGG TCG ACG TCC TAT GWG CTG ACT CAG CCA CC | 237 |
| OL4S (HuVL3B-SAL) | TGA GCA CAC AGG TCG ACG TCT TCT GAG CTG ACT CAG GAC CC | 238 |

TABLE 2 -continued

| Primer name | Primer nucleotide sequence | SEQ ID NO |
|---|---|---|
| Second round Vkappa, Vlambda and VH amplifications | | |
| OL5S (HuVL4B-SAL) | TGA GCA CAC AGG TCG ACG CAG CYT GTG CTG ACT CAA TC | 239 |
| OL6S (HuVL5-SAL) | TGA GCA CAC AGG TCG ACG CAG GCT GTG CTG ACT CAG CCG TC | 240 |
| OL7S (HuVL6-SAL) | TGA GCA CAC AGG TCG ACG AAT TTT ATG CTG ACT CAG CCC CA | 241 |
| OL8S (HuVL7/8-SAL) | TGA GCA CAC AGG TCG ACG CAG RCT GTG GTG ACY CAG GAG CC | 242 |
| OL9S (HuVL9-SAL) # | TGA GCA CAC AGG TCG ACG CWG CCT GTG CTG ACT CAG CCM CC | 243 |
| OL9S (HuVL10-SAL) # | TGA GCA CAC AGG TCG ACG CAG GCA GGG CTG ACT CAG | 244 |
| OJL1 (HuJL1-NOT) | GAG TCA TTC TCG ACT TGC GGC CGC ACC TAG GAC GGT GAC CTT GGT CCC | 245 |
| OJL2 (HuJL2/3-NOT) | GAG TCA TTC TCG ACT TGC GGC CGC ACC TAG GAC GGT CAG CTT GGT CCC | 246 |
| OJL3 (HuJL7-NOT) | GAG TCA TTC TCG ACT TGC GGC CGC ACC GAG GAC GGT CAG CTG GGT GCC | 247 |
| OH1S (HuVH1B-SFI) + | GTC CTC GCA ACT GCG GCC CAG CCG GCC ATG GCC CAG RTG CAG CTG GTG CAR TCT GG | 248 |
| OH1S (HuVH1C-SFI) + | GTC CTC GCA ACT GCG GCC CAG CCG GCC ATG GCC SAG GTC CAG CTG GTR CAG TCT GG | 249 |
| OH2S (HuVH2B-SFI) | GTC CTC GCA ACT GCG GCC CAG CCG GCC ATG GCC CAG RTC ACC TTG AAG GAG TCT GG | 250 |
| OH3S (HuVH3A-SFI) | GTC CTC GCA ACT GCG GCC CAG CCG GCC ATG GCC GAG GTG CAG CTG GTG GAG | 251 |
| OH4S (HuVH3C-SFI) | GTC CTC GCA ACT GCG GCC CAG CCG GCC ATG GCC GAG GTG CAG CTG GTG GAG WCY GG | 252 |
| OH5S (HuVH4B-SFI) | GTC CTC GCA ACT GCG GCC CAG CCG GCC ATG GCC CAG GTG CAG CTA CAG CAG TGG GG | 253 |
| OH6S (HuVH4C-SFI) | GTC CTC GCA ACT GCG GCC CAG CCG GCC ATG GCC CAG STG CAG CTG CAG GAG TCS GG | 254 |
| OH7S (HuVH6A-SFI) | GTC CTC GCA ACT GCG GCC CAG CCG GCC ATG GCC CAG GTA CAG CTG CAG CAG TCA GG | 255 |
| OJH1 (HuJH1/2-XHO) | GAG TCA TTC TCG ACT CGA GAC RGT GAC CAG GGT GCC | 256 |
| OJH2 (HuJH3-XHO) | GAG TCA TTC TCG ACT CGA GAC GGT GAC CAT TGT CCC | 257 |
| OJH3 (HuJH4/5-XHO) | GAG TCA TTC TCG ACT CGA GAC GGT GAC CAG GGT TCC | 258 |
| OJH4 (HuJH6-XHO) | GAG TCA TTC TCG ACT CGA GAC GGT GAC CGT GGT CCC | 259 |

* Mix in 1:1:1 ratio

Mix in 1:1 ratio

+ Mix in 1:1 ratio

TABLE 3

Second round VL regions amplification overview

| Template | 5' primer | 3' primer | Product | Share in PK/PL (%) | Pool | Share in VL (%) |
|---|---|---|---|---|---|---|
| K1 | OK1S | OJK1 | K1J1 | 25 | PK1 | 30 |
| | OK1S | OJK2 | K1J2 | 25 | | |
| | OK1S | OJK3 | K1J3 | 10 | | |
| | OK1S | OJK4 | K1J4 | 25 | | |
| | OK1S | OJK5 | K1J5 | 15 | | |
| K2 | OK2S | OJK1 | K2J1 | 25 | PK2 | 4 |
| | OK2S | OJK2 | K2J2 | 25 | | |
| | OK2S | OJK3 | K2J3 | 10 | | |
| | OK2S | OJK4 | K2J4 | 25 | | |
| | OK2S | OJK5 | K2J5 | 15 | | |
| K3 | OK3S | OJK1 | K3J1 | 25 | PK3 | 1 |
| | OK3S | OJK2 | K3J2 | 25 | | |
| | OK3S | OJK3 | K3J3 | 10 | | |
| | OK3S | OJK4 | K3J4 | 25 | | |
| | OK3S | OJK5 | K3J5 | 15 | | |
| K4 | OK4S | OJK1 | K4J1 | 25 | PK4 | 19 |
| | OK4S | OJK2 | K4J2 | 25 | | |
| | OK4S | OJK3 | K4J3 | 10 | | |
| | OK4S | OJK4 | K4J4 | 25 | | |
| | OK4S | OJK5 | K4J5 | 15 | | |
| K5 | OK5S | OJK1 | K5J1 | 25 | PK5 | 1 |
| | OK5S | OJK2 | K5J2 | 25 | | |
| | OK5S | OJK3 | K5J3 | 10 | | |
| | OK5S | OJK4 | K5J4 | 25 | | |
| | OK5S | OJK5 | K5J5 | 15 | | |
| K6 | OK6S | OJK1 | K6J1 | 25 | PK6 | 5 |
| | OK6S | OJK2 | K6J2 | 25 | | |
| | OK6S | OJK3 | K6J3 | 10 | | |
| | OK6S | OJK4 | K6J4 | 25 | | |
| | OK6S | OJK5 | K6J5 | 15 | | |
| L1 | OL1S | OJL1 | L1J1 | 30 | PL1 | 14 |
| | OL1S | OJL2 | L1J2 | 60 | | |
| | OL1S | OJL3 | L1J3 | 10 | | |
| L2 | OL2S | OJL1 | L2J1 | 30 | PL2 | 10 |
| | OL2S | OJL2 | L2J2 | 60 | | |
| | OL2S | OJL3 | L2J3 | 10 | | |
| L3 | OL3S | OJL1 | L3J1 | 30 | PL3 | 10 |
| | OL3S | OJL2 | L3J2 | 60 | | |
| | OL3S | OJL3 | L3J3 | 10 | | |
| L4 | OL4S | OJL1 | L4J1 | 30 | PL4 | 1 |
| | OL4S | OJL2 | L4J2 | 60 | | |
| | OL4S | OJL3 | L4J3 | 10 | | |
| L5 | OL5S | OJL1 | L5J1 | 30 | PL5 | 1 |
| | OL5S | OJL2 | L5J2 | 60 | | |
| | OL5S | OJL3 | L5J3 | 10 | | |
| L6 | OL6S | OJL1 | L6J1 | 30 | PL6 | 1 |
| | OL6S | OJL2 | L6J2 | 60 | | |
| | OL6S | OJL3 | L6J3 | 10 | | |
| L7 | OL7S | OJL1 | L7J1 | 30 | PL7 | 1 |
| | OL7S | OJL2 | L7J2 | 60 | | |
| | OL7S | OJL3 | L7J3 | 10 | | |
| L8 | OL8S | OJL1 | L8J1 | 30 | PL8 | 1 |
| | OL8S | OJL2 | L8J2 | 60 | | |
| | OL8S | OJL3 | L8J3 | 10 | | |
| L9 | OL9S | OJL1 | L9J1 | 30 | PL9 | 1 |
| | OL9S | OJL2 | L9J2 | 60 | | |
| | OL9S | OJL3 | L9J3 | 10 | | |
| | | | | | | VL 100% |

TABLE 4

Second round VH regions amplification overview

| Template | 5' primer | 3' primer | Product | Share in PK/PL (%) | Pool | Share in VH (%) |
|---|---|---|---|---|---|---|
| H1 | OH1S | OJH1 | H1J1 | 10 | PH1 | 25 |
| | OH1S | OJH2 | H1J2 | 10 | | |
| | OH1S | OJH3 | H1J3 | 60 | | |
| | OH1S | OJH4 | H1J4 | 20 | | |
| H2 | OH2S | OJH1 | H2J1 | 10 | PH2 | 2 |
| | OH2S | OJH2 | H2J2 | 10 | | |
| | OH2S | OJH3 | H2J3 | 60 | | |
| | OH2S | OJH4 | H2J4 | 20 | | |
| H3 | OH3S | OJH1 | H3J1 | 10 | PH3 | 25 |
| | OH3S | OJH2 | H3J2 | 10 | | |
| | OH3S | OJH3 | H3J3 | 60 | | |
| | OH3S | OJH4 | H3J4 | 20 | | |
| H4 | OH4S | OJH1 | H4J1 | 10 | PH4 | 25 |
| | OH4S | OJH2 | H4J2 | 10 | | |
| | OH4S | OJH3 | H4J3 | 60 | | |
| | OH4S | OJH4 | H4J4 | 20 | | |
| H5 | OH5S | OJH1 | H5J1 | 10 | PH5 | 2 |
| | OH5S | OJH2 | H5J2 | 10 | | |
| | OH5S | OJH3 | H5J3 | 60 | | |
| | OH5S | OJH4 | H5J4 | 20 | | |
| H6 | OH6S | OJH1 | H6J1 | 10 | PH6 | 20 |
| | OH6S | OJH2 | H6J2 | 10 | | |
| | OH6S | OJH3 | H6J3 | 60 | | |
| | OH6S | OJH4 | H6J4 | 20 | | |
| H7 | OH7S | OJH1 | H7J1 | 10 | PH7 | 1 |
| | OH7S | OJH2 | H7J2 | 10 | | |
| | OH7S | OJH3 | H7J3 | 60 | | |
| | OH7S | OJH4 | H7J4 | 20 | | |
| | | | | | | VH 100% |

TABLE 5

Characteristics of the individual IgM memory B cell libraries.
IgM memory libraries

| | Cells | | Libraries | | | |
|---|---|---|---|---|---|---|
| Donor | Total PBL ($\times 10^6$) | % memory B cells | Size ($\times 10^6$) | % Insert frequency | % ORF | % Unique |
| Individual 1 | | | 3 | 96 | 74 | 98 |
| Individual 2 | 72.5 | 1.7 | 5 | 98 | 79 | 98 |
| Individual 3 | 67.5 | 1.4 | 3 | 96 | 79 | 98 |
| Individual 4 | 132.5 | 2.3 | 6 | 98 | 69 | 99 |

TABLE 6

Cross-binding activity of single-chain phage antibodies to HA molecules of different HA subtypes as measured by ELISA (ELISA titer; OD 492 nm).

| SC # | H3 | H7 | HB |
|---|---|---|---|
| sc08-001 | 0.885 | 2.451 | x |
| sc08-003 | 1.320 | 0.222 | x |
| sc08-006 | 0.511 | 0.227 | x |
| sc08-007 | 0.074 | 2.365 | x |
| sc08-009 | 0.095 | 1.130 | x |
| sc08-010 | 0.165 | 1.242 | x |
| sc08-011 | 0.090 | 1.802 | x |
| sc08-013 | 0.078 | 1.400 | x |
| sc08-014 | 0.239 | 0.834 | x |
| sc08-015 | 0.727 | 0.165 | x |
| sc08-016 | 1.112 | 0.164 | x |
| sc08-017 | 1.158 | 0.285 | x |
| sc08-018 | 0.711 | 0.221 | x |

x = not determined;
H3 = HA of H3 subtype;
H7 = HA of H7 subtype;
HB = HA of influenza virus B.

TABLE 7

Cross-binding activity of PEG/NACl-precipitated and filter-sterilized phage antibodies to HA molecules of different HA subtypes as measured by ELISA (OD 492 nm).

| SC # | H1 | H3 | H5 | H7 | B(o) |
|---|---|---|---|---|---|
| sc08-001 | + | + | − | + | − |
| sc08-003 | − | + | − | − | − |
| sc08-006 | − | + | − | − | − |
| sc08-007 | − | − | − | + | − |
| sc08-009 | − | − | − | + | − |
| sc08-010 | − | − | − | + | − |
| sc08-011 | − | − | − | + | − |
| sc08-013 | − | − | − | + | − |
| sc08-014 | + | + | − | + | − |
| sc08-015 | − | + | − | − | − |
| sc08-016 | − | + | − | − | − |
| sc08-017 | − | + | − | − | − |
| sc08-018 | − | + | − | − | − |

H1 = HA of H1 subtype,
H3 = HA of H3 subtype;
H5 = HA of H5 subtype;
H7 = HA of H7 subtype;
B(o) = HA of influenza virus B/Ohio/01/2005.

TABLE 8

FACS analysis of PEG/NACl-precipitated and filter-sterilized phage antibodies (expressed as MFI = mean fluorescence intensity). PER.C6 = untransfected PER.C6 ® cells (control); mH1, mH3, mH5, mH7, mHB = membrane bound HA of the subtypes H1, H3, H5, H7 and influenza B subtypes respectively.

| SC # | PER.C6 ® | mH1 | mH3 | mH5 | mH7 | mHB |
|---|---|---|---|---|---|---|
| sc08-001 | 2 | 27 | 68 | 5 | 62 | x |
| sc08-003 | 5 | 9 | 77 | 7 | 7 | x |
| sc08-006 | 2 | 6 | 69 | 5 | 6 | x |
| sc08-007 | 1 | 5 | 4 | 4 | 73 | x |
| sc08-009 | 11 | 12 | 11 | 10 | 15 | x |
| sc08-010 | 2 | 4 | 3 | 4 | 60 | x |
| sc08-011 | 1 | 3 | 4 | 4 | 73 | x |
| sc08-013 | 2 | 5 | 3 | 7 | 61 | x |
| sc08-014 | 10 | 26 | 82 | 17 | 32 | x |
| sc08-015 | 3 | 7 | 79 | 7 | 6 | x |
| sc08-016 | 1 | 7 | 82 | 5 | 5 | x |
| sc08-017 | 1 | 6 | 81 | 5 | 5 | x |
| sc08-018 | 2 | 6 | 74 | 6 | 7 | x |

TABLE 9

Data of the CDR regions of the HA specific immunoglobulins (SEQ ID NO:).

| IgG# | Vh locus | HCDR1 | HCDR2 | HCDR3 | Vl locus | LCDR1 | LCDR2 | LCDR3 |
|---|---|---|---|---|---|---|---|---|
| CR8001 | 3-53 | SNYVS (81) | LIYTGGTTYYADSVKG (82) | VSALRFLQWPNYAMDV (83) | 1-4 | SGTRSDVGGHNYVS (84) | EVSHRPS (85) | SSYTGEGPLGV (86) |
| CR8003 | 3-7 | SYWMS (87) | NMKQDGSEKYYVDSVKG (88) | GSCDDSWTGCHDAFDI (89) | 2-14 | GGNNIGSKSVH (90) | DSARPS (91) | QVWESGSDLRLL (92) |
| CR8015 | 3-7 | SYWMS (87) | NMKQDGSEKYYVDSVKG (88) | GSCDDSWTGCHDAFDI (89) | 2-14 | GGDNIGRKSVH (93) | DNSDRPS (94) | HVWGSSRDHYV (95) |
| CR8016 | 3-7 | SYWMS (87) | NMKQDGSEKYYVDSVKG (88) | GSCDDSWTGCHDAFDI (89) | 1-13 | TGSSSNIGAGYDVH (96) | GNN (97)RPS | QSYDSSLSVYV (98) |
| CR8017 | 3-7 | SYWMS (87) | NMKQDGSEKYYVDSVKG (88) | GSCDDSWTGCHDAFDI (89) | 2-13 | QGDSLRSYYAS (99) | AKTNRPS (100) | NSRDSSGNHVV (101) |
| CR8018 | 3-7 | SYWMS (87) | NMKQDGSEKYYVDSVKG (88) | GSCDDSWTGCHDAFDI (89) | 1-4 | TGTSSDVGGYNYVS (102) | EVSHRPS (85) | SSYTGEGPLGV (86) |
| CR8019 | 3-23 | TSAMS (103) | GISGSGATTYYAGSVKG (104) | DTSLFEYDTSGFTAPGNAFDI (105) | O12 | RASQSISGYLN (106) | GASTLQS (107) | QQTYTSPPYA (108) |
| CR8020 | 1-18 | RFGVS (109) | WISAYNGDTYYAQKFQA (110) | EPPLFYSSWSLDN (111) | A27 | ARASQSVSMNYLA (112) | GASRRAT (113) | QQYGTSPRT (114) |
| CR8021 | 3-23 | AYAMN (115) | AIGGSGGSTYYADSVKG (116) | GRDWTGGYFFDS (117) | B3 | KSSQSIFYSSNNKNYLT (118) | WASTRES (119) | QQYYSIPYT (120) |
| CR8038 | 3-23 | GYAMS (121) | DIGGSGGGTYYADSVKG (122) | SSSWDRAYFFDS (123) | B3 | KSSQSVLYSSIHKNYLA (124) | WASTRES (119) | QQYYRSPPT (125) |
| CR8039 | 4-59 | SYYWS (126) | YIYYRGGTSYNPSLKS (127) | KDWGSAAGSVWYFDL (128) | 1-2 | TGTSSDVGGYNYVS (129) | EVSKRPS (130) | SSYAGSNNLI (131) |
| CR8040 | 3-33 | SYGMH (132) | FIWYDGSNKHYADSMKG (133) | DGGYSTWEWYFDL (134) | A26 | RASQGIGSNLH (135) | YASQSIT (136) | HQSSSLPLT (137) |
| CR8041 | 1-18 | SFGLS (138) | WISAYNGEIKYAQKFQG (139) | EPPLYFSSWSLDF (140) | A27 | ARASQSVSSNYLA (141) | GASRRAT (142) | QQYDSSPRT (143) |
| CR8043 | 1-03 | AYSMH (144) | WINTAIGNTQYSQKFQD (145) | GASWDARGWSGY (146) | B3 | KSSQSVFSSSTNKNYLA (147) | WSSTRES (148) | HQYYTAPWT (149) |
| CR8049 | 2-26 | NTRMGVS (150) | HIFSNDETSYRTSLKR (151) | IGSGYESSAYSTWLDP (152) | 2-14 | EGDTIGSKSVH (153) | NDRDRPS (154) | QVWESGGDQTV (155) |

TABLE 9 -continued

Data of the CDR regions of the HA specific immunoglobulins (SEQ ID NO:).

| IgG# | Vh locus | HCDR1 | HCDR2 | HCDR3 | Vl locus | LCDR1 | LCDR2 | LCDR3 |
|---|---|---|---|---|---|---|---|---|
| CR8050 | 4-34 | DHYWS (156) | EVVHSGDTNYTPSLRN (157) | GRNVAVVGAIQRHYDY (158) | A27 | RASQSVSRNYLA (159) | GASSRAT (160) | QHYGSVLVA (161) |
| CR8052 | 4-61 | SGTYYWS (162) | DISYSGSTNYNPSLKS (163) | AMAAYNYDRGGYNDYYYMDV (164) | O12 | RASQGINTYLN (165) | AASTLQS (166) | QQSYSTAIT (167) |
| CR8055 | 3-33 | TYGMH (168) | FIWYDGSNKHYQDSVKG (169) | DGGYSTWEWYFDL (170) | A26 | RASRSIGSDLH (171) | FASQSMS (172) | HQSSSLPLT (137) |
| CR8057 | 3-53 | VIFMS (173) | IIYIDDSTYYADSVKG (174) | ESGDFGDQTGPYHYYAMDV (175) | 2-14 | TGSSGDIGGYNAVS (176) | EVTSRPS (177) | CSFADSNILI (178) |
| CR8069 | 3-43 | DYTMH (179) | LISWDGGMSNYADSVKG (180) | DIRPRMPARHFMDV (181) | L2 | RASQNVNYNLA (182) | VASTRAT (183) | QQYNNWPPAIT (184) |

TABLE 10

Data of the HA-specific IgGs. SEQ ID NOs of the nucleotide and amino acid sequences of the variable regions of the heavy and light chains

| Name IgG | SEQ ID NO of nucleotide sequence heavy chain variable region | SEQ ID NO of amino acid sequence heavy chain variable region | SEQ ID NO of nucleotide sequence light chain variable region | SEQ ID NO of amino acid sequence light chain variable region |
|---|---|---|---|---|
| CR8001 | 1 | 2 | 3 | 4 |
| CR8003 | 5 | 6 | 7 | 8 |
| CR8015 | 9 | 10 | 11 | 12 |
| CR8016 | 13 | 14 | 15 | 16 |
| CR8017 | 17 | 18 | 19 | 20 |
| CR8018 | 21 | 22 | 23 | 24 |
| CR8019 | 25 | 26 | 27 | 28 |
| CR8020 | 29 | 30 | 31 | 32 |
| CR8021 | 33 | 34 | 35 | 36 |
| CR8038 | 37 | 38 | 39 | 40 |
| CR8039 | 41 | 42 | 43 | 44 |
| CR8040 | 45 | 46 | 47 | 48 |
| CR8041 | 49 | 50 | 51 | 52 |
| CR8043 | 53 | 54 | 55 | 56 |
| CR8049 | 57 | 58 | 59 | 60 |
| CR8050 | 61 | 62 | 63 | 64 |
| CR8052 | 65 | 66 | 67 | 68 |
| CR8055 | 69 | 70 | 71 | 72 |
| CR8057 | 73 | 74 | 75 | 76 |
| CR8069 | 77 | 78 | 79 | 80 |

TABLE 11

In vitro neutralization of influenza virus H3N2 by selected IgGs Neutralization titer SK50 (μg/ml)

| IgG # | A/Wisconsin/67/2005 |
|---|---|
| CR8001 | 11.95 |
| CR8003 | 5.31 |
| CR8015 | 23.78 |
| CR8016 | 1.77 |
| CR8017 | 2.82 |
| CR8018 | 6.03 |
| CR8019 | 1.98 |
| CR8020 | 8.45 |
| CR8021 | 1.77 |
| CR8038 | 3.54 |
| CR8039 | 1.8 |
| CR8040 | >40 |
| CR8041 | 3.99 |
| CR8043 | 1.49 |
| CR8049 | 3.26 |
| CR8050 | 1.77 |
| CR8052 | >40 |
| CR8055 | 1.07 |
| CR8057 | 0.011 |
| CR8069 | ND |

TABLE 12

Cross-binding reactivity of anti-H3N2 IgGs. NCal. = A/New Caledonia/20/1999 (H1N1); Wisc. = A/Wisconsin/67/2005 (H3N2); NY. = A/New York/55/2004 (H3N2), Wyo. = A/Wyoming/3/2003 (H3N2); Neth. = A/Netherlands/219/2003 (H7N7); ND = not done.

| | IgG Elisa binding (titration) | | | | | Facs binding, [IgG] = 5 μg/ml, MFI | | | |
|---|---|---|---|---|---|---|---|---|---|
| | H1 | H3 | H3 | H3 | H7 | | | | |
| IgG # | NCal. | Wisc | NY | Wyo | Neth | PerC6 | H1 | H3 | H7 |
| CR8001 | + | + | + | + | + | 4 | 100 | 763 | 106 |
| CR8003 | − | + | + | + | − | 3 | 3 | 657 | 5 |
| CR8015 | − | + | + | + | − | 3 | 4 | 600 | 4 |
| CR8016 | − | + | + | + | − | 3 | 3 | 840 | 5 |
| CR8017 | − | + | + | + | − | 3 | 3 | 558 | 4 |
| CR8018 | − | + | + | + | − | 3 | 3 | 348 | 4 |
| CR8019 | − | + | − | + | − | 3 | 4 | 685 | 6 |
| CR8020 | − | + | + | + | + | 4 | 3 | 657 | 140 |

TABLE 12-continued

Cross-binding reactivity of anti-H3N2 IgGs. NCal. = A/New Caledonia/20/1999 (H1N1); Wisc. = A/Wisconsin/67/2005 (H3N2); NY. = A/New York/55/2004 (H3N2), Wyo. = A/Wyoming/3/2003 (H3N2); Neth. = A/Netherlands/219/2003 (H7N7); ND = not done.

| | IgG Elisa binding (titration) | | | | | Facs binding, [IgG] = 5 μg/ml, | | | |
|---|---|---|---|---|---|---|---|---|---|
| | H1 | H3 | H3 | H3 | H7 | MFI | | | |
| IgG # | NCal. | Wisc | NY | Wyo | Neth | PerC6 | H1 | H3 | H7 |
| CR8021 | − | + | + | + | + | 4 | 4 | 678 | 4 |
| CR8038 | − | + | + | + | − | ND | ND | ND | ND |
| CR8039 | − | + | + | + | − | 4 | 4 | 503 | 4 |
| CR8040 | − | + | + | + | − | 4 | 5 | 446 | 4 |
| CR8041 | − | + | + | + | + | 4 | 4 | 364 | 120 |
| CR8043 | − | + | + | + | + | 4 | 4 | 646 | 11 |
| CR8049 | − | + | + | + | − | 3 | 3 | 542 | 4 |
| CR8050 | − | + | + | + | − | 6 | 8 | 282 | 6 |
| CR8052 | − | + | + | + | − | 4 | 4 | 364 | 5 |
| CR8055 | − | − | − | − | − | 21 | 31 | 433 | 26 |
| CR8057 | − | + | + | + | low | 7 | 8 | 943 | 15 |
| CR8069 | − | + | + | + | − | 4 | 6 | 447 | 5 |

TABLE 13

Cross-neutralizing activity of anti-H3N2 IgGs; ND = not done
Neutralization titer SK50 ( μg/ml)

| | H1 | | | H2 | | | | | | |
|---|---|---|---|---|---|---|---|---|---|---|
| IgG # | A/New Caledonia/ 20/1999 | A/ Brisbane/ 59/1007 | A/ Solomon islands/ IVR-145 | A/ Wisconsin/ 67/2005 | A/ Hiroshima/ 52/2005 | A/ Panama/ 2000/1999 | A/ Johannesburg/ 33/1994 | A/ Hong Kong/ 1/1968 | H7 A/Mallard/ Netherlands/ 12/2000 | H10 A/Chick/ Germany/ N/49 |
| CR8001 | >40 | >40 | >40 | 11.95 | 13.02 | >40 | 6.51 | 7.07 | >40 | >40 |
| CR8003 | >40 | >40 | >40 | 5.31 | 4.27 | >40 | >40 | ND | >40 | >40 |
| CR8015 | >40 | >40 | >40 | 23.78 | 28.28 | >40 | >40 | ND | >40 | >40 |
| CR8016 | >40 | >40 | >40 | 1.77 | 8.84 | 28.28 | >40 | ND | >40 | >40 |
| CR8017 | >40 | >40 | >40 | 2.82 | 13.55 | >40 | >40 | ND | >40 | >40 |
| CR8018 | >40 | >40 | >40 | 6.03 | 8.45 | >40 | >40 | ND | >40 | >40 |
| CR8019 | >40 | >40 | >40 | 1.98 | 0.88 | >40 | 0.88 | ND | >40 | >40 |
| CR8020 | >40 | >40 | >40 | 8.45 | 11.95 | 7.74 | 7.07 | 1.77 | 0.028 | 17.68 |
| CR8021 | ND | >40 | >40 | 1.77 | 2.5 | >40 | 3.54 | 14.14 | >40 | >40 |
| CR8038 | ND | ND | ND | 3.54 | 7.07 | >40 | 5.95 | ND | >40 | >40 |
| CR8039 | >40 | >40 | >40 | 1.8 | 3.26 | 4.6 | 1.33 | 2.97 | >40 | >40 |
| CR8040 | >40 | >40 | >40 | >40 | >40 | >40 | 6.77 | ND | >40 | >40 |
| CR8041 | >40 | >40 | >40 | 3.99 | 4.75 | 2.99 | 1.69 | 1.05 | 1.105 | 25 |
| CR8043 | >40 | >40 | >40 | 1.49 | 3.54 | 10.15 | 2.66 | 4.2 | >40 | 14.87 |
| CR8049 | >40 | >40 | >40 | 3.26 | 3.54 | >40 | >40 | ND | >40 | >40 |
| CR8050 | ND | ND | ND | 1.77 | ND | 6.5 | 1.49 | ND | >40 | >40 |
| CR8052 | >40 | >40 | >40 | >40 | >40 | 21.89 | >40 | ND | >40 | >40 |
| CR8055 | >40 | >40 | >40 | 1.07 | 1.15 | >40 | 3.38 | ND | >40 | >40 |
| CR8057 | >40 | >40 | >40 | 0.011 | 0.0068 | 0.022 | 2.17 | 2.17 | >40 | >40 |
| CR8069 | >40 | >40 | >40 | ND | 3.54 | 11.89 | 3.54 | 11.89 | >40 | >40 |

TABLE 14

Sequence conservation around the binding region of the H3 mAbs CR8020, CR8041 and CR8043

| | HA2 position | | | | | | | | | | | | | | | |
|---|---|---|---|---|---|---|---|---|---|---|---|---|---|---|---|---|
| | 14 | 15 | 16 | 17 | 18 | 19 | 20 | 21 | 22 | 23 | 24 | 25 | 26 | 27 | 28 | 29 |
| Consensus | W | E | G | M | V | D | G | W | Y | G | F | R | H | Q | N | S |
| Group_1 | — | — | — | — | — | — | — | — | — | — | — | — | — | — | — | — |
| Group_2 | — | — | — | — | — | — | — | — | — | — | — | — | — | — | — | — |
| Group_3 | — | — | — | — | M | — | — | — | — | — | — | — | — | — | — | — |
| Group_4 | — | — | — | — | — | — | — | — | — | — | — | — | — | — | — | — |
| Group_5 | — | — | — | — | I | — | — | — | — | — | — | — | — | — | — | — |
| Group_6 | — | — | — | — | — | — | — | — | — | — | — | — | — | — | — | — |
| Group_7 | — | — | — | — | — | — | — | — | — | — | — | — | — | L | — | — |
| Group_8 | — | — | — | — | M | — | — | — | — | — | — | — | — | — | — | — |
| Group_9 | — | — | — | — | — | — | — | — | — | — | — | — | — | — | — | A |

TABLE 14-continued

Sequence conservation around the binding region of the H3 mAbs CR8020, CR8041 and CR8043

| | | | | | | | | | | | | | | | | |
|---|---|---|---|---|---|---|---|---|---|---|---|---|---|---|---|---|
| Group_10 | — | — | — | — | K | — | — | — | — | — | — | — | — | — | — | — |
| Group_11 | — | — | — | — | — | — | — | — | — | — | — | — | — | — | — | — |
| Group_12 | — | — | — | — | — | — | — | — | — | — | — | — | — | — | — | Y |
| Group_13 | — | — | — | — | — | — | — | — | — | — | — | — | — | — | — | — |
| Group_14 | — | — | — | — | — | — | — | — | — | — | — | — | — | — | — | — |
| Group_15 | — | — | — | — | — | — | — | — | — | — | — | — | — | — | — | X |
| Group_16 | — | — | — | — | — | — | — | — | — | — | — | — | — | — | — | Y |
| Group_17 | — | — | — | — | — | — | — | — | N | — | — | — | — | — | — | — |
| Group_18 | — | — | — | — | — | — | — | C | — | — | — | — | — | — | — | — |
| Group_19 | — | — | — | — | — | N | — | — | — | — | — | — | — | — | — | — |
| Group_20 | — | — | — | — | I | — | — | — | — | — | — | — | — | R | — | — |
| Group_21 | — | — | — | — | M | — | — | — | — | — | — | — | — | — | — | — |
| Group_22 | — | — | — | — | M | — | — | — | — | — | — | — | — | H | — | — |
| Group_23 | — | K | — | — | — | — | — | R | — | — | — | — | — | — | — | — |

| | HA2 position | | | | | | | | | | | | |
|---|---|---|---|---|---|---|---|---|---|---|---|---|---|
| Consensus | 30 E | 31 G | 32 T | 33 G | 34 Q | 35 A | 36 A | 37 D | 38 L | 39 K | N | Years | Tested strains |
| Group_1 | — | — | — | — | — | — | — | — | — | — | 655 | 1972-2008 | Pa |
| Group_2 | — | — | I | — | — | — | — | — | — | — | 380 | 2004-2008 | Hs-Wi |
| Group_3 | — | — | — | — | — | — | — | — | — | — | 127 | 1999-2004 | |
| Group_4 | — | — | R | — | — | — | — | — | — | — | 91 | 2007-2009 | |
| Group_5 | — | — | — | — | — | — | — | — | — | — | 69 | 1968-1997 | HK |
| Group_6 | — | — | M | — | — | — | — | — | — | — | 10 | 2007 | |
| Group_7 | — | — | — | — | — | — | — | — | — | — | 6 | 1999-2004 | |
| Group_8 | — | — | I | — | — | — | — | — | — | — | 4 | 2002-2007 | |
| Group_9 | — | — | — | — | — | — | — | — | — | — | 3 | 2004 | |
| Group_10 | — | — | — | — | — | — | — | — | — | — | 3 | 1999 | |
| Group_11 | — | — | R | — | — | — | — | — | F | — | 2 | 2009 | |
| Group_12 | — | — | — | — | — | — | — | — | — | — | 2 | 2003-2004 | |
| Group_13 | — | — | I | — | — | — | — | — | F | — | 1 | 2006 | |
| Group_14 | — | — | V | — | — | — | — | — | — | — | 1 | 2007 | |
| Group_15 | — | — | I | — | — | — | — | — | — | — | 1 | 2007 | |
| Group_16 | — | — | R | — | — | — | — | — | — | — | 1 | 2008 | |
| Group_17 | — | — | — | — | — | — | — | — | — | — | 1 | 2003 | |
| Group_18 | — | — | — | — | — | — | — | — | — | — | 1 | 2001 | |
| Group_19 | — | — | — | — | — | — | — | — | — | — | 1 | 1999 | |
| Group_20 | — | — | — | — | — | — | — | — | — | — | 1 | 1975 | |
| Group_21 | — | — | R | — | — | — | — | — | — | — | 1 | 2008 | |
| Group_22 | — | — | — | — | — | — | — | — | — | — | 1 | 2002 | |
| Group_23 | — | — | — | — | — | — | — | — | — | — | 1 | 2002 | |

TABLE 15

Neutralization titers on various Influenza A strains

| | H1 | H3 | | | | | | | H7 | | H10 |
|---|---|---|---|---|---|---|---|---|---|---|---|
| IgG # | 3 H1N1 strains (1999-2007) | A/ Wisconsin/ 67/ 2005 | A/ Hiroshima/ 52/ 2005 | A/ Panama/ 2000/ 1999 | A/ Johannesburg/ 33/1994 | A/ Hong Kong/ 1/1968 | A/HK/1/ 68-M20 | A/HK/1/ 68-M2c | A/ Mallard/ Netherlands/ 12/2000 | A/Chick/ NL/ 621557/ 03-ma | A/ Chick/ Germany/ N/49 |
| CR8001 | >40 | 11.9 | 13.0 | >40 | 6.5 | 7.1 | 5.26 | tbd | >40 | 39.8 | >40 |
| CR8020 | >40 | 3.5 | 3.5 | 5.0 | 2.0 | 1.8 | 1.8 | 1.8 | 2.5 | 27.6 | 6.6 |
| CR8041 | >40 | 3.3 | 3.5 | 5.0 | 1.6 | 1.7 | 1.8 | 1.7 | 38.0 | 258.0 | 37.2 |
| CR8043 | >40 | 1.6 | 1.8 | 4.2 | 1.2 | 0.8 | 1.8 | 1.2 | >40 | >40 | 6.6 |
| CR8057 | >40 | 0.005 | 0.003 | 0.01 | >40 | >40 | >40 | >40 | >40 | — | >250 |

All SK50 titers in ug/ml; Mouse-adapted strains; Ma “pandemic” H7 strain

TABLE 16

| Study | Group | Mean AUC (g * day) | SD (g * day) | p-value[a] (mAb vs control) | p-value[b] |
|---|---|---|---|---|---|
| | Mean area under the curve of body weight change from baseline at day 0. | | | | |
| 1 | 30 mg/kg control | −82.86 | 14.15 | | |
| | 1 mg/kg CR8020 | −63.21 | 30.91 | 0.09 | |
| | 3 mg/kg CR8020 | 16.95 | 8.20 | <0.001 | <0.001 (1 vs 3 mg/kg) |
| | 10 mg/kg CR8020 | 31.44 | 9.09 | <0.001 | 0.454 (3 vs 10 mg/kg) |
| | 30 mg/kg CR8020 | 25.62 | 12.94 | <0.001 | ns |
| 2 | 30 mg/kg control | −86.51 | 8.83 | | |
| | 1 mg/kg CR8041 | −68.26 | 11.41 | 0.004 | |
| | 3 mg/kg CR8041 | 19.51 | 13.82 | <0.001 | <0.001 (1 vs 3 mg/kg) |
| | 10 mg/kg CR8041 | 35.23 | 11.06 | <0.001 | 0.061 (3 vs 10 mg/kg) |
| | 30 mg/kg CR8041 | 28.21 | 7.89 | <0.001 | ns |
| | 1 mg/kg CR8043 | −66.19 | 8.74 | <0.001 | |
| | 3 mg/kg CR8043 | 8.48 | 11.81 | <0.001 | <0.001 (1 vs 3 mg/kg) |
| | 10 mg/kg CR8043 | 31.57 | 7.90 | <0.001 | <0.001 (3 vs 10 mg/kg) |
| | 30 mg/kg CR8043 | 27.72 | 6.61 | <0.001 | 0.997 (10 vs 30 mg/kg) |

[a]Mean AUC values of the mAb dose groups were compared to the control Ab groups using analysis of variance with Dunnet's adjustment for multiple comparisons.
[b]Mean AUC values per antibody concentration were compared for each antibody using analysis of variance with Tukey's adjustment for multiple comparisons.
ns = not statistically significant

TABLE 17

Mean area under the curve of body weight change from baseline at day 0.

| Group | Mean AUC (g * day) | SD (g * day) | p-value[a] |
|---|---|---|---|
| 15 mg/kg CR8020 at day −1 | 33.44 | 10.06 | <0.001 |
| 15 mg/kg CR8020 at day 1 | 10.70 | 16.23 | <0.001 |
| 15 mg/kg CR8020 at day 2 | −15.23 | 11.60 | <0.001 |
| 15 mg/kg CR8020 at day 3 | −65.45 | 35.90 | 0.003 |
| 15 mg/kg CR8020 at day 4 | −85.95 | 23.14 | 0.742 |
| 15 mg/kg CR8020 at day 5 | −100.88 | 12.78 | 0.986 |
| 15 mg/kg CR8020 at day 6 | −84.91 | 12.28 | 0.653 |
| Control mAb at day 1 | −95.76 | 11.55 | |

[a]Mean AUC values of the 15 mg/kg mAb CR8020 dosed groups were compared to the control mAb group using analysis of variance with Dunnet's adjustment for multiple comparisons in the post-hoc analysis. Prophylactic treatment with 15 mg/kg mAb CR8020 resulted in a statistically significant reduction in weight loss compared to the control group ($p < 0.001$). Therapeutic treatment at day 1, day 2 or day 3 with 15 mg/kg mAb CR8020 also resulted in a statistically significant reduction in weight loss compared to the control group ($p < 0.001$, $p < 0.001$ and $p = 0.003$, respectively). Treatment at days 4, day 5 or day 6 with 15 mg/kg mAb CR8020 did not result in a statistically significant reduction in weight loss compared to the control group ($p > 0.05$ for all three groups).

TABLE 18

Median clinical scores. The interval with significant difference between clinical scores compared to the control mAb group are listed (e.g., between 15 mg/kg at day −1 and the control group the difference in clinical scores is significant from day 4 onwards).

| Group | Relative to control: Interval (day(s)) | p |
|---|---|---|
| 15 mg/kg CR8020 at day −1 | 4-21 | ≤0.001 |
| 15 mg/kg CR8020 at day 1 | 2-21 | ≤0.001 |
| 15 mg/kg CR8020 at day 2 | 3, 5-21 | ≤0.001 |
| 15 mg/kg CR8020 at day 3 | 3, 5-21 | ≤0.012 |
| 15 mg/kg CR8020 at day 4 | 3, 5-21 | ≤0.034 |
| 15 mg/kg CR8020 at day 5 | 3 | ≤0.001 |
| 15 mg/kg CR8020 at day 6 | 3 | ≤0.001 |

TABLE 19

Mean area under the curve of body weight change from baseline at day 0.

| Group | Mean AUC (g * day) | SD (g * day) | p-value[a] (mAb CR8020 vs control) |
|---|---|---|---|
| 30 mg/kg control | −93.06 | 10.88 | |
| 1 mg/kg CR8020 | −45.61 | 15.05 | <0.001 |
| 3 mg/kg CR8020 | −13.31 | 9.51 | <0.001 |
| 10 mg/kg CR8020 | −6.35 | 12.40 | <0.001 |
| 30 mg/kg CR8020 | −12.59 | 7.35 | <0.001 |

[a]Mean AUC values of the mAb CR8020 dosed groups were compared to the control mAb group using analysis of variance with Dunnet's adjustment for multiple comparisons in the post-hoc analysis.

TABLE 20

Summary of binding and neutralization properties of monoclonal antibodies specific for influenza virus HA.

| | H1 Binding | H3 VNA | Binding | VNA |
|---|---|---|---|---|
| CR6261 | + | + | − | − |
| CR6323 | + | + | − | − |
| CR8001 | + | − | + | + |
| CR8020 | − | − | + | + |
| CR8041 | − | − | + | + |
| CR8043 | − | − | + | + |

TABLE 21

Mean area under the curve of body weight change from baseline at day 0.

| Group | Mean AUC (g * day) | SD (g * day) | p-value (mAb vs control)[a] |
|---|---|---|---|
| 30 mg/kg control | −101.38 | 11.67 | |
| 1 mg/kg CR8020 | −82.58 | 34.71 | 0.356 |
| 3 mg/kg CR8020 | −5.70 | 23.97 | <0.001 |
| 10 mg/kg CR8020 | 2.13 | 13.13 | <0.001 |
| 1 mg/kg CR8041 | −105.05 | 17.04 | 1 |
| 3 mg/kg CR8041 | −32.22 | 30.87 | <0.001 |
| 10 mg/kg CR8041 | −20.06 | 17.92 | <0.001 |
| 30 mg/kg CR8041 | −10.01 | 10.11 | <0.001 |

TABLE 21-continued

Mean area under the curve of body weight change from baseline at day 0.

| Group | Mean AUC (g * day) | SD (g * day) | p-value (mAb vs control)[a] |
|---|---|---|---|
| 1 mg/kg CR8043 | −107.75 | 11.04 | 0.997 |
| 3 mg/kg CR8043 | −117.88 | 5.91 | 0.510 |
| 10 mg/kg CR8043 | −94.00 | 23.23 | 0.992 |
| 30 mg/kg CR8043 | −56.82 | 17.55 | <0.001 |

[a]Mean AUC values of the mAb CR8020 dosed groups were compared to the control mAb group using analysis of variance with Dunnet's adjustment for multiple comparisons in the post-hoc analysis.

TABLE 22

Mean area under the curve of body weight change from baseline at day 0.

| Group | Mean AUC (g * day) | SD (g * day) | p-value (mAb vs control)[a] |
|---|---|---|---|
| 15 mg/kg CR8020 at day −1 | −7.68 | 8.17 | <0.001 |
| 15 mg/kg CR8020 at day 1 | −20.43 | 8.41 | <0.001 |
| 15 mg/kg CR8020 at day 2 | −38.18 | 37.35 | <0.001 |
| 15 mg/kg CR8020 at day 3 | −28.27 | 9.63 | <0.001 |
| 15 mg/kg CR8020 at day 4 | −99.11 | 37.90 | 0.566 |
| 15 mg/kg CR8020 at day 5 | −93.62 | 10.29 | 0.979 |
| 15 mg/kg CR8020 at day 6 | −94.06 | 7.65 | 0.858 |
| Control antibody at day 1 | −93.33 | 10.58 | |

[a]Mean AUC values were compared using the RobustReg procedure (SAS) which allocates less weight to outliers.

TABLE 23

Median clinical scores.

| Group | Relative to control | |
|---|---|---|
| | Interval (day(s)) | p |
| 15 mg/kg CR8020 at day −1 | 4-21 | ≤0.001 |
| 15 mg/kg CR8020 at day 1 | 2, 5-21 | ≤0.012 |
| 15 mg/kg CR8020 at day 2 | 6-21 | ≤0.038 |
| 15 mg/kg CR8020 at day 3 | 7-21 | ≤0.035 |
| 15 mg/kg CR8020 at day 4 | 5, 6, 8-21 | ≤0.016 |
| 15 mg/kg CR8020 at day 5 | 8 | <0.001 |
| 15 mg/kg CR8020 at day 6 | — | ≥0.449 |

TABLE 24

Binding kinetics

| Fab | kon (1/Ms) | Kdis (1/s) | KD (nM) |
|---|---|---|---|
| A/Wisconsin | | | |
| CRF8020 | 2.03E+05 | 2.08E−03 | 11.2 |
| CRF8043 | 4.08E+05 | 9.86E−05 | 0.3 |
| A/Brisbane | | | |
| CRF8020 | 1.81E+05 | 1.43E−03 | 8.9 |
| CRF8043 | 3.12E+05 | 8.69E−05 | 0.3 |

REFERENCES

Air M. A. (1981), Sequence relationships among the hemagglutinin genes of 12 subtypes of influenza A virus. *Proc. Natl. Acad. Sci. U.S.A.* 78(12):7639-7643.

Boel E. et al. (2000), Functional human monoclonal antibodies of all isotypes constructed from phage display library-derived single-chain Fv antibody fragments. *J. Immunol. Methods* 239:153-166.

Brown E. G. et al. (2001), Pattern of mutation in the genome of influenza A virus on adaptation to increased virulence in the mouse lung: Identification of functional themes. *PNAS* 98:6883-6888.

Burton D. R. and C. F. Barbas (1994), Human antibodies from combinatorial libraries. *Adv. Immunol.* 57:191-280.

Chou T. C. and P. Talalay (1984), Quantitative analysis of dose-effect relationships: the combined effects of multiple drugs or enzyme inhibitors. *Adv. Enzyme Regul.* 22:27-55.

De Kruif J. et al. (1995a), Rapid selection of cell subpopulation-specific human monoclonal antibodies from a synthetic phage antibody library. *Proc. Natl. Acad. Sci. U.S.A.* 92:3938.

De Kruif J. et al. (1995b), Selection and application of human single-chain Fv antibody fragments from a semi-synthetic phage antibody display library with designed CDR3 regions. *J. Mol. Biol.* 248:97-105.

Ekiert et al. (2009), Antibody recognition of a highly conserved influenza virus epitope. *Science* 324:246-251.

Fouchier A. M. et al. (2005), Characterization of a novel influenza A virus hemagglutinin subtype (H16) obtained from black-headed gulls. *J. Virol.* 79(5):2814-2822.

Gocník M. et al. (2007), Antibodies specific to the HA2 glycopolypeptide of influenza A virus haemagglutinin with fusion-inhibition activity contribute to the protection of kice against lethal infection. *J. Gen. Virol.* 88:951-955.

Huls G. et al. (1999), Antitumor immune effector mechanisms recruited by phage display-derived fully human IgG1 and IgA1 monoclonal antibodies. *Cancer Res.* 59:5778-5784.

Östberg L. and E. Pursch (1983), Human×(Mouse×Human) hybridomas stably producing human antibodies. *Hybridoma* 2(4): 361-367.

Slootstra J. W. et al. (1996), Structural aspects of antibody-antigen interaction revealed through small random peptide libraries. *Mol. Divers.* 1:87-96.

Stropkovská A. et al. (2009), Broadly cross-reactive monoclonal antibodies against HA2 glycopeptide of influenza A virus hemagglutinin of H3 subtype reduce replication of influenza A viruses of human and avian origin. *Acta Virologica* 53:15-20.

The World Health Organization Global Influenza Program Surveillance Network (2005), Evolution of H5N1 Avian Influenza Viruses in Asia. *Emerg. Infect. Dis.* 11:1515-1521.

Varečková E. et al. (2003a), Inhibition of fusion activity of influenza A hemagglutinin-mediated by HA2-specific monoclonal antibodies. *Arch. Virol.* 148:469-486.

Varečková E. et al. (2003b), A monoclonal antibody specific to the HA2 glycoprotein of influenza A virus haemagglutinin that inhibits its fusion activity reduces replication of the virus. *Acta Virologica* 47:229-236.

Wang T. et al. (2010), Broadly protective monoclonal antibodies against H3 influenza viruses following sequential immunization with different hemagglutinins. *PLoS Pathogens* 6(2):1-9.

What is claimed is:

1. A binding molecule genetically engineered to specifically recognize and bind to an epitope in influenza hemagglutinin protein (HA), having neutralizing activity against influenza viruses comprising HA of the H3 subtype and having cross-neutralizing activity against at least an influenza virus comprising HA of the H7 subtype, and/or an influenza virus comprising HA of the H10 subtype, wherein the binding molecule is selected from the group consisting of:

a) a binding molecule comprising a heavy chain CDR1 region of SEQ ID NO:81, a heavy chain CDR2 region of SEQ ID NO:82, a heavy chain CDR3 region of SEQ ID NO:83, a light chain CDR1 region of SEQ ID NO:84, a light chain CDR2 region of SEQ ID NO:85, and a light chain CDR3 region of SEQ ID NO:86, b) a binding molecule comprising a heavy chain CDR1 region of SEQ ID NO:87, a heavy chain CDR2 region of SEQ ID NO:88, a heavy chain CDR3 region of SEQ ID NO:89, a light chain CDR1 region of SEQ ID NO:90, a light chain CDR2 region of SEQ ID NO:91, and a light chain CDR3 region of SEQ ID NO:92, c) a binding molecule comprising a heavy chain CDR1 region of SEQ ID NO:103, a heavy chain CDR2 region of SEQ ID NO:104, a heavy chain CDR3 region of SEQ ID NO:105, a light chain CDR1 region of SEQ ID NO:106, a light chain CDR2 region of SEQ ID NO:107, and a light chain CDR3 region of SEQ ID NO:108, d) a binding molecule comprising a heavy chain CDR1 region of SEQ ID NO:109, a heavy chain CDR2 region of SEQ ID NO:110, a heavy chain CDR3 region of SEQ ID NO:111, a light chain CDR1 region of SEQ ID NO:112, a light chain CDR2 region of SEQ ID NO:113, and a light chain CDR3 region of SEQ ID NO:114, e) a binding molecule comprising a heavy chain CDR1 region of SEQ ID NO:115, a heavy chain CDR2 region of SEQ ID NO:116, a heavy chain CDR3 region of SEQ ID NO:117, a light chain CDR1 region of SEQ ID NO:118, a light chain CDR2 region of SEQ ID NO:119, and a light chain CDR3 region of SEQ ID NO:120, f) a binding molecule comprising a heavy chain CDR1 region of SEQ ID NO:121, a heavy chain CDR2 region of SEQ ID NO:122, a heavy chain CDR3 region of SEQ ID NO:123, a light chain CDR1 region of SEQ ID NO:124, a light chain CDR2 region of SEQ ID NO:125, and a light chain CDR3 region of SEQ ID NO:126, g) a binding molecule comprising a heavy chain CDR1 region of SEQ ID NO:126, a heavy chain CDR2 region of SEQ ID NO:127, a heavy chain CDR3 region of SEQ ID NO:128, a light chain CDR1 region of SEQ ID NO:129, a light chain CDR2 region of SEQ ID NO:130, and a light chain CDR3 region of SEQ ID NO:131, h) a binding molecule comprising a heavy chain CDR1 region of SEQ ID NO:132, a heavy chain CDR2 region of SEQ ID NO:133, a heavy chain CDR3 region of SEQ ID NO:134, a light chain CDR1 region of SEQ ID NO:135, a light chain CDR2 region of SEQ ID NO:136, and a light chain CDR3 region of SEQ ID NO:137, i) a binding molecule comprising a heavy chain CDR1 region of SEQ ID NO:138, a heavy chain CDR2 region of SEQ ID NO:139, a heavy chain CDR3 region of SEQ ID NO:140, a light chain CDR1 region of SEQ ID NO:141, a light chain CDR2 region of SEQ ID NO:142, and a light chain CDR3 region of SEQ ID NO:143, and j) a binding molecule comprising a heavy chain CDR1 region of SEQ ID NO:144, a heavy chain CDR2 region of SEQ ID NO:145, a heavy chain CDR3 region of SEQ ID NO:146, a light chain CDR1 region of SEQ ID NO:147, a light chain CDR2 region of SEQ ID NO:148, and a light chain CDR3 region of SEQ ID NO:149, k) a binding molecule comprising a heavy chain CDR1 region of SEQ ID NO:150, a heavy chain CDR2 region of SEQ ID NO:151, a heavy chain CDR3 region of SEQ ID NO:152, a light chain CDR1 region of SEQ ID NO:153, a light chain CDR2 region of SEQ ID NO:154, and a light chain CDR3 region of SEQ ID NO:155, l) a binding molecule comprising a heavy chain CDR1 region of SEQ ID NO:156, a heavy chain CDR2 region of SEQ ID NO:157, a heavy chain CDR3 region of SEQ ID NO:158, a light chain CDR1 region of SEQ ID NO:159, a light chain CDR2 region of SEQ ID NO:160, and a light chain CDR3 region of SEQ ID NO:161, m) a binding molecule comprising a heavy chain CDR1 region of SEQ ID NO:162, a heavy chain CDR2 region of SEQ ID NO:163, a heavy chain CDR3 region of SEQ ID NO:164, a light chain CDR1 region of SEQ ID NO:165, a light chain CDR2 region of SEQ ID NO:166, and a light chain CDR3 region of SEQ ID NO:167, n) a binding molecule comprising a heavy chain CDR1 region of SEQ ID NO:168, a heavy chain CDR2 region of SEQ ID NO:169, a heavy chain CDR3 region of SEQ ID NO:170, a light chain CDR1 region of SEQ ID NO:171, a light chain CDR2 region of SEQ ID NO:172, and a light chain CDR3 region of SEQ ID NO:173, o) a binding molecule comprising a heavy chain CDR1 region of SEQ ID NO:173, a heavy chain CDR2 region of SEQ ID NO:174, a heavy chain CDR3 region of SEQ ID NO:175, a light chain CDR1 region of SEQ ID NO:176, a light chain CDR2 region of SEQ ID NO:177, and a light chain CDR3 region of SEQ ID NO:178, and p) a binding molecule comprising a heavy chain CDR1 region of SEQ ID NO:179, a heavy chain CDR2 region of SEQ ID NO:180, a heavy chain CDR3 region of SEQ ID NO:181, a light chain CDR1 region of SEQ ID NO:182, a light chain CDR2 region of SEQ ID NO:183, and a light chain CDR3 region of SEQ ID NO:184.

2. A binding molecule genetically engineered to specifically recognize and bind to an epitope in influenza hemagglutinin protein (HA), having neutralizing activity against influenza viruses comprising HA of the H3 subtype and having cross-neutralizing activity against at least an influenza virus comprising HA of the H7 subtype, and/or an influenza virus comprising HA of the H10 subtype, wherein the binding molecule is selected from the group consisting of:

a binding molecule comprising a heavy chain CDR1 region of SEQ ID NO:109, a heavy chain CDR2 region of SEQ ID NO:110, a heavy chain CDR3 region of SEQ ID NO:111, a light chain CDR1 region of SEQ ID NO:112, a light chain CDR2 region of SEQ ID NO:113, and a light chain CDR3 region of SEQ ID NO:114, a binding molecule comprising a heavy chain CDR1 region of SEQ ID NO:138, a heavy chain CDR2 region of SEQ ID NO:139, a heavy chain CDR3 region of SEQ ID NO:140, a light chain CDR1 region of SEQ ID NO:141, a light chain CDR2 region of SEQ ID NO:142, and a light chain CDR3 region of SEQ ID NO:143, and a binding molecule comprising a heavy chain CDR1 region of SEQ ID NO:144, a heavy chain CDR2 region of SEQ ID NO:145, a heavy chain CDR3 region of SEQ ID NO:146, a light chain CDR1 region of SEQ ID NO:147, a light chain CDR2 region of SEQ ID NO:148, and a light chain CDR3 region of SEQ ID NO:149.

3. A human monoclonal antibody specifically binding influenza HA protein, wherein the human monoclonal antibody comprises:

(a) a heavy chain CDR1 region of SEQ ID NO:109, a heavy chain CDR2 region of SEQ ID NO:110, a heavy chain CDR3 region of SEQ ID NO:111, a light chain CDR1 region of SEQ ID NO:112, a light chain CDR2 region of SEQ ID NO:113, and a light chain CDR3 region of SEQ ID NO:114, or (b) a heavy chain CDR1 region of SEQ ID NO:144, a heavy chain CDR2 region of SEQ ID NO:145, a heavy chain CDR3 region of SEQ ID NO:146, a light chain CDR1 region of SEQ ID NO:147, a light chain CDR2 region of SEQ ID NO:148, and a light chain CDR3 region of SEQ ID NO:149.

4. The human monoclonal antibody of claim 3, wherein the human monoclonal antibody comprises:

the heavy chain CDR1 region of SEQ ID NO:109,
the heavy chain CDR2 region of SEQ ID NO:110,
the heavy chain CDR3 region of SEQ ID NO:111,
the light chain CDR1 region of SEQ ID NO:112,
the light chain CDR2 region of SEQ ID NO:113, and
the light chain CDR3 region of SEQ ID NO:114.

5. The human monoclonal antibody of claim 3, wherein the human monoclonal antibody comprises:

the heavy chain CDR1 region of SEQ ID NO:144,
the heavy chain CDR2 region of SEQ ID NO:145,
the heavy chain CDR3 region of SEQ ID NO:146,
the light chain CDR1 region of SEQ ID NO:147,
the light chain CDR2 region of SEQ ID NO:148, and
the light chain CDR3 region of SEQ ID NO:149.

6. A method of diagnosing influenza infection in a subject, the method comprising:

contacting the human monoclonal antibody of claim 3 with a biological sample of the subject in order to diagnose the influenza infection in the subject.

7. A method of treating or prophylaxing against influenza infection in a subject, the method comprising:

administering the human monoclonal antibody of claim 3 to the subject to treat or prophylax the subject against an influenza infection caused by influenza virus comprising HA of the H3 subtype.

8. An immunoconjugate comprising:

the human monoclonal antibody of claim 3, and
at least one tag associated therewith.

9. A composition comprising:

the human monoclonal antibody of claim 3, and
a pharmaceutically acceptable excipient.

10. A process for producing a human monoclonal antibody having neutralizing activity against influenza viruses comprising hemagglutinin protein (HA) of the H3 subtype and having cross-neutralizing activity against at least an influenza virus comprising HA of the H7 subtype, and/or an influenza virus comprising HA of the H10 subtype, wherein the process comprises:

culturing a host cell comprising a vector comprising a polynucleotide encoding the human monoclonal antibody of claim 3 under conditions conducive to the expression of the human monoclonal antibody, and, optionally, recovering the expressed human monoclonal antibody.

11. The process of claim 10, wherein the host cell is a human cell.

* * * * *

UNITED STATES PATENT AND TRADEMARK OFFICE
CERTIFICATE OF CORRECTION

PATENT NO. : 9,611,317 B2
APPLICATION NO. : 13/897843
DATED : April 4, 2017
INVENTOR(S) : Mark Throsby et al.

Page 1 of 1

It is certified that error appears in the above-identified patent and that said Letters Patent is hereby corrected as shown below:

On the Title Page

Please add the following inventors:
Adrianus Quirinus BAKKER   Hoorn, The Netherlands
Tim BEAUMONT               Ouderkerk aan de Amstel, The Netherlands
Mark KWAKKENBOS            Amsterdam, The Netherlands
Hergen SPITS               Amsterdam, The Netherlands Signed and Sealed this
Twentieth Day of July, 2021

Drew Hirshfeld
*Performing the Functions and Duties of the
Under Secretary of Commerce for Intellectual Property and
Director of the United States Patent and Trademark Office*